(12) United States Patent
Pfeifer et al.

(10) Patent No.: US 8,124,353 B2
(45) Date of Patent: Feb. 28, 2012

(54) METHODS OF TREATING AND MONITORING DISEASE WITH ANTIBODIES

(75) Inventors: Andrea Pfeifer, St-Legier (CH); Maria Pihlgren, St. Sulpice (CH); Andreas Muhs, Pully (CH); Ryan Watts, San Mateo, CA (US)

(73) Assignees: AC Immune S.A., Lausanne (CH); Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/311,505

(22) PCT Filed: Oct. 2, 2007

(86) PCT No.: PCT/US2007/021134
§ 371 (c)(1),
(2), (4) Date: Jan. 19, 2010

(87) PCT Pub. No.: WO2008/060364
PCT Pub. Date: May 22, 2008

(65) Prior Publication Data
US 2010/0150906 A1    Jun. 17, 2010

Related U.S. Application Data

(60) Provisional application No. 60/943,289, filed on Jun. 11, 2007, provisional application No. 60/943,499, filed on Jun. 12, 2007.

(30) Foreign Application Priority Data

Oct. 2, 2006   (EP) .................................. 06020765
Oct. 2, 2006   (EP) .................................. 06020766
Dec. 8, 2006   (WO) ................. PCT/EP2006/011862
Jul. 13, 2007  (WO) ................. PCT/US2007/073504

(51) Int. Cl.
*G01N 33/53* (2006.01)
(52) U.S. Cl. ........................................... 435/7.1
(58) Field of Classification Search .................... None
See application file for complete search history.

(56) References Cited

U.S. PATENT DOCUMENTS

| | | |
|---|---|---|
| 4,666,829 A | 5/1987 | Glenner et al. |
| 5,218,100 A | 6/1993 | Muller-Hill et al. |
| 5,231,000 A | 7/1993 | Majocha et al. |
| 5,231,170 A | 7/1993 | Averback |
| 5,234,814 A | 8/1993 | Card et al. |
| 5,441,870 A | 8/1995 | Seubert et al. |
| 5,538,845 A | 7/1996 | Knops et al. |
| 5,567,720 A | 10/1996 | Averback |
| 5,589,154 A | 12/1996 | Anderson |
| 5,593,846 A | 1/1997 | Schenk et al. |
| 5,605,811 A | 2/1997 | Seubert et al. |
| 5,626,332 A | 5/1997 | Phillips |
| 5,665,355 A | 9/1997 | Primi |
| 5,679,531 A | 10/1997 | Konig |
| 5,688,651 A | 11/1997 | Solomon |
| 5,693,753 A | 12/1997 | Konig |
| 5,705,401 A | 1/1998 | Masters et al. |
| 5,721,130 A | 2/1998 | Seubert et al. |
| 5,750,349 A | 5/1998 | Suzuki et al. |
| 5,766,846 A | 6/1998 | Schlossmacher et al. |
| 5,773,218 A * | 6/1998 | Gallatin et al. .............. 435/6.11 |
| 5,786,180 A | 7/1998 | Konig |
| 5,955,285 A | 9/1999 | Averback |
| 5,955,317 A | 9/1999 | Suzuki et al. |
| 6,018,024 A | 1/2000 | Seubert et al. |
| 6,114,133 A | 9/2000 | Seubert et al. |
| 6,214,973 B1 | 4/2001 | Ohtomo et al. |
| 6,218,506 B1 | 4/2001 | Krafft et al. |
| 6,274,603 B1 | 8/2001 | Poirior |
| 6,284,221 B1 | 9/2001 | Schenk et al. |
| 6,287,793 B1 | 9/2001 | Schenk et al. |
| 6,294,171 B2 | 9/2001 | McMichael |
| 6,303,567 B1 | 10/2001 | Findeis et al. |
| 6,309,892 B1 | 10/2001 | Averback |
| 6,387,674 B1 | 5/2002 | Trasciatti et al. |
| 6,582,945 B1 | 6/2003 | Raso |
| 6,610,493 B1 | 8/2003 | Citron et al. |
| 6,664,442 B2 | 12/2003 | McConlogue et al. |
| 6,737,056 B1 | 5/2004 | Presta |
| 6,743,427 B1 | 6/2004 | Schenk |

(Continued)

FOREIGN PATENT DOCUMENTS

CN    1396183    2/2003

(Continued)

OTHER PUBLICATIONS

Ozawa et al. 2002 (Annals of the New York Academy of Sciences 977:149-154).*

(Continued)

*Primary Examiner* — Daniel E Kolker
(74) *Attorney, Agent, or Firm* — Jones Day

(57) ABSTRACT

The present invention is related to methods and compositions for the therapeutic and diagnostic use in the treatment of diseases and disorders which are caused by or associated with amyloid or amyloid-like proteins including amyloidosis, a group of disorders and abnormalities associated with amyloid protein such as Alzheimer's disease. The present invention provides novel methods and compositions comprising highly specific and highly effective antibodies having the ability to specifically recognize and bind to specific epitopes from a range of j3-amyloid proteins. The antibodies enabled by the teaching of the present invention are particularly useful for the treatment of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD).

11 Claims, 26 Drawing Sheets

U.S. PATENT DOCUMENTS

Figure 4:
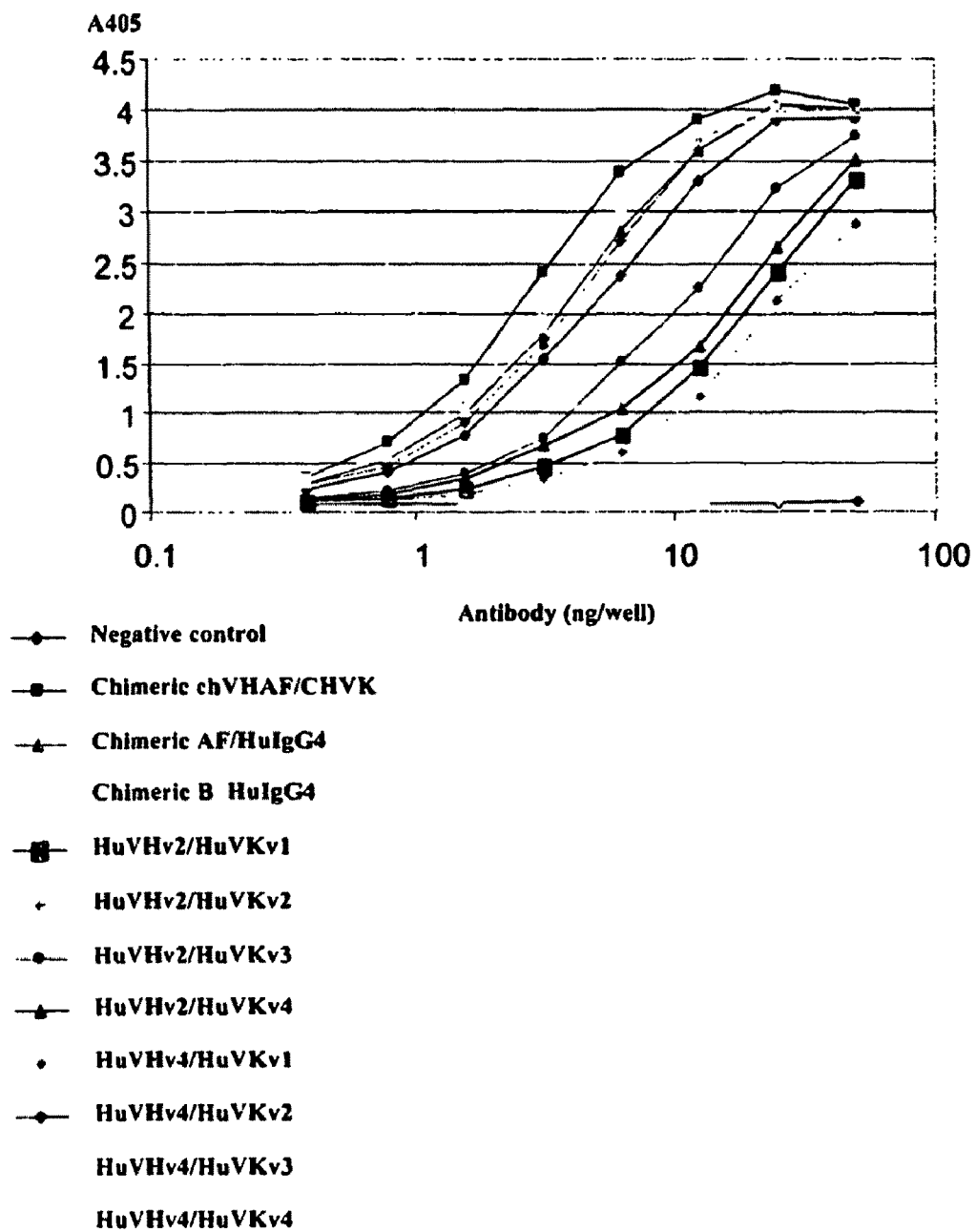

| | | |
|---|---|---|
| 6,750,324 B1 | 6/2004 | Schenk |
| 6,761,888 B1 | 7/2004 | Schenk |
| 6,787,138 B1 | 9/2004 | Schenk |
| 6,787,139 B1 | 9/2004 | Schenk |
| 6,787,140 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk |
| 6,815,175 B2 | 11/2004 | Weksler |
| 6,849,416 B2 | 2/2005 | Wiltfang et al. |
| 6,866,849 B2 | 3/2005 | Schenk |
| 6,866,850 B2 | 3/2005 | Schenk |
| 6,872,554 B2 | 3/2005 | Raso |
| 6,875,434 B1 | 4/2005 | Schenk |
| 6,905,686 B1 | 6/2005 | Schenk |
| 6,913,745 B1 | 7/2005 | Schenk |
| 6,972,127 B2 | 12/2005 | Schenk |
| 6,998,124 B1 | 2/2006 | Erickson-Miller et al. |
| 7,014,855 B2 | 3/2006 | Schenk |
| 7,022,500 B1 | 4/2006 | Queen et al. |
| 7,060,270 B2 | 6/2006 | Nicolau et al. |
| 7,067,133 B2 | 6/2006 | Nicolau |
| 7,129,084 B2 | 10/2006 | Bulow et al. |
| 7,179,892 B2 | 2/2007 | Basi et al. |
| 7,189,819 B2 | 3/2007 | Basi et al. |
| 7,195,761 B2 | 3/2007 | Holtzman et al. |
| 7,256,273 B2 | 8/2007 | Basi et al. |
| 7,318,923 B2 | 1/2008 | Tsurushita et al. |
| 7,320,790 B2 | 1/2008 | Hinton et al. |
| 7,335,491 B2 | 2/2008 | Drapeau et al. |
| 7,339,035 B2 | 3/2008 | Yanagisawa et al. |
| 7,371,365 B2 | 5/2008 | Poduslo et al. |
| 7,413,884 B2 | 8/2008 | Raso |
| 7,427,342 B2 | 9/2008 | Barber |
| 7,772,375 B2 * | 8/2010 | Greferath et al. ........ 530/388.85 |
| 7,892,544 B2 * | 2/2011 | Pfeifer et al. ............. 424/133.1 |
| 2001/0029293 A1 | 10/2001 | Gallatin et al. |
| 2002/0009445 A1 | 1/2002 | Du et al. |
| 2002/0086847 A1 | 7/2002 | Chain |
| 2002/0094335 A1 | 7/2002 | Chalifour et al. |
| 2002/0182660 A1 | 12/2002 | Fong |
| 2002/0197258 A1 | 12/2002 | Ghanbari et al. |
| 2003/0068316 A1 | 4/2003 | Klein et al. |
| 2003/0108551 A1 | 6/2003 | Nicolau |
| 2003/0147882 A1 | 8/2003 | Solomon et al. |
| 2003/0190689 A1 | 10/2003 | Crosby et al. |
| 2003/0232758 A1 | 12/2003 | St. George-Hyslop et al. |
| 2004/0043416 A1 | 3/2004 | Ji et al. |
| 2004/0043418 A1 | 3/2004 | Holtzman et al. |
| 2004/0058414 A1 | 3/2004 | Queen et al. |
| 2004/0142872 A1 | 7/2004 | Poduslo et al. |
| 2004/0146512 A1 | 7/2004 | Rosenthal et al. |
| 2004/0175394 A1 | 9/2004 | Schenk et al. |
| 2004/0181042 A1 | 9/2004 | Yanagisawa et al. |
| 2004/0191264 A1 | 9/2004 | Nielsen et al. |
| 2004/0192898 A1 | 9/2004 | Jia et al. |
| 2004/0213800 A1 | 10/2004 | Seubett et al. |
| 2004/0223912 A1 | 11/2004 | Montalto et al. |
| 2004/0241164 A1 | 12/2004 | Bales et al. |
| 2004/0242845 A1 | 12/2004 | Nicolau et al. |
| 2004/0248197 A1 | 12/2004 | Holtzman et al. |
| 2004/0265919 A1 | 12/2004 | Vanderstichele et al. |
| 2005/0013815 A1 | 1/2005 | Schenk |
| 2005/0019330 A1 | 1/2005 | Schenk |
| 2005/0031651 A1 | 2/2005 | Gervais et al. |
| 2005/0118651 A1 | 6/2005 | Basi et al. |
| 2005/0124016 A1 | 6/2005 | LaDu et al. |
| 2005/0129691 A1 | 6/2005 | Gerlai |
| 2005/0129695 A1 | 6/2005 | Mercken et al. |
| 2005/0147613 A1 | 7/2005 | Raso |
| 2005/0169925 A1 | 8/2005 | Bardroff et al. |
| 2005/0175626 A1 | 8/2005 | Delacourte et al. |
| 2006/0008458 A1 | 1/2006 | Solomon |
| 2006/0057646 A1 | 3/2006 | Wiltfang et al. |
| 2006/0057701 A1 | 3/2006 | Rosenthal et al. |
| 2006/0073149 A1 | 4/2006 | Bales et al. |
| 2006/0110388 A1 | 5/2006 | Davies et al. |
| 2006/0111301 A1 | 5/2006 | Mattner |
| 2006/0115477 A1 | 6/2006 | Unger et al. |
| 2006/0127954 A1 | 6/2006 | Mercken et al. |
| 2006/0160161 A1 | 7/2006 | Pavliakova et al. |
| 2006/0165682 A1 | 7/2006 | Basi et al. |
| 2006/0193850 A1 | 8/2006 | Warne et al. |
| 2006/0198851 A1 | 9/2006 | Basi et al. |
| 2006/0228349 A1 | 10/2006 | Acton et al. |
| 2006/0246075 A1 | 11/2006 | Mercken et al. |
| 2006/0280733 A1 | 12/2006 | Kayed et al. |
| 2006/0292152 A1 | 12/2006 | Rosenthal et al. |
| 2007/0010435 A1 | 1/2007 | Frangione et al. |
| 2007/0015218 A1 | 1/2007 | Cao et al. |
| 2007/0031416 A1 | 2/2007 | Shoji et al. |
| 2007/0072307 A1 | 3/2007 | Godavarti et al. |
| 2007/0098721 A1 | 5/2007 | Hillen et al. |
| 2007/0110750 A1 | 5/2007 | Glabe et al. |
| 2007/0128191 A1 | 6/2007 | Barrio |
| 2007/0190046 A1 | 8/2007 | DeMattos et al. |
| 2007/0213512 A1 | 9/2007 | Krafft et al. |
| 2007/0218499 A1 | 9/2007 | Lambert et al. |
| 2008/0025988 A1 | 1/2008 | Yamaguchi et al. |
| 2008/0107601 A1 | 5/2008 | Lauwereys et al. |
| 2008/0131422 A1 | 6/2008 | Sugimura et al. |
| 2008/0199879 A1 | 8/2008 | Takayama et al. |
| 2008/0292639 A1 | 11/2008 | Shen et al. |
| 2009/0017040 A1 | 1/2009 | Pfeifer et al. |
| 2009/0017041 A1 | 1/2009 | Pfeifer et al. |
| 2009/0023159 A1 | 1/2009 | Mendez |
| 2009/0035295 A1 | 2/2009 | Hillen et al. |
| 2009/0035307 A1 | 2/2009 | Barghorn et al. |
| 2009/0074775 A1 | 3/2009 | Holtzman et al. |
| 2009/0155246 A1 | 6/2009 | Gellerfors et al. |
| 2009/0156471 A1 | 6/2009 | Gazit et al. |
| 2009/0162362 A1 | 6/2009 | Sarasa |
| 2009/0162878 A1 | 6/2009 | Kim et al. |
| 2009/0175847 A1 | 7/2009 | Barghorn et al. |
| 2009/0191190 A1 | 7/2009 | Barghorn et al. |
| 2009/0214515 A1 | 8/2009 | Holzman et al. |
| 2009/0232801 A1 | 9/2009 | Hillen et al. |
| 2009/0238831 A1 | 9/2009 | Hillen et al. |
| 2010/0080800 A1 | 4/2010 | Pfeifer et al. |
| 2010/0291097 A1 | 11/2010 | Pfeifer et al. |
| 2010/0297012 A1 | 11/2010 | Pfeifer et al. |
| 2010/0297013 A1 | 11/2010 | Pfeifer et al. |
| 2010/0297132 A1 * | 11/2010 | Greferath et al. .......... 424/139.1 |
| 2011/0070613 A1 | 3/2011 | Greferath et al. |

FOREIGN PATENT DOCUMENTS

| | | |
|---|---|---|
| EP | 0613007 | 8/1994 |
| EP | 0623675 | 11/1994 |
| EP | 0304013 | 6/1996 |
| EP | 0783104 | 7/1997 |
| EP | 1130032 | 9/2001 |
| EP | 1420032 | 5/2004 |
| EP | 1741783 | 1/2007 |
| EP | 1861422 | 12/2007 |
| EP | 1954718 | 8/2008 |
| EP | 1963363 | 9/2008 |
| EP | 1976877 | 10/2008 |
| JP | 07238096 | 9/1995 |
| JP | 2005 185281 | 7/2005 |
| JP | 2007077103 | 3/2007 |
| WO | WO 89/07657 | 8/1989 |
| WO | WO 90/05746 | 5/1990 |
| WO | WO 92/11018 | 7/1992 |
| WO | WO 95/11994 | 5/1995 |
| WO | WO 96/01359 | 1/1996 |
| WO | WO 96/28187 | 9/1996 |
| WO | WO 96/29605 | 9/1996 |
| WO | WO 96/03631 | 11/1996 |
| WO | WO 96/40731 | 12/1996 |
| WO | WO 97/10505 | 3/1997 |
| WO | WO 97/18476 | 5/1997 |
| WO | WO 97/21728 | 6/1997 |
| WO | WO 99/05175 | 2/1999 |
| WO | WO 99/27944 | 6/1999 |
| WO | WO 99/40837 | 8/1999 |
| WO | WO 99/40909 | 8/1999 |
| WO | WO 99/59571 | 11/1999 |

| | | |
|---|---|---|
| WO | WO 00/56771 | 9/2000 |
| WO | WO 00/72880 | 12/2000 |
| WO | WO 01/16364 | 3/2001 |
| WO | WO 01/18169 | 3/2001 |
| WO | 01/62801 * | 8/2001 |
| WO | WO 01/62801 | 8/2001 |
| WO | WO 01/85093 | 11/2001 |
| WO | WO 02/46237 | 6/2002 |
| WO | WO 02/096937 | 12/2002 |
| WO | WO 03/014162 | 2/2003 |
| WO | WO 03/016466 | 2/2003 |
| WO | WO 03/070760 | 8/2003 |
| WO | WO 03/076006 | 9/2003 |
| WO | WO 03/077858 | 9/2003 |
| WO | WO 03/090772 | 11/2003 |
| WO | WO 2004/024090 | 3/2004 |
| WO | WO 2004/029093 | 4/2004 |
| WO | WO 2004/050707 | 6/2004 |
| WO | WO 2004/058258 | 7/2004 |
| WO | WO 2004/065569 | 8/2004 |
| WO | WO 2004/067561 | 8/2004 |
| WO | WO 2004/071408 | 8/2004 |
| WO | WO 2004/108895 | 12/2004 |
| WO | WO 2005/005638 | 1/2005 |
| WO | WO 2005/018424 | 3/2005 |
| WO | WO 2005/025516 | 3/2005 |
| WO | WO 2005/053604 | 6/2005 |
| WO | WO 2005/058941 | 6/2005 |
| WO | WO 2005/081872 | 9/2005 |
| WO | WO 2005/105998 | 11/2005 |
| WO | WO 2005/120571 | 12/2005 |
| WO | WO 2006/016644 | 2/2006 |
| WO | WO 2006/036291 | 4/2006 |
| WO | WO 2006/037604 | 4/2006 |
| WO | WO 2006/039327 | 4/2006 |
| WO | WO 2006/055178 | 5/2006 |
| WO | WO 2006/066049 | 6/2006 |
| WO | WO 2006/066089 | 6/2006 |
| WO | WO 2006/066171 | 6/2006 |
| WO | WO 2006/081171 | 8/2006 |
| WO | WO 2006/083533 | 8/2006 |
| WO | WO 2006/083689 | 8/2006 |
| WO | WO 2006/094724 | 9/2006 |
| WO | WO 2006/103116 | 10/2006 |
| WO | WO 2006/118959 | 11/2006 |
| WO | WO 2006/121656 | 11/2006 |
| WO | WO 2007/011639 | 1/2007 |
| WO | WO 2007/017686 | 2/2007 |
| WO | WO 2007/022416 | 2/2007 |
| WO | WO 2007/042261 | 4/2007 |
| WO | WO 2007/050359 | 5/2007 |
| WO | WO 2007/062088 | 5/2007 |
| WO | WO 2007/062852 | 6/2007 |
| WO | WO 2007/064917 | 6/2007 |
| WO | WO 2007/064919 | 6/2007 |
| WO | WO 2007/064972 | 6/2007 |
| WO | WO 2007/068412 | 6/2007 |
| WO | WO 2007/068429 | 6/2007 |
| WO | WO 2007/106617 | 9/2007 |
| WO | WO 2007/108756 | 9/2007 |
| WO | WO 2007/113172 | 10/2007 |
| WO | WO 2007/123345 | 11/2007 |
| WO | WO 2008/002893 | 1/2008 |
| WO | WO 2008/011348 | 1/2008 |
| WO | WO 2008/012101 | 1/2008 |
| WO | WO 2008/030251 | 3/2008 |
| WO | WO 2008/045962 | 4/2008 |
| WO | WO 2008/060364 | 5/2008 |
| WO | WO 2008/061795 | 5/2008 |
| WO | WO 2008/067464 | 6/2008 |
| WO | WO 2008/070229 | 6/2008 |
| WO | WO 2008/071394 | 6/2008 |
| WO | WO 2008/104385 | 9/2008 |
| WO | WO 2008/104386 | 9/2008 |
| WO | WO 2008/143708 | 11/2008 |
| WO | WO 2008/150946 | 12/2008 |
| WO | WO 2008/150949 | 12/2008 |
| WO | WO 2008/156621 | 12/2008 |
| WO | WO 2008/156622 | 12/2008 |
| WO | WO 2009/048537 | 4/2009 |
| WO | WO 2009/048538 | 4/2009 |
| WO | WO 2009/048539 | 4/2009 |

OTHER PUBLICATIONS

Acha-Orbea et al., 1993, "Anti-T-cell receptor V beta antibodies in autoimmunity", Immunol. Ser.; 59:193-202.

Amendment And Response as filed on Jul. 27, 2009 in U.S. Appl. No. 11/637,213.

Anderson et al., 2004, "Characterization of beta amyloid assemblies in drusen: the deposits associated with aging and age-related macular degeneration", Experimental Eye Research; 78:243-256.

Bard et al., 2000, "Peripherally administered antibodies against amyloid bipeptide enter the central nervous system and reduce pathology in a mouse model of Alzheimer disease", Nature Med.; 6:916-919.

Bard et al., 2003, "Epitope and isotype specificities of antibodies to beta-amyloid peptide for protection against Alzheimer's disease-like neuropathology", Proc Natl Acad Sci USA; 100(4): 2023-2028.

Barghorn et al., 2005, "Globular amyloid beta-peptide 1-42 oligomer—a homogeneous and stable neuropatholgical protein in Alzheimer's disease", J Neurochem; 95(31):834-847.

Barrow et al., 1992, "Solution conformations and aggregational properties of synthetic amyloid beta-peptides of Alzheimer's disease. Analysis of circular dichroism spectra", J. Mol. Biol.: 225:1075-1093.

Blond et al., 1987, "Partly native epitopes are already present on early intermediates in the folding of trytophan synthase", Proc Natl Acad Sci USA: 84:1147-1151.

Burdick et al., 1992, "Assembly and aggregation properties of synthetic Alzheimer's A4/beta amyloid peptide analogs", J Biol Chem; 267:546-554.

Campbell et al., 1984, "General properties and applications of monoclonal antibodies", Elsevier Science Publishers B.V., pp. 1-32.

Casset et al., 2003, "A peptide mimetic of an anti-CD4 monoclonal antibody by rational design", Biochemical and Biophysical Research Communications.

Celli et al., 1998, "Origin and pathogenesis of antiphospholipid antibodies", Braz J Med Biol Res; 31(6):723-732.

Chen et al., 1999, "Selection and analysis of an optimized anti-VEGF antibody: crystal structure of an affinity-matured Fab in complex with antigen". J Mol Biol; 293:865-881.

Chinese Office Action of Chinese application No. 200680046466.9, dated Feb. 24, 2011.

Clackson et al., 1991, "Making antibody fragments using phage display libraries". Nature: 352(15):624-328.

"Comparison of 8F5 and FP12H3-C2/ACI-01-Ab-7-C2 antibodies", AC Immune, Aug. 2009, pp. 1-3.

Database EMBL [Online], 1988, "Mouse immunoglobulin rearranged kappa-chain V-region V 105 gene from C.AL20-TEPC-105 myeloma, exons 1 and 2", retrieved from EBI accession No. EMBL:M12183 Database accession No. M12183.

Database EMBL [Online], 1999, "Mus musculus F5.20G3 low-affinity anti-phosphorylcholine IgG antibody mRNA, partial cds", retrieved from EBI accession No. EMBL:AF044238 Database accession No. AF044238.

Database Geneseq [Online], 1988, "L chain subunit of FAS specific antibody coding sequence", retrieved from EBI accession No. GSN:AAT88870 Database accession No. AAT88870.

Database Geneseq [Online], 1999, "Anti-human FAS monoclonal antibody CH11 light chain cDNA", retrieved from EBI accession No. GSN:AAV66736 Database accession No. AAV66736.

Database Geneseq [Online], 2003, "Mouse DNA encoding antibody 3D8 heavy chain variable region", retrieved from EBI accession No. GSN:ABX16569 Database accession No. ABX16569.

Database Geneseq [Online], 2005, "Humanized monoclonal antibody Hu4785-2 heavy chain", retrieved from EBI accession No. GSP:ADX39139 Database accession No. ADX39139.

Database Geneseq [Online], 2005, "Humanized monoclonal antibody Hu4785-2 VH region", retrieved from EBI accession No. GSP:ADX39143 Database accession No. ADX39143.

Database Geneseq [Online], 2005, "Humanized monoclonal antibody Hu4785-2 partial protein", retrieved from EBI accession No. GSP:ADX39104 Database accession No. ADX39104.
Database Geneseq [Online], 2005, "Mouse monoclonal antibody 4785 heavy chain SEQ ID 38", retrieved from EBI accession No. GSP:ADX39137 Database accession No. ADX39137.
Database Geneseq [Online], 2005, "Mouse monoclonal antibody 4785 heavy chain SEQ ID 1", retrieved from EBI accession No. GSP:ADX39100 Database accession No. ADX39100.
Database NCBI Protein [Online] dated Apr. 11, 1996, accession No. AAA96779.
Database NCBI Protein [Online] dated Aug. 30, 1993, accession No. AAA38584.
Database NCBI Protein [Online] dated Mar. 23, 2002, accession No. AAL92941.
Database NCBI Protein [Online] dated Mar. 23, 2002, accession No. AAL92933.
David et al., 1991, "A significant reduction in the incidence of collagen induced arthritis in mice treated with anti-TCRV—beta antibodies", J Cell Biochem; Suppl. 15E, p. 179.
Davies et al., 1995, "Antibody VH domains as small recognition units", Biotechnology; 13:475-479.
De Giorgi et al., 1993, "Induction of foetal lethality in AKR offspring after repeated inoculations into AKR females of anti-TCR/V beta 6 monoclonal antibody", Res Immunol; 144(4):245-255.
De Giorgi et al., 1993, "Murine hybridomas secreting monoclonal antibodies reacting with MIsa antigens", Exp Clin Immunogenet; 10(4):219-223.
DeMattos et al., 2001, "Peripheral anti-Aβ antibody alters CNS and plasma Aβ clearance and decreases brain Aβ burden in a mouse model of Alzheimer's disease", Proc Natl Acad Sci USA; 98:8850-8855.
DeWachter et al., 2000, "Aging increased amyloid peptide and caused amyloid plaques in brain of old APP/V7171 transgenic mice by a different mechanism than mutant presenilin I", J Neurosci; 20:6452-6458.
DeWachter et al., 2002, "Neuronal deficiency of presenilin I inhibits amyloid plaque formation and corrects hippocampal long-term potentiation but not a cognitive defect of amyloid precursor protein [V7171] transgenic mice". J Neurosci: 22:3445-3453.
Ding et al., 2007, "Targeting age-related macular degeneration with Alzheimer's disease based immunotherapies: anti-amyloid-beta antibody attenuates pathologies in an age-related macular degeneration mouse model", Vision Research, Pergamon Press, Oxford, GB: 48(3):339-345.
Dorronsoro et al., 2003, "Peripheral and dual binding site inhibitors of acetylcholinesterase as neurodegenerative disease-modifying agents". Expert Opin Ther Pat; 13(11):1725-1732.
Dumoulin et al., 2002, "Single-domain antibody fragments with high conformational stability", Protein Sci; 11:500-515.
European Office Action dated May 18, 2010 of European application No. 08836966.5-2406.
European Office Action dated Oct. 21, 2010 of European application No. 08837467.3-2406.
European Office Action dated Dec. 23, 2008 of European application No. 06829456.0-2402.
European Office Action dated Jul. 30, 2010 of European application No. 06829456.0-2402.
European Office Action dated May 3, 2010 of European Application No. 08768370.2-1222.
European Office Action dated Feb. 8, 2011 of European application No. 08768371.0-2406.
European Office Action dated Oct. 21, 2010 of European application No. 08838455.7-2406.
Ewert et al., 2003, "Biophysical properties of human antibody variable domains", J Mol Biol; 325:531-553.
Frenkel et al., 2000, "Modulation of Alzheimer's beta-amyloid neurotoxicity by site-directed single-chain antibody", J Neuroimmunol; 106(1-2):23-31.
Fujimuro et al., 1994, "Production and characterization of monoclonal antibodies specific to multi-ubiquitin chains of polyubiquitinated proteins", FEBS; 349:173-180.
Fujimuro et al., 2005, "Production of antipolyubiquitin monoclonal antibodies and their use for characterization and isolation of polyubiquitinated proteins", Meth Enzymol; 399:75-86.
Fukuchi et al., 2006, "Amelioration of amyloid load by anti-Abeta single-chain antibody in Alzheimer mouse model", Biochem Biophys Res Commun; 344(1):79-86.
Glenner et al., 1984, "Alzheimer's disease: initial report of the purification and characterization of a novel cerebrovascular amyloid protein", Biochem Biophys Res Comm; 129:885-890.
Gulf Cooperation Council Office Action dated Mar. 5, 2010 of Gulf Cooperation Council application No. GCC/P/2006/7389.
Guo et al., 2007, "Targeting amyloid-beta in glaucoma treatment", Proc Natl Acad Sci USA; 104(33):13444-13449.
Hanan et al., 1996, "Inhibitory effect of monoclonal antibodies on Alzheime's β-amyloid peptide aggregation", Amyloid: Int J Exp Clin Invest; 3:130-133.
Heneka et al., 2005, "Focal glial activation coincides with increased with increased BACE1 activation and precedes amyloid plaque deposition in APP[V7171] transgenic mice", J Neuroinflammation; 2:22.
Hicke, 2001, "Protein regulation by monoubiquitin", Nat Rev; 2:196-201.
Holm et al., 2007, "Functional mapping and single chain construction of the anti-cytokeratin 8 monoclonal antibody TS1", Mol Immunol: 44:1075-1084.
Hungarian Search Report dated Dec. 17, 2010 of Singaporean application No. 200908189-4.
Indonesian Office Action dated Feb. 25, 2011 of Indonesian application No. W-00200801821.
International Preliminary Report on Patentability dated Apr. 15, 2010 of International application No. PCT/US2008/011491.
International Preliminary Report on Patentability dated Apr. 15, 2010 of International application No. PCT/US2008/011492.
International Preliminary Report on Patentability dated Apr. 15, 2010 of International application No. PCT/US2008/011493.
International Preliminary Report on Patentability dated Apr. 15, 2010 of International application No. PCT/US2007/073504.
International Preliminary Report on Patentability dated Jun. 26, 2008 of International application No. PCT/EP2006/011862.
International Preliminary Report on Patentability dated Dec. 17, 2009 of International application No. PCT/US2008/007317.
International Preliminary Report on Patentability dated Dec. 17, 2009 of International application No. PCT/US2008/007318.
International Preliminary Report on Patentability dated Dec. 17, 2009 of International application No. PCT/US2007/021134.
International Search Report dated Jun. 12, 2007 of International Application No. PCT/EP2006/011862.
International Search Report dated May 14, 2008 of International Application No. PCT/US2007/073504.
International Search Report dated Nov. 21, 2008 of International application No. PCT/US2008/007318.
International Search Report dated Dec. 15, 2000 of International application No. PCT/US2000/014810.
International Search Report dated Dec. 19, 2008 of International application No. PCT/US2007/021134.
International Search Report dated Oct. 12, 2009 of International application No. PCT/US2008/011493.
International Search Report dated Sep. 7, 2009 of International application No. PCT/US2008/011492.
International Search Report dated Sep. 20, 2009 of International application No. PCT/US2008/011491.
International Search Report dated Oct. 28, 2008 of International application No. PCT/US2008/007317.
Johnson-Wood et al., 1997, "Amyloid precursor protein processing and A beta42 deposition in a transgenic mouse model of Alzheimer disease", Proc. Natl. Acad. Sci. USA; 94(4):1550-1555.
Jung et al., 1996, "Alzheimer's beta-amyloid precursor protein is expressed on the surface of immediately ex vivo brain cells: a flow cytometric study", J. Neurosci. Res.; 46(3):336-348.
Khaw et al., 1982, "Technetium-99m labeling of antibodies to cardiac myosin fab and to human fibrinogen", J Nucl Med; 23:1011-1019.

Kim et al., 2004, "Development of conformation-specific antibodies for neutralization of beta-amyloid oligomers", Neurobiol Aging; 25(1):S145, P1-175 Abstract.

Kirschner et al., 1986, "X-ray diffraction from intraneuronal paired helical filaments and extraneuronal amyloid fibers in Alzheimer disease indices cross-beta conformation", Proc Natl Acad Sci USA; 83:503-507.

Kisilevsky et al., 1995, "Arresting amyloidosis in vivo using small-molecule anionic sulphonates or sulphates: Implications for Alzheimer's disease", Nat Med; 1(2):143-148.

Kisilevsky, 1996, "Anti-amyloid drugs potential in the treatment of diseases associated with aging", Drugs Aging; 8(2):75-83.

Klein et al., 2002, "Abeta toxicity in Alzheimer's disease: globular oligomers (ADDLs) as new vaccine and drug targets", Neurochem Int: 41(5):345-352.

Klimka et al., 2000, "Human anti-CD30 recombinant antibodies by guided phage antibody selection using cell panning", Brit J Cancer; 83(2):252-260.

Lambert et al., 2007, "Monoclonal antibodies that target pathological assemblies of Abeta", J Neurochem; 100(1): 23-35.

Langdon et al., 2000, "Germline sequences of $V_H$7183 gene family members in C57BL/6 mice demonstrate natural selection of particular sequences during recent evolution", Immunogen; 51:241-245.

Lee et al., 2002, "Molecular cloning of agonistic and antagonistic monoclonal antibodies against human 4-IBB", Eur J Immunogenet; 29(5):449-452.

Levine et al., 2002, "4,4'-dianilino-1,1'-binaphthyl-5-disulfonate (bis-ANS) reports on non-β-sheet conformers of Alzheimer's peptide β (1-40)", Arch Biochem Biophys; 404:106-115.

Liu Ruitian et al., 2004, "Single chain variable fragments against beta-amyloid (Abeta) can inhibit Abeta aggregation and prevent Abeta-induced neurotoxicity", Biochem; 43(22):6959-6967.

Lund et al., 1995, "Oligosaccharide-protein interactions in IgG can modulate recognition by Fc-gamma receptors", FASEB J; 9(1):115-119.

MacCallum et al., 1996, "Antibody-antigen interactions: contact analysis and binding site topography", J Mol Biol; 262:732-745.

Marks et al., 1992, "By-passing immunization: Building high affinity human antibodies by chain shuffling", Biotechnology; 10:779-783.

McGreer et al., 1994, "Pathological proteins in senile plaques", Tohoku J Exp Med; 174:269-277.

McKinnon et al., 2002, "Caspase activation and amyloid precursor protein cleavage in rat ocular hypertension", Invest Ophthamol & Vis Sci; 43(4):1077-1087.

McLaurin et al., 2002, "Therapeutically effective antibodies against amyloid-beta peptide target amyloid-beta residues 4-10 and inhibit cytotoxicity and fibrillogenesis", Nat Med; 8(11):1263-1269.

Mexican Office Action (translation) dated Dec. 28, 2010 of Mexican application No. MX/a/2009/013503.

Moechars et al., 1999, "Early phenotypic changes in transgenic mice that overexpress different mutants of amyloid precursor protein in brain", J Biol Chem; 274:6483-6492.

Moretto et al., 2007, "Conformation-sensitive antibodies against Alzheimer amyloid-beta by immunization with a thioredoxin-constrained B-cell epitope peptide", J Biol Chem; 282(15):11436-11445.

Nelson et al., 2006, "Recent atomic models of amyloid fibril structure", Curr Opin Struct Biol; 16:260-265.

Nemes et al., 2004, "Cross-linking of ubiquitin, HSP27, parkin, and α-synuclein by γ-glutamyl-ε-lysine bonds in Alzheimer's neurofibrillary tangles", FASEB J; 18:1135-37.

New Zealand Examination Report dated Jun. 23, 2010 of New Zealand application No. 574188.

New Zealand Examination Report dated Oct. 29, 2010 of New Zealand application No. 581834.

New Zealand Examination Report dated Nov. 2, 2010 of New Zealand application No. 581835.

New Zealand Examination Report dated Jan. 19, 2011 of New Zealand application No. 585110.

Nicolau et al., 2002, "A liposome-based therapeutic vaccine against beta-amyloid plaques on the pancreas of transgenic norba mice", Proc Natl Acad Sci USA; 99(4): 2332-2337.

Notice of Allowance and Fees Due dated Dec. 14, 2009 of U.S. Appl. No. 11/637,213.

Notice of Allowance dated Jul. 30, 2010 of U.S. Appl. No. 11/777,777.

Office Action dated Apr. 27, 2009 of U.S. Appl. No. 11/637,213.
Office Action dated Aug. 10, 2009 of U.S. Appl. No. 11/777,777.
Office Action dated Aug. 31, 2009 of U.S. Appl. No 11/637,213.
Office Action dated Feb. 17, 2009 of U.S. Appl. No. 11/637,213.
Office Action dated Jan. 12, 2011 of U.S. Appl. No. 11/777,777.
Office Action dated Jan. 27, 2010 of U.S. Appl. No. 11/777,777.
Office Action dated Jul. 1, 2010 of U.S. Appl. No. 11/777,777.
Office Action dated May 5, 2010 of U.S. Appl. No. 11/777,777.
Office Action dated Oct. 4, 2010 of U.S. Appl. No. 11/777,777.
Office Action dated Sep. 11, 2009 of U.S. Appl. No. 11/637,213.
Office Action dated Apr. 4, 2011 of U.S. Appl. No. 12/311,505.
Office Action dated Jun. 28, 2010 of European application No. 08768371.0-2406.
Office Action dated Jun. 7, 2010 of U.S. Appl. No. 12/213,006.
Office Action dated Jun. 4, 2010 of U.S. Appl. No. 12/213,007.
European Office Action, dated Jul. 18, 2011 of European application No. 06829456.0-2402.
Chilean Office Action dated Apr. 13, 2011 with English Technical Report of Chilean application No. 3485-2006.
Office Action dated Nov. 15, 2010 of U.S. Appl. No. 12/213,006.
Office Action dated Nov. 19, 2010 of U.S. Appl. No. 12/213,007.

Padlan et al., 1989, "Structure of an antibody-antigen complex: crystal structure of the HyHEL-10 Fab-lysozyme complex", Proc Natl Acad Sci USA: 86(15):5938-42.

Paul eds., 1993, "Fv structure and diversity in three dimensions", Fundamental Immunology; pp. 292-295.

Pereira et al., 1998, "Cardiolipin binding a light chain from lupus-prone mice", Biochemistry; 37(5):1430-1437.

Petkova et al., 2002, "A structural model for Alzheimer's β-amyloid fibrils based on experimental constraints from solid state NMR", Proc Natl Acad Sci USA; 99:16742-16747.

Petkova et al., 2004, "Solid state NMR reveals a pH-dependent antiparallel β-sheet registry in fibrils formed by a β-amyloid peptide", J Mol Biol; 335:247-260.

Pihlgren, M., "Binding of the murine monoclonal anti-Abeta antibody ACI-01-Ab7 to Abeta1-42 monomers, oligomers, and fibers", AC Immune, 2006, pp. 1-4.

Pihlgren, M., "Study ACI-ACI-2009.03 Disaggregation of Abeta1-42 fibers by ACI-01-Ab-7C2", AC Immune, 2009. pp. 1-4.

Piorkowska, K., and Pihlgren, M., "Study ACI-ACI-2009.02; Binding of ACI-01-Ab-7C2 to plaques". AC Immune, 2009, pp. 1-3.

Portolano et al., 1993, "Lack of promiscuity in autoantigen-specific H and L chain combination as revealed by human H and L chain "roulette"", J. Immunol; 150(3):880-887.

Racke et al., 2005, "Exacerbation of cerebral amyloid angiopathy-associated microhemorrhage in amyloid precursor protein transgenic mice by immunotherapy is dependent on antibody recognition of deposited forms of amyloid beta", J. Neurosci.; 25(3):629-636.

Rader et al., 1998, "A phage display approach for rapid antibody humanization:designed combinatorial V gene libraries", Proc Natl Acad Sci USA; 95:8910-8915.

Rebe et al., 2005, "Deglycosylation of anti-β amyloid antibodies inhibits microglia activation in BV-2 cellular model". American Journal of Alzheimer's Disease and Other Dimentias; 20(5):303-313.

Rudikoff et al., 1982, "Single amino acid substitution altering antigen-binding specificity", Proc Natl Acad Sci USA; 79(6):1979-1983.

Russian Office Action (translation) dated Feb. 15, 2011 of Russian application No. 2009104769.

Russian Office Action dated Jul. 13, 2010 of Russian application No. 2008128139.

Russian Office Action dated Nov. 8, 2010 of Russian application No. 2008128139.

Rzepecki et al., 2004, "Prevention of Alzheimer's disease-associated Aβ aggregation by rationally designed non-peptide β-sheet ligands", J Biol Chem; 279(46):47497-47505.

Schable et al., 1999, "Characteristics of the immunoglobulin V kappa genes, pseudogenes, relics and orphons in the mouse genome", Eur J Immunol; 29:2082-2086.

Schenk et al., 1999, "Immunization with amyloid-beta attenuates Alzheimer-disease-like pathology in the PDAPP mouse", Nature; 400:173-177.

Sergeant, 2003, "Truncated beta-amyloid peptide species in preclinical Alzheimer's disease as new targets for the vaccination approach", J Neurochem; 85(6):1581-91.

Seubert et al., 1992, "Isolation and quantification of soluble Alzheimer's beta-peptide from biological fluids", Nature 359(6393):325-327.

Singapore Office Action dated Aug. 23, 2010, with Examination Report, dated Jun. 9. 2010 of Singaporean patent application No. 200804129-5.

Singapore Written Opinion dated Nov. 30, 2009 of Singaporean application No. 200900163-7.

Smith et al., 1995, "Determination of helix-helix interactions in membranes by rotational resonance NMR", Proc Natl Acad Sci USA; 92:488-491.

Solomon et al., 1996, "Monoclonal antibodies inhibit in vitro fibrillar aggregation of the Alzheimer beta-amyloid amyloid peptide", Proc Natl Acad Sci USA;93:452-455.

Solomon et al., 1997, "Disaggregation of Alzheimer β-amyloid by site-directed mAb", Proc Natl Acad Sci USA; 94:4109-4112.

Solomon, 2007, "Beta-amyloid based immunotherapy as a treatment of Alzheimer's disease", Drugs of Today: 43(5):333-342.

Soto et al., 1995, "The alpha-helical to beta-strand transition in the amino-terminal fragment of the amyloid beta-peptide modulates amyloid formation", J. Biol. Chem.; 270(7):3063-3067.

"Staining of human Brain Sections with AC Immune's humanized ACI-01-Ab7 Antibody". Study ACI-Bonn-01, AC Immune, Sep. 26, 2006, pp. 1-4.

"Studies of Influence of Passive Vaccination with ACI-01-Ab7 on Memory Capacity in single transgenic hAPP Mice" AC Immune, 2006, pp. 1-3.

"Studies to map the Epitope of AC Immune's monoclonal Antibody ACI-01-Ab7"AC Immune, 2006, pp. 1-5.

"Study to analyze the Binding of AC Immune's monoclonal Antibody ACI-01-Ab7 to Amyloid Species in Western Blot and Dot Blot", AC Immune, 2006, pp. 1-4.

"Study to analyze the Binding of AC Immune's murine monoclonal Antibody ACI-01-Ab7 to Amyloid Species in ELISA", AC Immune, 2006. pp. 1-2.

Tenno et al., 1994, "Structural basis for distinct roles of Lys63- and Lys48-linked polyubiquitin chains", Genes to Cells; 9:865-875.

Vajdos et al., 2002, "Comprehensive functional maps of the antigen-binding site of an anti-ErbB2 antibody obtained with shotgun scanning mutagenesis", J Mol Biol; 320(2):415-428.

Van Den Beucken et al., 2001, "Building novel binding ligands to B7.1 and B7.2 based on human antibody single variable light chain domains", J Mol Biol; 310:591-601.

Van Der Auwera et al., 2005, "A ketogenic diet reduces amyloid beta 40 and 42 in a mouse model of Alzheimer's disease", Nutr Metab (Lond); 2:28.

Van Gool et al., 1994, "Concentrations of amyloid-beta protein in cerebrospinal fluid increase with age in patients free from neurodegenerative disease", Neurosci Let; 172(1-2):122-124.

Vietnamese Office Action dated Dec. 1, 2009 of Vietnamese application No. 1-2008-01736.

Vietnamese Office Action dated Jul. 22, 2009 of Vietnamese application No. 1-2008-01736.

Vietnamese Office Action dated Dec. 1, 2008 of Vietnamese application No. 1-2008-01736.

Ward et al., 1989, "Binding activities of a repertoire of single immunoglobulin variable domains secreted from *Escherichia coli*", Letters to Nature; 341(12):544-546.

Weaver-Feldhaus et al., 2004, "Yeast mating for combinatorial Fab library generation and surface display", FEBS Letters; 564(2):24-34.

Written Opinion dated Oct. 12, 2009 of International application No. PCT/US2008/011493.

Written Opinion dated Jun. 12, 2007 of International application No. PCT/EP2006/011862.

Written Opinion dated Dec. 19, 2008 of International Application No. PCT/US2007/021134.

Written Opinion dated May 14, 2008 of International Application No. PCT/US2007/073504.

Written Opinion dated Nov. 21, 2008 of International application No. PCT/US2008/007318.

Written Opinion dated Oct. 28, 2008 of International application No. PCT/US2008/007317.

Written Opinion dated Sep. 7, 2009 of International application No. PCT/US2008/011492.

Written Opinion dated Sep. 20, 2009 of International application No. PCT/US2008/011491.

Written Opinion dated Oct. 18, 2010 of Singapore application No. 201002372-9.

Chilean Office Action of application No. 2007-2070 with English Technical Report, dated Mar. 14, 2011.

Davies et al., 1996, "Affinity improvement of single antibody VH domains: residues in all three hypervariable regions affect antigen binding", Immunotechnology; 2(3):169-179.

Holt et al., 2003, "Domain antibodies: proteins for therapy", Trends in Biotechnology; 21(11):484-490.

Maynard et al., 2000, "Antibody engineering", Annu Rev Biomed Eng; 2:339-376.

Mexican Office Action (translation) of application No. MX/a/2009/000476, dated Mar. 30, 2011.

Office Action dated Apr. 19, 2011 of U.S. Appl. No. 12/213,006.

Pini et al., 1998, "Design and use of a phage display library. Human antibodies with subnanomolar affinity against a marker of angiogenesis eluted from a two-dimensional gel", J Biol Chem; 273(34):21769-21776.

Mexican Office Action of Mexican application no. MX/a/2008/007477, dated Mar. 17, 2011.

Mitchell et al., 2007, "Prevention of intracerebral haemorrhage". Current Drug Targets; 8:832-838.

Office Action, dated Jun. 8, 2011 of U.S. Appl. No. 12/460,747.

Russian Office Action, dated Mar. 17, 2011 of Russian application No. 2009104769.

Russian Office Action, dated Oct. 1, 2008 of Russian application No. 2008128139.

Singapore Examination Report of application No. 200900163-7, dated Sep. 30, 2010.

Vickers, 2002, "A vaccine against Alzheimer's disease", Drugs Aging; 19(7):487-494.

Ukrainian Office Action, dated Jun. 1, 2011 of Ukrainian application No. 200808792.

* cited by examiner

FIG. 1
(Example 2)

FIG. 2
(Example 2)

```
                    10              20              30
C2VHAF    E V Q L V E S G G G L V Q P G G S L K L S C A A S G F T F S
AF120466  E V [K] L V E S G G G L V [K] P G G S L K L S C A A S G F T F S 40              50              60
C2VHAF    S Y G M S W V R Q T P D K R L E L V A S I N S N G G S T Y Y
AF120466  S Y G M S W V R Q T P D K R L E [W] V A [T] I [S] S [G] G [S Y] T Y Y 70              80              90
C2VHAF    P D S V K G R F T I S R D N A K N T L Y L Q M S S L K S E D
AF120466  P D S V K G R F T I S R D N A K N T L Y L Q M S S L K S E D 100             110
C2VHAF    T A M Y Y C A S G D Y W G Q G S T L T V S S
AF120466  T A M Y Y C A [R R]
```

FIG. 3

(Example 5.2)

(Example 8)

(Example 9)

C: Antibody hC2

A: Chimeric antibody

Control patient

Temporal neocortex region I, 40 x

CA4 (Cornu ammonis region 4), 40 x

AD patient

Temporal neocortex region I, 40 x

Temporal neocortex region I, 40 x preAD patient

Temporal neocortex region I, 40 x

Temporal neocortex region I, 40 x

FIG. 6 (Example 11)

A)

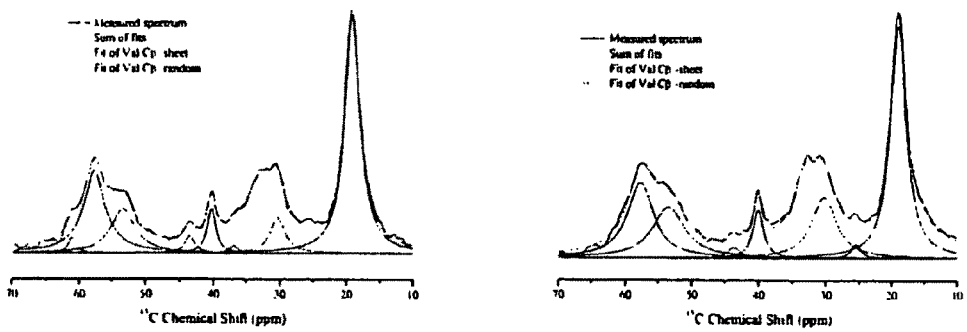

B)

| Resonance | PBS | | | Mouse C2 | | |
|---|---|---|---|---|---|---|
| | δ ISO (ppm) | FWHH (Hz) | % Integral Intensity | δ ISO (ppm) | FWHH (Hz) | % Integral Intensity |
| Val Cβ -sheet | 32.60 | 479 | 81.7 | 33.09 | 366 | 53.5 |
| Val Cβ -random | 30.27 | 200 | 18.3 | 30.27 | 340 | 46.5 |

A) Comparison of $^{13}$C CPMAS spectra and fits for U-$^{13}$C Tyr10 and Val12 labelled amyloid β1-42 fibres incubated with PBS (left; served as control) or AC1-7-C2 (right) for 24 hrs and then lyophilised. The fits for the two conformations of Val12 Cβ are shown in green (sheet) and blue (random coil). The peak at c33 ppm corresponds to the beta sheet conformation of the fibres whilst that at 30 ppm is a result of random coil conformation.

B): Comparison of the fitted parameters for the two conformations of Val 12 Cβ. The fitted chemical shifts for the two conformations are quite similar but the integral intensities are very different, reflecting a reduction in the original beta sheet conformation by approx 35% (1-(53.5/81.7)). This is in very close agreement with the value we obtained from the fluorescence measurement.

FIG. 7

(Example 12)

(Example 12)

(Example 13)

```
                        10                    20                       30
C2VK     D V V M T Q T P L S L P V S L G D Q A S I S C R S S Q S L V
C2HuVK1  D I V M T Q S P L S L P V T P G E P A S I S C R S S Q S L V
C2HuVK2  D I V M T Q S P L S L P V T P G E P A S I S C R S S Q S L V
C2HuVK3  D I V M T Q S P L S L P V T P G E P A S I S C R S S Q S L V
C2HuVK4  D I V M T Q S P L S L P V T P G E P A S I S C R S S Q S L V
dpk15    D I V M T Q S P L S L P V T P G E P A S I S C R S S Q S L L
JK1      - - - - - - - - - - - - - - - - - - - - - - - - - - - - - -

40                    50                       60
C2VK     Y S N G D T Y L H W Y L Q K P G Q S P K L L I Y K V S N R F
C2HuVK1  Y S N G D T Y L H W Y L Q K P G Q S P Q L L I Y K V S N R F
C2HuVK2  Y S N G D T Y L H W Y L Q K P G Q S P Q L L I Y K V S N R F
C2HuVK3  Y S N G D T Y L H W Y L Q K P G Q S P K L L I Y K V S N R F
C2HuVK4  Y S N G D T Y L H W Y L Q K P G Q S P K L L I Y K V S N R F
dpk15    H S N G Y N Y L D W Y L Q K P G Q S P Q L L I Y L G S N R A
JK1      - - - - - - - - - - - - - - - - - - - - - - - - - - - - - -

70                    80                       90
C2VK     S G V P D R F S G S G S G T D F T L K I S R V E A E D L G V
C2HuVK1  S G V P D R F S G S G S G T D F T L K I S R V E A E D V G V
C2HuVK2  S G V P D R F S G S G S G T D F T L K I S R V E A E D V G V
C2HuVK3  S G V P D R F S G S G S G T D F T L K I S R V E A E D V G V
C2HuVK4  S G V P D R F S G S G S G T D F T L K I S R V E A E D V G V
dpk15    S G V P D R F S G S G S G T D F T L K I S R V E A E D V G V
JK1      - - - - - - - - - - - - - - - - - - - - - - - - - - - - - -

100                   110
C2VK     Y F C S Q S T H V P W T F G G G T K L E I K
C2HuVK1  Y Y C S Q S T H V P W T F G Q G T K V E I K
C2HuVK2  Y F C S Q S T H V P W T F G Q G T K V E I K
C2HuVK3  Y Y C S Q S T H V P W T F G Q G T K V E I K
C2HuVK4  Y F C S Q S T H V P W T F G Q G T K V E I K
dpk15    Y Y C M Q - - - - - - - - - - A - L Q T P
JK1      - - - - - - - - - - - W T F G Q G T K V E I K
```

FIG. 10

```
                              10                  20                  30
C2VHAF     E V Q L V E S G G G L V Q P G G S L K L S C A A S G F T F S
C2HuVHAF1  E V Q L V E S G G G L V Q P G G S L R L S C A A S G F T F S
C2HuVHAF2  E V Q L V E S G G G L V Q P G G S L R L S C A A S G F T F S
C2HuVHAF3  E V Q L V E S G G G L V Q P G G S L R L S C A A S G F T F S
C2HuVHAF4  E V Q L V E S G G G L V Q P G G S L R L S C A A S G F T F S
DP-54      E V Q L V E S G G G L V Q P G G S L R L S C A A S G F T F S
HUJH6      - - - - - - - - - - - - - - - - - - - - - - - - - - - - - -

40                  50                  60
C2VHAF     S Y G M S W V R Q T P D K R L E L V A S I N S N G G S T Y Y
C2HuVHAF1  S Y G M S W V R Q A P G K G L E W V A S I N S N G G S T Y Y
C2HuVHAF2  S Y G M S W V R Q A P G K G L E W V A S I N S N G G S T Y Y
C2HuVHAF3  S Y G M S W V R Q A P G K G L E L V A S I N S N G G S T Y Y
C2HuVHAF4  S Y G M S W V R Q A P G K G L E L V A S I N S N G G S T Y Y
DP-54      S Y W M S W V R Q A P G K G L E W V A N I K Q D G S E K Y Y
HUJH6      - - - - - - - - - - - - - - - - - - - - - - - - - - - - Y Y 70                  80                  90
C2VHAF     P D S V K G R F T I S R D N A K N T L Y L Q M S S L K S E D
C2HuVHAF1  P D S V K G R F T I S R D N A K N S L Y L Q M N S L R A E D
C2HuVHAF2  P D S V K G R F T I S R D N A K N S L Y L Q M N S L R A E D
C2HuVHAF3  P D S V K G R F T I S R D N A K N S L Y L Q M N S L R A E D
C2HuVHAF4  P D S V K G R F T I S R D N A K N S L Y L Q M N S L R A E D
DP-54      V D S V K G R F T I S R D N A K N S L Y L Q M N S L R A E D
HUJH6      - - - - - - - - - - - - - - - - - - - - - - - - - - - - - -

100                 110
C2VHAF     T A M Y Y C A S G D Y W G Q G S T L T V S S
C2HuVHAF1  T A V Y Y C A R G D Y W G Q G T T V T V S S
C2HuVHAF2  T A V Y Y C A S G D Y W G Q G T T V T V S S
C2HuVHAF3  T A V Y Y C A R G D Y W G Q G T T V T V S S
C2HuVHAF4  T A V Y Y C A S G D Y W G Q G T T V T V S S
DP-54      T A V Y Y C A R
HUJH6      - - - - Y Y Y G M - D V W G Q G T T V T V S S
```

```
          Xmnl                                                                    Bglll
AATTATAGGGATAGAGAACAGATTCTGGTTGCCAGGGGTTAGGGTGGTGGAGAAAGAAGAGTAGGCGAAACTATAAAGGGAGATCTTTGTGATCATGGGA
                                                                                                      53C
TTAATATCCCTATCTCTTGTCTAAGACCAACGGTCCCCAATCCCACCACCTCTTTCTTCTCATCCGCTTTGATATTTCCCTCTAGAAACACTAGTACCCT Xbal
TAAATCTGTATCTTGATTGCAGTGGTAGTTGCAGGCATCTAGACATGTGATAAAATGACATAGAACTGTACACACTTATTTTTATCAATGTCAAATTCTTG
                                                                                                      54C
ATTTAGACATAGAACTAACGTCACCATCAACGTCCGTAGATCTGTACACTATTTTACTGTATCTTGACATGTGTGAATAAAATAGTTACAGTTTAAGAAC Bsgl
GTTTTAATATCGTACTGTAATTACGTAAGAAGTAACCAACAGGAGAAACTGGGTGCAGGACACATCAGACCTCTGTGCTTTATATCCTGTCTTTGCTACT
                                                                                                      55C
CAAAATTATAGCATGACATTAATGCATTCTTCATTGGTTGTCCTCTTTGACCCACGTCCTGTGTAGTCTGGAGACACGAAATATAGGACAGAAACGATGA TTCTGTGAATCTATAATTATTTCCAAATAATTTTTTTAAACTTTTTTTTTTATGCTGGATCG
                                                                5561
AAGACACTTAGATATTAATAAAGGTTTATTAAAAAAATTTGAAAAAAAAAATACGACCTAGC
```

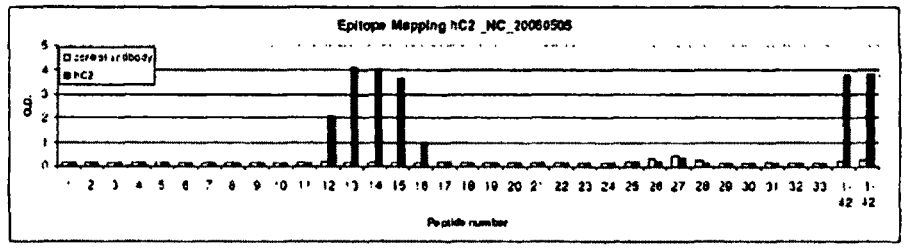

Figure 1. hC2 binds to peptides 12, 13, 14, 15 and 16 of the Aβ 1-42 peptide library.
Binding of hC2 to overlapping peptides of Aβ 1-42 was analyzed by ELISA. Binding to the complete Aβ 1-42 and binding of a non-binding chimeric antibody (control antibody) was used as positive and negative controls respectively. The peptide number corresponds to the amino acid in the Aβ 1-42 sequence on which the peptide starts. Results are expressed as OD.

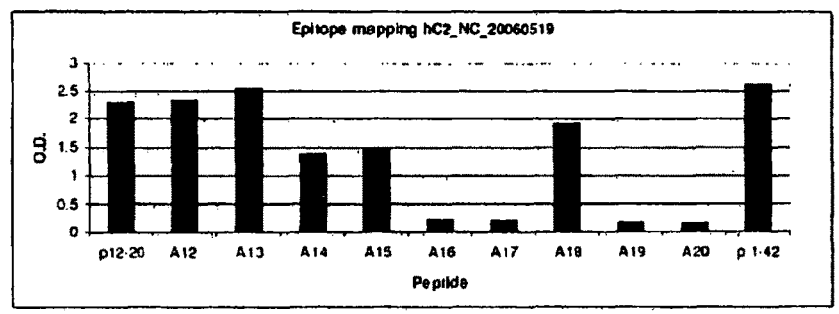

Figure 2. hC2 binding to Aβ 12-20 is completely dependent on aa 16,17,19 and 20 and partially dependent on aa 14,15 and 18.
Binding of hC2 to Aβ 12-20 and alanine substituted Aβ 12-20 was analyzed by ELISA. Binding to the complete Aβ 1-42 was used as positive control. The number corresponds to the aa that is substituted by alanine. Results are expressed as OD.

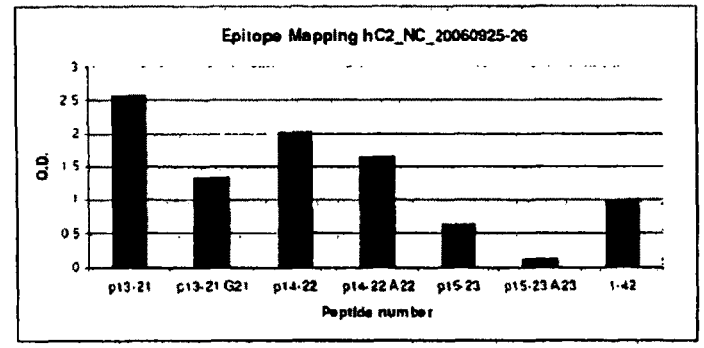

Figure 3. hC2 binding to Aβ 15-23 is dependent on aa 23 and partially on aa 21 and slightly dependent on aa 22
Binding of hC2 to Aβ 13-21, 14-22 or 15-23 and to 13-21G21, 14-22A22 or 15-23A23 was analyzed by ELISA. Binding to the complete Aβ 1-42 was used as positive control. Results are expressed as OD

FIG. 15

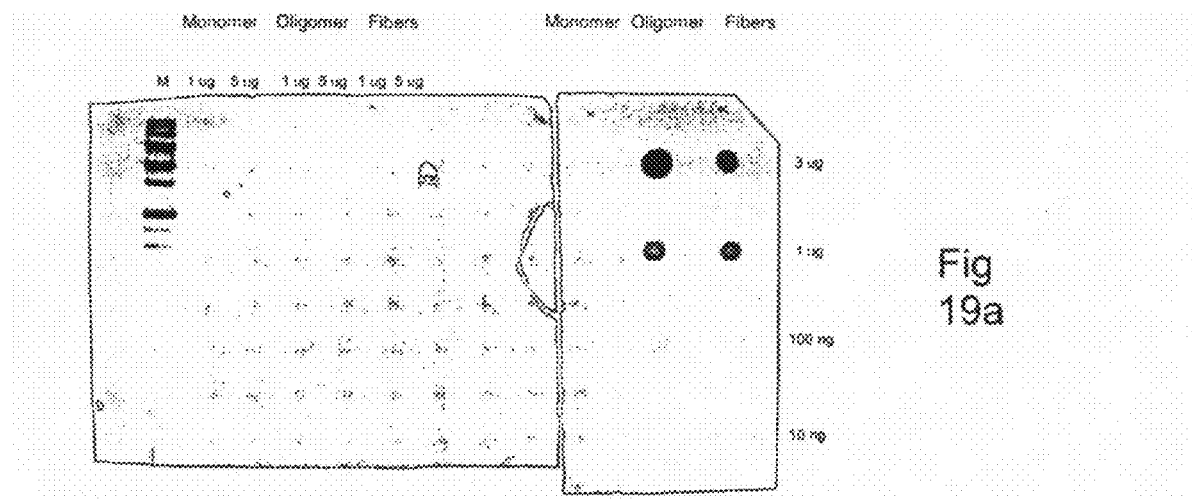
Fig 19a
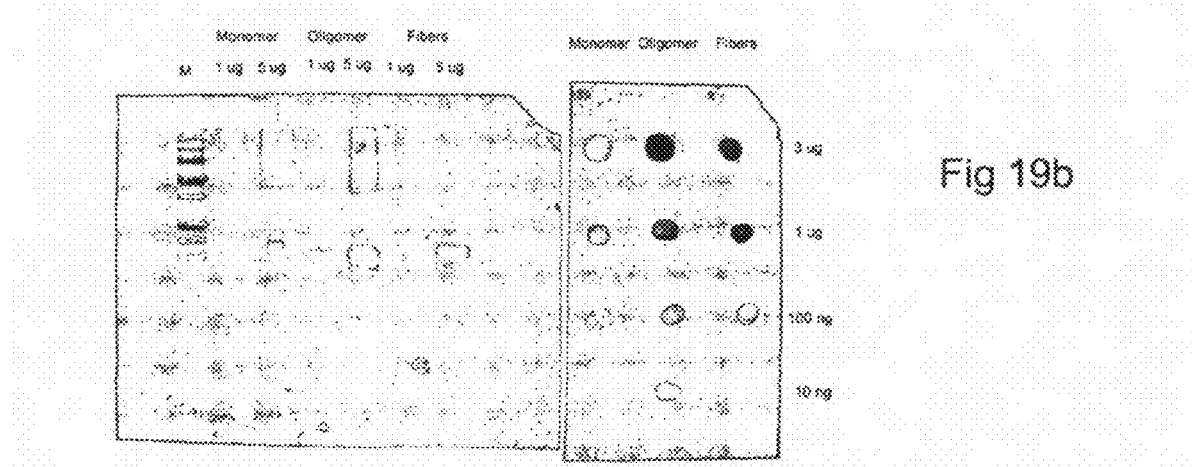
Fig 19b
FIG. 19

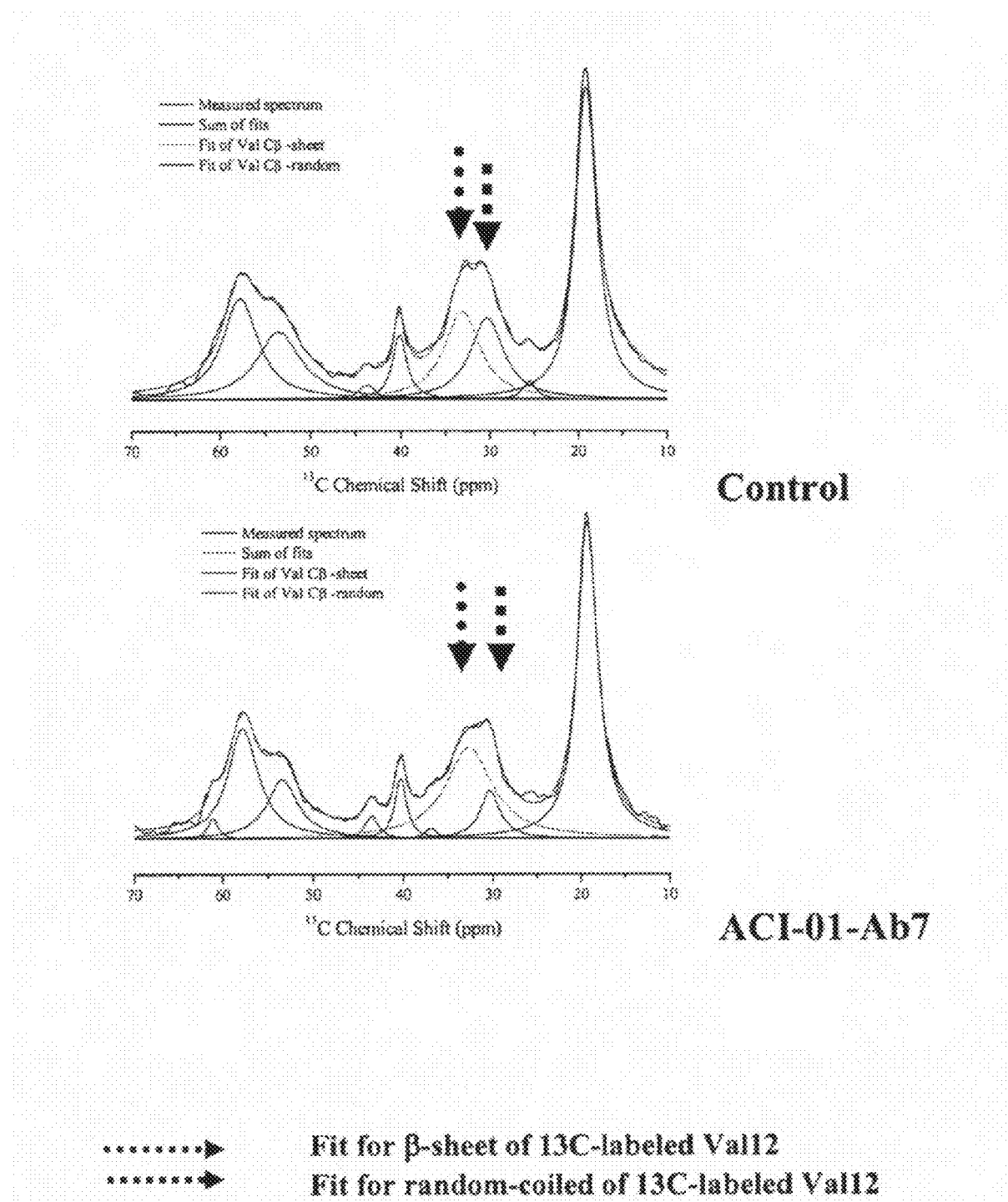
FIG: 21

SEQUENCE LISTING

<160> NUMBER OF SEQ ID NOS: 101

<210> SEQ ID NO 1
<211> LENGTH: 10
<212> TYPE: PRT
<213> ORGANISM: Artificial Sequence
<220> FEATURE:
<223> OTHER INFORMATION: /note="Description of artificial sequence:
     Synthetic peptide"

<400> SEQUENCE: 1

Gly Phe Thr Phe Ser Ser Tyr Gly Met Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: /note="Description of artificial sequence:
     Synthetic peptide"

<400> SEQUENCE: 2

Ser Ile Asn Ser Asn Gly Gly Ser Thr Tyr Tyr Pro Asp Ser Val Lys

```
1               5                   10                  15
Gly

<210> SEQ ID NO 3
<211> LENGTH: 3
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 3

Gly Asp Tyr
1

<210> SEQ ID NO 4
<211> LENGTH: 16
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 4

Arg Ser Ser Gln Ser Leu Val Tyr Ser Asn Gly Asp Thr Tyr Leu His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 6

Ser Gln Ser Thr His Val Pro Trp Thr
1               5

<210> SEQ ID NO 7
<211> LENGTH: 6
<212> TYPE: PRT
<213> ORGANISM: Homo sapiens

<400> SEQUENCE: 7

Val Phe Phe Ala Glu Asp
1               5

<210> SEQ ID NO 8
<211> LENGTH: 5
<212> TYPE: PRT
<213> ORGANISM: Homo sapiens

<400> SEQUENCE: 8

His Gln Lys Leu Val
```

```
<210> SEQ ID NO 9
<211> LENGTH: 6
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="Val" "Leu" "norleucine" "Met"
      "Phe" or "Ile"
<220> FEATURE:
<221> NAME/KEY: misc_feature
<222> LOCATION: (1)..(1)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (4)..(4)
<223> OTHER INFORMATION: /replace="Val" "Leu" "Ser" or "Ile"
<220> FEATURE:
<221> NAME/KEY: VARIANT
<222> LOCATION: (5)..(5)
<223> OTHER INFORMATION: /replace="Asp"
<220> FEATURE:
<221> NAME/KEY: VARIANT
<222> LOCATION: (6)..(6)
<223> OTHER INFORMATION: /replace="Asp"
<220> FEATURE:
<221> NAME/KEY: misc_feature
<222> LOCATION: (4)..(6)
<223> OTHER INFORMATION: /notes="Residues given in the sequence have no
      preference with respect to those in the annotations for said
      positions"

<400> SEQUENCE: 9

Ala Phe Phe Ala Glu Glu
1               5

<210> SEQ ID NO 10
<211> LENGTH: 5
<212> TYPE: PRT
<213> ORGANISM: Artificial Sequence
<220> FEATURE:
<223> OTHER INFORMATION: /note="Description of artificial sequence:
      Synthetic peptide"
<220> FEATURE:
<221> NAME/KEY: VARIANT
<222> LOCATION: (1)..(1)
<223> OTHER INFORMATION: /replace="Asn" "Gln" "Lys" or "Arg"
<220> FEATURE:
<221> NAME/KEY: VARIANT
<222> LOCATION: (2)..(2)
<223> OTHER INFORMATION: /replace="Gln"
<220> FEATURE:
<221> NAME/KEY: misc_feature
<222> LOCATION: (1)..(2)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (5)..(5)
<223> OTHER INFORMATION: /replace="Val" "Leu" "norleucine" "Met"
      "Phe" or "Ile"
<220> FEATURE:
<221> NAME/KEY: misc_feature
<222> LOCATION: (5)..(5)
<223> OTHER INFORMATION: /notes="Residues given in the sequence have no
      preference with respect to those in the annotations for said
      positions"

<400> SEQUENCE: 10

His Asn Lys Leu Ala
1               5
```

```
<210> SEQ ID NO 11
<211> LENGTH: 10
<212> TYPE: PRT
<213> ORGANISM: Artificial Sequence
<220> FEATURE:
<223> OTHER INFORMATION: /note="Description of artificial sequence:
      Synthetic peptide"
<220> FEATURE:
<221> NAME/KEY: VARIANT
<222> LOCATION: (1)..(1)
<223> OTHER INFORMATION: /replace="Asn" or "Gln"
<220> FEATURE:
<221> NAME/KEY: VARIANT
<222> LOCATION: (2)..(2)
<223> OTHER INFORMATION: /replace="Asn"
<220> FEATURE:
<221> NAME/KEY: VARIANT
<222> LOCATION: (5)..(5)
<223> OTHER INFORMATION: /replace="Leu" or "Ile"
<220> FEATURE:
<221> NAME/KEY: VARIANT
<222> LOCATION: (8)..(8)
<223> OTHER INFORMATION: /replace="Val"
<220> FEATURE:
<221> NAME/KEY: VARIANT
<222> LOCATION: (9)..(9)
<223> OTHER INFORMATION: /replace="Asp"
<220> FEATURE:
<221> NAME/KEY: VARIANT
<222> LOCATION: (10)..(10)
<223> OTHER INFORMATION: /replace="Glu"

<400> SEQUENCE: 11

His Gln Lys Leu Val Phe Phe Ala Glu Asp
1               5                   10

<210> SEQ ID NO 12
<211> LENGTH: 112
<212> TYPE: PRT
<213> ORGANISM: Artificial Sequence
<220> FEATURE:
<223> OTHER INFORMATION: /note="Description of artificial sequence:
      Synthetic polypeptide"

<400> SEQUENCE: 12

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
                20                  25                  30

Asn Gly Asp Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

<210> SEQ ID NO 13
<211> LENGTH: 219
<212> TYPE: PRT
<213> ORGANISM: Artificial Sequence
<220> FEATURE:
<223> OTHER INFORMATION: /note="Description of artificial sequence:
      Synthetic polypeptide"
```

-continued

```
<400> SEQUENCE: 13

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 14
<211> LENGTH: 107
<212> TYPE: PRT
<213> ORGANISM: Artificial Sequence
<220> FEATURE:
<223> OTHER INFORMATION: /note="Description of artificial sequence:
      Synthetic polypeptide"

<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 15
<211> LENGTH: 112
<212> TYPE: PRT
```

<213> ORGANISM: Artificial Sequence
<220> FEATURE:
<223> OTHER INFORMATION: /note="Description of artificial sequence: Synthetic polypeptide"

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser
            100                 105                 110

<210> SEQ ID NO 16
<211> LENGTH: 439
<212> TYPE: PRT
<213> ORGANISM: Artificial Sequence
<220> FEATURE:
<223> OTHER INFORMATION: /note="Description of artificial sequence: Synthetic polypeptide"

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser
            100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220

Glu Phe Leu Gly Gly Pro Ser Val Phe Leu Phe Pro Lys Pro Lys
225                 230                 235                 240

Asp Thr Leu Met Ile Ser Arg Thr Pro Glu Val Thr Cys Val Val Val
            245                 250                 255

Asp Val Ser Gln Glu Asp Pro Glu Val Gln Phe Asn Trp Tyr Val Asp
        260                 265                 270

Gly Val Glu Val His Asn Ala Lys Thr Lys Pro Arg Glu Glu Gln Phe
    275                 280                 285

Asn Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
            325                 330                 335

Glu Pro Gln Val Tyr Thr Leu Pro Pro Ser Gln Glu Glu Met Thr Lys
        340                 345                 350

Asn Gln Val Ser Leu Thr Cys Leu Val Lys Gly Phe Tyr Pro Ser Asp
    355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
            405                 410                 415

Cys Ser Val Met His Glu Ala Leu His Asn His Tyr Thr Gln Lys Ser
        420                 425                 430

Leu Ser Leu Ser Leu Gly Lys
        435

<210> SEQ ID NO 17
<211> LENGTH: 326
<212> TYPE: PRT
<213> ORGANISM: Homo sapiens

<400> SEQUENCE: 17

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
        100                 105                 110

Glu Phe Leu Gly Gly Pro Ser Val Phe Leu Phe Pro Pro Lys Pro Lys
    115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

```
Gly Val Glu Val His Asn Ala Lys Thr Lys Pro Arg Glu Gln Phe
            165                 170                 175

Asn Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 18
<211> LENGTH: 51
<212> TYPE: DNA
<213> ORGANISM: Artificial Sequence
<220> FEATURE:
<223> OTHER INFORMATION: /note="Description of artificial sequence:
      Synthetic oligonucleotide"

<400> SEQUENCE: 18
agcatcaata gtaatggtgg tagcacctat tatccagaca gtgtgaaggg c         51

<210> SEQ ID NO 19
<211> LENGTH: 9
<212> TYPE: DNA
<213> ORGANISM: Artificial Sequence
<220> FEATURE:
<223> OTHER INFORMATION: /note="Description of artificial sequence:
      Synthetic oligonucleotide"

<400> SEQUENCE: 19 ggtgactac                                                         9

<210> SEQ ID NO 20
<211> LENGTH: 49
<212> TYPE: DNA
<213> ORGANISM: Artificial Sequence
<220> FEATURE:
<223> OTHER INFORMATION: /note="Description of artificial sequence:
      Synthetic oligonucleotide"

<400> SEQUENCE: 20
agatctagtc agagccttgt atatagtaat ggagacacct atttacatt             49

<210> SEQ ID NO 21
<211> LENGTH: 336
<212> TYPE: DNA
<213> ORGANISM: Artificial Sequence
<220> FEATURE:
<223> OTHER INFORMATION: /note="Description of artificial sequence:
```

Synthetic polynucleotide"

<400> SEQUENCE: 21

```
gatattgtga tgacccaatc tccactctcc ctgcctgtca ctcctggtga gcctgcctcc    60
atctcttgca gatctagtca gagccttgta tatagtaatg gagacaccta tttacattgg   120
tacctgcaga agccaggcca gtctccacag ctcctgatct acaaagtttc caaccgattt   180
tctggggtcc cagacaggtt cagtggcagt ggatcaggga cagatttcac actcaagatc   240
agcagagtgg aggctgagga tgtgggagtt tattactgct ctcaaagtac acatgttcct   300
tggacgttcg gccaaggcac caaggtggaa atcaaa                             336
```

<210> SEQ ID NO 22
<211> LENGTH: 657
<212> TYPE: DNA
<213> ORGANISM: Artificial Sequence
<220> FEATURE:
<223> OTHER INFORMATION: /note="Description of artificial sequence:
      Synthetic polynucleotide"

<400> SEQUENCE: 22

```
gatattgtga tgacccaatc tccactctcc ctgcctgtca ctcctggtga gcctgcctcc    60
atctcttgca gatctagtca gagccttgta tatagtaatg gagacaccta tttacattgg   120
tacctgcaga agccaggcca gtctccacag ctcctgatct acaaagtttc caaccgattt   180
tctggggtcc cagacaggtt cagtggcagt ggatcaggga cagatttcac actcaagatc   240
agcagagtgg aggctgagga tgtgggagtt tattactgct ctcaaagtac acatgttcct   300
tggacgttcg gccaaggcac caaggtggaa atcaaagga ctgtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt      657
```

<210> SEQ ID NO 23
<211> LENGTH: 321
<212> TYPE: DNA
<213> ORGANISM: Artificial Sequence
<220> FEATURE:
<223> OTHER INFORMATION: /note="Description of artificial sequence:
      Synthetic polynucleotide"

<400> SEQUENCE: 23

```
aggactgtgg ctgcaccatc tgtcttcatc ttcccgccat ctgatgagca gttgaaatct   60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                             321
```

<210> SEQ ID NO 24
<211> LENGTH: 336
<212> TYPE: DNA
<213> ORGANISM: Artificial Sequence
<220> FEATURE:
<223> OTHER INFORMATION: /note="Description of artificial sequence:
      Synthetic polynucleotide"

<400> SEQUENCE: 24

| | |
|---|---|
| gaggtgcagc tggtcgagtc tggggggaggc ttagtgcagc ctggagggtc cctgagactc | 60 |
| tcctgtgcag cctctggatt cactttcagt agctatggca tgtcttgggt tcgccaggct | 120 |
| ccaggcaagg gtctcgaatt ggtcgcaagc atcaatagta atggtggtag cacctattat | 180 |
| ccagacagtg tgaagggccg attcaccatc tccagagaca atgccaagaa ctccctgtac | 240 |
| ctgcaaatga acagtctgag agctgaggac accgccgtgt attactgtgc aagtggtgac | 300 |
| tactggggcc aaggcaccac tgtcacagtc tcctca | 336 |

<210> SEQ ID NO 25
<211> LENGTH: 1317
<212> TYPE: DNA
<213> ORGANISM: Artificial Sequence
<220> FEATURE:
<223> OTHER INFORMATION: /note="Description of artificial sequence: Synthetic polynucleotide"

<400> SEQUENCE: 25

| | |
|---|---|
| gaggtgcagc tggtcgagtc tggggggaggc ttagtgcagc ctggagggtc cctgagactc | 60 |
| tcctgtgcag cctctggatt cactttcagt agctatggca tgtcttgggt tcgccaggct | 120 |
| ccaggcaagg gtctcgaatt ggtcgcaagc atcaatagta atggtggtag cacctattat | 180 |
| ccagacagtg tgaagggccg attcaccatc tccagagaca atgccaagaa ctccctgtac | 240 |
| ctgcaaatga acagtctgag agctgaggac accgccgtgt attactgtgc aagtggtgac | 300 |
| tactggggcc aaggcaccac tgtcacagtc tcctcagctt ccaccaaggg cccatccgtc | 360 |
| ttccccctgg cgccctgctc cagatcgacc tccgagagca cagccgccct gggctgcctg | 420 |
| gtcaaggact acttccccga accggtgacg gtgtcgtgga actcaggcgc cctgaccagc | 480 |
| ggcgtgcaca ccttcccggc tgtcctacag tcctcaggac tctactccct cagcagcgtg | 540 |
| gtgaccgtgc cctccagcag cttgggcacg aagacctaca cctgcaacgt agatcacaag | 600 |
| cccagcaaca ccaaggtgga caagagagtt gagtcccaaa tatggtcccc cgtgtcccca | 660 |
| tgcccagcac ctgagttcct ggggggacca tcagtcttcc tgttcccccc aaaacccaag | 720 |
| gacactctca tgatctcccg gacccctgag gtcacgtgcg tggtggtgga cgtgagccag | 780 |
| gaagaccccg aggtccagtt caactggtac gtggatggcg tggaggtgca taatgccaag | 840 |
| acaaagccgc gggaggagca gttcaacagc acgtaccgtg tggtcagcgt cctcaccgtc | 900 |
| ctgcaccagg actggctgaa cggcaaggag tacaagtgca aggtctccaa caaaggcctc | 960 |
| ccgtcctcca tcgagaaaac catctccaaa gccaaagggc agccccgaga gccacaggtg | 1020 |
| tacaccctgc cccatcccca ggaggagatg accaagaacc aggtcagcct gacctgcctg | 1080 |
| gtcaaaggct tctaccccag cgacatcgcc gtggagtggg agagcaatgg gcagccggag | 1140 |
| aacaactaca agaccacgcc tcccgtcctc gattccgacg gctccttctt cctctacagc | 1200 |
| aggctaaccg tggacaagag caggtggcag gaggggaatg tcttctcatg ctccgtgatg | 1260 |
| catgaggctc tgcacaacca ctacacacag aagagcctct ccctgtctct gggtaaa | 1317 |

<210> SEQ ID NO 26
<211> LENGTH: 981
<212> TYPE: DNA
<213> ORGANISM: Artificial Sequence
<220> FEATURE:
<223> OTHER INFORMATION: /note="Description of artificial sequence: Synthetic polynucleotide"

<400> SEQUENCE: 26

```
gcttccacca agggcccatc cgtcttcccc ctggcgccct gctccagatc gacctccgag    60
agcacagccg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacgaagacc   240
tacacctgca acgtagatca caagcccagc aacaccaagg tggacaagag agttgagtcc   300
aaatatggtc ccccgtgtcc cccatgccca gcacctgagt tcctgggggg accatcagtc   360
ttcctgttcc ccccaaaacc caaggacact ctcatgatct cccggacccc tgaggtcacg   420
tgcgtggtgg tggacgtgag ccaggaagac cccgaggtcc agttcaactg gtacgtggat   480
ggcgtggagg tgcataatgc caagacaaag ccgcgggagg agcagttcaa cagcacgtac   540
cgtgtggtca gcgtcctcac cgtcctgcac caggactggc tgaacggcaa ggagtacaag   600
tgcaaggtct ccaacaaagg cctcccgtcc tccatcgaga aaaccatctc caaagccaaa   660
gggcagcccc gagagccaca ggtgtacacc ctgcccccat cccaggagga gatgaccaag   720
aaccaggtca gcctgacctg cctggtcaaa ggcttctacc ccagcgacat cgccgtggag   780
tgggagagca atgggcagcc ggagaacaac tacaagacca cgcctcccgt cctcgattcc   840
gacggctcct tcttcctcta cagcaggcta accgtggaca gagcaggtg gcaggagggg   900 aatgtcttct catgctccgt gatgcatgag gctctgcaca accactacac acagaagagc   960
ctctccctgt ctctgggtaa a                                             981
```

<210> SEQ ID NO 27
<211> LENGTH: 112
<212> TYPE: PRT
<213> ORGANISM: Mus musculus
<400> SEQUENCE: 27

```
Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110
```

<210> SEQ ID NO 28
<211> LENGTH: 112
<212> TYPE: PRT
<213> ORGANISM: Mus musculus
<400> SEQUENCE: 28

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Leu Val
        35                  40                  45
```

```
Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Ser Gly Asp Tyr Trp Gly Gln Gly Ser Thr Leu Thr Val Ser Ser
            100                 105                 110
```

<210> SEQ ID NO 29
<211> LENGTH: 336
<212> TYPE: DNA
<213> ORGANISM: Mus musculus

<400> SEQUENCE: 29

```
gatgttgtga tgacccaaac tccactctcc ctgcctgtca gtcttggaga tcaagcctcc    60
atctcttgca gatctagtca gagccttgta tatagtaatg gagacaccta tttacattgg   120
tacctgcaga agccaggcca gtctccaaag ctcctgatct acaaagtttc aaccgatttt   180
tctggggtcc cagacaggtt cagtggcagt ggatcaggga cagatttcac actcaagatc   240
agcagagtgg aggctgagga tctgggagtt tatttctgct ctcaaagtac acatgttcct   300
tggacgttcg gtggaggcac caagctagaa atcaaa                              336
```

<210> SEQ ID NO 30
<211> LENGTH: 417
<212> TYPE: DNA
<213> ORGANISM: Mus musculus

<400> SEQUENCE: 30

```
atgaagttgc ctgttaggct gttggtgctg atgttctgga ttcctgcttc cagcagtgat    60
gttgtgatga cccaaactcc actctccctg cctgtcagtc ttggagatca agcctccatc   120
tcttgcagat ctagtcagag ccttgtatat agtaatggag acacctattt acattggtac   180
ctgcagaagc caggccagtc tccaaagctc ctgatctaca agtttccaa ccgattttct    240
ggggtcccag acaggttcag tggcagtgga tcagggacag atttcacact caagatcagc   300
agagtggagg ctgaggatct gggagtttat ttctgctctc aaagtacaca tgttccttgg   360
acgttcggtg gaggcaccaa gctagaaatc aaacgggctg atgctgcacc aactgta      417
```

<210> SEQ ID NO 31
<211> LENGTH: 336
<212> TYPE: DNA
<213> ORGANISM: Mus musculus

<400> SEQUENCE: 31

```
gaggtgcagc tggtggagtc tgggggaggc ttagtgcagc ctggagggtc cctgaaactc    60
tcctgtgcag cctctggatt cactttcagt agctatggca tgtcttgggt tcgccagact   120
ccagacaaga ggctggaatt ggtcgcaagc atcaatagta atggtggtag cacctattat   180
ccagacagtg tgaagggccg attcaccatc tccagagaca atgccaagaa caccctgtac   240
ctgcaaatga gcagtctgaa gtctgaggac acagccatgt attactgtgc aagtggtgac   300
tactggggcc aaggctccac tctcacagtc tcctca                              336
```

<210> SEQ ID NO 32
<211> LENGTH: 408
<212> TYPE: DNA
<213> ORGANISM: Mus musculus

<400> SEQUENCE: 32

```
atgrasttsg ggytcagmtt grttttcctt gcccttattt taaaaggtgt ccaatgtgag      60
gtgcagctgg tggagtctgg gggaggctta gtgcagcctg agggtccct gaaactctcc     120 tgtgcagcct ctggattcac tttcagtagc tatggcatgt cttgggttcg ccagactcca    180
gacaagaggc tggaattggt cgcaagcatc aatagtaatg gtggtagcac ctattatcca    240
gacagtgtga agggccgatt caccatctcc agagacaatg ccaagaacac cctgtacctg    300
caaatgagca gtctgaagtc tgaggacaca gccatgtatt actgtgcaag tggtgactac    360
tggggccaag gctccactct cacagtctcc tcagccaaaa caacaccc                 408
```

```
<210> SEQ ID NO 33
<211> LENGTH: 10
<212> TYPE: PRT
<213> ORGANISM: Artificial Sequence
<220> FEATURE:
<223> OTHER INFORMATION: /note="Description of artificial sequence:
      Synthetic peptide"
<220> FEATURE:
<221> NAME/KEY: VARIANT
<222> LOCATION: (2)..(2)
<223> OTHER INFORMATION: /replace="Gln"
<220> FEATURE:
<221> NAME/KEY: misc_feature
<222> LOCATION: (2)..(2)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (5)..(5)
<223> OTHER INFORMATION: /replace="Val" "Leu" "norleucine" "Met"
      "Phe" or "Ile"
<220> FEATURE:
<221> NAME/KEY: VARIANT
<222> LOCATION: (6)..(6)
<223> OTHER INFORMATION: /replace="Val" "Leu" "norleucine" "Met"
      "Phe" or "Ile"
<220> FEATURE:
<221> NAME/KEY: VARIANT
<222> LOCATION: (7)..(7)
<223> OTHER INFORMATION: /replace="Val" "Leu" "norleucine" "Met"
      "Phe" or "Ile"
<220> FEATURE:
<221> NAME/KEY: VARIANT
<222> LOCATION: (8)..(8)
<223> OTHER INFORMATION: /replace="Val" "Leu" "Ser" or "Ile"
<220> FEATURE:
<221> NAME/KEY: VARIANT
<222> LOCATION: (9)..(9)
<223> OTHER INFORMATION: /replace="Asp"
<220> FEATURE:
<221> NAME/KEY: VARIANT
<222> LOCATION: (10)..(10)
<223> OTHER INFORMATION: /replace="Asp"
<220> FEATURE:
<221> NAME/KEY: misc_feature
<222> LOCATION: (5)..(10)
<223> OTHER INFORMATION: /notes="Residues given in the sequence have no
      preference with respect to those in the annotations for said
      positions"
```

<400> SEQUENCE: 33

```
His Asn Lys Leu Ala Ala Ala Ala Glu Glu
1               5                   10
```

```
<210> SEQ ID NO 34
<211> LENGTH: 11
<212> TYPE: PRT
<213> ORGANISM: Artificial Sequence
<220> FEATURE:
```

```
<223> OTHER INFORMATION: /note="Description of artificial sequence:
      Synthetic peptide"
<220> FEATURE:
<221> NAME/KEY: VARIANT
<222> LOCATION: (1)..(1)
<223> OTHER INFORMATION: /replace="Asn" "Gln" "Lys" or "Arg"
<220> FEATURE:
<221> NAME/KEY: misc_feature
<222> LOCATION: (1)..(1)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (3)..(3)
<223> OTHER INFORMATION: /replace="Gln"
<220> FEATURE:
<221> NAME/KEY: VARIANT
<222> LOCATION: (4)..(4)
<223> OTHER INFORMATION: /replace="Asn" "Gln" "Lys" or "Arg"
<220> FEATURE:
<221> NAME/KEY: VARIANT
<222> LOCATION: (5)..(5)
<223> OTHER INFORMATION: /replace="Val" "Leu" "Ser" or "Ile"
<220> FEATURE:
<221> NAME/KEY: VARIANT
<222> LOCATION: (6)..(6)
<223> OTHER INFORMATION: /replace="Val" "Leu" "Ser" or "Ile"
<220> FEATURE:
<221> NAME/KEY: misc_feature
<222> LOCATION: (3)..(6)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (9)..(9)
<223> OTHER INFORMATION: /replace="Val" "Leu" "Ser" or "Ile"
<220> FEATURE:
<221> NAME/KEY: VARIANT
<222> LOCATION: (10)..(10)
<223> OTHER INFORMATION: /replace="Asp"
<220> FEATURE:
<221> NAME/KEY: VARIANT
<222> LOCATION: (11)..(11)
<223> OTHER INFORMATION: /replace="Asp"
<220> FEATURE:
<221> NAME/KEY: misc_feature
<222> LOCATION: (9)..(11)
<223> OTHER INFORMATION: /notes="Residues given in the sequence have no
      preference with respect to those in the annotations for said
      positions"

<400> SEQUENCE: 34

His His Asn His Ala Ala Phe Phe Ala Glu Glu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: /note="Description of artificial sequence:
      Synthetic peptide"
<220> FEATURE:
<221> NAME/KEY: VARIANT
<222> LOCATION: (1)..(1)
<223> OTHER INFORMATION: /replace="Asn" "Gln" "Lys" or "Arg"
<220> FEATURE:
<221> NAME/KEY: VARIANT
<222> LOCATION: (2)..(2)
<223> OTHER INFORMATION: /replace="Gln"
<220> FEATURE:
<221> NAME/KEY: misc_feature
<222> LOCATION: (1)..(2)
<223> OTHER INFORMATION: /notes="Residues given in the sequence have no
      preference with respect to those in the annotations for said
      positions"
```

```
<220> FEATURE:
<221> NAME/KEY: VARIANT
<222> LOCATION: (5)..(5)
<223> OTHER INFORMATION: /replace="Val" "Leu" "norleucine" "Met"
      "Phe" or "Ile"
<220> FEATURE:
<221> NAME/KEY: misc_feature
<222> LOCATION: (5)..(5)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (8)..(8)
<223> OTHER INFORMATION: /replace="Val" "Leu" "Ser" or "Ile"
<220> FEATURE:
<221> NAME/KEY: VARIANT
<222> LOCATION: (9)..(9)
<223> OTHER INFORMATION: /replace="Asp"
<220> FEATURE:
<221> NAME/KEY: VARIANT
<222> LOCATION: (10)..(10)
<223> OTHER INFORMATION: /replace="Asp"
<220> FEATURE:
<221> NAME/KEY: misc_feature
<222> LOCATION: (8)..(10)
<223> OTHER INFORMATION: /notes="Residues given in the sequence have no
      preference with respect to those in the annotations for said
      positions"

<400> SEQUENCE: 35

His Asn Lys Leu Ala Phe Phe Ala Glu Glu
1               5                   10

<210> SEQ ID NO 36
<211> LENGTH: 10
<212> TYPE: PRT
<213> ORGANISM: Artificial Sequence
<220> FEATURE:
<223> OTHER INFORMATION: /note="Description of artificial sequence:
      Synthetic peptide"
<220> FEATURE:
<221> NAME/KEY: VARIANT
<222> LOCATION: (2)..(2)
<223> OTHER INFORMATION: /replace="Gln"
<220> FEATURE:
<221> NAME/KEY: misc_feature
<222> LOCATION: (2)..(2)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (5)..(5)
<223> OTHER INFORMATION: /replace="Val" "Leu" "norleucine" "Met"
      "Phe" or "Ile"
<220> FEATURE:
<221> NAME/KEY: misc_feature
<222> LOCATION: (5)..(5)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (8)..(8)
<223> OTHER INFORMATION: /replace="Val" "Leu" "Ser" or "Ile"
<220> FEATURE:
<221> NAME/KEY: VARIANT
<222> LOCATION: (9)..(9)
<223> OTHER INFORMATION: /replace="Asp"
<220> FEATURE:
<221> NAME/KEY: VARIANT
<222> LOCATION: (10)..(10)
<223> OTHER INFORMATION: /replace="Asp"
<220> FEATURE:
<221> NAME/KEY: misc_feature
<222> LOCATION: (8)..(10)
<223> OTHER INFORMATION: /notes="Residues given in the sequence have no
``` preference with respect to those in the annotations for said
       positions"

<400> SEQUENCE: 36

His Asn Lys Leu Ala Phe Phe Ala Glu Glu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: /note="Description of artificial sequence:
       Synthetic peptide"
<220> FEATURE:
<221> NAME/KEY: VARIANT
<222> LOCATION: (1)..(1)
<223> OTHER INFORMATION: /replace="Asn" "Gln" "Lys" or "Arg"
<220> FEATURE:
<221> NAME/KEY: VARIANT
<222> LOCATION: (2)..(2)
<223> OTHER INFORMATION: /replace="Gln"
<220> FEATURE:
<221> NAME/KEY: misc_feature
<222> LOCATION: (1)..(2)
<223> OTHER INFORMATION: /notes="Residues given in the sequence have no
       preference with respect to those in the annotations for said
       positions"
<220> FEATURE:
<221> NAME/KEY: VARIANT
<222> LOCATION: (5)..(5)
<223> OTHER INFORMATION: /replace="Val" "Leu" "norleucine" "Met"
       "Phe" or "Ile"
<220> FEATURE:
<221> NAME/KEY: misc_feature
<222> LOCATION: (5)..(5)
<223> OTHER INFORMATION: /notes="Residues given in the sequence have no
       preference with respect to those in the annotations for said
       positions"
<220> FEATURE:
<221> NAME/KEY: VARIANT
<222> LOCATION: (8)..(8)
<223> OTHER INFORMATION: /replace="Val" "Leu" "Ser" or "Ile"
<220> FEATURE:
<221> NAME/KEY: VARIANT
<222> LOCATION: (9)..(9)
<223> OTHER INFORMATION: /replace="Asp"
<220> FEATURE:
<221> NAME/KEY: misc_feature
<222> LOCATION: (8)..(9)
<223> OTHER INFORMATION: /notes="Residues given in the sequence have no
       preference with respect to those in the annotations for said
       positions"

<400> SEQUENCE: 37

His Asn Lys Leu Ala Phe Phe Ala Glu Asp
1               5                   10

<210> SEQ ID NO 38
<211> LENGTH: 10
<212> TYPE: PRT
<213> ORGANISM: Artificial Sequence
<220> FEATURE:
<223> OTHER INFORMATION: /note="Description of artificial sequence:
       Synthetic peptide"
<220> FEATURE:
<221> NAME/KEY: VARIANT
<222> LOCATION: (2)..(2)
<223> OTHER INFORMATION: /replace="Gln"
<220> FEATURE:
<221> NAME/KEY: misc_feature
<222> LOCATION: (2)..(2)
<223> OTHER INFORMATION: /notes="Residues given in the sequence have no
       preference with respect to those in the annotations for said
       positions"
<220> FEATURE:

```
-continued

<221> NAME/KEY: VARIANT
<222> LOCATION: (5)..(5)
<223> OTHER INFORMATION: /replace="Val" "Leu" "norleucine" "Met"
      "Phe" or "Ile"
<220> FEATURE:
<221> NAME/KEY: misc_feature
<222> LOCATION: (5)..(5)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (8)..(8)
<223> OTHER INFORMATION: /replace="Val" "Leu" "Ser" or "Ile"
<220> FEATURE:
<221> NAME/KEY: VARIANT
<222> LOCATION: (9)..(9)
<223> OTHER INFORMATION: /replace="Asp"
<220> FEATURE:
<221> NAME/KEY: misc_feature
<222> LOCATION: (8)..(9)
<223> OTHER INFORMATION: /notes="Residues given in the sequence have no
      preference with respect to those in the annotations for said
      positions"

<400> SEQUENCE: 38

His Asn Lys Leu Ala Phe Phe Ala Glu Asp
1               5                   10

<210> SEQ ID NO 39
<211> LENGTH: 10
<212> TYPE: PRT
<213> ORGANISM: Artificial Sequence
<220> FEATURE:
<223> OTHER INFORMATION: /note="Description of artificial sequence:
      Synthetic peptide"
<220> FEATURE:
<221> NAME/KEY: VARIANT
<222> LOCATION: (1)..(1)
<223> OTHER INFORMATION: /replace="Asn" "Gln" "Lys" or "Arg"
<220> FEATURE:
<221> NAME/KEY: VARIANT
<222> LOCATION: (2)..(2)
<223> OTHER INFORMATION: /replace="Gln"
<220> FEATURE:
<221> NAME/KEY: VARIANT
<222> LOCATION: (3)..(3)
<223> OTHER INFORMATION: /replace="His" "Asn" "Gln" or "Arg"
<220> FEATURE:
<221> NAME/KEY: misc_feature
<222> LOCATION: (1)..(3)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (5)..(5)
<223> OTHER INFORMATION: /replace="Val" "Leu" "norleucine" "Met"
      "Phe" or "Ile"
<220> FEATURE:
<221> NAME/KEY: misc_feature
<222> LOCATION: (5)..(5)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (8)..(8)
<223> OTHER INFORMATION: /replace="Val" "Leu" "Ser" or "Ile"
<220> FEATURE:
<221> NAME/KEY: VARIANT
<222> LOCATION: (9)..(9)
<223> OTHER INFORMATION: /replace="Asp"
<220> FEATURE:
<221> NAME/KEY: VARIANT
<222> LOCATION: (10)..(10)
<223> OTHER INFORMATION: /replace="Asp"
<220> FEATURE:
```

```
<221> NAME/KEY: misc_feature
<222> LOCATION: (8)..(10)
<223> OTHER INFORMATION: /notes="Residues given in the sequence have no
      preference with respect to those in the annotations for said
      positions"

<400> SEQUENCE: 39

His Asn Lys Leu Ala Phe Phe Ala Glu Glu
1               5                   10

<210> SEQ ID NO 40
<211> LENGTH: 11
<212> TYPE: PRT
<213> ORGANISM: Homo sapiens

<400> SEQUENCE: 40

Val His His Lys Leu Val Phe Phe Ala Glu Asp
1               5                   10

<210> SEQ ID NO 41
<211> LENGTH: 219
<212> TYPE: PRT
<213> ORGANISM: Mus musculus

<400> SEQUENCE: 41

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 42
<211> LENGTH: 448
<212> TYPE: PRT
<213> ORGANISM: Mus musculus

<400> SEQUENCE: 42
```

-continued

```
Glu Val Gln Leu Val Glu Ser Gly Gly Leu Val Gln Pro Gly
1               5                   10                  15
Ser Leu Lys Leu Ser Cys Ala Ala Ser Gly Phe Thr Phe Ser Ser Tyr
            20                  25                  30
Gly Met Ser Trp Val Arg Gln Thr Pro Asp Lys Arg Leu Glu Leu Val
        35                  40                  45
Ala Ser Ile Asn Ser Asn Gly Gly Ser Thr Tyr Tyr Pro Asp Ser Val
    50                  55                  60
Lys Gly Arg Phe Thr Ile Ser Arg Asp Asn Ala Lys Asn Thr Leu Tyr
65                  70                  75                  80
Leu Gln Met Ser Ser Leu Lys Ser Glu Asp Thr Ala Met Tyr Tyr Cys
                85                  90                  95
Ala Ser Gly Asp Tyr Trp Gly Gln Gly Ser Thr Leu Thr Val Ser Ser
            100                 105                 110
Ala Lys Thr Thr Pro Pro Ser Val Tyr Pro Leu Ala Pro Gly Cys Gly
        115                 120                 125
Asp Thr Thr Gly Ser Ser Val Thr Leu Gly Cys Leu Val Lys Gly Tyr
    130                 135                 140
Phe Pro Glu Ser Val Thr Val Thr Trp Asn Ser Gly Ser Leu Ser Ser
145                 150                 155                 160
Ser Val His Thr Phe Pro Ala Leu Leu Gln Ser Gly Leu Tyr Thr Met
                165                 170                 175
Ser Ser Ser Val Thr Val Pro Ser Ser Thr Trp Pro Ser Gln Thr Val
            180                 185                 190
Thr Cys Ser Val Ala His Pro Ala Ser Ser Thr Val Asp Lys Lys
        195                 200                 205
Leu Glu Pro Ser Gly Pro Ile Ser Thr Ile Asn Pro Cys Pro Pro Cys
    210                 215                 220
Lys Glu Cys His Lys Cys Pro Ala Pro Asn Leu Glu Gly Gly Pro Ser
225                 230                 235                 240
Val Phe Ile Phe Pro Pro Asn Ile Lys Asp Val Leu Met Ile Ser Leu
                245                 250                 255
Thr Pro Lys Val Thr Cys Val Val Val Asp Val Ser Glu Asp Asp Pro
            260                 265                 270
Asp Val Gln Ile Ser Trp Phe Val Asn Asn Val Glu Val His Thr Ala
        275                 280                 285
Gln Thr Gln Thr His Arg Glu Asp Tyr Asn Ser Thr Ile Arg Val Val
    290                 295                 300
Ser Thr Leu Pro Ile Gln His Gln Asp Trp Met Ser Gly Lys Glu Phe
305                 310                 315                 320
Lys Cys Lys Val Asn Asn Lys Asp Leu Pro Ser Pro Ile Glu Arg Thr
                325                 330                 335
Ile Ser Lys Ile Lys Gly Leu Val Arg Ala Pro Gln Val Tyr Ile Leu
            340                 345                 350
Pro Pro Pro Ala Glu Gln Leu Ser Arg Lys Asp Val Ser Leu Thr Cys
        355                 360                 365
Leu Val Val Gly Phe Asn Pro Gly Asp Ile Ser Val Glu Trp Thr Ser
    370                 375                 380
Asn Gly His Thr Glu Glu Asn Tyr Lys Asp Thr Ala Pro Val Leu Asp
385                 390                 395                 400
Ser Asp Gly Ser Tyr Phe Ile Tyr Ser Lys Leu Asn Met Lys Thr Ser
                405                 410                 415
Lys Trp Glu Lys Thr Asp Ser Phe Ser Cys Asn Val Arg His Glu Gly
            420                 425                 430
```

Leu Lys Asn Tyr Tyr Leu Lys Lys Thr Ile Ser Arg Ser Pro Gly Lys
         435                 440                 445

<210> SEQ ID NO 43
<211> LENGTH: 15
<212> TYPE: PRT
<213> ORGANISM: Homo sapiens

<400> SEQUENCE: 43

Asp Ala Glu Phe Arg His Asp Ser Gly Tyr Glu Val His His Gln
1               5                   10                  15

<210> SEQ ID NO 44
<211> LENGTH: 16
<212> TYPE: PRT
<213> ORGANISM: Homo sapiens

<400> SEQUENCE: 44

Asp Ala Glu Phe Arg His Asp Ser Gly Tyr Glu Val His His Gln Lys
1               5                   10                  15

<210> SEQ ID NO 45
<211> LENGTH: 15
<212> TYPE: PRT
<213> ORGANISM: Homo sapiens

<400> SEQUENCE: 45

Asp Ala Glu Phe Arg His Asp Ser Gly Tyr Glu Val His Gln Lys
1               5                   10                  15

<210> SEQ ID NO 46
<211> LENGTH: 14
<212> TYPE: PRT
<213> ORGANISM: Homo sapiens

<400> SEQUENCE: 46

Glu Asp Val Gly Ser Asn Lys Gly Ala Ile Ile Gly Leu Met
1               5                   10

<210> SEQ ID NO 47
<211> LENGTH: 12
<212> TYPE: PRT
<213> ORGANISM: Homo sapiens

<400> SEQUENCE: 47

Gly Ala Ile Ile Gly Leu Met Val Gly Gly Val Val
1               5                   10

<210> SEQ ID NO 48
<211> LENGTH: 17
<212> TYPE: PRT
<213> ORGANISM: Homo sapiens

<400> SEQUENCE: 48

Asp Ala Glu Phe Arg His Asp Ser Gly Tyr Glu Val His His Gln Lys
1               5                   10                  15
Leu

<210> SEQ ID NO 49
<211> LENGTH: 11
<212> TYPE: PRT
<213> ORGANISM: Artificial Sequence
<220> FEATURE:
<223> OTHER INFORMATION: /note="Description of artificial sequence:
      Synthetic peptide"

```
<220> FEATURE:
<221> NAME/KEY: VARIANT
<222> LOCATION: (1)..(1)
<223> OTHER INFORMATION: /replace="Asn" "Gln" "Lys" or "Arg"
<220> FEATURE:
<221> NAME/KEY: misc_feature
<222> LOCATION: (1)..(1)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (3)..(3)
<223> OTHER INFORMATION: /replace="Gln"
<220> FEATURE:
<221> NAME/KEY: VARIANT
<222> LOCATION: (4)..(4)
<223> OTHER INFORMATION: /replace="Asn" "Gln" "Lys" or "Arg"
<220> FEATURE:
<221> NAME/KEY: VARIANT
<222> LOCATION: (5)..(5)
<223> OTHER INFORMATION: /replace="Val" "Leu" "Ser" or "Ile"
<220> FEATURE:
<221> NAME/KEY: VARIANT
<222> LOCATION: (6)..(6)
<223> OTHER INFORMATION: /replace="Val" "Leu" "norleucine" "Met"
      "Phe" or "Ile"
<220> FEATURE:
<221> NAME/KEY: misc_feature
<222> LOCATION: (3)..(6)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (9)..(9)
<223> OTHER INFORMATION: /replace="Val" "Leu" or "Ile"
<220> FEATURE:
<221> NAME/KEY: VARIANT
<222> LOCATION: (10)..(10)
<223> OTHER INFORMATION: /replace="Asp"
<220> FEATURE:
<221> NAME/KEY: VARIANT
<222> LOCATION: (11)..(11)
<223> OTHER INFORMATION: /replace="Asp"
<220> FEATURE:
<221> NAME/KEY: misc_feature
<222> LOCATION: (9)..(11)
<223> OTHER INFORMATION: /notes="Residues given in the sequence have no
      preference with respect to those in the annotations for said
      positions"

<400> SEQUENCE: 49

His His Asn His Ala Ala Phe Phe Ala Glu Glu
1               5                   10

<210> SEQ ID NO 50
<211> LENGTH: 10
<212> TYPE: PRT
<213> ORGANISM: Artificial Sequence
<220> FEATURE:
<223> OTHER INFORMATION: /note="Description of artificial sequence:
      Synthetic peptide"
<220> FEATURE:
<221> NAME/KEY: VARIANT
<222> LOCATION: (1)..(1)
<223> OTHER INFORMATION: /replace="Asn" "Gln" "Lys" or "Arg"
<220> FEATURE:
<221> NAME/KEY: VARIANT
<222> LOCATION: (2)..(2)
<223> OTHER INFORMATION: /replace="Gln"
<220> FEATURE:
<221> NAME/KEY: misc_feature
<222> LOCATION: (1)..(2)
<223> OTHER INFORMATION: /notes="Residues given in the sequence have no
      preference with respect to those in the annotations for said
      positions"
<220> FEATURE:
```

```
<221> NAME/KEY: VARIANT
<222> LOCATION: (5)..(5)
<223> OTHER INFORMATION: /replace="Ala" "Leu" "Met" "Phe" "norleucine"
      or "Ile"
<220> FEATURE:
<221> NAME/KEY: misc_feature
<222> LOCATION: (5)..(5)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (8)..(8)
<223> OTHER INFORMATION: /replace="Val" "Leu" or "Ile"
<220> FEATURE:
<221> NAME/KEY: VARIANT
<222> LOCATION: (9)..(9)
<223> OTHER INFORMATION: /replace="Asp"
<220> FEATURE:
<221> NAME/KEY: VARIANT
<222> LOCATION: (10)..(10)
<223> OTHER INFORMATION: /replace="Asp"
<220> FEATURE:
<221> NAME/KEY: misc_feature
<222> LOCATION: (8)..(10)
<223> OTHER INFORMATION: /notes="Residues given in the sequence have no
      preference with respect to those in the annotations for said
      positions"

<400> SEQUENCE: 50

His Asn Lys Leu Val Phe Phe Ala Glu Glu
1               5                   10

<210> SEQ ID NO 51
<211> LENGTH: 4
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 51

Phe Phe Ala Glu
1

<210> SEQ ID NO 52
<211> LENGTH: 12
<212> TYPE: PRT
<213> ORGANISM: Artificial Sequence
<220> FEATURE:
<223> OTHER INFORMATION: /note="Description of artificial sequence:
      Synthetic peptide"
<220> FEATURE:
<221> NAME/KEY: VARIANT
<222> LOCATION: (1)..(1)
<223> OTHER INFORMATION: /replace="Asn" "Gln" "Lys" or "Arg"
<220> FEATURE:
<221> NAME/KEY: VARIANT
<222> LOCATION: (3)..(3)
<223> OTHER INFORMATION: /replace="Asn"
<220> FEATURE:
<221> NAME/KEY: VARIANT
<222> LOCATION: (6)..(6)
<223> OTHER INFORMATION: /replace="Ala" "Leu" "norleucine" "Met"
      "Phe" or "Ile"
<220> FEATURE:
<221> NAME/KEY: VARIANT
<222> LOCATION: (9)..(9)
<223> OTHER INFORMATION: /replace="Val" "Leu" "Ser" or "Ile"
<220> FEATURE:
<221> NAME/KEY: VARIANT
<222> LOCATION: (10)..(10)
<223> OTHER INFORMATION: /replace="Asp"
<220> FEATURE:
<221> NAME/KEY: VARIANT
<222> LOCATION: (12)..(12)
```

-continued

```
<223> OTHER INFORMATION: /replace="Ala" "Leu" "norleucine" "Met"
      "Phe" or "Ile"

<400> SEQUENCE: 52

His His Gln Lys Leu Val Phe Phe Ala Glu Asp Val
1               5                   10

<210> SEQ ID NO 53
<211> LENGTH: 10
<212> TYPE: PRT
<213> ORGANISM: Homo sapiens
<220> FEATURE:
<221> NAME/KEY: VARIANT
<222> LOCATION: (2)..(2)
<223> OTHER INFORMATION: /replace="Asn"
<220> FEATURE:
<221> NAME/KEY: VARIANT
<222> LOCATION: (5)..(5)
<223> OTHER INFORMATION: /replace="Leu" or "Ile"
<220> FEATURE:
<221> NAME/KEY: VARIANT
<222> LOCATION: (8)..(8)
<223> OTHER INFORMATION: /replace="Val"
<220> FEATURE:
<221> NAME/KEY: VARIANT
<222> LOCATION: (9)..(9)
<223> OTHER INFORMATION: /replace="Asp"
<220> FEATURE:
<221> NAME/KEY: VARIANT
<222> LOCATION: (10)..(10)
<223> OTHER INFORMATION: /replace="Asp"

<400> SEQUENCE: 53

His Gln Lys Leu Val Phe Phe Ala Glu Glu
1               5                   10

<210> SEQ ID NO 54
<211> LENGTH: 11
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="Asn" "Gln" "Lys" or "Arg"
<220> FEATURE:
<221> NAME/KEY: misc_feature
<222> LOCATION: (1)..(1)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (3)..(3)
<223> OTHER INFORMATION: /replace="Gln"
<220> FEATURE:
<221> NAME/KEY: VARIANT
<222> LOCATION: (4)..(4)
<223> OTHER INFORMATION: /replace="Asn" "Gln" "Lys" or "Arg"
<220> FEATURE:
<221> NAME/KEY: VARIANT
<222> LOCATION: (5)..(5)
<223> OTHER INFORMATION: /replace="Val" "Leu" "Ser" or "Ile"
<220> FEATURE:
<221> NAME/KEY: VARIANT
<222> LOCATION: (6)..(6)
<223> OTHER INFORMATION: /replace="Val" "Leu" or "Ile"
<220> FEATURE:
<221> NAME/KEY: misc_feature
<222> LOCATION: (3)..(6)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (9)..(9)
<223> OTHER INFORMATION: /replace="Val" "Leu" or "Ile"
```

```
<220> FEATURE:
<221> NAME/KEY: VARIANT
<222> LOCATION: (10)..(10)
<223> OTHER INFORMATION: /replace="Asp"
<220> FEATURE:
<221> NAME/KEY: VARIANT
<222> LOCATION: (11)..(11)
<223> OTHER INFORMATION: /replace="Asp"
<220> FEATURE:
<221> NAME/KEY: misc_feature
<222> LOCATION: (9)..(11)
<223> OTHER INFORMATION: /notes="Residues given in the sequence have no
      preference with respect to those in the annotations for said
      positions"

<400> SEQUENCE: 54

His His Asn His Ala Ala Phe Phe Ala Glu Glu
1               5                   10

<210> SEQ ID NO 55
<211> LENGTH: 12
<212> TYPE: PRT
<213> ORGANISM: Homo sapiens

<400> SEQUENCE: 55

Val His His Gln Lys Leu Val Phe Phe Ala Glu Asp
1               5                   10

<210> SEQ ID NO 56
<211> LENGTH: 5
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 56

Leu Glu Trp Ile Gly
1               5

<210> SEQ ID NO 57
<211> LENGTH: 7
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 57

Arg Val Ser Asn Arg Phe Ser
1               5

<210> SEQ ID NO 58
<211> LENGTH: 7
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 58

Lys Val Ser Ser Arg Phe Ser
1               5

<210> SEQ ID NO 59
<211> LENGTH: 9
<212> TYPE: PRT
<213> ORGANISM: Artificial Sequence
<220> FEATURE:
<223> OTHER INFORMATION: /note="Description of artificial sequence:
```

Synthetic peptide"

<400> SEQUENCE: 59

Val His His Gln Lys Leu Val Phe Phe
1               5

<210> SEQ ID NO 60
<211> LENGTH: 9
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 60

Ala His His Gln Lys Leu Val Phe Phe
1               5

<210> SEQ ID NO 61
<211> LENGTH: 9
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 61

Val Ala His Gln Lys Leu Val Phe Phe
1               5

<210> SEQ ID NO 62
<211> LENGTH: 9
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 62

Val His Ala Gln Lys Leu Val Phe Phe
1               5

<210> SEQ ID NO 63
<211> LENGTH: 9
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 63

Val His His Ala Lys Leu Val Phe Phe
1               5

<210> SEQ ID NO 64
<211> LENGTH: 9
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 64

Val His His Gln Ala Leu Val Phe Phe
1               5

<210> SEQ ID NO 65
<211> LENGTH: 9

```
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 65

Val His His Gln Lys Ala Val Phe Phe
1               5

<210> SEQ ID NO 66
<211> LENGTH: 9
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 66

Val His His Gln Lys Leu Ala Phe Phe
1               5

<210> SEQ ID NO 67
<211> LENGTH: 9
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 67

Val His His Gln Lys Leu Val Ala Phe
1               5

<210> SEQ ID NO 68
<211> LENGTH: 9
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 68

Val His His Gln Lys Leu Val Phe Ala
1               5

<210> SEQ ID NO 69
<211> LENGTH: 9
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 69

His His Gln Lys Leu Val Phe Phe Ala
1               5

<210> SEQ ID NO 70
<211> LENGTH: 9
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 70

His His Gln Lys Leu Val Phe Phe Gly
1               5
```

-continued

```
<210> SEQ ID NO 71
<211> LENGTH: 9
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 71

His Gln Lys Leu Val Phe Phe Ala Glu
1               5

<210> SEQ ID NO 72
<211> LENGTH: 9
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 72

His Gln Lys Leu Val Phe Phe Ala Ala
1               5

<210> SEQ ID NO 73
<211> LENGTH: 9
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 73

Gln Lys Leu Val Phe Phe Ala Glu Asp
1               5

<210> SEQ ID NO 74
<211> LENGTH: 9
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 74

Gln Lys Leu Val Phe Phe Ala Glu Ala
1               5

<210> SEQ ID NO 75
<211> LENGTH: 10
<212> TYPE: PRT
<213> ORGANISM: Artificial Sequence
<220> FEATURE:
<223> OTHER INFORMATION: /note="Description of artificial sequence:
      Synthetic peptide"
<220> FEATURE:
<221> NAME/KEY: VARIANT
<222> LOCATION: (1)..(1)
<223> OTHER INFORMATION: /replace="Asn" or "Gln"
<220> FEATURE:
<221> NAME/KEY: VARIANT
<222> LOCATION: (2)..(2)
<223> OTHER INFORMATION: /replace="Asn"
<220> FEATURE:
<221> NAME/KEY: VARIANT
<222> LOCATION: (5)..(5)
<223> OTHER INFORMATION: /replace="Leu" or "Ile"
<220> FEATURE:
<221> NAME/KEY: VARIANT
<222> LOCATION: (8)..(8)
```

```
<223> OTHER INFORMATION: /replace="Val"
<220> FEATURE:
<221> NAME/KEY: VARIANT
<222> LOCATION: (9)..(9)
<223> OTHER INFORMATION: /replace="Asp"
<220> FEATURE:
<221> NAME/KEY: VARIANT
<222> LOCATION: (10)..(10)
<223> OTHER INFORMATION: /replace="Glu"

<400> SEQUENCE: 75

His Gln Lys Leu Val Phe Phe Ala Glu Asp
1               5                   10

<210> SEQ ID NO 76
<211> LENGTH: 11
<212> TYPE: PRT
<213> ORGANISM: Artificial Sequence
<220> FEATURE:
<223> OTHER INFORMATION: /note="Description of artificial sequence:
      Synthetic peptide"
<220> FEATURE:
<221> NAME/KEY: VARIANT
<222> LOCATION: (1)..(1)
<223> OTHER INFORMATION: /replace="Asn" "Gln" "Lys" or "Arg"
<220> FEATURE:
<221> NAME/KEY: misc_feature
<222> LOCATION: (1)..(1)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (3)..(3)
<223> OTHER INFORMATION: /replace="Gln"
<220> FEATURE:
<221> NAME/KEY: VARIANT
<222> LOCATION: (4)..(4)
<223> OTHER INFORMATION: /replace="Asn" "Gln" "Lys" or "Arg"
<220> FEATURE:
<221> NAME/KEY: VARIANT
<222> LOCATION: (5)..(5)
<223> OTHER INFORMATION: /replace="Val" "Leu" "Ser" or "Ile"
<220> FEATURE:
<221> NAME/KEY: VARIANT
<222> LOCATION: (6)..(6)
<223> OTHER INFORMATION: /replace="Val" "Leu" or "Ile"
<220> FEATURE:
<221> NAME/KEY: misc_feature
<222> LOCATION: (3)..(6)
<223> OTHER INFORMATION: /notes="Residues given in the sequence have no
      preference with respect to those in the annotations for said
      positions"
<220> FEATURE:
<221> NAME/KEY: VARIANT
<222> LOCATION: (9)..(11)
<223> OTHER INFORMATION: /replace="Val" "Leu" or "Ile"
<220> FEATURE:
<221> NAME/KEY: VARIANT
<222> LOCATION: (9)..(11)
<223> OTHER INFORMATION: /replace="Asp"
<220> FEATURE:
<221> NAME/KEY: VARIANT
<222> LOCATION: (9)..(11)
<223> OTHER INFORMATION: /replace="Asp"
<220> FEATURE:
<221> NAME/KEY: misc_feature
<222> LOCATION: (9)..(11)
<223> OTHER INFORMATION: /notes="Residues given in the sequence have no
      preference with respect to those in the annotations for said
      positions"

<400> SEQUENCE: 76

His His Asn His Ala Ala Phe Phe Ala Glu Glu
1               5                   10
```

```
<210> SEQ ID NO 77
<211> LENGTH: 635
<212> TYPE: DNA
<213> ORGANISM: Artificial Sequence
<220> FEATURE:
<223> OTHER INFORMATION: /note="Description of artificial sequence:
      Synthetic polynucleotide"
<220> FEATURE:
<221> NAME/KEY: CDS
<222> LOCATION: (122)..(166)
<220> FEATURE:
<221> NAME/KEY: CDS
<222> LOCATION: (249)..(596)

<400> SEQUENCE: 77
aagcttatga atatgcaaat cctctgaatc tacatggtaa atataggttt gtctatacca    60
caaacagaaa aacatgagat cacagttctc tctacagtta ctgagcacac aggacctcac   120 c atg gga tgg agc tgt atc atc ctc ttc ttg gta gca aca gct aca       166
  Met Gly Trp Ser Cys Ile Ile Leu Phe Leu Val Ala Thr Ala Thr
  1               5                  10                 15 ggtaaggggc tcacagtagc aggcttgagg tctggacata tatgggtg acaatgacat     226 ccactttgcc tttctctcca ca ggt gtc cac tcc gat gtt gtg atg acc caa   278
                         Gly Val His Ser Asp Val Val Met Thr Gln
                                                20                  25 act cca ctc tcc ctg cct gtc agt ctt gga gat caa gcc tcc atc tct    326
Thr Pro Leu Ser Leu Pro Val Ser Leu Gly Asp Gln Ala Ser Ile Ser
                30                  35                  40 tgc aga tct agt cag agc ctt gta tat agt aat gga gac acc tat tta    374
Cys Arg Ser Ser Gln Ser Leu Val Tyr Ser Asn Gly Asp Thr Tyr Leu
            45                  50                  55 cat tgg tac ctg cag aag cca ggc cag tct cca aag ctc ctg atc tac    422
His Trp Tyr Leu Gln Lys Pro Gly Gln Ser Pro Lys Leu Leu Ile Tyr
        60                  65                  70 aaa gtt tcc aac cga ttt tct ggg gtc cca gac agg ttc agt ggc agt    470
Lys Val Ser Asn Arg Phe Ser Gly Val Pro Asp Arg Phe Ser Gly Ser
    75                  80                  85 gga tca ggg aca gat ttc aca ctc aag atc agc aga gtg gag gct gag    518
Gly Ser Gly Thr Asp Phe Thr Leu Lys Ile Ser Arg Val Glu Ala Glu
90                  95                 100                 105 gat ctg gga gtt tat ttc tgc tct caa agt aca cat gtt cct tgg acg    566
Asp Leu Gly Val Tyr Phe Cys Ser Gln Ser Thr His Val Pro Trp Thr
                110                 115                 120 ttc ggc gga ggc acc aag ctg gaa atc aaa cgtgagtaga atttaaactt       616
Phe Gly Gly Gly Thr Lys Leu Glu Ile Lys
            125                 130 tgcttcctca gttggatcc                                                635

<210> SEQ ID NO 78
<211> LENGTH: 15
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 78

Met Gly Trp Ser Cys Ile Ile Leu Phe Leu Val Ala Thr Ala Thr
1               5                  10                  15

<210> SEQ ID NO 79
<211> LENGTH: 116
<212> TYPE: PRT
<213> ORGANISM: Artificial Sequence
<220> FEATURE:
```

<223> OTHER INFORMATION: /note="Description of artificial sequence: Synthetic polypeptide"

<400> SEQUENCE: 79

```
Gly Val His Ser Asp Val Val Met Thr Gln Thr Pro Leu Ser Leu Pro
1               5                   10                  15
Val Ser Leu Gly Asp Gln Ala Ser Ile Ser Cys Arg Ser Ser Gln Ser
            20                  25                  30
Leu Val Tyr Ser Asn Gly Asp Thr Tyr Leu His Trp Tyr Leu Gln Lys
        35                  40                  45
Pro Gly Gln Ser Pro Lys Leu Leu Ile Tyr Lys Val Ser Asn Arg Phe
    50                  55                  60
Ser Gly Val Pro Asp Arg Phe Ser Gly Ser Gly Ser Gly Thr Asp Phe
65                  70                  75                  80
Thr Leu Lys Ile Ser Arg Val Glu Ala Glu Asp Leu Gly Val Tyr Phe
                85                  90                  95
Cys Ser Gln Ser Thr His Val Pro Trp Thr Phe Gly Gly Gly Thr Lys
            100                 105                 110
Leu Glu Ile Lys
        115
```

<210> SEQ ID NO 80
<211> LENGTH: 798
<212> TYPE: DNA
<213> ORGANISM: Artificial Sequence
<220> FEATURE:
<223> OTHER INFORMATION: /note="Description of artificial sequence: Synthetic polynucleotide"
<220> FEATURE:
<221> NAME/KEY: CDS
<222> LOCATION: (122)..(166)
<220> FEATURE:
<221> NAME/KEY: CDS
<222> LOCATION: (249)..(596)

<400> SEQUENCE: 80

```
aagcttatga atatgcaaat cctctgaatc tacatggtaa atataggttt gtctatacca      60
caaacagaaa aacatgagat cacagttctc tctacagtta ctgagcacac aggacctcac     120 c atg gga tgg agc tgt atc atc ctc ttc ttg gta gca aca gct aca         166
  Met Gly Trp Ser Cys Ile Ile Leu Phe Leu Val Ala Thr Ala Thr
  1               5                   10                  15 ggtaaggggc tcacagtagc aggcttgagg tctggacata tatatgggtg acaatgacat     226
ccactttgcc tttctctcca ca ggt gtc cac tcc gag gtg cag ctg gtc gag     278
                         Gly Val His Ser Glu Val Gln Leu Val Glu
                                             20                  25 tct ggg gga ggc tta gtg cag cct gga ggg tcc ctg aaa ctc tcc tgt     326
Ser Gly Gly Gly Leu Val Gln Pro Gly Gly Ser Leu Lys Leu Ser Cys
            30                  35                  40 gca gcc tct gga ttc act ttc agt agc tat ggc atg tct tgg gtt cgc     374
Ala Ala Ser Gly Phe Thr Phe Ser Ser Tyr Gly Met Ser Trp Val Arg
        45                  50                  55 cag act cca gac aag agg ctg gaa ttg gtc gca agc atc aat agt aat     422
Gln Thr Pro Asp Lys Arg Leu Glu Leu Val Ala Ser Ile Asn Ser Asn
    60                  65                  70 ggt ggt agc acc tat tat cca gac agt gtg aag ggc cga ttc acc atc     470
Gly Gly Ser Thr Tyr Tyr Pro Asp Ser Val Lys Gly Arg Phe Thr Ile
75                  80                  85 tcc aga gac aat gcc aag aac acc ctg tac ctg caa atg agc agt ctg     518
Ser Arg Asp Asn Ala Lys Asn Thr Leu Tyr Leu Gln Met Ser Ser Leu
90                  95                  100                 105
```

```
aag tct gag gac aca gcc atg tat tac tgt gca agt ggt gac tac tgg        566
Lys Ser Glu Asp Thr Ala Met Tyr Tyr Cys Ala Ser Gly Asp Tyr Trp
            110                 115                 120 ggc caa ggc tcc act ctc aca gtc tcc tca ggtgagtcct tacaacctct          616
Gly Gln Gly Ser Thr Leu Thr Val Ser Ser
            125                 130 ctcttctatt cagcttaaat agatttact gcatttgttg gggggaaat gtgtgtatct        676 gaatttcagg tcatgaagga ctagggacac cttgggagtc agaaagggtc attgggagcc      736
cgggctgatg cagacagaca tcctcagctc ccagacttca tggccagaga tttataggat      796
cc                                                                     798

<210> SEQ ID NO 81
<211> LENGTH: 116
<212> TYPE: PRT
<213> ORGANISM: Artificial Sequence
<220> FEATURE:
<223> OTHER INFORMATION: /note="Description of artificial sequence:
      Synthetic polypeptide"

<400> SEQUENCE: 81

Gly Val His Ser Glu Val Gln Leu Val Glu Ser Gly Gly Gly Leu Val
1               5                   10                  15

Gln Pro Gly Gly Ser Leu Lys Leu Ser Cys Ala Ala Ser Gly Phe Thr
            20                  25                  30

Phe Ser Ser Tyr Gly Met Ser Trp Val Arg Gln Thr Pro Asp Lys Arg
        35                  40                  45

Leu Glu Leu Val Ala Ser Ile Asn Ser Asn Gly Gly Ser Thr Tyr Tyr
    50                  55                  60

Pro Asp Ser Val Lys Gly Arg Phe Thr Ile Ser Arg Asp Asn Ala Lys
65                  70                  75                  80

Asn Thr Leu Tyr Leu Gln Met Ser Ser Leu Lys Ser Glu Asp Thr Ala
                85                  90                  95

Met Tyr Tyr Cys Ala Ser Gly Asp Tyr Trp Gly Gln Gly Ser Thr Leu
            100                 105                 110

Thr Val Ser Ser
        115

<210> SEQ ID NO 82
<211> LENGTH: 99
<212> TYPE: PRT
<213> ORGANISM: Mus sp.

<400> SEQUENCE: 82

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Arg
```

```
<210> SEQ ID NO 83
<211> LENGTH: 112
<212> TYPE: PRT
<213> ORGANISM: Artificial Sequence
<220> FEATURE:
<223> OTHER INFORMATION: /note="Description of artificial sequence:
      Synthetic polypeptide"

<400> SEQUENCE: 83

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gln Gly Thr Lys Val Glu Ile Lys
            100                 105                 110

<210> SEQ ID NO 84
<211> LENGTH: 112
<212> TYPE: PRT
<213> ORGANISM: Artificial Sequence
<220> FEATURE:
<223> OTHER INFORMATION: /note="Description of artificial sequence:
      Synthetic polypeptide"

<400> SEQUENCE: 84

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

<210> SEQ ID NO 85
<211> LENGTH: 112
<212> TYPE: PRT
<213> ORGANISM: Artificial Sequence
<220> FEATURE:
<223> OTHER INFORMATION: /note="Description of artificial sequence:
      Synthetic polypeptide"

<400> SEQUENCE: 85

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30
```

```
Asn Gly Asp Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Ser
                 85                  90                  95

Thr His Val Pro Trp Thr Phe Gly Gln Gly Thr Lys Val Glu Ile Lys
            100                 105                 110
```

<210> SEQ ID NO 86
<211> LENGTH: 100
<212> TYPE: PRT
<213> ORGANISM: Mus sp.

<400> SEQUENCE: 86

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro
            100
```

<210> SEQ ID NO 87
<211> LENGTH: 12
<212> TYPE: PRT
<213> ORGANISM: Homo sapiens

<400> SEQUENCE: 87

```
Trp Thr Phe Gly Gln Gly Thr Lys Val Glu Ile Lys
 1               5                  10
```

<210> SEQ ID NO 88
<211> LENGTH: 112
<212> TYPE: PRT
<213> ORGANISM: Artificial Sequence
<220> FEATURE:
<223> OTHER INFORMATION: /note="Description of artificial sequence: Synthetic polypeptide"

<400> SEQUENCE: 88

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Gly Met Ser Trp Val Arg Gln Ala Pro Gly Lys Gly Leu Glu Trp Val
            35                  40                  45

Ala Ser Ile Asn Ser Asn Gly Gly Ser Thr Tyr Tyr Pro Asp Ser Val
 50                  55                  60

Lys Gly Arg Phe Thr Ile Ser Arg Asp Asn Ala Lys Asn Ser Leu Tyr
 65                  70                  75                  80
```

```
Leu Gln Met Asn Ser Leu Arg Ala Glu Asp Thr Ala Val Tyr Tyr Cys
                85                  90                  95

Ala Arg Gly Asp Tyr Trp Gly Gln Gly Thr Thr Val Thr Val Ser Ser
            100                 105                 110

<210> SEQ ID NO 89
<211> LENGTH: 112
<212> TYPE: PRT
<213> ORGANISM: Artificial Sequence
<220> FEATURE:
<223> OTHER INFORMATION: /note="Description of artificial sequence:
      Synthetic polypeptide"

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
            35                  40                  45

Ala Ser Ile Asn Ser Asn Gly Gly Ser Thr Tyr Tyr Pro Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser
            100                 105                 110

<210> SEQ ID NO 90
<211> LENGTH: 112
<212> TYPE: PRT
<213> ORGANISM: Artificial Sequence
<220> FEATURE:
<223> OTHER INFORMATION: /note="Description of artificial sequence:
      Synthetic polypeptide"

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
            35                  40                  45

Ala Ser Ile Asn Ser Asn Gly Gly Ser Thr Tyr Tyr Pro Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Trp Gly Gln Gly Thr Thr Val Thr Val Ser Ser
            100                 105                 110

<210> SEQ ID NO 91
<211> LENGTH: 98
<212> TYPE: PRT
<213> ORGANISM: Mus sp.

<400> SEQUENCE: 91

Glu Val Gln Leu Val Glu Ser Gly Gly Gly Leu Val Gln Pro Gly Gly
```

```
                   1               5                  10                  15
               Ser Leu Arg Leu Ser Cys Ala Ala Ser Gly Phe Thr Phe Ser Ser Tyr
                             20                  25                  30

Trp Met Ser Trp Val Arg Gln Ala Pro Gly Lys Gly Leu Glu Trp Val
                             35                  40                  45

Ala Asn Ile Lys Gln Asp Gly Ser Glu Lys Tyr Tyr Val Asp Ser Val
                             50                  55                  60

Lys Gly Arg Phe Thr Ile Ser Arg Asp Asn Ala Lys Asn Ser Leu Tyr
               65                  70                  75                  80

Leu Gln Met Asn Ser Leu Arg Ala Glu Asp Thr Ala Val Tyr Tyr Cys
                             85                  90                  95

Ala Arg

<210> SEQ ID NO 92
               <211> LENGTH: 20
               <212> TYPE: PRT
               <213> ORGANISM: Homo sapiens

<400> SEQUENCE: 92

Tyr Tyr Tyr Tyr Tyr Gly Met Asp Val Trp Gly Gln Gly Thr Thr Val
               1               5                  10                  15

Thr Val Ser Ser
                             20

<210> SEQ ID NO 93
               <211> LENGTH: 635
               <212> TYPE: DNA
               <213> ORGANISM: Artificial Sequence
               <220> FEATURE:
               <223> OTHER INFORMATION: /note="Description of artificial sequence:
                     Synthetic polynucleotide"
               <220> FEATURE:
               <221> NAME/KEY: CDS
               <222> LOCATION: (122)..(166)
               <220> FEATURE:
               <221> NAME/KEY: CDS
               <222> LOCATION: (249)..(596)

<400> SEQUENCE: 93
aagcttatga aatatgcaaat cctctgaatc tacatggtaa atataggttt gtctatacca       60
caaacagaaa aacatgagat cacagttctc tctacagtta ctgagcacac aggacctcac      120 c atg gga tgg agc tgt atc atc ctc ttc ttg gta gca aca gct aca            166
                 Met Gly Trp Ser Cys Ile Ile Leu Phe Leu Val Ala Thr Ala Thr
                 1               5                  10                  15 ggtaagggc tcacagtagc aggcttgagg tctggacata tatatgggtg acaatgacat       226
ccactttgcc tttctctcca ca ggt gtc cac tcc gat att gtg atg acc caa        278
                                        Gly Val His Ser Asp Ile Val Met Thr Gln
                                                            20                  25 tct cca ctc tcc ctg cct gtc act cct ggt gag cct gcc tcc atc tct        326
               Ser Pro Leu Ser Leu Pro Val Thr Pro Gly Glu Pro Ala Ser Ile Ser
                             30                  35                  40 tgc aga tct agt cag agc ctt gta tat agt aat gga gac acc tat tta        374
               Cys Arg Ser Ser Gln Ser Leu Val Tyr Ser Asn Gly Asp Thr Tyr Leu
                             45                  50                  55 cat tgg tac ctg cag aag cca ggc cag tct cca cag ctc ctg atc tac        422
               His Trp Tyr Leu Gln Lys Pro Gly Gln Ser Pro Gln Leu Leu Ile Tyr
                             60                  65                  70 aaa gtt tcc aac cga ttt tct ggg gtc cca gac agg ttc agt ggc agt        470
               Lys Val Ser Asn Arg Phe Ser Gly Val Pro Asp Arg Phe Ser Gly Ser
                             75                  80                  85
```

```
gga tca ggg aca gat ttc aca ctc aag atc agc aga gtg gag gct gag    518
Gly Ser Gly Thr Asp Phe Thr Leu Lys Ile Ser Arg Val Glu Ala Glu
 90                  95                 100                 105 gat gtg gga gtt tat tac tgc tct caa agt aca cat gtt cct tgg acg    566
Asp Val Gly Val Tyr Tyr Cys Ser Gln Ser Thr His Val Pro Trp Thr
            110                 115                 120 ttc ggc caa ggc acc aag gtg gaa atc aaa cgtgagtaga atttaaactt      616
Phe Gly Gln Gly Thr Lys Val Glu Ile Lys
        125                 130 tgcttcctca gttggatcc                                               635

<210> SEQ ID NO 94
<211> LENGTH: 116
<212> TYPE: PRT
<213> ORGANISM: Artificial Sequence
<220> FEATURE:
<223> OTHER INFORMATION: /note="Description of artificial sequence:
      Synthetic polypeptide"

<400> SEQUENCE: 94

Gly Val His Ser Asp Ile Val Met Thr Gln Ser Pro Leu Ser Leu Pro
1               5                   10                  15

Val Thr Pro Gly Glu Pro Ala Ser Ile Ser Cys Arg Ser Ser Gln Ser
            20                  25                  30

Leu Val Tyr Ser Asn Gly Asp Thr Tyr Leu His Trp Tyr Leu Gln Lys
        35                  40                  45

Pro Gly Gln Ser Pro Gln Leu Leu Ile Tyr Lys Val Ser Asn Arg Phe
    50                  55                  60

Ser Gly Val Pro Asp Arg Phe Ser Gly Ser Gly Ser Gly Thr Asp Phe
65                  70                  75                  80

Thr Leu Lys Ile Ser Arg Val Glu Ala Glu Asp Val Gly Val Tyr Tyr
                85                  90                  95

Cys Ser Gln Ser Thr His Val Pro Trp Thr Phe Gly Gln Gly Thr Lys
            100                 105                 110

Val Glu Ile Lys
        115

<210> SEQ ID NO 95
<211> LENGTH: 5561
<212> TYPE: DNA
<213> ORGANISM: Artificial Sequence
<220> FEATURE:
<223> OTHER INFORMATION: /note="Description of artificial sequence:
      Synthetic polynucleotide"
<220> FEATURE:
<221> NAME/KEY: CDS
<222> LOCATION: (2138)..(2455)

<400> SEQUENCE: 95
ggatcctggc agagtctcac agatgcttct gagacaacat ttgctttcaa aaaatgaacc     60
acacacatcc taaagatctc agccacttcc catgtttcat tttatgttac agcaaacatc    120
acaacaatca ttcctacaga tcaccactgc atgtgatcaa taaaatagtt tttgcaacaa    180
tggtacttat gataatcatc ttttattgtt tacaaatact gctttacaat agttattcgg    240
ttgcactgtt catattagat ttccaattag ctcacttagg aacataagtc cctcgaacag    300
ctcagtcatc tttttcattc ctgtttctat ccccctacatc tctttccttt gcagacgact    360
atctcctaca ctgaaacagg aaagctagct ttttttttc agtgctattt aattatttca     420
atatcctctc atcaaatgta tttaaataac aaaagctcaa ccaaaagaa agaaatatgt    480 aattctttca gagtaaaaat cacacccatg acctggccac tgagggcttg atcaattcac    540
```

```
tttgaatttg gcattaaata ccattaaggt atattaactg attttaaaat aagatatatt    600
cgtgaccatg ttttaactt tcaaaaatgt agctgccagt gtgtgatttt atttcagttg    660
tacaaaatat ctaaacctat agcaatgtga ttaataaaaa cttaaacata ttttccagta   720
ccttaattct gtgataggaa aatttaatc tgagtatttt aatttcataa tctctaaaat    780
agtttaatga tttgtcattg tgttgctgtc gtttacccca gctgatctca aaagtgatat   840
ttaaggagat tattttggtc tgcaacaact tgataggact attttagggc cttttaaag    900 ctctattaaa actaacttac aacgattcaa aactgtttta aactatttca aaatgatttt   960
agagcctttt gaaaactctt ttaaacactt tttaaactct attaaaacta ataagataac  1020
ttgaaataat tttcatgtca aatacattaa ctgtttaatg tttaaatgcc agatgaaaaa  1080
tgtaaagcta tcaagaattc acccagatag gagtatcttc atagcatgtt tttccctgct  1140 tatttccag tgatcacatt attttgctac catggttatt ttatacaatt atctgaaaaa  1200
aattagttat gaagattaaa agagaagaaa atattaaaca taagagattc agtctttcat  1260
gttgaactgc ttggttaaca gtgaagttag tttaaaaaa aaaaaaact atttctgtta   1320 tcagctgact tctccctatc tgttgacttc tcccagcaaa agattcttat tttacatttt   1380
aactactgct ctcccaccca acgggtggaa tcccccagag ggggatttcc aagaggccac   1440
ctggcagttg ctgagggtca gaagtgaagc tagccacttc ctcttaggca ggtggccaag   1500
attacagttg acctctcctg gtatggctga aaattgctgc atatggttac aggccttgag   1560
gcctttggga gggcttagag agttgctgga acagtcagaa ggtggagggg ctgacaccac   1620
ccaggcgcag aggcagggct cagggcctgc tctgcaggga ggttttagcc cagccagccc   1680
aaagtaaccc ccgggagcct gttatcccag cacagtcctg gaagaggcac aggggaaata   1740
aaagcggacg gaggctttcc ttgactcagc cgctgcctgg tcttcttcag acctgttctg   1800
aattctaaac tctgagggg tcggatgacg tggccattct ttgcctaaag cattgagttt    1860
actgcaaggt cagaaaagca tgcaaagccc tcagaatggc tgcaaagagc tccaacaaaa   1920 caattagaa cttattaag gaatagggg aagctaggaa gaaactcaaa acatcaagat     1980
tttaaatacg cttcttggtc tccttgctat aattatctgg gataagcatg ctgttttctg   2040
tctgtcccta acatgccctg tgattatccg caaacaacac acccaagggc agaactttgt   2100
tacttaaaca ccatcctgtt tgcttctttc ctcagga act gtg gct gca cca tct    2155
                                          Thr Val Ala Ala Pro Ser
                                            1               5 gtc ttc atc ttc ccg cca tct gat gag cag ttg aaa tct gga act gcc    2203
Val Phe Ile Phe Pro Pro Ser Asp Glu Gln Leu Lys Ser Gly Thr Ala
             10                  15                  20 tct gtt gtg tgc ctg ctg aat aac ttc tat ccc aga gag gcc aaa gta    2251
Ser Val Val Cys Leu Leu Asn Asn Phe Tyr Pro Arg Glu Ala Lys Val
     25                  30                  35 cag tgg aag gtg gat aac gcc ctc caa tcg ggt aac tcc cag gag agt    2299
Gln Trp Lys Val Asp Asn Ala Leu Gln Ser Gly Asn Ser Gln Glu Ser
 40                  45                  50 gtc aca gag cag gac agc aag gac agc acc tac agc ctc agc agc acc    2347
Val Thr Glu Gln Asp Ser Lys Asp Ser Thr Tyr Ser Leu Ser Ser Thr
 55                  60                  65                  70 ctg acg ctg agc aaa gca gac tac gag aaa cac aaa gtc tac gcc tgc    2395
Leu Thr Leu Ser Lys Ala Asp Tyr Glu Lys His Lys Val Tyr Ala Cys
             75                  80                  85 gaa gtc acc cat cag ggc ctg agc tcg ccc gtc aca aag agc ttc aac    2443
Glu Val Thr His Gln Gly Leu Ser Ser Pro Val Thr Lys Ser Phe Asn
         90                  95                 100
```

```
agg gga gag tgt tagagggaga agtgccccca cctgctcctc agttccagcc    2495
Arg Gly Glu Cys
        105 tgacccccte ccatcctttg gcctctgacc cttttteccac aggggaccta cccctattgc    2555
ggtcctccag ctcatctttc acctcacccc cctcctcctc cttggcttta attatgctaa    2615
tgttggagga gaatgaataa ataaagtgaa tctttgcacc tgtggtttct ctctttcctc    2675
atttaataat tattatctgt tgttttacca actactcaat ttctcttata agggactaaa    2735
tatgtagtca tcctaaggcg cataaccatt tataaaaatc atccttcatt ctattttacc    2795
ctatcatcct ctgcaagaca gtcctccctc aaacccacaa gccttctgtc ctcacagtcc    2855
cctgggccat ggtaggagag acttgcttcc ttgttttccc ctcctcagca agccctcata    2915 gtcctttta agggtgacag gtcttacagt catatatcct ttgattcaat tccctgagaa    2975
tcaaccaaag caaattttte aaaagaagaa acctgctata agagaatca ttcattgcaa    3035 catgatataa ataacaaca caataaaagc aattaaataa acaaacaata gggaaatgtt    3095
taagttcatc atggtactta gacttaatgg aatgtcatgc cttatttaca tttttaaaca    3155
ggtactgagg gactcctgtc tgccaagggc cgtattgagt actttccaca acctaattta    3215
atccacacta tactgtgaga ttaaaaacat tcattaaaat gttgcaaagg ttctataaag    3275
ctgagagaca aatatattct ataactcagc aatcccactt ctagatgact gagtgtcccc    3335
acccaccaaa aaactatgca agaatgttca aagcagcttt atttacaaaa gccaaaaatt    3395
ggaaatagcc cgattgtcca acaatagaat gagttattaa actgtggtat gtttatacat    3455
tagaataccc aatgaggaga attaacaagc tacaactata cctactcaca cagatgaatc    3515
tcataaaaat aatgttacat aagagaaact caatgcaaaa gatatgttct gtatgttttc    3575
atccatataa agttcaaaac caggtaaaaa taaagttaga aatttggatg gaaattactc    3635
ttagctgggg gtgggcgagt tagtgcctgg gagaagacaa gaaggggctt ctggggtctt    3695
ggtaatgttc tgttcctcgt gtggggttgt gcagttatga tctgtgcact gttctgtata    3755
cacattatgc ttcaaaataa cttcacataa agaacatctt atacccagtt aatagataga    3815
agaggaataa gtaataggtc aagaccatgc agctggtaag tgggggggcc tgggatcaaa    3875
tagctacctg cctaatcctg ccctcttgag ccctgaatga gtctgccttc cagggctcaa    3935
ggtgctcaac aaaacaacag gcctgctatt ttcctggcat ctgtgccctg tttggctagc    3995
taggagcaca catacataga aattaaatga aacagacctt cagcaagggg acagaggaca    4055 gaattaaccct tgcccagaca ctggaaaccc atgtatgaac actcacatgt ttgggaaggg    4115
ggaagggcac atgtaaatga ggactcttcc tcattctatg gggcactctg gccctgcccc    4175
tctcagctac tcatccatcc aacacacctt tctaagtacc tctctctgcc tacactctga    4235
aggggttcag gagtaactaa cacagcatcc cttccctcaa atgactgacc atcccttgt    4295 cctgctttgt ttttctttcc agtcagtact gggaaagtgg ggaaggacag tcatggaaaa    4355
actacataag gaagcacctt gcccttctgc ctcttgagaa tgttgatgag tatcaaatct    4415
ttcaaacttt ggaggtttga gtaggggtga gactcagtaa tgtcccttcc aatgacatga    4475
acttgctcac tcatccctgg gggccaaatt gaacaatcaa aggcaggcat aatccagtta    4535
tgaattcaaa ccttcttctc agaagataac actctgaagg gaaacccacc cataacctaa    4595
gcaagtgaag acaggtgctg caggtggaat tgtgtccttc aaaaaggtat gctcaactcc    4655
ttgctcttgg tactcataaa tgggtcacat aaatgtgact ttatttggaa ataggtctt    4715 tgcagaggta atcaagtcaa aattaggtca tactgaaatg tttgtgagga tgcggtgaaa    4775
```

-continued

```
atggatcatt catatattgc tggtgggaat ataaaagggt atagctactc tagaaaatag    4835
ttgtcagttt cttgaaaaac taaacaaaag acacctacca tatgacccag gaattgtact    4895
ccttgggaat ttaccccag gaaataaaaa cttatgtcca cacagaaccc atacatgatt    4955
gttcacagca gctttatttg ttgtagccaa agctagaaag agccaaccca tccctcaata    5015
ggcaactagc ctaacaaatt gtaatatatc catgccatag aatgctatga ggcaataaaa    5075
aggaacgaag tgttgataca gagaactgga gtgattctga aggactttct actgagtgaa    5135
aaaagccaat ctgaaagggt cacataccat gtgattcctt ttatgtaaca ttgttgaagt    5195
gacaaaatta tagggataga aacagattc tggttgccag gggttagggt ggtggagaaa    5255
gaagagtagg cgaaactata aagggagatc tttgtgatca tgggataaat ctgtatcttg    5315
attgcagtgg tagttgcagg catctagaca tgtgataaaa tgacatagaa ctgtacacac    5375
ttattttatc aatgtcaaat tcttggtttt aatatcgtac tgtaattacg taagaagtaa    5435
ccaacaggag aaactgggtg caggacacat cagacctctg tgctttatat cctgtctttg    5495
ctactttctg tgaatctata attatttcca ataattttt ttaaactttt tttttatgct    5555
ggatcg                                                              5561
```

<210> SEQ ID NO 96
<211> LENGTH: 106
<212> TYPE: PRT
<213> ORGANISM: Artificial Sequence
<220> FEATURE:
<223> OTHER INFORMATION: /note="Description of artificial sequence:
      Synthetic polypeptide"

<400> SEQUENCE: 96

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 97
<211> LENGTH: 2027
<212> TYPE: DNA
<213> ORGANISM: Artificial Sequence
<220> FEATURE:
<223> OTHER INFORMATION: /note="Description of artificial sequence:
      Synthetic polynucleotide"
<220> FEATURE:
<221> NAME/KEY: CDS
<222> LOCATION: (230)..(523)
<220> FEATURE:
<221> NAME/KEY: CDS
<222> LOCATION: (920)..(955)
<220> FEATURE:
<221> NAME/KEY: CDS
<222> LOCATION: (1074)..(1403)
<220> FEATURE:
<221> NAME/KEY: CDS

<222> LOCATION: (1501)..(1821)

<400> SEQUENCE: 97

```
ggatcctcta gattgagctt tctggggcag gccaggcctg accttggctg ggggcaggga      60 ggggggctaag gtgacgcagg tggcgccagc caggtgcaca cccaatgccc atgagcccag     120
acactggacc ctgcatggac catcgcggat agacaagaac cgaggggcct ctgcgccctg     180
ggcccagctc tgtcccacac cgcggtcaca tggcaccacc tctcttgca gct tcc acc    238
                                                        Ala Ser Thr
                                                          1
```

| | | | | | | | | | | | | | | | | |
|---|---|---|---|---|---|---|---|---|---|---|---|---|---|---|---|---|
| aag | ggc | cca | tcc | gtc | ttc | ccc | ctg | gcg | ccc | tgc | tcc | aga | tcg | acc | tcc | 286 |
| Lys | Gly | Pro | Ser | Val | Phe | Pro | Leu | Ala | Pro | Cys | Ser | Arg | Ser | Thr | Ser | |
| | 5 | | | | 10 | | | | | 15 | | | | | | |

| | | | | | | | | | | | | | | | | |
|---|---|---|---|---|---|---|---|---|---|---|---|---|---|---|---|---|
| gag | agc | aca | gcc | gcc | ctg | ggc | tgc | ctg | gtc | aag | gac | tac | ttc | ccc | gaa | 334 |
| Glu | Ser | Thr | Ala | Ala | Leu | Gly | Cys | Leu | Val | Lys | Asp | Tyr | Phe | Pro | Glu | |
| 20 | | | | 25 | | | | | 30 | | | | | 35 | | |

| | | | | | | | | | | | | | | | | |
|---|---|---|---|---|---|---|---|---|---|---|---|---|---|---|---|---|
| ccg | gtg | acg | gtg | tcg | tgg | aac | tca | ggc | gcc | ctg | acc | agc | ggc | gtg | cac | 382 |
| Pro | Val | Thr | Val | Ser | Trp | Asn | Ser | Gly | Ala | Leu | Thr | Ser | Gly | Val | His | |
| | | | 40 | | | | | 45 | | | | | 50 | | | |

| | | | | | | | | | | | | | | | | |
|---|---|---|---|---|---|---|---|---|---|---|---|---|---|---|---|---|
| acc | ttc | ccg | gct | gtc | cta | cag | tcc | tca | gga | ctc | tac | tcc | ctc | agc | agc | 430 |
| Thr | Phe | Pro | Ala | Val | Leu | Gln | Ser | Ser | Gly | Leu | Tyr | Ser | Leu | Ser | Ser | |
| | | | 55 | | | | | 60 | | | | | 65 | | | |

| | | | | | | | | | | | | | | | | |
|---|---|---|---|---|---|---|---|---|---|---|---|---|---|---|---|---|
| gtg | gtg | acc | gtg | ccc | tcc | agc | agc | ttg | ggc | acg | aag | acc | tac | acc | tgc | 478 |
| Val | Val | Thr | Val | Pro | Ser | Ser | Ser | Leu | Gly | Thr | Lys | Thr | Tyr | Thr | Cys | |
| | | 70 | | | | | 75 | | | | | 80 | | | | |

| | | | | | | | | | | | | | | |
|---|---|---|---|---|---|---|---|---|---|---|---|---|---|---|
| aac | gta | gat | cac | aag | ccc | agc | aac | acc | aag | gtg | gac | aag | aga | gtt | 523 |
| Asn | Val | Asp | His | Lys | Pro | Ser | Asn | Thr | Lys | Val | Asp | Lys | Arg | Val | |
| | 85 | | | | 90 | | | | | 95 | | | | | |

```
ggtgagaggc cagcacaggg agggaggggtg tctgctggaa gccaggctca gccctcctgc     583
ctggacgcac cccggctgtg cagccccagc ccagggcagc aaggcatgcc ccatctgtct     643 cctcaccccgg aggcctctga ccaccccact catgctcagg gagagggtct tctggatttt    703
tccaccaggc tccgggcagc acaggctgg atgcccctac ccaggccct gcgcatacag      763 gggcaggtgc tgcgctcaga cctgccaaga gccatatccg ggaggaccct gcccctgacc    823
taagcccacc ccaaaggcca aactctccac tcccctcagct cagacacctt ctctcctccc    883
agatcgatct gagtaactcc caatcttctc tctgca gag tcc aaa tat ggt ccc      937
                                     Glu Ser Lys Tyr Gly Pro
                                                      100
```

| | | | | | | |
|---|---|---|---|---|---|---|
| ccg | tgt | ccc | cca | tgc | cca | ggtaagccaa cccaggcctc gccctccagc | 985 |
| Pro | Cys | Pro | Pro | Cys | Pro | |
| 105 | | | | 110 | | |

```
tcaaggcggg acaggtgccc tagagtagcc tgcatccagg acaggcccc agccgggtgc     1045 tgacgcatcc acctccatct cttcctca gca cct gag ttc ctg ggg gga cca       1097
                                Ala Pro Glu Phe Leu Gly Gly Pro
                                                     115
```

| | | | | | | | | | | | | | |
|---|---|---|---|---|---|---|---|---|---|---|---|---|---|
| tca | gtc | ttc | ctg | ttc | ccc | cca | aaa | ccc | aag | gac | act | ctc | atg | atc | tcc | 1145 |
| Ser | Val | Phe | Leu | Phe | Pro | Pro | Lys | Pro | Lys | Asp | Thr | Leu | Met | Ile | Ser | |
| | 120 | | | | | 125 | | | | | 130 | | | | | |

| | | | | | | | | | | | | | | | | |
|---|---|---|---|---|---|---|---|---|---|---|---|---|---|---|---|---|
| cgg | acc | cct | gag | gtc | acg | tgc | gtg | gtg | gtg | gac | gtg | agc | cag | gaa | gac | 1193 |
| Arg | Thr | Pro | Glu | Val | Thr | Cys | Val | Val | Val | Asp | Val | Ser | Gln | Glu | Asp | |
| 135 | | | | 140 | | | | | 145 | | | | | 150 | | |

| | | | | | | | | | | | | | | | | |
|---|---|---|---|---|---|---|---|---|---|---|---|---|---|---|---|---|
| ccc | gag | gtc | cag | ttc | aac | tgg | tac | gtg | gat | ggc | gtg | gag | gtg | cat | aat | 1241 |
| Pro | Glu | Val | Gln | Phe | Asn | Trp | Tyr | Val | Asp | Gly | Val | Glu | Val | His | Asn | |
| | | | | 155 | | | | | 160 | | | | | 165 | | |

| | | | | | | | | | | | | | | | | |
|---|---|---|---|---|---|---|---|---|---|---|---|---|---|---|---|---|
| gcc | aag | aca | aag | ccg | cgg | gag | gag | cag | ttc | aac | agc | acg | tac | cgt | gtg | 1289 |
| Ala | Lys | Thr | Lys | Pro | Arg | Glu | Glu | Gln | Phe | Asn | Ser | Thr | Tyr | Arg | Val | |
| | 170 | | | | | 175 | | | | | 180 | | | | | |

```
gtc agc gtc ctc acc gtc ctg cac cag gac tgg ctg aac ggc aag gag         1337
Val Ser Val Leu Thr Val Leu His Gln Asp Trp Leu Asn Gly Lys Glu
        185                 190                 195 tac aag tgc aag gtc tcc aac aaa ggc ctc ccg tcc tcc atc gag aaa         1385
Tyr Lys Cys Lys Val Ser Asn Lys Gly Leu Pro Ser Ser Ile Glu Lys
    200                 205                 210 acc atc tcc aaa gcc aaa ggtgggaccc acggggtgcg agggccacat                1433
Thr Ile Ser Lys Ala Lys
215                 220 ggacagaggt cagctcggcc caccctctgc cctgggagtg accgctgtgc caacctctgt      1493 ccctaca ggg cag ccc cga gag cca cag gtg tac acc ctg ccc cca tcc        1542
        Gly Gln Pro Arg Glu Pro Gln Val Tyr Thr Leu Pro Pro Ser
                        225                 230 cag gag gag atg acc aag aac cag gtc agc ctg acc tgc ctg gtc aaa        1590
Gln Glu Glu Met Thr Lys Asn Gln Val Ser Leu Thr Cys Leu Val Lys
235                 240                 245                 250 ggc ttc tac ccc agc gac atc gcc gtg gag tgg gag agc aat ggg cag        1638
Gly Phe Tyr Pro Ser Asp Ile Ala Val Glu Trp Glu Ser Asn Gly Gln
                255                 260                 265 ccg gag aac aac tac aag acc acg cct ccc gtc ctc gat tcc gac ggc        1686
Pro Glu Asn Asn Tyr Lys Thr Thr Pro Pro Val Leu Asp Ser Asp Gly
        270                 275                 280 tcc ttc ttc ctc tac agc agg cta acc gtg gac aag agc agg tgg cag        1734
Ser Phe Phe Leu Tyr Ser Arg Leu Thr Val Asp Lys Ser Arg Trp Gln
    285                 290                 295 gag ggg aat gtc ttc tca tgc tcc gtg atg cat gag gct ctg cac aac        1782
Glu Gly Asn Val Phe Ser Cys Ser Val Met His Glu Ala Leu His Asn
300                 305                 310 cac tac aca cag aag agc ctc tcc ctg tct ctg ggt aaa tgagtgccag         1831
His Tyr Thr Gln Lys Ser Leu Ser Leu Ser Leu Gly Lys
315                 320                 325 ggccggcaag cccccgctcc ccgggctctc ggggtcgcgc gaggatgctt ggcacgtacc      1891
ccgtctacat acttcccagg cacccagcat ggaaataaag cacccaccac tgccctgggc      1951
ccctgtgaga ctgtgatggt tctttccacg ggtcaggccg agtctgaggc ctgagtgaca      2011
tgagggaggc agatcc                                                       2027

<210> SEQ ID NO 98
<211> LENGTH: 98
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 98

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val
```

```
<210> SEQ ID NO 99
<211> LENGTH: 12
<212> TYPE: PRT
<213> ORGANISM: Artificial Sequence
<220> FEATURE:
<223> OTHER INFORMATION: /note="Description of artificial sequence:
      Synthetic peptide"

<400> SEQUENCE: 99

Glu Ser Lys Tyr Gly Pro Pro Cys Pro Pro Cys Pro
1               5                   10

<210> SEQ ID NO 100
<211> LENGTH: 110
<212> TYPE: PRT
<213> ORGANISM: Artificial Sequence
<220> FEATURE:
<223> OTHER INFORMATION: /note="Description of artificial sequence:
      Synthetic polypeptide"

<400> SEQUENCE: 100

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 101
<211> LENGTH: 107
<212> TYPE: PRT
<213> ORGANISM: Artificial Sequence
<220> FEATURE:
<223> OTHER INFORMATION: /note="Description of artificial sequence:
      Synthetic polypeptide"

<400> SEQUENCE: 101

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105
```

METHODS OF TREATING AND MONITORING DISEASE WITH ANTIBODIES

The present application is a National Stage application of PCT/US2007/021134 filed Oct. 2, 2007, which published as WO 2008/060364 on May 22, 2008 and claims priority benefit from International Application No: PCT/EP2006/011862, filed Dec. 8, 2006; International Application No: PCT/US2007/073504, filed Jul. 13, 2007; European Patent Application No. 060 207 65.1, filed Oct. 2, 2006; European Patent Application No. 060 207 66.9, filed Oct. 2, 2006; U.S. Provisional Application No. 60/943,289, filed Jun. 11, 2007; and U.S. Provisional Application No. 60/943,499, filed Jun. 12, 2007, all of which are incorporated herein by reference in their entireties.

The present invention is related to methods and compositions for diagnosis and treatment of amyloidosis, a group of disorders and abnormalities associated with amyloid protein such as Alzheimer's disease.

Amyloidosis is not a single disease entity but rather a diverse group of progressive disease processes characterized by extracellular tissue deposits of a waxy, starch-like protein called amyloid, which accumulates in one or more organs or body systems. As the amyloid deposits accumulate, they begin to interfere with the normal function of the organ or body system. There are at least 15 different types of amyloidosis. The major forms are primary amyloidosis without known antecedent, secondary amyloidosis following some other condition, and hereditary amyloidosis.

Secondary amyloidosis occurs during chronic infection or inflammatory disease, such as tuberculosis, a bacterial infection called familial Mediterranean fever, bone infections (osteomyelitis), rheumatoid arthritis, inflammation of the small intestine (granulomatous ileitis), Hodgkin's disease, and leprosy.

Amyloid deposits include amyloid P (pentagonal) component (AP), a glycoprotein related to normal serum amyloid P (SAP), and sulphated glycosaminoglycans (GAG), complex carbohydrates of connective tissue. Amyloid protein fibrils, which account for about 90% of the amyloid material, comprise one of several different types of proteins. These proteins are capable of folding into so-called "beta-pleated" sheet fibrils, a unique protein configuration which exhibits binding sites for Congo red resulting in the unique staining properties of the amyloid protein.

Many diseases of aging are based on or associated with amyloid-like proteins and are characterized, in part, by the buildup of extracellular deposits of amyloid or amyloid-like material that contribute to the pathogenesis, as well as the progression of the disease. These diseases include, but are not limited to, neurological disorders such as Alzheimer's Disease (AD), including diseases or conditions characterized by a loss of cognitive memory capacity such as, for example, mild cognitive impairment (MCI), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex. Other diseases which are based on or associated with amyloid-like proteins are progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes; senile cardiac amyloidosis; endocrine tumors, and others, including macular degeneration.

Although pathogenesis of these diseases may be diverse, their characteristic deposits often contain many shared molecular constituents. To a significant degree, this may be attributable to the local activation of pro-inflammatory pathways thereby leading to the concurrent deposition of activated complement components, acute phase reactants, immune modulators, and other inflammatory mediators (McGeer et al., 1994).

Alzheimer's Disease (AD) is a neurological disorder primarily thought to be caused by amyloid plaques, an accumulation of abnormal deposit of proteins in the brain. The most frequent type of amyloid found in the brain of affected individuals is composed primarily of Aβ fibrils. Scientific evidence demonstrates that an increase in the production and accumulation of beta-amyloid protein in plaques leads to nerve cell death, which contributes to the development and progression of AD. Loss of nerve cells in strategic brain areas, in turn, causes reduction in the neurotransmitters and impairment of memory. The proteins principally responsible for the plaque build up include amyloid precursor protein (APP) and two presenilins (presenilin I and presenilin II). Sequential cleavage of the amyloid precursor protein (APP), which is constitutively expressed and catabolized in most cells, by the enzymes β and γ secretase leads to the release of a 39 to 43 amino acid Aβ peptide. The degradation of APPs likely increases their propensity to aggregate in plaques. It is especially the Aβ(1-42) fragment that has a high propensity of building aggregates due to two very hydrophobic amino acid residues at its C-terminus. The Aβ(1-42) fragment is therefore believed to be mainly involved and responsible for the initiation of neuritic plaque formation in AD and to have, therefore, a high pathological potential. There is therefore a need for agents to prevent the formation of amyloid plaques and to diffuse existing plaques in AD.

The symptoms of AD manifest slowly and the first symptom may only be mild forgetfulness. In this stage, individuals may forget recent events, activities, the names of familiar people or things and may not be able to solve simple math problems. As the disease progresses, symptoms are more easily noticed and become serious enough to cause people with AD or their family members to seek medical help. Mid-stage symptoms of AD include forgetting how to do simple tasks such as grooming, and problems develop with speaking, understanding, reading, or writing. Later stage AD patients may become anxious or aggressive, may wander away from home and ultimately need total care.

Presently, the only definite way to diagnose AD is to identify plaques and tangles in brain tissue in an autopsy after death of the individual. Therefore, doctors can only make a diagnosis of "possible" or "probable" AD while the person is still alive. Using current methods, physicians can diagnose AD correctly up to 90 percent of the time using several tools to diagnose "probable" AD. Physicians ask questions about the person's general health, past medical problems, and the history of any difficulties the person has carrying out daily activities. Behavioral tests of memory, problem solving, attention, counting, and language provide information on cognitive degeneration and medical tests such as tests of blood, urine, or spinal fluid, and brain scans can provide some further information.

The management of AD consists of medication-based and non-medication based treatments. Treatments aimed at changing the underlying course of the disease (delaying or reversing the progression) have so far been largely unsuccessful. Medicines that restore the deficit (defect), or malfunctioning, in the chemical messengers of the nerve cells (neurotransmitters), in particular the cholinesterase inhibitors (ChEIs) such as tacrine and rivastigmine, have been shown to improve symptoms. ChEIs impede the enzymatic degradation of neurotransmitters thereby increasing the amount of chemical messengers available to transmit the nerve signals in the brain.

For some people in the early and middle stages of the disease, the drugs tacrine (COGNEX®, Morris Plains, N.J.), donepezil (ARICEPT®, Tokyo, JP), rivastigmine (EXELON®, East Hanover, N.J.), or galantamine (REMINYL®, New Brunswick, N.J.) may help prevent some symptoms from becoming worse for a limited time. Another drug, memantine (NAMENDA®, New York, N.Y.), has been approved for treatment of moderate to severe AD. Medications are also available to address the psychiatric manifestations of AD. Also, some medicines may help control behavioral symptoms of AD such as sleeplessness, agitation, wandering, anxiety, and depression. Treating these symptoms often makes patients more comfortable and makes their care easier for caregivers. Unfortunately, despite significant treatment advances showing that this class of agents is consistently better than a placebo, the disease continues to progress, and the average effect on mental functioning has only been modest. Many of the drugs used in AD medication such as, for example, ChEIs also have side effects that include gastrointestinal dysfunction, liver toxicity and weight loss.

Lewy body dementia (LBD) is a neurodegenerative disorder that can occur in persons older than 65 years of age, which typically causes symptoms of cognitive (thinking) impairment and abnormal behavioral changes. Symptoms can include cognitive impairment, neurological signs, sleep disorder, and autonomic failure. Cognitive impairment is the presenting feature of LBD in most cases. Patients have recurrent episodes of confusion that progressively worsen. The fluctuation in cognitive ability is often associated with shifting degrees of attention and alertness. Cognitive impairment and fluctuations of thinking may vary over minutes, hours, or days.

Lewy bodies are formed from phosphorylated and non-phosphorylated neurofilament proteins; they contain the synaptic protein alpha-synuclein as well as ubiquitin, which is involved in the elimination of damaged or abnormal proteins. In addition to Lewy Bodies, Lewy neurites, which are inclusion bodies in the cell processes of the nerve cells, may also be present. Amyloid plaques may form in the brains of patients afflicted with DLB, however they tend to be fewer in number than seen in patients with Alzheimer's disease. Neurofibrillary tangles, the other micropathological hallmark of AD, are not a main characteristic of DLB but are frequently present in addition to amyloid plaques.

Amyotrophic lateral sclerosis (ALS) is characterized by degeneration of upper and lower motor neurons. In some ALS patients, dementia or aphasia may be present (ALS-D). The dementia is most commonly a frontotemporal dementia (FTD), and many of these cases have ubiquitin-positive, tau-negative inclusions in neurons of the dentate gyrus and superficial layers of the frontal and temporal lobes.

Inclusion-body myositis (IBM) is a crippling disease usually found in people over age 50, in which muscle fibers develop inflammation and begin to atrophy—but in which the brain is spared and patients retain their full intellect. Two enzymes involved in the production of amyloid-β protein were found to be increased inside the muscle cells of patients with this most common, progressive muscle disease of older people, in which amyloid-β is also increased.

Another disease that is based on or associated with the accumulation and deposit of amyloid-like protein is macular degeneration.

Macular degeneration is a common eye disease that causes deterioration of the macula, which is the central area of the retina (the paper-thin tissue at the back of the eye where light-sensitive cells send visual signals to the brain). Sharp, clear, 'straight ahead' vision is processed by the macula. Damage to the macula results in the development of blind spots and blurred or distorted vision. Age-related macular degeneration (AMD) is a major cause of visual impairment in the United States and for people over age 65 it is the leading cause of legal blindness among Caucasians. Approximately 1.8 million Americans age 40 and older have advanced AMD, and another 7.3 million people with intermediate AMD are at substantial risk for vision loss. The government estimates that by 2020 there will be 2.9 million people with advanced AMD. Victims of AMD are often surprised and frustrated to find out how little is known about the causes and treatment of this blinding condition.

There are two forms of macular degeneration: dry macular degeneration and wet macular degeneration. The dry form, in which the cells of the macula slowly begin to break down, is diagnosed in 85 percent of macular degeneration cases. Both eyes are usually affected by dry AMD, although one eye can lose vision while the other eye remains unaffected. Drusen, which are yellow deposits under the retina, are common early signs of dry AMD. The risk of developing advanced dry AMD or wet AMD increases as the number or size of the drusen increases. It is possible for dry AMD to advance and cause loss of vision without turning into the wet form of the disease; however, it is also possible for early-stage dry AMD to suddenly change into the wet form.

The wet form, although it only accounts for 15 percent of the cases, results in 90 percent of the blindness, and is considered advanced AMD (there is no early or intermediate stage of wet AMD). Wet AMD is always preceded by the dry form of the disease. As the dry form worsens, some people begin to have abnormal blood vessels growing behind the macula. These vessels are very fragile and will leak fluid and blood (hence 'wet' macular degeneration), causing rapid damage to the macula.

The dry form of AMD will initially often cause slightly blurred vision. The center of vision in particular may then become blurred and this region grows larger as the disease progresses. No symptoms may be noticed if only one eye is affected. In wet AMD, straight lines may appear wavy and central vision loss can occur rapidly.

Diagnosis of macular degeneration typically involves a dilated eye exam, visual acuity test, and a viewing of the back of the eye using a procedure called fundoscopy to help diagnose AMD, and—if wet AMD is suspected—fluorescein angiography may also be performed. If dry AMD reaches the advanced stages, there is no current treatment to prevent vision loss. However, a specific high dose formula of antioxidants and zinc may delay or prevent intermediate AMD from progressing to the advanced stage. Macugen® (pegaptanib sodium injection), laser photocoagulation and photodynamic therapy can control the abnormal blood vessel growth and bleeding in the macula, which is helpful for some people who have wet AMD; however, vision that is already lost will not be restored by these techniques. If vision is already lost, low vision aids exist that can help improve the quality of life.

One of the earliest signs of age-related macular degeneration (AMD) is the accumulation of extracellular deposits known as drusen between the basal lamina of the retinal pigmented epithelium (RPE) and Bruch's membrane (BM). Recent studies conducted by Anderson et al. have confirmed that drusen contains amyloid beta. (Experimental Eye Research 78 (2004) 243-256).

Ongoing research continues with studies exploring environmental, genetic, and dietary factors that may contribute to AMD. New treatment strategies are also being explored, including retinal cell transplants, drugs that will prevent or slow down the progress of the disease, radiation therapy, gene therapies, a computer chip implanted in the retina that may help stimulate vision and agents that will prevent the growth of new blood vessels under the macula.

An important factor to consider when developing new drugs is the ease of use for the target patients. Oral drug delivery, —specifically tablets, capsules and softgels—, account for 70% of all dosage forms consumed because of patient convenience. Drug developers agree that patients prefer oral delivery rather than subjecting themselves to injections or other, more invasive forms of medicinal administration. Formulations resulting in low dosing intervals (i.e. once a day or sustained release) are also preferable. The ease of administering antibiotics in oral dosage forms results in an increase of patient compliance during treatment.

What is needed are effective methods and compositions for preventing or addressing the complications associated with amyloidosis, a group of diseases and disorders associated with amyloid plaque formation including secondary amyloidosis and age-related amyloidosis including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration. In particular what is needed are agents capable of counteracting the physiological manifestations of the disease such as the formation of plaques associated with aggregation of fibers of the amyloid or amyloid-like peptide.

Anti-amyloid antibodies elicited by the inoculation of $A\beta_{1-42}$ mixed with Freund complete or incomplete adjuvant were reported to reduce the amyloid burden in transgenic mice for human Alzheimer disease (Schenk et al., 1999). Intraperitoneal inoculation of tetrapalmitoylated $A\beta_{1-16}$ reconstituted in liposomes to NORBA transgenic mice elicited significant titers of anti-amyloid antibodies, which were reported to solubilize amyloid fibers and plaques in vitro and in vivo. (Nicolau et al., 2002).

A possible mechanism by which the dissolution of amyloid plaques and fibres occurred was first suggested by Bard et al., (2000), who concluded that the antibodies opsonized the plaques, which were subsequently destroyed by the macrophages of the microglia. De Mattos et al., (2001) indicated that a mAb directed against the central domain of β-amyloid was able to bind and completely sequester plasma amyloid. They argued that the presence of these mAbs in circulation shifted the equilibrium of Aβ between brain and plasma, favoring the peripheral clearing and catabolism instead of deposition within the brain.

Prolonged human therapy with rodent antibodies may result in an antiglobulin response which is detectable at about 8-12 days after administration and reaches a peak at about 20-30 days. If such an antiglobulin response is encountered, the treatment must be discontinued after not more than about 10 days and re-treatment at a latter date is usually precluded because it will lead to rapid onset of a secondary antiglobulin response. Although rodent antibodies share a considerable degree of sequence conservation with that of human antibodies, there are many sequence differences between rodents and human antibodies sufficient for the rodent antibodies to be immunogenic in humans.

This problem may be overcome by generating antibodies directly in humans or by the creation of "humanized' (a.k.a. "reshaped' antibodies). Humanized antibodies have a variable region amino acid sequence that contains the rodent-derived CDRs interspersed into human or human-like framework sequences. Since the specificity of the humanized antibody is provided by the rodent-derived CDRs, their residues are to be used essentially unchanged with only minor modifications being allowable, which do not significantly interfere with the affinity and specificity of the antibody for its target antigen. Framework residues may be derived from any primate or, particularly, from any human variable region or may be a combination thereof and the resultant designed variable region would be considered reshaped.

To maximise the likelihood that affinity will be retained in the reshaped antibody it is important to make a proper selection of the framework region. It is known that the framework sequences serve to hold the CDRs in their correct spatial orientation for interaction with antigen, and that framework residues can sometimes even participate in antigen binding. In order to maintain the affinity of the antibody for its antigen it is advantageous to select human framework sequences that are most similar to the sequences of the rodent frameworks. It then may still be necessary to replace one or more amino acids in the human framework sequence with the corresponding residue in the rodent framework to avoid losses with the affinity. This replacement may be aided by computer modelling.

The present invention provides novel methods and compositions comprising highly specific and highly effective antibodies, particularly chimeric antibodies including fragments thereof, more particularly partially or fully humanized antibodies including fragments thereof, having the ability to specifically recognize and bind to specific epitopes from a range of β-amyloid antigens, which my be presented to the antibody in a monomeric, dimeric, trimeric, etc, a polymeric form, in form of an aggregate, fibers, filaments or in the condensed form of a plaque. The antibodies enabled by the teaching of the present invention are particularly useful for the treatment of amyloidosis, a group of diseases and disorders associated with amyloid plaque formation including secondary amyloidosis and age-related amyloidosis including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, hereditary cerebral hemorrhage with amyloidosis Dutch type, Parkinson's disease, HIV-related dementia, ALS (amyotropic lateral sclerosis), Adult Onset Diabetes; senile cardiac amyloidosis; endocrine tumors, and others, including macular degeneration, to name just a few.

SUMMARY OF THE INVENTION

In one embodiment, the invention relates to a chimeric antibody or a fragment thereof, or a humanized antibody or a fragment thereof, which recognizes and binds to at least one distinct binding site, particularly to a least two distinct binding sites, and more particularly to at least three distinct binding sites on the β-amyloid protein wherein said one, said at least two and said at least three binding sites each comprise at least one or two consecutive amino acid residues predominantly involved in the binding of the antibody.

In particular, the chimeric antibody or a fragment thereof, or the humanized antibody or a fragment thereof according to the invention binds to at least two, particularly to at least three distinct binding sites on the β-amyloid protein wherein at least two of the three distinct binding sites comprise at least two consecutive amino acid residues predominantly involved in the binding of the antibody and at least one of the three distinct binding sites comprise at least one amino acid residue.

The at least two distinct binding sites comprising at least two consecutive amino acid residues predominantly involved in the binding of the antibody are located in close proximity to each other on the antigen, separated and/or flanked by at least one amino acid residue not involved in antibody binding or to a significantly smaller extent as compared to said at least two consecutive amino acid residues, thus forming a conformational discontinuous epitope.

The at least three distinct binding sites comprising at least two consecutive amino acid residues and at least one amino acid residue, respectively, which are predominantly involved in the binding of the antibody are located in close proximity to each other on the epitope, separated and/or flanked by at least one amino acid residue not involved in antibody binding or to a significantly smaller extent as compared to the amino acid residues, which are predominantly involved in the binding of the antibody, thus forming a conformational discontinuous epitope.

In particular, a chimeric antibody or a fragment thereof, or a humanized antibody or a fragment thereof is provided, which recognizes and binds to at least one distinct binding site, particularly to a least two distinct binding sites, more particularly to at least three distinct binding sites on the β-amyloid protein wherein said at least one or said at least two distinct binding sites each comprise at least two consecutive amino acid residues predominantly involved in the binding of the antibody, wherein the at least two consecutive amino acid residues representing a first binding site are -Phe-Phe-embedded within the following core sequence (SEQ ID NO: 9):

$Xaa_3$-Phe-Phe-$Xaa_4$-$Xaa_5$-$Xaa_6$, wherein
$Xaa_3$ is an amino acid residue selected from the group consisting of Ala, Val, Leu, norleucine, Met, Phe, and Ile;
$Xaa_4$ is an amino acid residue selected from the group consisting of Ala, Val, Leu, Ser and Ile;
$Xaa_5$ is an amino acid residue selected from the group consisting of Glu and Asp,
$Xaa_6$ is an amino acid residue selected from the group consisting of Glu and Asp, and wherein said amino acid residues $Xaa_3$ $Xaa_4$, $Xaa_5$ and $Xaa_6$ are not involved in antibody binding or to a significantly smaller extent as compared to the -Phe-Phe-binding site.

In another embodiment of the invention, a chimeric antibody or a fragment thereof, or a humanized antibody or a fragment thereof is provided, wherein
$Xaa_3$ is Val or Leu, but particularly Val;
$Xaa_4$ is Ala or Val, but particularly Ala;
$Xaa_5$ is Glu or Asp, but particularly Glu;
$Xaa_6$ is Glu or Asp, but particularly Asp.

In particular, a chimeric antibody or a fragment thereof, or a humanized antibody or a fragment thereof is provided, which recognizes and binds to at least one distinct binding site, particularly to a least two distinct binding sites, more particularly to at least three distinct binding sites on the β-amyloid protein wherein said distinct binding sites comprise at least one and at least two consecutive amino acid residues, respectively, predominantly involved in the binding of the antibody, wherein the at least two consecutive amino acid residues representing a first binding site are -Phe-Phe- and the at least one amino acid residue is -His-embedded within the following core sequence:

-$Xaa_1$-His-$Xaa_3$-$Xaa_4$-$Xaa_5$-$Xaa_6$-Phe-Phe-$Xaa_7$-$Xaa_8$-$Xaa_9$-, wherein
$Xaa_1$ is an amino acid residue selected from the group consisting of His, Asn, Gln, Lys and Arg
$Xaa_3$ is an amino acid residue selected from the group consisting of Asn and Gln
$Xaa_4$ is an amino acid residue selected from the group consisting of His, Asn, Gln, Lys and Arg
$Xaa_5$ is an amino acid residue selected from the group consisting of Ala, Val, Leu, Ser and Ile;
$Xaa_6$ is an amino acid residue selected from the group consisting of Ala, Val, Leu, norleucine, Met, Phe, and Ile
$Xaa_7$ is an amino acid residue selected from the group consisting of Ala, Val, Leu and Ile
$Xaa_8$ is an amino acid residue selected from the group consisting of Glu and Asp,
$Xaa_9$ is an amino acid residue selected from the group consisting of Glu and Asp, and wherein said amino acid residues $Xaa_1$, $Xaa_3$, $Xaa_8$, $Xaa_7$, $Xaa_8$ and $Xaa_9$, are not involved in antibody binding or to a smaller to significantly smaller extent as compared to the -His- and the -Phe-Phe-binding site, respectively.

In another embodiment of the invention, a chimeric antibody or a fragment thereof, or a humanized antibody or a fragment thereof is provided, wherein
$Xaa_3$ is Gln or Asn, but particularly Gln;
$Xaa_4$ is Lys
$Xaa_5$ is Leu
$Xaa_6$ is Val or Leu, but particularly Val;
$Xaa_7$ is Ala or Val, but particularly Ala;
$Xaa_8$ is Glu or Asp, but particularly Glu; and
$Xaa_9$ is Asp or Glu, but particularly Asp.

In another embodiment of the invention, a chimeric antibody or a fragment thereof, or a humanized antibody or a fragment thereof is provided, which recognizes and binds to at least one distinct binding site, particularly to a least two distinct binding sites, more particularly to at least three distinct binding sites on the β-amyloid protein, wherein said at least one or said at least two distinct binding sites each comprise at least two consecutive amino acid residues predominantly involved in the binding of the antibody, wherein the at least two consecutive amino acid residues representing a second binding site are -Lys-Leu-embedded within the following core sequence (SEQ ID NO: 10):

$Xaa_1$-$Xaa_2$-Lys-Leu-$Xaa_3$ wherein
$Xaa_1$ is an amino acid residue selected from the group consisting of His, Asn, Gln Lys, and Arg;
$Xaa_2$ is an amino acid residue selected from the group consisting of Asn and Gln;
$Xaa_3$ is an amino acid residue selected from the group consisting of Ala, Val, Leu, norleucine, Met, Phe, and Ile; and wherein said amino acid residues $Xaa_2$, $Xaa_3$, are not involved in antibody binding or to a smaller to significantly smaller extent as compared to the -Lys-Leu-binding site.

In another embodiment of the invention, a chimeric antibody or a fragment thereof, or a humanized antibody or a fragment thereof is provided, which recognizes and binds to at least one distinct binding site, particularly to a least two distinct binding sites, more particularly to at least three distinct binding sites on the β-amyloid protein wherein said distinct binding sites comprise at least one and at least two consecutive amino acid residues, respectively, predominantly involved in the binding of the antibody, wherein the at least one and the at least two consecutive amino acids, which are separated by at least one amino acid residue not involved in antibody binding or to a significantly smaller extent as compared to the amino acid residues predominantly involved in the binding of the antibody, are -His- and -Lys-Leu-, respectively, embedded within the following core sequence:

His-$Xaa_2$-Lys-Leu-$Xaa_3$-$Xaa_4$-$Xaa_5$-$Xaa_6$- -$Xaa_7$-$Xaa_8$- wherein
$Xaa_2$ is an amino acid residue selected from the group consisting of Asn and Gln;
$Xaa_3$ is an amino acid residue selected from the group consisting of Ala, Val, Leu, norleucine, Met, Phe, and Ile;
$Xaa_4$ is an amino acid residue selected from the group consisting of Ala, Val, Leu, norleucine, Met, Phe, and Ile
$Xaa_5$ is an amino acid residue selected from the group consisting of Ala, Val, Leu, norleucine, Met, Phe, and Ile
$Xaa_6$ is an amino acid residue selected from the group consisting of Ala, Val, Leu, Ser and Ile;
$Xaa_7$ is an amino acid residue selected from the group consisting of Glu and Asp,
$Xaa_8$ is an amino acid residue selected from the group consisting of Glu and Asp
and wherein said amino acid residues $Xaa_2$, $Xaa_3$, $Xaa_6$, $Xaa_7$, $Xaa_8$, are not involved in antibody binding or to a smaller to significantly smaller extent as compared to the -His- and the -Lys-Leu-binding site, respectively.

In another embodiment of the invention, a chimeric antibody or a fragment thereof, or a humanized antibody or a fragment thereof is provided, wherein
$Xaa_2$ is Gln or Asn, but particularly Gln;
$Xaa_3$ is Val or Leu, but particularly Val;
$Xaa_4$ is Phe
$Xaa_5$ is Phe
$Xaa_6$ is Ala or Val, but particularly Ala;
$Xaa_7$ is Glu or Asp, but particularly Glu; and
$Xaa_8$ is Asp or Glu, but particularly Asp.

In another embodiment of the invention, a chimeric antibody or a fragment thereof, or a humanized antibody or a fragment thereof is provided, which recognizes and binds to at least two distinct binding sites on the β-amyloid protein wherein said at least two distinct binding sites each comprise at least two consecutive amino acid residues predominantly involved in the binding of the antibody, wherein the at least two consecutive amino acids are separated by at least one amino acid residue not involved in antibody binding or to a significantly smaller extent than said consecutive amino acid residues, which are -Phe-Phe- and -Lys-Leu-, respectively, representing a first and second binding site embedded within the following core sequence:

$Xaa_1$-$Xaa_2$-Lys-Leu-$Xaa_3$-Phe-Phe-$Xaa_4$-$Xaa_5$-$Xaa_6$, wherein
$Xaa_1$ is an amino acid residue selected from the group consisting of His, Asn, Gln Lys, and Arg;
$Xaa_2$ is an amino acid residue selected from the group consisting of Asn and Gln;
$Xaa_3$ is an amino acid residue selected from the group consisting of Ala, Val, Leu, norleucine, Met, Phe, and Ile;
$Xaa_4$ is an amino acid residue selected from the group consisting of Ala, Val, Leu, Ser and Ile;
$Xaa_5$ is an amino acid residue selected from the group consisting of Glu and Asp,
$Xaa_6$ is an amino acid residue selected from the group consisting of Glu and Asp and wherein said amino acid residues $Xaa_2$, $Xaa_3$, $Xaa_4$, $Xaa_5$ and $Xaa_6$ are not involved in antibody binding or to a smaller to significantly smaller extent as compared to the -Lys-Leu- and -Phe-Phe-binding site, respectively.

In another embodiment of the invention, a chimeric antibody or a fragment thereof, or a humanized antibody or a fragment thereof is provided, which recognizes and binds to at least one distinct binding site, particularly to a least two distinct binding sites, more particularly to at least three distinct binding sites on the β-amyloid protein wherein said distinct binding sites comprise at least one and at least two consecutive amino acid residues, respectively, predominantly involved in the binding of the antibody, wherein the at least one and the at least two consecutive amino acids are separated by at least one amino acid residue not involved in antibody binding or to a significantly smaller extent as compared to the amino acid residues, which are predominantly involved in the binding of the antibody, and wherein said amino acid residues are -His- and -Phe-Phe- and -Lys-Leu-, respectively, embedded within the following core sequence:

His-$Xaa_2$-Lys-Leu-$Xaa_3$-Phe-Phe-$Xaa_4$-$Xaa_5$-$Xaa_6$, wherein
$Xaa_2$ is an amino acid residue selected from the group consisting of Asn and Gln;
$Xaa_3$ is an amino acid residue selected from the group consisting of Ala, Val, Leu, norleucine, Met, Phe, and Ile;
$Xaa_4$ is an amino acid residue selected from the group consisting of Ala, Val, Leu, Ser and Ile;
$Xaa_5$ is an amino acid residue selected from the group consisting of Glu and Asp,
$Xaa_6$ is an amino acid residue selected from the group consisting of Glu and Asp, and wherein said amino acid residues $Xaa_2$, $Xaa_3$, $Xaa_4$, $Xaa_5$, $Xaa_6$, are not involved in antibody binding or to a smaller to significantly smaller extent as compared to the -His-, the -Lys-Leu- and the -Phe-Phe-binding site, respectively.

In another embodiment of the invention, a chimeric antibody or a fragment thereof, or a humanized antibody or a fragment thereof is provided, wherein
$Xaa_2$ is Gln or Asn, but particularly Gln;
$Xaa_3$ is Val or Leu, but particularly Val;
$Xaa_4$ is Ala or Val, but particularly Ala;
$Xaa_5$ is Glu or Asp, but particularly Glu; and
$Xaa_6$ is Asp or Glu, but particularly Asp.

In another embodiment of the invention, a chimeric antibody or a fragment thereof, or a humanized antibody or a fragment thereof is provided, which recognizes and binds to at least two distinct binding sites on the β-amyloid protein wherein said at least two distinct binding sites each comprise at least two consecutive amino acid residues predominantly involved in the binding of the antibody, wherein the at least two consecutive amino acids are separated by at least one amino acid residue not involved in antibody binding or to a significantly smaller extent than said consecutive amino acid residues, which are -Phe-Phe- and -Lys-Leu-, respectively, representing a first and second binding site embedded within the following core sequence:

$Xaa_1$-$Xaa_2$-Lys-Leu-$Xaa_3$-Phe-Phe-$Xaa_4$-$Xaa_5$-$Xaa_6$, wherein
- $Xaa_1$ is an amino acid residue selected from the group consisting of His, Asn, Gln, Lys and Arg;
- $Xaa_2$ is an amino acid residue selected from the group consisting of Asn and Gln;
- $Xaa_3$ is an amino acid residue selected from the group consisting of Val, Ala, Leu, Met, Phe, norleucine and Ile
- $Xaa_4$ is an amino acid residue selected from the group consisting of Ala, Val, Leu and Ile;
- $Xaa_5$ is an amino acid residue selected from the group consisting of Glu and Asp,
- $Xaa_6$ is an amino acid residue selected from the group consisting of Glu and Asp, and wherein said amino acid residues $Xaa_2$, $Xaa_3$, $Xaa_4$, $Xaa_s$, $Xaa_6$, are not involved in antibody binding or to a smaller to significantly smaller extent as compared to the -Lys-Leu- and the -Phe-Phe binding site, respectively.

In another embodiment of the invention, a chimeric antibody or a fragment thereof, or a humanized antibody or a fragment thereof is provided, wherein
- $Xaa_1$ is His or Arg, but particularly His;
- $Xaa_2$ is Gln or Asn, but particularly Gln;
- $Xaa_3$ is Val or Leu, but particularly Val;
- $Xaa_4$ is Ala or Val, but particularly Ala;
- $Xaa_5$ is Glu or Asp, but particularly Glu; and
- $Xaa_6$ is Asp or Glu, but particularly Asp.

In one embodiment of the invention, a chimeric antibody or a fragment thereof, or a humanized antibody or a fragment thereof is provided which recognizes and binds to at least two distinct binding sites on the β-amyloid protein wherein said at least two distinct binding sites each comprise at least two consecutive amino acid residues predominantly involved in the binding of the antibody, which are -Phe-Phe-Ala-Glu-, particularly -Phe-Phe-Ala-, but especially -Phe-Phe- and -Lys-Leu-, respectively, and wherein said at least two distinct binding sites exhibit amino acid sequence -Val-Phe-Phe-Ala-Glu-Asp- shown in SEQ ID NO: 7 and amino acid sequence His-Gln-Lys-Leu-Val- shown in SEQ ID NO: 8, respectively.

In one embodiment of the invention, a chimeric antibody or a fragment thereof, or a humanized antibody or a fragment thereof is provided, which recognizes and binds to at least one distinct binding site, particularly to a least two distinct binding sites, more particularly to at least three distinct binding sites on the β-amyloid protein wherein the said at least one or said at least two distinct binding sites comprise at least one and at least two consecutive amino acid residues, respectively, predominantly involved in the binding of the antibody, which are -Phe-Phe- and -Lys-Leu-, and -His-, respectively, wherein said distinct binding sites are embedded in the amino acid sequence -Val-Phe-Phe-Ala-Glu-, and amino acid sequence -His-Gln-Lys-Leu-Val-, respectively.

In another embodiment of the invention, the chimeric antibody or a fragment thereof, or a humanized antibody or a fragment thereof comprises an antigen recognition and binding site which recognizes and binds to at least two distinct binding sites on the β-amyloid protein wherein said at least two distinct binding sites each comprise at least two consecutive amino acid residues within the amino acid sequence given in SEQ ID NOs: 7 and 8, respectively, wherein said consecutive amino acid residues, particularly -Phe-Phe- and -Lys-Leu-, are predominantly involved in the binding of the β-amyloid protein.

In a further specific embodiment of the invention, an antibody or a fragment thereof according to the invention is provided, which binds to 4 distinct binding sites on the β-amyloid protein wherein said 4 distinct binding sites include 2 binding sites each comprising one amino acid residue and 2 binding sites each comprising two consecutive amino acid residues, which residues are predominantly involved in the binding of the antibody, wherein said 4 distinct binding sites are located in close proximity to each other on the β-amyloid protein, and wherein said 4 binding sites are separated by at least one amino acid residue not involved in antibody binding or involved in binding but to a significantly smaller extent as compared to said one amino acid residue and said two consecutive amino acid residues of the 4 distinct binding sites thus forming a conformational discontinuous epitope.

In particular, the first of the two consecutive amino acid residues predominantly involved in the binding of the antibody is -Lys-Leu-, and the second of the at least two consecutive amino acid residues is -Phe-Phe-, the first of the single amino acid residues is -His- and the second of the single amino acid residues is -Asp-embedded within the following core sequence:

-$Xaa_1$-His-$Xaa_2$-Lys-Leu-$Xaa_3$-Phe-Phe-$Xaa_4$-$Xaa_5$-Asp-$Xaa_6$ wherein
- $Xaa_1$ is an amino acid residue selected from the group consisting of His, Asn, Gln, Lys and Arg, but particularly His;
- $Xaa_2$ is an amino acid residue selected from the group consisting of Asn and Gln, but particularly Gln ;
- $Xaa_3$ is an amino acid residue selected from the group consisting of Ala, Val, Leu, norleucine, Met, Phe, and Ile, particularly Val;
- $Xaa_4$ is an amino acid residue selected from the group consisting of Ala, Val, Leu, Ser and Ile, particularly Ala;
- $Xaa_5$ is an amino acid residue selected from the group consisting of Glu and Asp, particularly Glu;
- $Xaa_6$ is an amino acid residue selected from the group consisting of Ala, Val, Leu, norleucine, Met, Phe, and Ile, particularly Val; and wherein said amino acid residues $Xaa_1$, $Xaa_2$, $Xaa_3$, $Xaa_4$, $Xaa_5$, $Xaa_6$, are not involved in antibody binding or are involved in binding but to a significantly smaller extent as compared to the -His-, -Asp-, the -Lys-Leu, and the -Phe-Phe-binding site.

In one embodiment, the invention relates to an antibody or a fragment thereof according to the invention, which binds to 4 distinct binding sites on the β-amyloid protein, wherein said 4 distinct binding sites include two binding sites each comprising one amino acid residue and two binding sites each comprising two consecutive amino acid residues, wherein the first of the two consecutive amino acid residues predominantly involved in the binding of the antibody is -Lys-Leu-, and the second of the at least two consecutive amino acid residues is -Phe-Phe-, the first of the single amino acid residues is -His- and the second of the single amino acid residues is -Asp-embedded within the following core sequence:

-Xaa₁-His-Xaa₂-Lys-Leu-Xaa₃-Phe-Phe-Xaa₄-Xaa₅-Asp-Xaa₆ wherein
Xaa₁ is an amino acid residue selected from the group consisting of His, Asn, Gln, Lys and Arg, but particularly His;
Xaa₂ is an amino acid residue selected from the group consisting of Asn and Gln, but particularly Gln ;
Xaa₃ is an amino acid residue selected from the group consisting of Ala, Val, Leu, norleucine, Met, Phe, and Ile, particularly Val;
Xaa₄ is an amino acid residue selected from the group consisting of Ala, Val, Leu, Ser and Ile, particularly Ala;
Xaa₅ is an amino acid residue selected from the group consisting of Glu and Asp, particularly Glu;
Xaa₆ is an amino acid residue selected from the group consisting of Ala, Val, Leu, norleucine, Met, Phe, and Ile, particularly Val; and wherein said amino acid residues Xaa₁, Xaa₂, Xaa₃, Xaa₄, Xaa₅, Xaa₆, are not involved in antibody binding or Xaa$_4$ is an amino acid residue selected from the group consisting of Ala and Val, but particularly Ala;

Xaa$_5$ is an amino acid residue selected from the group consisting of Glu and Asp, but particularly Glu;

Xaa$_6$ is an amino acid residue selected from the group consisting of Glu and Asp, but particularly Glu; and wherein said amino acid residues Xaa$_2$, Xaa$_3$, Xaa$_4$, Xaa$_5$, Xaa$_6$, are not involved in antibody binding or to a smaller extent as compared to the -His- and the -Lys-Leu- and the -Phe-Phe-binding site.

In a specific embodiment of the invention, the CDR of non-human origin is obtained from a donor antibody, but particularly from a murine donor antibody, raised against an antigen fragment which does not contain said distinct binding site. This shift in the epitopic region may have at least partially been caused by the use of a supramolecular antigenic construct comprising an antigenic peptide corresponding to the amino acid sequence of the β-amyloid peptide, particularly of β-amyloid peptide Aβ$_{1-16}$, modified with a hydrophilic moiety such as, for example, polyethylene glycol (PEG), wherein said hydrophilic moiety is covalently bound to each of the termini of the antigenic peptide through at least one, particularly one or two amino acids such as, for example, lysine, glutamic acid and cysteine or any other suitable amino acid or amino acid analogue capable of serving as a connecting device for coupling the hydrophilic moiety to the peptide fragment, as described herein below in the immunization process. When a PEG is used as the hydrophilic moiety, the free PEG termini are covalently bound to phosphatidylethanolamine or any other compound suitable to function as the anchoring element, for example, to embed the antigenic construct in the bilayer of a liposome as described herein.

In particular, the CDR of non-human origin is obtained from a murine donor antibody which exhibits the characteristic properties of ACI-01-Ab7C2 (also named "mC2" throughout the application) deposited 1 Dec. 2005 with the "Deutsche Sammlung von Mikroorganismen und Zellkulturen GmbH (DSMZ) in Braunschweig, Mascheroder Weg 1 B, 38124 Branuschweig, under the provisions of the Budapest Treaty under accession no DSM ACC2750).

In one embodiment of the invention, the CDR of non-human origin is obtained from murine donor antibody ACI-01-Ab7C2 (also named "mC2" throughout the application) deposited 1 Dec. 2005 with the "Deutsche Sammlung von Mikroorganismen und Zellkulturen GmbH (DSMZ) in Braunschweig, Mascheroder Weg 1 B, 38124 Branuschweig, under the provisions of the Budapest Treaty under accession no DSM ACC2750).

Also the use of lipid A as part of the immunization protocol may have contributed to a shift in the epitopic region.

In a specific embodiment, the invention relates to a humanized antibody or a fragment thereof comprising integrated into human- or primate-derived framework regions at least one peptide with an amino acid sequence selected from the group of sequences consisting of SEQ ID NO: 2 representing CDR2 and SEQ ID NO: 3 representing CDR3 of the Heavy Chain Variable Region (HCVR) and SEQ ID NO: 4 representing CDR1 of the Light Chain Variable Region (LCVR).

In another embodiment, the invention relates to a humanized antibody or a fragment thereof, wherein said humanized antibody comprises integrated into human- or primate-derived heavy chain framework regions at least one peptide with an amino acid sequence selected from the group of sequences consisting of SEQ ID NO: 2 representing CDR2 and SEQ ID NO: 3 representing CDR3 of the Heavy Chain Variable Region (HCVR).

In still another embodiment, the invention relates to a humanized antibody or a fragment thereof, wherein said humanized antibody comprises integrated into human- or primate-derived light chain framework regions a peptide with an amino acid sequence of SEQ ID NO: 4 representing CDR1 of the Light Chain Variable Region (LCVR).

In particular, the invention relates to a Light Chain Variable Region (LCVR) comprising integrated into human- or primate-derived framework regions at least one peptide with an amino acid sequence of SEQ ID NO: 4 representing CDR1 of the Light Chain Variable Region (LCVR).

In another specific embodiment, the invention relates to a Heavy Chain Variable Region (HCVR) comprising integrated into human- or primate-derived framework regions at least one peptide with an amino acid sequence selected from the group of sequences consisting of SEQ ID NO: 2 representing CDR2 and SEQ ID NO: 3 representing CDR3 of the Heavy Chain Variable Region (HCVR).

The invention further relates to a humanized antibody or a fragment thereof, which comprises integrated into human- or primate-derived framework regions at least two peptides, which peptides are different and exhibit an amino acid sequence selected from the group of sequences consisting of SEQ ID NO:1 representing CDR1, SEQ ID NO: 2 representing CDR2 and SEQ ID NO: 3 representing CDR3 of the Heavy Chain Variable Region (HCVR) and SEQ ID NO: 4 representing CDR1, SEQ ID NO: 5 representing CDR2 and SEQ ID NO: 6 representing CDR3 of the Light Chain Variable Region (LCVR) wherein the same CDR cannot be present twice in the antibody. In particular, if the at least two CDRs present are both CDRs of the Light Chain Variable Region (LCVR), at least on of said CDRs must be CDR1 represented by SEQ ID NO: 4.

Also comprised by the invention is a humanized antibody or a fragment thereof comprising integrated into human- or primate-derived heavy chain framework regions at least two peptides with an amino acid sequence selected from the group of sequences consisting of SEQ ID NO: 1 representing CDR1, SEQ ID NO: 2 representing CDR2 and SEQ ID NO: 3 representing CDR3 of the Heavy Chain Variable Region (HCVR), but particularly a humanized antibody or a fragment thereof wherein the same CDR cannot be present twice in the antibody.

In particular, the invention relates to a Heavy Chain Variable Region (HCVR) comprising integrated into human- or primate-derived heavy chain framework regions at least two peptides with an amino acid sequence selected from the group of sequences consisting of SEQ ID NO: 1 representing CDR1, SEQ ID NO: 2 representing CDR2 and SEQ ID NO: 3 representing CDR3 of the Heavy Chain Variable Region (HCVR).

In a further embodiment, the invention relates to a humanized antibody or a fragment thereof, comprising integrated into human- or primate-derived light chain framework regions at least two peptides with an amino acid sequence selected from the group of sequences consisting of SEQ ID NO: 4 representing CDR1, SEQ ID NO: 5 representing CDR2 and SEQ ID NO: 6 representing CDR3 of the Light Chain Variable Region (LCVR).

In particular, the invention relates to a Light Chain Variable Region (LCVR), which has integrated into human- or primate-derived light chain framework regions at least two peptides with an amino acid sequence selected from the group of sequences consisting of SEQ ID NO: 4 representing CDR1, SEQ ID NO: 5 representing CDR2 and SEQ ID NO: 6 representing CDR3 of the Light Chain Variable Region (LCVR), wherein the same CDR cannot be present twice in the antibody and, in particular, at least on of said CDRs must be CDR1 represented by SEQ ID NO: 4.

The invention also relates to a humanized antibody or a fragment thereof, comprising integrated into human- or primate-derived heavy chain framework regions peptides with an amino acid sequence of SEQ ID NO: 1 representing CDR1, SEQ ID NO: 2 representing CDR2 and SEQ ID NO: 3 representing CDR3 of the Heavy Chain Variable Region (HCVR), particularly in the order indicated above.

In particular, the invention relates to a Heavy Chain Variable Region (HCVR) comprising integrated into human- or primate-derived heavy chain framework regions peptides with an amino acid sequence of SEQ ID NO: 1 representing CDR1, SEQ ID NO: 2 representing CDR2 and SEQ ID NO: 3 representing CDR3 of the Heavy Chain Variable Region (HCVR), particularly in the order indicated above.

Also comprised by the invention is a humanized antibody or a fragment thereof comprising integrated into human- or primate-derived light chain framework regions peptides with an amino acid sequence of SEQ ID NO: 4 representing CDR1, SEQ ID NO: 5 representing CDR2 and SEQ ID NO: 6 representing CDR3 of the Light Chain Variable Region (LCVR), particularly in the order indicated above.

In particular, the invention relates to a Light Chain Variable Region (LCVR) comprising integrated into human- or primate-derived light chain framework regions peptides with an amino acid sequence of SEQ ID NO: 4 representing CDR1, SEQ ID NO: 5 representing CDR2 and SEQ ID NO: 6 representing CDR3 of the Light Chain Variable Region (LCVR), particularly in the order indicated above.

The invention also relates to a humanized antibody or a fragment thereof, which comprises integrated into human- or primate-derived framework regions at least three peptides with an amino acid sequence selected from the group of sequences consisting of SEQ ID NO: 1 representing CDR1, SEQ ID NO: 2 representing CDR2 and SEQ ID NO: 3 representing CDR3 of the Heavy Chain Variable Region (HCVR) and SEQ ID NO: 4 representing CDR1, SEQ ID NO: 5 representing CDR2 and SEQ ID NO: 6 representing. CDR3 of the Light Chain Variable Region (LCVR), but particularly a humanized antibody or a fragment thereof wherein the same CDR cannot be present twice in the antibody.

In another embodiment the invention relates to a humanized antibody or a fragment thereof, which antibody comprises integrated into human- or primate-derived framework regions at least four peptides with an amino acid sequence selected from the group of sequences consisting of SEQ ID NO: 1 representing CDR1, SEQ ID NO: 2 representing CDR2 and SEQ ID NO:3 representing CDR3 of the Heavy Chain Variable Region (HCVR) and SEQ ID NO: 4 representing CDR1, SEQ ID NO: 5 representing CDR2 and SEQ ID NO: 6 representing CDR3 of the Light Chain Variable Region (LCVR), but particularly a humanized antibody or a fragment thereof wherein the same CDR cannot be present twice in the antibody.

In still another embodiment, the invention relates to a humanized antibody or a fragment thereof, which comprises integrated into human- or primate-derived framework regions at least five peptides with an amino acid sequence selected from the group of sequences consisting of SEQ ID NO: 1 representing CDR1, SEQ ID NO: 2 representing CDR2 and SEQ ID NO:3 representing CDR3 of the Heavy Chain Variable Region (HCVR) and SEQ ID NO: 4 representing CDR1, SEQ ID NO: 5 representing CDR2 and SEQ ID NO: 6 representing CDR3 of the Light Chain Variable Region (LCVR), but particularly a humanized antibody or a fragment thereof wherein the same CDR cannot be present twice in the antibody.

In still another embodiment, the invention relates to a humanized antibody or a fragment thereof, which comprises integrated into human- or primate-derived framework regions peptides with an amino acid sequence of SEQ ID NO: 1 representing CDR1, SEQ ID NO: 2 representing CDR2 and SEQ ID NO: 3 representing CDR3 of the Heavy Chain Variable Region (HCVR) and SEQ ID NO: 4 representing CDR1, SEQ ID NO: 5 representing CDR2 and SEQ ID NO: 6 representing CDR3 of the Light Chain Variable Region (LCVR).

In a specific embodiment, the invention relates to a humanized antibody, a Heavy Chain Variable Region (HCVR), or a fragment thereof, wherein said humanized antibody, Heavy Chain Variable Region (HCVR) or fragment thereof comprises integrated into human- or primate-derived heavy chain framework regions at least a peptide with an amino acid sequence of SEQ ID NO: 2 representing CDR2 of the Heavy Chain Variable Region (HCVR).

In another specific embodiment, the invention relates to a humanized antibody, a Heavy Chain Variable Region (HCVR) or a fragment thereof, wherein said humanized antibody, Heavy Chain Variable Region (HCVR) or fragment thereof comprises integrated into human- or primate-derived heavy chain framework regions at least a peptide with an amino acid sequence of SEQ ID NO: 3 representing CDR3 of the Heavy Chain Variable Region (HCVR).

In another specific embodiment, the invention relates to a humanized antibody, Heavy Chain Variable Region (HCVR) or a fragment thereof, which antibody, Heavy Chain Variable Region (HCVR) or fragment thereof comprises integrated into human- or primate-derived heavy chain framework regions at least two peptides with an amino acid sequence of SEQ ID NO: 1 representing CDR1 and SEQ ID NO: 2 representing CDR2 of the Heavy Chain Variable Region (HCVR).

In another specific embodiment, the invention relates to a humanized antibody, a Heavy Chain Variable Region (HCVR) or a fragment thereof, which antibody, Heavy Chain Variable Region (HCVR) or fragment thereof comprises integrated into human- or primate-derived heavy chain framework regions at least two peptides with an amino acid sequence of SEQ ID NO: 1 representing CDR1 and SEQ ID NO: 3 representing CDR3 of the Heavy Chain Variable Region (HCVR).

In another specific embodiment, the invention relates to a humanized antibody, a Heavy Chain Variable Region (HCVR) or a fragment thereof, which antibody, Heavy Chain Variable Region (HCVR) or fragment thereof comprises integrated into human- or primate-derived heavy chain framework regions at least two peptides with an amino acid sequence of SEQ ID NO: 2 representing CDR2 and SEQ ID NO: 3 representing CDR3 of the Heavy Chain Variable Region (HCVR).

In another specific embodiment, the invention relates to a humanized antibody, a Light Chain Variable Region (LCVR) or a fragment thereof, which antibody, Light Chain Variable Region (LCVR) or fragment thereof comprises integrated into human- or primate-derived heavy chain framework regions at least two peptides with an amino acid sequence of SEQ ID NO: 4 representing CDR1 and SEQ ID NO: 5 representing CDR2 of the Light Chain Variable Region (LCVR).

In another specific embodiment, the invention relates to a humanized antibody, a Light Chain Variable Region (LCVR) or a fragment thereof, which antibody, Light Chain Variable Region (LCVR) or fragment thereof comprises integrated into human- or primate-derived heavy chain framework regions at least two peptides with an amino acid sequence of SEQ ID NO: 4 representing CDR1 and SEQ ID NO: 6 representing CDR3 of the Light Chain Variable Region (LCVR).

Further comprised by the invention is a humanized antibody or a fragment thereof, wherein both the Heavy Chain Variable Region (HCVR) and the Light Chain Variable Region (LCVR) of the mouse C2 antibody each contributes at least one of its CDR regions to the at least two CDR regions of the humanized antibody. The resulting humanized antibody or a fragment thereof thus may comprise

- at least an amino acid sequence of SEQ ID NO: 1 representing CDR1 (HCVR) in combination with an amino acid sequence of SEQ ID NO: 4 representing CDR1 (LCVR);
- at least an amino acid sequence of SEQ ID NO: 2 representing CDR2 (HCVR) in combination with an amino acid sequence of SEQ ID NO: 4 representing CDR1 (LCVR);
- at least an amino acid sequence of SEQ ID NO: 3 representing CDR3 (HCVR) in combination with an amino acid sequence of SEQ ID NO: 4 representing CDR1 (LCVR);
- at least an amino acid sequence of SEQ ID NO: 1 representing CDR1 (HCVR) in combination with an amino acid sequence of SEQ ID NO: 5 representing CDR2 (LCVR);
- at least an amino acid sequence of SEQ ID NO: 2 representing CDR2 (HCVR) in combination with an amino acid sequence of SEQ ID NO: 5 representing CDR2 (LCVR);
- at least an amino acid sequence of SEQ ID NO:2 representing CDR2 (HCVR) in combination with an amino acid sequence of SEQ ID NO: 6 representing CDR3 (LCVR);
- at least an amino acid sequence of SEQ ID NO:1 representing CDR1 (HCVR) in combination with an amino acid sequence of SEQ ID NO: 6 representing CDR3 (LCVR);
- at least an amino acid sequence of SEQ ID NO: 3 representing CDR3 (HCVR) in combination with an amino acid sequence of SEQ ID NO: 5 representing CDR2 (LCVR);
- at least an amino acid sequence of SEQ ID NO: 3 representing CDR3 (HCVR) in combination with an amino acid sequence of SEQ ID NO: 6 representing CDR3 (LCVR).

In still another embodiment, the invention relates to a chimeric antibody or a fragment thereof, or a humanized antibody or a fragment thereof as described herein before, which antibody comprises a light chain and/or a heavy chain constant region of human or primate origin.

In a further embodiment, the invention relates to a chimeric antibody or a fragment thereof, or a humanized antibody or a fragment thereof, wherein at least one, particularly at least one but not more than 5, more particularly at least one but not more than 4, even more particularly at least one but not more than 3, but especially at least one but not more than 2, of the amino acids representative of the light chain and/or heavy chain CDR regions as given in SEQ ID NOs: 1-6 is changed through a conservative substitution such that the antibody maintains its full functionality.

In particular, the invention relates to a chimeric antibody or a fragment thereof, or a humanized antibody or a fragment thereof, wherein in CDR2 of the light chain variable region (LCVR) as given in SEQ ID NO: 5, the Lys at Kabat position 50 is replaced by an amino acid residue selected from the group consisting of Arg, Gln and Glu, particularly by Arg.

In particular, the invention relates to a light chain variable region (LCVR) wherein in CDR2 as given in SEQ ID NO: 5, the Lys at Kabat position 50 is replaced by an amino acid residue selected from the group consisting of Arg, Gln and Glu, particularly by Arg.

In another embodiment, the invention relates to a chimeric antibody or a fragment thereof, or a humanized antibody or a fragment thereof, wherein in CDR2 of the light chain variable region (LCVR) as given in SEQ ID NO: 5, the Ser at Kabat position 53 is replaced by an amino acid residue selected from the group consisting of Asn or Thr, but particularly by Asn.

In particular, the invention relates to a light chain variable region (LCVR) wherein in CDR2 as given in SEQ ID NO: 5, the Ser at Kabat position 53 is replaced by an amino acid residue selected from the group consisting of Asn or Thr, but particularly by Asn.

In one embodiment of the invention, a chimeric antibody or a fragment thereof, or a humanized antibody or a fragment thereof is provided, wherein the Heavy Chain Variable Region (HCVR) has an amino acid sequence that is 90%, particularly 95%, more particularly 98% identical to the sequence given in SEQ ID NO: 15 and 16, respectively.

In another embodiment of the invention, a chimeric antibody or a fragment thereof, or a humanized antibody or a fragment thereof is provided, wherein the Light Chain Variable Region (LCVR) has an amino acid sequence that is 90%, particularly 95%, more particularly 98% identical to the sequence given in SEQ ID NO: 12 and 13, respectively.

In still another embodiment of the invention, a humanized antibody or a fragment thereof is provided, wherein at least two, but especially three, of the CDR regions of the Heavy Chain Variable Region (HCVR) have an amino acid sequence that is 90%, particularly 95%, more particularly 98% identical to the corresponding CDR region as given in SEQ ID NO: 1-3.

In a further embodiment of the invention, a humanized antibody or a fragment thereof is provided, wherein at least two, but especially three, of the CDR regions of the Light Chain Variable Region (LCVR) have an amino acid sequence that is 90%, particularly 95%, more particularly 98% identical to the corresponding CDR region as given in SEQ ID NO: 4-6.

In still another embodiment, the invention relates to a chimeric antibody or a fragment thereof, or a humanized antibody or a fragment thereof according to the present invention as described herein before wherein the Heavy Chain Variable Region (HCVR) has an amino acid sequence that is 90%, 91%, 92%, 93%, 94%, 95%, 96%, 97%, 98% or 99% identical to the sequence given in SEQ ID NO: 15 and 16, respectively.

In still another embodiment, the invention relates to a chimeric antibody or a fragment thereof, or a humanized antibody or a fragment thereof according to the present invention as described herein before wherein the Light Chain Variable Region (LCVR) has an amino acid sequence that is 90%, 91%, 92%, 93%, 94%, 95%, 96%, 97%, 98% or 99% identical to the sequence given in SEQ ID NO: 12 and 13, respectively.

In still another embodiment, the invention relates to a chimeric antibody or a fragment thereof, or a humanized antibody or a fragment thereof according to the present invention as described herein before, wherein at least one, particularly at least two, but especially three, of the CDR regions of the Heavy Chain Variable Region (HCVR) have an amino acid sequence that is 90%, 91%, 92%, 93%, 94%, 95%, 96%, 97%, 98% or 99% identical to the corresponding CDR region as given in SEQ ID NO: 1-3.

In still another embodiment, the invention relates to a chimeric antibody or a fragment thereof, or a humanized antibody or a fragment thereof according to the present invention as described herein before, wherein at least one, particularly at least two, but especially three, of the CDR regions of the Light Chain Variable Region (LCVR) have an amino acid sequence that is 90%, 91%, 92%, 93%, 94%, 95%, 96%, 97%, 98% or 99% identical to the corresponding CDR region as given in SEQ ID NO: 4-6.

In still another embodiment, the invention relates to a humanized antibody according to the present invention and as described herein before, wherein at least one of the amino acids representative of the acceptor framework sequences obtained from human germline $V_H$ and $V_K$ sequences, respectively is changed through a substitution to an amino acid from the corresponding region of murine antibody ACI-01-Ab7C2 or a substitution conservative thereto.

In particular, the invention relates to a Heavy Chain Variable Region and to a humanized antibody comprising this Heavy Chain Variable Region, respectively, wherein the Trp in Kabat position 47 in the acceptor framework sequence obtained from human germline $V_H$ sequences of KABAT subgroup $V_H$III of the Heavy Chain Variable Region is replaced by an amino acid selected from the group consisting of Leu, norleucine, Ile, Val, Met, Ala, and Phe, particularly Leu and Ile, but especially Leu such as shown in SEQ ID NO: 15.

The invention further relates to a Heavy Chain Variable Region and to a humanized antibody comprising this Heavy Chain Variable Region, respectively, wherein the Arg in Kabat position 94 in the acceptor framework sequence obtained from human germline $V_H$ sequences of KABAT subgroup $V_H$III of the Heavy Chain Variable Region is replaced by an amino acid selected from the group consisting of Ser and Thr, but especially by Ser such as shown in SEQ ID NO: 15.

In still another embodiment, the invention relates to a Heavy Chain Variable Region and to a humanized antibody comprising this Heavy Chain Variable Region, respectively, wherein the Trp in Kabat position 47 in the acceptor framework sequence obtained from human germline $V_H$ sequences of KABAT subgroup $V_H$III of the Heavy Chain Variable Region is replaced by an amino acid selected from the group consisting of Leu, norleucine, Ile, Val, Met, Ala, and Phe, particularly Leu and Ile, but especially Leu and the Arg in Kabat position 94 is replaced by an amino acid selected from the group consisting of Ser and Thr, but especially by Ser such as shown in SEQ ID NO: 15.

The invention further relates to a Light Chain Variable Region and to a humanized antibody comprising this Light Chain Variable Region, respectively, wherein the Gln in Kabat position 45 in the acceptor framework sequence obtained from human germline $V_K$ sequences of KABAT subgroup $V_K$II of the Light Chain Variable Region is replaced by an amino acid selected from the group consisting of Lys, Arg, Gln, and Asn, particularly by Lys and Arg, but especially by Lys.

The invention further relates to a Light Chain Variable Region and to a humanized antibody comprising this Light Chain Variable Region, respectively, wherein the Tyr in Kabat position 87 in the acceptor framework sequence obtained from human germline $V_K$ sequences of KABAT subgroup $V_K$II of the Light Chain Variable Region is replaced by an amino acid selected from the group consisting of Phe, Leu, Val, Ile, and Ala, particularly by Leu and Phe, but especially by Phe.

The invention further relates to a Light Chain Variable Region and to a humanized antibody comprising this Light Chain Variable Region, respectively, wherein the Lys in Kabat position 50 in the CDR2 region obtained from a mouse monoclonal antibody, particularly murine antibody ACI-01-Ab7C2, such as shown in SEQ ID NO: 12 is replaced by an amino acid selected from the group consisting of Arg, Gln, His, and Asn, but especially by Arg In still another embodiment, the invention relates to a Light Chain Variable Region and to a humanized antibody comprising this Light Chain Variable Region, respectively, wherein the Asn in Kabat position 53 in the CDR2 region obtained from a mouse monoclonal antibody, particularly murine antibody ACI-01-Ab7C2, such as shown in SEQ ID NO: 12 is replaced by an amino acid selected from the group consisting of Ala, Val, Leu, Ser and Ile; but especially Ser.

In still another embodiment, the invention relates to a humanized antibody, wherein the Trp in Kabat position 47 in the acceptor framework sequence obtained from human germline $V_H$ sequences of KABAT subgroup $V_H$III of the Heavy Chain Variable Region is replaced by an amino acid selected from the group consisting of Leu, norleucine, Ile, Val, Met, Ala, and Phe, particularly Leu and Ile, but especially Leu and the Arg in Kabat position 94 in the acceptor framework sequence obtained from human germline $V_H$ sequences of KABAT subgroup $V_H$III of the Heavy Chain Variable Region is replaced by an amino acid selected from the group consisting of Ser and Thr, but especially by Ser as shown in SEQ ID NO: 15, and the Tyr in Kabat position 87 in the acceptor framework sequence obtained from human germline $V_K$ sequences of KABAT subgroup $V_K$II of the Light Chain Variable Region is replaced by an amino acid selected from the group consisting of Phe, Leu, Val, Ile, and Ala, particularly by Leu and Phe, but especially by Phe.

In still another embodiment, the invention relates to a Heavy Chain Variable Region and to a humanized antibody comprising this Heavy Chain Variable Region, respectively, wherein the Trp in Kabat position 47 in the acceptor framework sequence obtained from human germline $V_H$ sequences of KABAT subgroup $V_H$III of the Heavy Chain Variable Region as shown in SEQ ID NO: 15 is replaced by Leu.

In still another embodiment, the invention relates to a Heavy Chain Variable Region and to a humanized antibody comprising this Heavy Chain Variable Region, respectively, wherein the Arg in Kabat position 94 in the acceptor framework sequence obtained from human germline $V_H$ sequences of KABAT subgroup $V_H$III of the Heavy Chain Variable Region is replaced by Ser such as shown in SEQ ID NO: 15.

In still another embodiment, the invention relates to a Heavy Chain Variable Region and to a humanized antibody comprising this Heavy Chain Variable Region, respectively, wherein the Trp in Kabat position 47 in the acceptor framework sequence obtained from human germline $V_H$ sequences of KABAT subgroup $V_H$III of the Heavy Chain Variable Region is replaced by Leu and Ile, but especially Leu and the Arg in Kabat position 94 in the acceptor framework sequence obtained from human germline $V_H$ sequences of KABAT subgroup $V_H$III of the Heavy Chain Variable Region is replaced by Ser such as shown in SEQ ID NO: 15.

In still another embodiment, the invention relates to a Light Chain Variable Region and to a humanized antibody comprising this Heavy Chain Variable Region, respectively, wherein the Tyr in Kabat position 87 in the acceptor framework sequence obtained from human germline $V_K$ sequences of KABAT subgroup $V_K$II of the Light Chain Variable Region is replaced by Phe.

In still another embodiment, the invention relates to a Heavy Chain Variable Region and to a humanized antibody comprising this Heavy Chain Variable Region, respectively, wherein the Trp in Kabat position 47 in the acceptor framework sequence obtained from human germline $V_H$ sequences of KABAT subgroup $V_H$III of the Heavy Chain Variable Region is replaced by Leu and Ile, but especially Leu and the Arg in Kabat position 94 in the acceptor framework sequence obtained from human germline $V_H$ sequences of KABAT subgroup $V_H$III of the Heavy Chain Variable Region is replaced by Ser such as shown in SEQ ID NO: 15 and the Tyr in Kabat position 87 in the acceptor framework sequence obtained from human germline $V_K$ sequences of KABAT subgroup $V_K$II of the Light Chain Variable Region is replaced by Phe.

In one embodiment, the invention relates to a Heavy Chain Variable Region and to a humanized antibody comprising this Heavy Chain Variable Region, respectively, wherein the Trp in Kabat position 47 in the acceptor framework sequence obtained from human germline $V_H$ sequences of KABAT subgroup $V_H$III of the Heavy Chain Variable Region is replaced by an amino acid selected from the group consisting of Leu, norleucine, Ile, Val, Met, Ala, and Phe, particularly Leu and Ile, but especially Leu and the Arg in Kabat position 94 is replaced by an amino acid selected from the group consisting of Ser and Thr, but especially by Ser such as shown in SEQ ID NO: 15 and wherein the Lys in Kabat position 50 in the CDR2 region obtained from a mouse monoclonal antibody, particularly murine antibody ACI-01-Ab7C2, is replaced by an amino acid selected from the group consisting of Arg, Gln, His, and Asn, but especially by Arg.

In one embodiment, the invention relates to a Heavy Chain Variable Region and to a humanized antibody comprising this Heavy Chain Variable Region, respectively, wherein the Trp in Kabat position 47 in the acceptor framework sequence obtained from human germline $V_H$ sequences of KABAT subgroup $V_H$III of the Heavy Chain Variable Region is replaced by an amino acid selected from the group consisting of Leu, norleucine, Ile, Val, Met, Ala, and Phe, particularly Leu and Ile, but especially Leu and the Arg in Kabat position 94 is replaced by an amino acid selected from the group consisting of Ser and Thr, but especially by Ser such as shown in SEQ ID NO: 15 and wherein the Asn in Kabat position 53 in the CDR2 region obtained from a mouse monoclonal antibody, particularly murine antibody ACI-01-Ab7C2, is replaced by an amino acid selected from the group consisting of Ala, Val, Leu, Ser and Ile; but especially Ser.

In a specific embodiment, the invention relates to the light chain variable region of SEQ ID NO: 12.

In another specific embodiment of the invention, a humanized antibody is provided, which comprises the light chain variable region of SEQ ID NO: 12.

In a specific embodiment, the invention relates to the light chain variable region including signal sequences as shown in SEQ ID NO: 13.

In another specific embodiment of the invention, a humanized antibody is provided, which comprises the complete light chain variable region including signal sequences as shown in SEQ ID NO: 13.

In another specific embodiment of the invention, a humanized antibody is provided, which comprises the light chain variable region of SEQ ID NO: 12 and the light chain constant region of SEQ ID NO: 14.

In another specific embodiment of the invention, a humanized antibody is provided, which comprises the complete light chain variable region of SEQ ID NO: 13 and the light chain constant region of SEQ ID NO: 14.

In a specific embodiment, the invention relates to the heavy chain variable region of SEQ ID NO: 15.

In another specific embodiment of the invention, a humanized antibody is provided, which comprises the heavy chain variable region of SEQ ID NO: 15.

In a specific embodiment, the invention relates to the heavy chain variable region including signal sequences as shown in SEQ ID NO: 16.

In another specific embodiment of the invention, a humanized antibody is provided, which comprises the complete heavy chain variable region including signal sequences as shown in SEQ ID NO: 16.

In another specific embodiment of the invention, a humanized antibody is provided, which comprises the heavy chain variable region of SEQ ID NO: 15 and the heavy chain constant region of SEQ ID NO: 17.

In another specific embodiment of the invention, a humanized antibody is provided, which comprises the heavy chain variable region of SEQ ID NO: 16 and the heavy chain constant region of SEQ ID NO: 17.

In one embodiment the humanized antibody according to the invention and as described herein, upon co-incubation with an Aβ monomeric peptide having at least 30, particularly at least 35, more particularly at least 38, even more particularly at least 40 amino acid residues and/or an Aβ polymeric soluble amyloid peptide comprising a plurality of said Aβ monomeric units, but especially with an $A\beta_{1-42}$ monomeric and/or an Aβ polymeric soluble amyloid peptide comprising a plurality of said $A\beta_{1-42}$ monomeric units, particularly at a molar concentration ratio of antibody to Aβ1-42 of up to 1:1000, particularly of up to 1:500, more particularly of up to 1:300, even more particularly of up to 1:200, but especially at a molar concentration ratio of between 1:10 and 1:100, inhibits the aggregation of the Aβ monomers to high molecular polymeric fibrils.

In particular, the co-incubation of the antibody according to the invention with amyloid monomeric and/or polymeric soluble amyloid peptides is carried out for 24 hours to 60 hours, particularly for 30 hours to 50 hours, more particularly for 48 hours, but especially 24 hours, at a temperature of between 28° C. and 40° C., particularly of between 32° C. and 38° C., more particularly at 37° C.

In a specific embodiment of the invention, co-incubation with amyloid monomeric and/or polymeric soluble amyloid peptides is accomplished for 24 hours at a temperature of 37° C.

In particular, the antibody, particularly the humanized antibody according to the invention including any functionally equivalent antibody or functional parts thereof binds to $A\beta_{1-42}$ monomeric peptide and/or Aβ polymeric soluble amyloid peptide comprising a plurality of said $A\beta_{1-42}$ monomeric units and, upon co-incubation with $A\beta_{1-42}$ monomeric peptide and/or Aβ polymeric soluble amyloid peptide comprising a plurality of said $A\beta_{1-42}$ monomeric units inhibits the aggregation of the Aβ monomers and/or polymers to high molecular polymeric fibrils.

In one embodiment, the antibody, particularly the humanized antibody according to the invention including any functionally equivalent antibody or functional parts thereof inhibits the aggregation of the Aβ monomers and/or Aβ soluble polymers comprising a plurality of said Aβ monomeric units to high molecular polymeric fibrils by at least 50%, particularly by at least 60%, particularly by at least 65%, more particularly by at least 75%, even more particularly by at least 80%, but especially by at least 85%-90%, or more as compared to the respective amyloid peptide monomers incubated in buffer (control), at a molar concentration ratio of antibody to Aβ1-42 of up to 1:1000, particularly at a molar concentration ratio of between 1:10 and 1:100, but especially at a molar concentration ratio of 1:10.

In a specific embodiment of the invention, the antibody, particularly the humanized antibody according to the invention including any functionally equivalent antibody or functional parts thereof inhibits the aggregation of the Aβ monomers and/or Aβ soluble polymers comprising a plurality of said Aβ monomeric units to high molecular polymeric fibrils by at least 30% at a molar concentration ratio of antibody to Aβ1-42 of 1:100.

In another specific embodiment of the invention, the antibody, particularly the humanized antibody according to the invention including any functionally equivalent antibody or functional parts thereof inhibits the aggregation of the Aβ monomers and/or Aβ soluble polymers comprising a plurality of said Aβ monomeric units to high molecular polymeric fibrils by at least 80% at a molar concentration ratio of antibody to Aβ1-42 of 1:10.

Binding of the antibodies according to the invention and as described herein to amyloidogenic monomeric and/or polymeric peptides but, particularly, to the amyloid form (1-42) leads to inhibition of the aggregation of monomeric and/or polymeric amyloidogenic peptides to high molecular fibrils or filaments. Through the inhibition of the aggregation of amyloidogenic monomeric and/or polymeric peptides the antibodies according to the present invention are capable of preventing or slowing down the formation of amyloid plaques, particularly the amyloid form (1-42), which is know to become insoluble by change of secondary conformation and to be the major part of amyloid plaques in brains of diseased animals or humans.

The aggregation inhibition potential of the antibody according to the invention may be determined by any suitable method known in the art, particularly by density-gradient ultracentrifugation followed by a SDS-PAGE sedimentation analysis on a preformed gradient and/or by a thioflavin T (Th-T) fluorescent assay.

In one embodiment, the invention relates to an antibody, particularly a humanized antibody as described herein including any functionally equivalent antibody or functional parts thereof, which antibody, upon co-incubation, particularly at a molar concentration ratio of between 1:5 and 1:1000, particularly of between 1:10 and 1:500, more particularly at a ratio of 1:10 to 1:300, even more particularly at a ratio of between 1:10 and 1:100, with preformed high molecular polymeric amyloid fibrils or filaments formed by the aggregation of Aβ monomeric peptides having at least 30, particularly at least 35, more particularly at least 38, even more particularly at least 40 amino acid residues and, but especially Aβ$_{1-42}$ monomeric peptides, is capable of disaggregating the preformed polymeric fibrils or filaments by at least 20%, particularly by at least 30%, more particularly by at least 35%, even more particularly by at least 40%, but especially by at least 50% or more.

In a specific embodiment of the invention, the aggregation inhibition and the disaggregation potential of the antibody, respectively, is determined by density-gradient ultracentrifugation followed by a SDS-PAGE sedimentation analysis on a preformed gradient.

In another specific embodiment of the invention, the aggregation inhibition and the disaggregation potential of the antibody, respectively, is determined by thioflavin T (Th-T) fluorescent assay.

In another specific embodiment, the antibody according to the invention is co-incubated with amyloid preformed high molecular polymeric amyloid fibrils or filaments for 12 hours to 36 hours, particularly for 18 hours to 30 hours, more particularly for 24 hours at a temperature of between 28° C. and 40° C., particularly of between 32° C. and 38° C., more particularly at 37° C.

In particular, the co-incubation with preformed high molecular polymeric amyloid fibrils or filaments is done for 24 hours at a temperature of 37° C.

In a specific embodiment of the invention, the antibody, particularly the humanized antibody according to the invention including any functionally equivalent antibody or functional parts thereof is capable of disaggregating the preformed polymeric fibrils or filaments by at least 24% at a molar concentration ratio of antibody to Aβ1-42 of 1:100.

In another specific embodiment of the invention, the antibody, particularly the humanized antibody according to the invention including any functionally equivalent antibody or functional parts thereof is capable of disaggregating the preformed polymeric fibrils or filaments by at least 32% at a molar concentration ratio of antibody to Aβ1-42 of 1:10.

Through the disaggregation of amyloidogenic polymeric fibrils or filaments the antibodies according to the present invention are capable of preventing or slowing down the formation of amyloid plaques which leads to an alleviation of the symptoms associated with the disease and a delay or reversal of its progression.

Accordingly, it is a further embodiment of the invention to provide an antibody, particularly a humanized antibody, including any functionally equivalent antibody or functional parts thereof as described herein, which antibody is capable of decreasing the total amount of Aβ in the brain of an animal, particularly a mammal, but especially a human suffering from a disease or condition leading to increased concentration of Aβ in the brain.

In another embodiment, the invention relates to a humanized antibody according to the invention and as described herein before, which antibody is bi-effective in that it exhibits both an aggregation inhibition property as well as a disaggregation property, particularly paired with a high degree of conformational sensitivity.

In particular, the invention relates to a chimeric antibody or a fragment thereof, or a humanized antibody or a fragment thereof according to the invention and as described herein before, which antibody, upon co-incubation with amyloid monomeric and/or polymeric soluble amyloid peptides, particularly with β-amyloid monomeric peptides such as, for example, Aβ monomeric peptides 1-39; 1-40, 1-41, or 1-42, and/or a polymeric soluble β-amyloid peptide comprising a plurality of said Aβ monomeric units, but especially with an Aβ$_{1-42}$ monomeric and/or an Aβ polymeric soluble amyloid peptide comprising a plurality of said Aβ$_{1-42}$ monomeric units, inhibits the aggregation of the Aβ monomers into high molecular polymeric fibrils or filaments and, in addition, upon co-incubation with preformed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, or 1-42, but especially Aβ$_{1-42}$ monomeric peptides, is capable of disaggregating the preformed polymeric fibrils or filaments.

In another aspect, the invention relates to a chimeric antibody or a fragment thereof, or a humanized antibody or a fragment thereof according to the present invention and as described herein before, which antibody is capable of inducing a transition of the β-sheet conformation towards an α-helix and/or a random coil conformation, but particularly a random coil conformation, even more particularly a random coil conformation at a given location in the molecule, especially in the environment of Tyr 10 and Val12 of the Aβ protein, which leads to an increase of the random coil conformation at the expense of the β-sheet conformation and an improved solubilization of the preformed high molecular polymeric amyloid fibrils or filaments. In particular the decrease of the O-sheet conformation amounts to at least 30%, particularly to at least 35%, and more particularly to at least 40% and more as compared to the respective preformed amyloid polymeric fibrils or filaments incubated in buffer (control).

The antibody's potential in inducing a transition in the secondary structure is determined by solid state 13C NMR spectroscopy but, in particular, by measuring the integral intensities of the conformations of Tyr 10 and Val 12 Cβ in the $A\beta_{1-42}$ peptide.

In a further embodiment of the invention, a chimeric antibody or a fragment thereof, or a humanized antibody or a fragment thereof according to the present invention and as described herein before, is provided comprising at least one light chain or a fragment thereof or at least one heavy chain or a fragment thereof, wherein said antibody or fragment binds to an Aβ monomer with a high binding affinity with a $K_D$ in a range of between at least about $1\times10^{-7}$ M to at least about $1\times10^{-12}$ M, particularly of at least about $1\times10^{-8}$ M to at least about $1\times10^{-11}$ M, more particularly of at least about $1\times10^{-9}$ M to at least about $1\times10^{-10}$ M, even more particularly of at least about $1\times10^{-8}$ M to at least about $2\times10^{-8}$ M but, preferably, does not show any significant cross-reactivity with amyloid precursor protein (APP).

In another embodiment of the invention, a chimeric antibody or a fragment thereof, or a humanized antibody or a fragment thereof according to the present invention and as described herein before, is provided comprising at least one light chain or a fragment thereof or at least one heavy chain or a fragment thereof, wherein said antibody or fragment binds to an Aβ fiber, fibril or filament with a high binding affinity with a $K_D$ in a range of between at least about $1\times10^{-7}$ M to at least about $1\times10^{-12}$ M, particularly of at least about $1\times10^{-8}$ M to at least about $1\times10^{-11}$ M, more particularly of at least about $1\times10^{-9}$ M to at least about $1\times10^{-10}$ M, even more particularly of at least about $2\times10^{-9}$ M to at least about $5\times10^{-9}$ M, but, preferably, does not show any significant cross-reactivity with amyloid precursor protein (APP).

In another embodiment, the antibody according to the invention and as described herein before or a fragment thereof, exhibits an binding affinity to an Aβ fiber, fibril or filament which is at least 2 times, particularly at least 4 times, particularly at least 10 times, particularly at least 15 times, more particularly at least 20 times, but especially at least 25 times higher than the binding affinity to an Aβ monomer.

In still another embodiment, a chimeric antibody or a fragment thereof, or a humanized antibody or a fragment thereof is provided as described herein before, which antibody substantially binds to aggregated Aβ, including Aβ plaques, in the mammalian, particularly the human brain but, preferably, does not show any significant cross-reactivity with amyloid precursor protein (APP).

In another aspect of the invention, the chimeric antibody or a fragment thereof, or a humanized antibody or a fragment thereof is provided as described herein before, which antibody substantially binds to soluble polymeric amyloid, particularly amyloid β (Aβ), including Aβ monomers, in the mammalian, particularly the human brain but, preferably, does not show any significant cross-reactivity with amyloid precursor protein (APP).

Further provided is a chimeric antibody or a fragment thereof, or a humanized antibody or a fragment thereof according to the invention and as described herein before, which antibody significantly reduces Aβ plaque burden in the mammalian, particularly the human brain. This can be achieved by either binding of the antibody to the plaque or by shifting the equilibrium between amyloid, particularly amyloid β (Aβ), in its insoluble and aggregated state towards its soluble form by disaggregating fibers to soluble poly- and monomeric forms by inducing a shift in conformation and binding and stabilizing the disaggregated and solubilized amyloid forms, particularly amyloid β (Aβ) forms, in the tissue and/or body fluids, particularly the brain. Through the activity of the antibody according to the invention the peripheral clearing and catabolism is thus favored rather than deposition within the tissue and/or body fluids, particularly the brain. The beneficial effect of the antibody according to the invention can thus be obtained without binding of the antibody to the plaque.

Through this stabilizing activity, the antibody according to the invention is able to neutralize the toxic effects of the polymeric and less aggregated soluble amyloid protein, particularly amyloid β (Aβ) protein, in the tissue and/or body fluids. In a specific embodiment of the invention the antibody according to the invention may thus achieve its beneficial effects without necessarily binding aggregated amyloid beta in the brain.

In a further aspect of the invention a humanized antibody or a fragment thereof according to the present invention and as described herein before, is provided comprising at least one light chain or a fragment thereof or at least one heavy chain or a fragment thereof incorporating at least one, particularly two and more particularly three CDR regions obtained form a mouse donor antibody, particularly from mouse antibody ACI-01-Ab7C2 (named "mC2" and hC2 for the humanized C2 antibody, throughout the application) deposited 1 Dec. 2005 with the "Deutsche Sammlung von Mikroorganismen and Zellkulturen GmbH (DSMZ) in Braunschweig, Mascheroder Weg 1 B, 38124 Braunschweig, under accession no DSM ACC2750, wherein said antibody or fragment thereof has an affinity to the Aβ antigen which is at least 5 times, particularly at least 8 times, more particularly at least 10 times, but especially at least 15 times higher than that of the mouse donor antibody.

The antibody of this invention can be, in one embodiment, a whole antibody (e.g., with two full length light chains and two full length heavy chains) of any isotype and subtype (e.g., IgM, IgD, IgG1, IgG2, IgG3, IgG4, IgE, IgA1 and IgA2); but especially an antibody of the IgG4 isotype; alternatively, in another embodiment, it can be an antigen-binding fragment (e.g., Fab, F(ab')$_2$, and Fv) of a whole antibody.

The invention thus also relates to antigen-binding fragments of the antibodies described herein. In one embodiment of the invention, the fragment is selected from the group consisting of a Fab fragment, a Fab' fragment, a F(ab)$_2$ fragment, and a F$_v$ fragment, including the products of an Fab immunoglobulin expression library and epitope-binding fragments of any of the antibodies and fragments mentioned above.

In another embodiment, the antibody or antigen-binding fragment of the invention is conjugated to polyethylene glycol. In yet another embodiment, the constant region of the antibody of the invention is modified to reduce at least one constant region-mediated biological effector function relative to an unmodified antibody. In still another embodiment, the antibody or antigen-binding fragment of the invention comprises a Fc region having an altered effector function.

The invention further relates to a nucleotide molecule comprising a nucleotide sequence encoding a chimeric antibody or a fragment thereof, or a humanized antibody or a fragment thereof according to the invention and as disclosed herein before.

In particular, the invention relates to a nucleotide molecule comprising a nucleotide sequence encoding a stretch of contiguous amino acid molecules as given in SEQ ID NO: 2 and 3, respectively, or the complementary sequence, representing the Complementarity Determining Regions (CDRs) 2 and 3 of the Heavy Chain Variable Region (HCVR).

More particularly, the invention relates to a nucleotide molecule comprising a nucleotide sequence encoding a stretch of contiguous amino acid molecules as given in SEQ ID NO: 4, or the complementary sequence, representing the Complementarity Determining Regions (CDRs) 1 of the Light Chain Variable Region (LCVR).

In another embodiment of the invention a nucleotide molecule is provided comprising a nucleotide sequence as given in SEQ ID NO: 18 and SEQ ID NO: 19, or the complementary sequence, encoding the amino acid sequence of CDR 2 and CDR 3, respectively, of the Heavy Chain Variable Region (HCVR).

In another embodiment of the invention a nucleotide molecule is provided comprising a nucleotide sequence as given in SEQ ID NO: 20, or the complementary sequence, encoding the nucleotide sequence of CDR 1 of the Light Chain Variable Region (LCVR).

In another embodiment of the invention a nucleotide molecule is provided comprising a nucleotide sequence of SEQ ID NO: 21, or the complementary sequence, encoding the light chain variable region.

In another embodiment of the invention a nucleotide molecule is provided comprising a nucleotide sequence of SEQ ID NO: 22, or the complementary sequence, encoding the complete light chain variable region including signal sequences.

In another embodiment of the invention a nucleotide molecule is provided comprising a nucleotide sequence encoding the light chain variable region of SEQ ID NO: 22 and the light chain constant region of SEQ ID NO: 23. The invention also comprises the complementary strand of said nucleotide molecule.

In another embodiment of the invention a nucleotide molecule is provided comprising a nucleotide sequence of SEQ ID NO: 24 encoding the heavy chain variable region. The invention also comprises the complementary strand of said nucleotide molecule.

In another embodiment of the invention a nucleotide molecule is provided comprising a nucleotide sequence of SEQ ID NO: 25 encoding the complete heavy chain variable region including signal sequences. The invention also comprises the complementary strand of said nucleotide molecule.

In another embodiment of the invention a nucleotide molecule is provided comprising a nucleotide sequence encoding the heavy chain variable region of SEQ ID NO: 25 and the heavy chain constant region of SEQ ID NO: 26. The invention also comprises the complementary strand of said nucleotide molecule.

Also comprised by the present invention is a nucleotide sequence which hybridizes to one of the above-described antibody-encoding nucleotide sequences of the invention, particularly to the complementary strand thereof, either in isolation or as part of larger nucleotide molecule.

In particular, the invention relates to a nucleotide sequence that hybridizes under conventional hybridization conditions, particularly under stringent hybridization conditions, to any of the nucleotide sequences given in SEQ ID NOs: 18-26 and 29-32, particularly to the complementary strand thereof.

In another embodiment of the invention an expression vector is provided comprising the nucleic acid molecule according to the invention and as mentioned herein before.

In another embodiment of the invention a cell is provided comprising an expression vector comprising the nucleic acid according to the invention and as mentioned herein before.

In still another embodiment, the invention relates to a composition comprising the antibody according to the invention, but particularly a chimeric antibody or a fragment thereof, or a humanized antibody or a fragment thereof according to the invention and as described herein before including any functionally equivalent antibody or any derivative or functional parts thereof, in a therapeutically effective amount, in particular a composition which is a pharmaceutical composition optionally further comprising a pharmaceutically acceptable carrier. In another embodiment of the invention, said composition comprises the antibody in a therapeutically effective amount.

Further comprised by the invention is a mixture comprising an antibody, particularly a monoclonal antibody according to the invention, but particularly a chimeric antibody or a fragment thereof, or a humanized antibody or a fragment thereof according to the invention and as described herein before including any functionally equivalent antibody or any derivative or functional parts thereof, in a therapeutically effective amount and, optionally, a further biologically active substance and/or a pharmaceutically acceptable carrier and/or a diluent and/or an excipient.

In particular, the invention relates to a mixture, wherein the further biologically active substance is a compound used in the medication of amyloidosis, a group of diseases and disorders associated with amyloid or amyloid-like protein such as the Aβ protein involved in Alzheimer's disease.

In another embodiment of the invention, the other biologically active substance or compound may also be a therapeutic agent that may be used in the treatment of amyloidosis caused by amyloid β or may be used in the medication of other neurological disorders.

The other biologically active substance or compound may exert its biological effect by the same or a similar mechanism as the antibody according to the invention or by an unrelated mechanism of action or by a multiplicity of related and/or unrelated mechanisms of action.

Generally, the other biologically active compound may include neutron-transmission enhancers, psychotherapeutic drugs, acetylcholine esterase inhibitors, calcium-channel blockers, biogenic amines, benzodiazepine tranquilizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists.

More particularly, the invention relates to a mixture comprising at least one compound selected from the group consisting of compounds effective against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), α-secretase activators, β- and γ-secretase inhibitors, tau proteins, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, or cholinesterase inhibitors (ChEIs) such as tacrine, rivastigmine, donepezil, and/or galantamine, M1 agonists and other drugs including any amyloid or tau modifying drug and nutritive supplements, and nutritive supplements, together with an antibody according to the present invention and, optionally, a pharmaceutically acceptable carrier and/or a diluent and/or an excipient.

The invention further relates to a mixture, wherein the compound is a cholinesterase inhibitor (ChEIs), particularly a mixture, wherein the compound is one selected from the group consisting of tacrine, rivastigmine, donepezil, galantamine, niacin and memantine.

In a further embodiment, the mixtures according to the invention may comprise niacin or memantine together with an antibody according to the present invention and, optionally, a pharmaceutically acceptable carrier and/or a diluent and/or an excipient.

In still another embodiment of the invention mixtures are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with an antibody, particularly a monoclonal antibody according to the invention, but particularly a chimeric antibody or a fragment thereof, or a humanized antibody or a fragment thereof according to the invention and as described herein and, optionally, a pharmaceutically acceptable carrier and/or a diluent and/or an excipient.

In a specific embodiment of the invention, the compositions and mixtures according to the invention and as described herein before comprise the antibody and the biologically active substance, respectively, in a therapeutically effective amount.

Other compounds that can be suitably used in mixtures in combination with the antibody according to the present invention are described in WO 2004/058258 (see especially pages 16 and 17) including therapeutic drug targets (page 36-39), alkanesulfonic acids and alkanolsulfuric acids (pages 39-51), cholinesterase inhibitors (pages 51-56), NMDA receptor antagonists (pages 56-58), estrogens (pages 58-59), non-steroidal anti-inflammatory drugs (pages 60-61), antioxidants (pages 61-62), peroxisome proliferators-activated receptor (PPAR) agonists (pages 63-67), cholesterol-lowering agents (pages 68-75); amyloid inhibitors (pages 75-77), amyloid formation inhibitors (pages 77-78), metal chelators (pages 78-79), anti-psychotics and anti-depressants (pages 80-82), nutritional supplements (pages 83-89) and compounds increasing the availability of biologically active substances in the brain (see pages 89-93) and prodrugs (pages 93 and 94), which document is incorporated herein by reference.

In another embodiment, the invention relates to a mixture comprising the antibody, particularly a monoclonal antibody according to the invention, but particularly a chimeric antibody or a fragment thereof, or a humanized antibody or a fragment thereof according to the invention and as described herein before and/or the biologically active substance in a therapeutically effective amount.

The invention further relates to the use of an antibody, particularly a monoclonal antibody according to the invention, but particularly a chimeric antibody or a fragment thereof, or a humanized antibody or a fragment thereof according to the invention and as described herein before and/or a functional part thereof and/or a pharmaceutical composition, or a mixture comprising said antibody, for the preparation of a medicament for treating or alleviating the effects of amyloidosis, a group of diseases and disorders associated with amyloid plaque formation including secondary amyloidosis and age-related amyloidosis such as diseases including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration.

Also comprised by the present invention is a method for the preparation of an antibody, particularly a monoclonal antibody according to the invention, but particularly a chimeric antibody or a fragment thereof, or a humanized antibody or a fragment thereof according to the invention and as described herein before and/or a functional part thereof and/or a pharmaceutical composition, or a mixture comprising said antibody and/or a functional part, thereof, particularly in a therapeutically effective amount, for use in a method of preventing, treating or alleviating the effects of amyloidosis, a group of diseases and disorders associated with amyloid plaque formation including secondary amyloidosis and age-related amyloidosis such as diseases including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration comprising formulating an antibody, particularly a monoclonal antibody according to the invention, but particularly a chimeric antibody or a fragment thereof, or a humanized antibody or a fragment thereof according to the invention in a pharmaceutically acceptable form.

Further comprised by the present invention is a method for preventing, treating or alleviating the effects of amyloidosis, a group of diseases and disorders associated with amyloid plaque formation including secondary amyloidosis and age-related amyloidosis such as diseases including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration by administering an antibody and/or a functional part thereof, but particularly a humanized antibody and/or a functional part thereof, or a composition or mixture comprising such an antibody and/or a functional part thereof, to a an animal or a human affected by such a disorder comprising administering the antibody in a therapeutically effective amount.

It is also an object of the invention to provide a method for the treatment of amyloidosis, a group of diseases and disorders associated with amyloid plaque formation including secondary amyloidosis and age-related amyloidosis including, but not limited to, neurological disorders such as Alzheimer's Disease (AD), particularly a disease or condition characterized by a loss of cognitive memory capacity by administering to an animal, particularly a mammal or a human, an antibody, particularly a pharmaceutical composition according to the invention and as described herein.

In a specific embodiment the invention provides a method for retaining or increasing cognitive memory capacity but, particularly, for restoring the cognitive memory capacity of an animal, particularly a mammal or a human, suffering from memory impairment by administering to an animal, particularly a mammal or a human, an antibody, particularly a pharmaceutical composition according to the invention and as described herein before.

It is a further object of the invention to provide a therapeutic composition and a method of producing such a composition as well as a method for the treatment of amyloidosis, a group of diseases and disorders associated with amyloid plaque formation including secondary amyloidosis and age-related amyloidosis including, but not limited to, neurological disorders such as Alzheimer's Disease (AD), particularly a disease or condition characterized by a loss of cognitive memory capacity, using an antibody according to the invention and as described herein before.

In particular, the invention relates to the treatment of an animal, particularly a mammal or a human, suffering from an amyloid-associated condition characterized by a loss of cognitive memory capacity leads to the retention of cognitive memory capacity.

The invention further relates to a method of diagnosis of an amyloid-associated disease or condition in a patient comprising detecting the immunospecific binding of an antibody or an active fragment thereof to an epitope of the amyloid protein in a sample or in situ which includes the steps of (a) bringing the sample or a specific body part or body area suspected to contain the amyloid protein into contact with an antibody, particularly a monoclonal antibody according to the invention, but particularly a chimeric antibody or a fragment thereof, or a humanized antibody or a fragment thereof according to the invention and as described herein before, and/or a functional part thereof, which antibody binds an epitope of the amyloid protein;

(b) allowing the antibody and/or a functional part thereof, to bind to the amyloid protein to form an immunological complex;

(c) detecting the formation of the immunological complex; and (d) correlating the presence or absence of the immunological complex with the presence or absence of amyloid protein in the sample or specific body part or area.

Also comprised is a method of determining the extent of amyloidogenic plaque burden in a tissue and/or body fluids comprising (a) obtaining a sample representative of the tissue and/or body fluids under investigation;

(b) testing said sample for the presence of amyloid protein with an antibody, particularly a monoclonal antibody according to the invention, but particularly a chimeric antibody or a fragment thereof, or a humanized antibody or a fragment thereof according to the invention and as described herein before, and/or a functional part thereof;

(c) determining the amount of antibody bound to the protein; and (d) calculating the plaque burden in the tissue and/or body fluids.

In particular, the invention relates to a method of determining the extent of amyloidogenic plaque burden in a tissue and/or body fluids, wherein the formation of the immunological complex in step c) is determined such that presence or absence of the immunological complex correlates with presence or absence of amyloid protein.

In another embodiment of the invention, a test kit for detection and diagnosis of amyloid-associated diseases and conditions is provided comprising an antibody, particularly a monoclonal antibody according to the invention, but particularly a chimeric antibody or a fragment thereof, or a humanized antibody or a fragment thereof according to the invention and as described herein before, and/or a functional part thereof.

In particular, the invention relates to a test kit for detection and diagnosis of amyloid-associated diseases and conditions comprising a container holding one or more antibodies according to the present invention, and/or a functional part thereof, and instructions for using the antibodies for the purpose of binding to amyloid protein to form an immunological complex and detecting the formation of the immunological complex such that presence or absence of the immunological complex correlates with presence or absence of amyloid protein.

In another aspect, the invention provides an antibody comprising a variable region as recited in SEQ ID NO: 27, or a variant thereof. In one embodiment, a cell line expressing the antibody.

In another aspect, the invention provides an antibody gene comprising a variable region as recited in SEQ ID NO: 29, or a variant thereof. In one embodiment, a cell line expresses the antibody.

In another aspect, the invention provides a method for disaggregating preformed beta-amyloid fibers, comprising interacting an hC2 antibody with preformed beta-amyloid fibers.

In another aspect, the invention provides a humanized antibody or a fragment thereof according to any of the preceding claims, wherein said antibody or fragment thereof protects neurons from Abeta-induced degradation.

In another aspect, the invention provides a method of preventing Abeta-induced neuron degradation comprising treating neurons with an effective amount of a humanized antibody or a fragment thereof according to the disclosure herein.

In another aspect, the invention provides use of a humanized antibody or a fragment thereof according to the description herein for the preparation of a medicament for preventing degeneration of neurons upon exposure to Abeta oligomer.

In another embodiment of the invention, an antibody, particularly a monoclonal antibody, including any functionally equivalent antibody or functional parts thereof is provided, which recognized the native conformation of amyloid in that it specifically binds to amyloid oligomers and fibers, but not to not linearized amyloid species.

In a further embodiment of the invention, an antibody, particularly a monoclonal antibody, including any functionally equivalent antibody or functional parts thereof according to the present invention and as described herein before, is provided which antibody or fragment binds to an Aβ monomer with a binding affinity of at least about $1\times10^{-6}$ to at least about $1\times10^{-8}$, particularly of at least about $1\times10^{-6}$ to at least about $1\times10^{-7}$, more particularly of at least about $1\times10^{-7}$ to at least about $1\times10^{-8}$, even more particularly of at least about $1\times10^{-7}$ to at least about $4\times10^{-7}$ but, preferably, does not show any significant cross-reactivity with amyloid precursor protein (APP).

In another embodiment of the invention, an antibody, particularly a monoclonal antibody, including any functionally equivalent antibody or functional parts thereof according to the present invention and as described herein before, is provided which antibody or fragment binds to an Aβ fiber, fibril or filament with a binding affinity of at least about $1\times10^{-7}$ to at least about $1\times10^{-9}$, particularly of at least about $1\times10^{-7}$ to at least about $1\times10^{-8}$, more particularly of at least about $1\times10^{-8}$ to at least about $1\times10^{-9}$, even more particularly of at least about $1\times10^{-8}$ to at least about $5\times10^{-8}$, but, preferably, does not show any significant cross-reactivity with amyloid precursor protein (APP).

In another embodiment, the antibody, particularly a monoclonal antibody, including any functionally equivalent antibody or functional parts thereof according to the present invention and as described herein before exhibits an binding affinity to an Aβ fiber, fibril or filament which is at least 5 times, particularly at least 10 times, more particularly at least 15 times, higher than the binding affinity to an Aβ monomer.

Through the disaggregation of amyloidogenic polymeric fibrils or filaments the antibodies according to the present invention are capable of preventing or slowing down the formation of amyloid plaques which leads to an alleviation of the symptoms associated with the disease and a delay or reversal of its progression.

Accordingly, it is a further embodiment of the invention to provide an antibody, particularly a monoclonal antibody, including any functionally equivalent antibody or functional parts thereof as described herein before, which antibody is capable of decreasing the total amount of Aβ in the brain of an animal, particularly a mammal, but especially a human suffering from a disease or condition leading to increased concentration of Aβ in the brain.

In another embodiment of the invention an antibody, particularly a monoclonal antibody, including any functionally equivalent antibody or functional parts thereof as described herein before is provided, which antibody is capable of disrupting plaques thus decreasing the plaque load in the brain of an animal, particularly a mammal, but especially a human suffering from a disease or condition leading to an increased plaque load in the brain. The antibody according to the invention including any functionally equivalent antibody or functional parts thereof decreases the plaque load in the brain by at least 20%, particularly by at least 25%, more particularly by at least 30%, even more particularly more than 30%.

In still another embodiment of the invention an antibody, particularly a monoclonal antibody, including any functionally equivalent antibody or functional parts thereof as described herein before is provided, which antibody is capable of solubilizing plaques leading to a reduction of the amount of plaques in the brain of an animal, particularly a mammal, but especially a human suffering from a disease or condition leading to an increased plaque load in the brain. The antibody according to the invention including any functionally equivalent antibody or functional parts thereof reduces the amount of plaques in the brain by at least 10%, particularly by at least 15%, more particularly by at least 20%.

It is to be understood that the antibody according to the invention can exhibit one, two or more of the specific properties described herein before in various combinations.

In particular, an antibody or a fragment thereof is provided, which recognizes and binds to at least one distinct binding site, particularly to a least two distinct binding sites on the β-amyloid protein wherein the said at least one or said at least two distinct binding sites comprise at least one amino acid residue and at least two consecutive amino acid residues, respectively, predominantly involved in the binding of the antibody, wherein, in a specific embodiment of the invention, the at least one residue constituting the first distinct binding site is Leu and the at least two consecutive amino acid residues, constituting the second distinct binding site, are -Phe-Phe-embedded within the following core sequence:

-Xaa$_1$-Xaa$_2$-Xaa$_3$-Leu-Xaa$_4$-Phe-Phe-Xaa$_5$-Xaa$_6$-Xaa$_7$- wherein

Xaa$_1$ is an amino acid residue selected from the group comprising His, Asn, Gln Lys, and Arg;

Xaa$_2$ is an amino acid residue selected from the group comprising Asn and Gln;

Xaa$_3$ is an amino acid residue selected from the group comprising Lys, His, Asn, Gln and Arg Xaa$_4$ is an amino acid residue selected from the group comprising Ala, Val, Leu, norleucine, Met, Phe, and Ile;

Xaa$_5$ is an amino acid residue selected from the group comprising Ala, Val, Leu, Ser and Ile;

Xaa$_6$ is an amino acid residue selected from the group comprising Glu and Asp, Xaa$_7$ is an amino acid residue selected from the group comprising Glu and Asp.

In another aspect, the invention relates to an antibody or a fragment thereof, which recognizes and binds to at least one distinct binding site, particularly to a least two distinct binding sites, more particularly to at least three distinct binding sites on the β-amyloid protein, wherein said one or the at least two or the at least three distinct binding sites each comprise at least one, particularly at least two consecutive amino acid residues predominantly involved in the binding of the antibody.

In particular, the antibody or a fragment thereof according to the invention binds to at least two distinct binding sites on the β-amyloid protein, wherein said at least two distinct binding sites each comprise at least two consecutive amino acid residues predominantly involved in the binding of the antibody, wherein said at least two distinct binding sites are located in close proximity to each other on the antigen, separated by at least one amino acid residue not involved in antibody binding or to a significantly smaller extent as compared to said at least two consecutive amino acid residues, thus forming a conformational discontinuous epitope.

In another embodiment of the invention, an antibody or a fragment thereof according to the invention is provided, which recognizes and binds to at least one distinct binding site, particularly to a least two distinct binding sites, more particularly to at least three distinct binding sites on the β-amyloid protein wherein said distinct binding sites comprise at least one and at least two consecutive amino acid residues, respectively, predominantly involved in the binding of the antibody, wherein the at least one and the at least two consecutive amino acids, which are separated by at least one amino acid residue not involved in antibody binding or to a significantly smaller extent as compared to the amino acid residues predominantly involved in the binding of the antibody, are -His- and -Lys-Leu-, respectively, embedded within the following core sequence:

-His-Xaa$_2$-Lys-Leu-Xaa$_3$-Xaa$_4$-Xaa$_5$-Xaa$_6$--Xaa$_7$-Xaa$_8$- wherein
- Xaa$_2$ is an amino acid residue selected from the group comprising Asn and Gln;
- Xaa$_3$ is an amino acid residue selected from the group comprising Ala, Val, Leu, norleucine, Met, Phe, and Ile;
- Xaa$_4$ is an amino acid residue selected from the group comprising Ala, Val, Leu, norleucine, Met, Phe, and Ile
- Xaa$_5$ is an amino acid residue selected from the group comprising Ala, Val, Leu, norleucine, Met, Phe, and Ile
- Xaa$_6$ is an amino acid residue selected from the group comprising Ala, Val, Leu, Ser and Ile;
- Xaa$_7$ is an amino acid residue selected from the group comprising Glu and Asp,
- Xaa$_8$ is an amino acid residue selected from the group comprising Glu and Asp and wherein said amino acid residues Xaa$_2$, Xaa$_3$, Xaa$_6$, Xaa$_7$, Xaa$_8$, are not involved in antibody binding or to a significantly smaller extent as compared to the -His- and the -Lys-Leu-binding site.

In another embodiment, an antibody or a fragment thereof is provided, which recognizes and binds to at least one distinct binding site, particularly to a least two distinct binding sites, more particularly to at least three distinct binding sites on the β-amyloid protein wherein said distinct binding sites comprise at least one and at least two consecutive amino acid residues, respectively, predominantly involved in the binding of the antibody, wherein the at least two consecutive amino acid residues representing a first binding site are -Phe-Phe- and the at least one amino acid residue is -His-embedded within the following core sequence:

-Xaa$_1$-His-Xaa$_3$-Xaa$_4$-Xaa$_5$-Xaa$_6$-Phe-Phe-Xaa$_7$-Xaa$_8$-Xaa$_9$, wherein
- Xaa$_1$ is an amino acid residue selected from the group comprising His, Asn, Gln, Lys and Arg
- Xaa$_3$ is an amino acid residue selected from the group comprising Asn and Gln
- Xaa$_4$ is an amino acid residue selected from the group comprising His, Asn, Gln, Lys and Arg
- Xaa$_5$ is an amino acid residue selected from the group comprising Ala, Val, Leu, Ser and Ile;
- Xaa$_6$ is an amino acid residue selected from the group comprising Ala, Val, Leu and Ile
- Xaa$_7$ is an amino acid residue selected from the group comprising Ala, Val, Leu and Ile
- Xaa$_8$ is an amino acid residue selected from the group comprising Glu and Asp,
- Xaa$_9$ is an amino acid residue selected from the group comprising Glu and Asp, and wherein said amino acid residues Xaa$_1$, Xaa$_3$, Xaa$_6$, Xaa$_7$, Xaa$_8$ and Xaa$_9$, are not involved in antibody binding or to a significantly smaller extent as compared to the His and the -Phe-Phe-binding site.

In a specific embodiment of the invention, the first of at least two consecutive amino acid residues predominantly involved in the binding of the antibody involve -Lys- and -Leu-, and the second of the at least two consecutive amino acid residues involve -Phe-Phe-embedded within the following core sequence:

-Xaa$_1$-Xaa$_2$-Lys-Leu-Xaa$_4$-Phe-Phe-Xaa$_5$-Xaa$_6$-Xaa$_7$- wherein
- Xaa$_1$ is an amino acid residue selected from the group comprising His, Asn, Gln Lys, and Arg;
- Xaa$_2$ is an amino acid residue selected from the group comprising Asn and Gln;
- Xaa$_4$ is an amino acid residue selected from the group comprising Ala, Val, Leu, norleucine, Met, Phe, and Ile;
- Xaa$_5$ is an amino acid residue selected from the group comprising Ala, Val, Leu, Ser and Ile;
- Xaa$_6$ is an amino acid residue selected from the group comprising Glu and Asp,
- Xaa$_7$ is an amino acid residue selected from the group comprising Glu and Asp, and wherein said amino acid residues Xaa$_2$, Xaa$_3$, Xaa$_4$, Xaa$_5$, Xaa$_6$, Xaa$_7$ are not involved in antibody binding or to a significantly smaller extent as compared to the -Lys-Leu and the -Phe-Phe-binding site.

In another embodiment of the invention, an antibody or a fragment thereof is provided, wherein
- Xaa$_1$ is His or Arg, but particularly His;
- Xaa$_2$ is Gln or Asn, but particularly Gln;
- Xaa$_4$ is Val or Leu, but particularly Val;
- Xaa$_5$ is Ala or Val, but particularly Ala;
- Xaa$_6$ is Glu or Asp, but particularly Glu; and
- Xaa$_7$ is Asp or Glu, but particularly Asp.

In a further embodiment of the invention, the antibody or a fragment thereof according to the invention binds to at least three distinct binding sites on the β-amyloid protein wherein said at least three distinct binding sites comprise at least one amino acid residue and at least two consecutive amino acid residues, respectively, which residues are predominantly involved in the binding of the antibody, wherein said at least three distinct binding sites are located in close proximity to each other on the antigen, separated by at least one amino acid residue not involved in antibody binding or to a significantly smaller extent as compared to said at least one amino acid residue and said at least two consecutive amino acid residues, respectively, thus forming a conformational discontinuous epitope.

In a specific embodiment of the invention, the first of the at least two consecutive amino acid residues predominantly involved in the binding of the antibody involve -Lys-Leu-, and the second of the at least two consecutive amino acid residues involve -Phe-Phe-, and the third at least one amino residue involves -His-embedded within the following core sequence:

-His-Xaa$_2$-Lys-Leu-Xaa$_4$-Phe-Phe-Xaa$_5$-Xaa$_6$-Xaa$_7$- wherein
- Xaa$_2$ is an amino acid residue selected from the group comprising Asn and Gln;
- Xaa$_4$ is an amino acid residue selected from the group comprising Ala, Val, Leu, norleucine, Met, Phe, and Ile;
- Xaa$_5$ is an amino acid residue selected from the group comprising Ala, Val, Leu, Ser and Ile;
- Xaa$_6$ is an amino acid residue selected from the group comprising Glu and Asp,
- Xaa$_7$ is an amino acid residue selected from the group comprising Glu and Asp, and wherein said amino acid residues Xaa$_2$, Xaa$_3$, Xaa$_4$, Xaa$_5$, Xaa$_6$, Xaa$_7$ are not involved in antibody binding or to a significantly smaller extent as compared to the -His-, the -Lys-Leu, and the -Phe-Phe-binding site.

In another embodiment of the invention, an antibody or a fragment thereof is provided, wherein $Xaa_2$ is Gln or Asn, but particularly Gln;
$Xaa_4$ is Val or Leu, but particularly Val;
$Xaa_5$ is Ala or Val, but particularly Ala;
$Xaa_6$ is Glu or Asp, but particularly Glu; and
$Xaa_7$ is Glu or Asp, but particularly Asp;

In a specific embodiment of the invention, the first of the at least two consecutive amino acid residues predominantly involved in the binding of the antibody involve -Lys-Leu-, and the second of the at least two consecutive amino acid residues involve -Phe-Phe-, and the third at least one amino residue involves -Asp- embedded within the following core sequence:

$-Xaa_1-Xaa_2-Lys-Leu-Xaa_4-Phe-Phe-Xaa_5-Xaa_6-Asp-$ wherein $Xaa_1$ is an amino acid residue selected from the group comprising His, Asn, Gln Lys, and Arg;
$Xaa_2$ is an amino acid residue selected from the group comprising Asn and Gln;
$Xaa_4$ is an amino acid residue selected from the group comprising Ala, Val, Leu, norleucine, Met, Phe, and Ile;
$Xaa_5$ is an amino acid residue selected from the group comprising Ala, Val, Leu, Ser and Ile;
$Xaa_6$ is an amino acid residue selected from the group comprising Glu and Asp, and wherein said amino acid residues $Xaa_2$, $Xaa_3$, $Xaa_4$, $Xaa_5$, $Xaa_6$, $Xaa_7$ are not involved in antibody binding or to a significantly smaller extent as compared to the -Asp-, the -Lys-Leu, and the -Phe-Phe-binding site.

In another embodiment of the invention, an antibody or a fragment thereof is provided, wherein $Xaa_1$ is His or Arg, but particularly His;
$Xaa_2$ is Gln or Asn, but particularly Gln;
$Xaa_4$ is Val or Leu, but particularly Val;
$Xaa_5$ is Ala or Val, but particularly Ala; and
$Xaa_6$ is Glu or Asp, but particularly Glu In a further specific embodiment of the invention, an antibody or a fragment thereof according to the invention is provided, which binds to 4 distinct binding sites on the β-amyloid protein wherein said 4 distinct binding sites comprise one amino acid residue and two consecutive amino acid residues, respectively, which residues are predominantly involved in the binding of the antibody, wherein said 4 distinct binding sites are located in close proximity to each other on the antigen, separated by at least one amino acid residue not involved in antibody binding or to a significantly smaller extent as compared to said one amino acid residue and said two consecutive amino acid residues of the 4 distinct binding sites thus forming a conformational discontinuous epitope.

In particular, the first of the two consecutive amino acid residues predominantly involved in the binding of the antibody are -Lys-Leu-, and the second of the at least two consecutive amino acid residues are -Phe-Phe-, the first of the single amino residues is -His- and the second of the single amino residues is -Asp- embedded within the following core sequence:

$-His-Xaa_2-Lys-Leu-Xaa_4-Phe-Phe-Xaa_5-Xaa_6-Asp-$ wherein $Xaa_2$ is an amino acid residue selected from the group comprising Asn and Gln;
$Xaa_4$ is an amino acid residue selected from the group comprising Ala, Val, Leu, norleucine, Met, Phe, and Ile;
$Xaa_5$ is an amino acid residue selected from the group comprising Ala, Val, Leu, Ser and Ile;
$Xaa_6$ is an amino acid residue selected from the group comprising Glu and Asp, and wherein said amino acid residues $Xaa_2$, $Xaa_3$, $Xaa_4$, $Xaa_5$, $Xaa_6$, $Xaa_7$ are not involved in antibody binding or to a significantly smaller extent as compared to the -His-, -Asp-, the -Lys-Leu, and the -Phe-Phe-binding site.

In a specific embodiment of the invention, the recognition and binding sites as defined herein before are forming a conformational discontinuous epitope localized in a region of the β-amyloid protein between amino acid residue 12 to 24, particularly between residues 14 to 23, more particularly between amino acid residues 14 and 20, wherein the three distinct recognition and binding sites comprising 1 and 2 amino acid residues, respectively, are located at position 16, 17, and at position 19 and 20, and at position 14, respectively, which residues are predominantly involved in the binding of the β-amyloid protein and wherein said three distinct recognition and binding sites are separated by one amino acid residue located at position 15 and 18, respectively, which amino acids are not involved in the binding of the antigen or, at least, to a substantially smaller extent.

In a specific embodiment, said consecutive amino acid residues, particularly -Lys-Leu- at position 16 and 17 and -Phe-Phe- at position 19 and 20, which are predominantly involved in the binding of the β-amyloid protein, are embedded into the following core region:

| Val- | His- | His- | Gln- | Lys- | Leu- | Val- | Phe- | Phe- | Ala- |
|------|------|------|------|------|------|------|------|------|------|
| 12   | 13   | 14   | 15   | 16   | 17   | 18   | 19   | 20   | 21   |

| Glu- | Asp |
|------|-----|
| 22   | 23  |

In a further specific embodiment, said consecutive amino acid residues, particularly -Lys- at position 16, -Leu- at position 17 and -Phe-Phe- at position 19 and 20, and -His- at position 14, which are predominantly involved in the binding of the β-amyloid protein are embedded into the following core region:

| Val- | His- | His- | Gln- | Lys- | Leu- | Val- | Phe- | Phe- | Ala- |
|------|------|------|------|------|------|------|------|------|------|
| 12   | 13   | 14   | 15   | 16   | 17   | 18   | 19   | 20   | 21   |

| Glu- | Asp- |
|------|------|
| 22   | 23   |

Also part of the invention is the use of a monoclonal antibody and/or a functional part thereof according to the invention and as described herein before and/or a pharmaceutical composition, or a mixture comprising said antibody, for the preparation of a medicament for treating or alleviating the effects of diseases and disorders which are caused by or associated with amyloid or amyloid-like proteins including amyloidosis, a group of diseases and disorders associated with amyloid plaque formation including secondary amyloidosis and age-related amyloidosis such as diseases including, but not limited to, neurological disorders such as Alzheimer's Disease (AD and diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes; senile cardiac amyloidosis; endocrine tumors, and others, including macular degeneration.

In another embodiment of the present invention a method is provided for the preparation of a pharmaceutical composition using an antibody according to the invention and/or a functional part thereof but especially a monoclonal antibody and/or a functional part thereof or a functionally equivalent antibody, for use in treating or alleviating the effects of diseases and disorders which are caused by or associated with amyloid or amyloid-like proteins including amyloidosis, a group of diseases and disorders associated with amyloid plaque formation including secondary amyloidosis and age-related amyloidosis such as diseases including, but not limited to, neurological disorders such as Alzheimer's Disease (AD) and diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration comprising formulating an antibody according to the invention in a pharmaceutically acceptable form.

The antibodies and/or functional parts thereof but especially the monoclonal antibodies and/or functional parts thereof or a functionally equivalent antibody and the compositions and mixtures comprising said antibody according to the present invention may be used for the preparation of a medicament for preventing, treating or alleviating the effects of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes; senile cardiac amyloidosis; endocrine tumors, and others, including macular degeneration.

In a further embodiment of the invention a method is provided for reducing the plaque load in the brain of an animal, particularly a mammal, but especially a human suffering from a disease or condition leading to an increased plaque load in the brain comprising administering to an animal, particularly a mammal, more particularly a human in need of such a treatment, a therapeutically effective amount of an antibody and/or a functional part thereof but especially of the monoclonal antibody and/or a functional part thereof or of a functionally equivalent antibody according to the invention and as described herein before, or a composition or a mixture comprising said antibody.

In particular, the plaque load is reduced by at least 20%, particularly by at least 25%, more particularly by at least 30%, even more particularly by more than 30%.

In a further embodiment of the invention a method for reducing the amount of plaques in the brain of an animal, particularly a mammal, but especially a human suffering from a disease or condition leading to an increased plaque load in the brain comprising administering to an animal, particularly a mammal, more particularly a human in need of such a treatment, a therapeutically effective amount of an antibody and/or a functional part thereof but especially of the monoclonal antibody and/or a functional part thereof or of a functionally equivalent antibody according to the invention and as described herein before, or a composition or a mixture comprising said antibody.

In particular, the amount of plaques in the brain is reduced by at least 10%, particularly by at least 15%, more particularly by more than 15%.

In still another embodiment of the invention a method for decreasing the total amount of soluble $A\beta$ in the brain of an animal, particularly a mammal, but especially a human suffering from a disease or condition leading to increased concentrations of soluble $A\beta$ in the brain comprising administering to an animal, particularly a mammal, more particularly a human in need of such a treatment, a therapeutically effective amount of an antibody and/or a functional part thereof but especially of the monoclonal antibody and/or a functional part thereof or of a functionally equivalent antibody according to the invention and as described herein before, or a composition or a mixture comprising said antibody.

It is an objective of the present invention to provide a method for preventing, treating or alleviating the effects of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes; senile cardiac amyloidosis; endocrine tumors, and others, including macular degeneration, by administering an antibody, but particularly a monoclonal antibody or a composition or mixture comprising such an antibody according to the invention to an animal or a human affected by such a disorder comprising administering to an animal, particularly a mammal, more particularly a human in need of such a treatment, a therapeutically effective amount of an antibody and/or a functional part thereof but especially of the monoclonal antibody and/or a functional part thereof or of a functionally equivalent antibody according to the invention and as described herein before, or a composition or a mixture comprising said antibody.

In a specific embodiment the invention provides a method for retaining or increasing cognitive memory capacity of an animal, particularly a mammal or a human suffering from memory impairment by administering to an animal, particularly a mammal or a human in need of such a treatment, an antibody, but particularly a monoclonal antibody according to the invention or a composition or mixture comprising such an antibody according to the invention and as described herein before.

In another embodiment of the present invention a method is provided for the preparation of a pharmaceutical composition using an antibody according to the invention and/or a functional part thereof but especially a monoclonal antibody and/or a functional part thereof or a functionally equivalent antibody for preventing, treating or alleviating the effects of diseases and disorders which are caused by or associated with amyloid or amyloid-like proteins including amyloidosis, a group of diseases and disorders associated with amyloid plaque formation including secondary amyloidosis and age-related amyloidosis such as diseases including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes; senile cardiac amyloidosis; endocrine tumors, and others, including macular degeneration.

In a specific embodiment the invention provides a method for the preparation of a pharmaceutical composition using an antibody according to the invention and/or a functional part thereof but especially a monoclonal antibody and/or a functional part thereof or a functionally equivalent antibody for retaining or increasing cognitive memory capacity of an animal, particularly a mammal or a human, suffering from memory impairment by administering to an animal, particularly a mammal or a human, an antibody, but particularly a monoclonal antibody or a composition or mixture comprising such an antibody according to the invention and as described herein before.

These and other objects, features and advantages of the present invention will become apparent after a review of the following detailed description of the disclosed embodiment and the appended claims.

BRIEF DESCRIPTION OF FIGURES AND SEQUENCES

Figure 5:
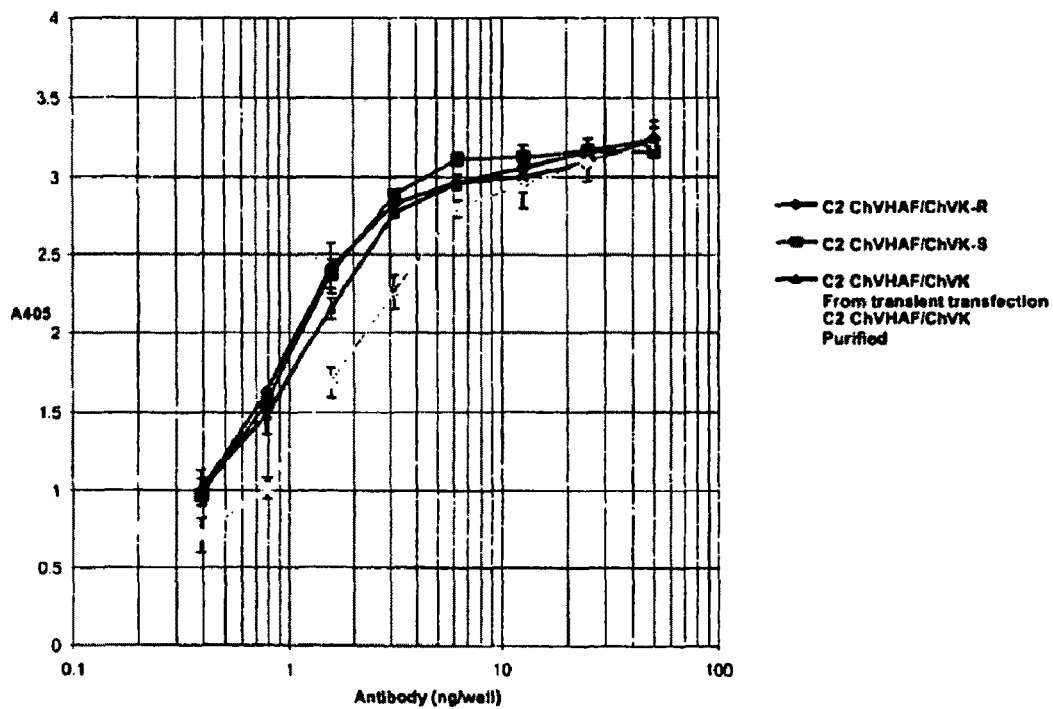
Figure 8:
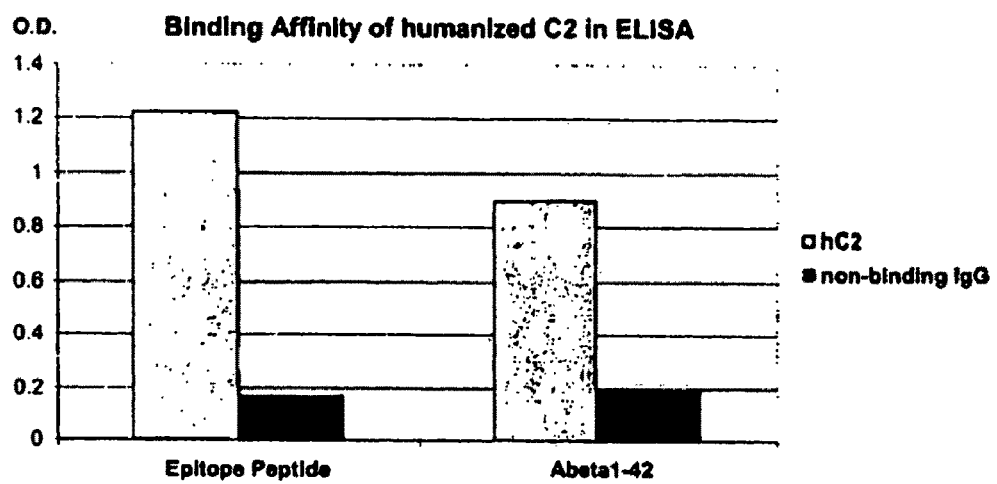
Figure 9:
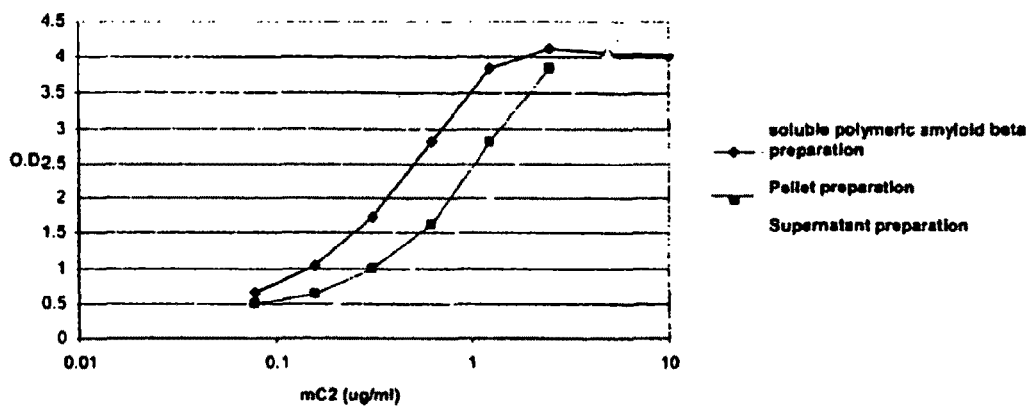
Figure 16:
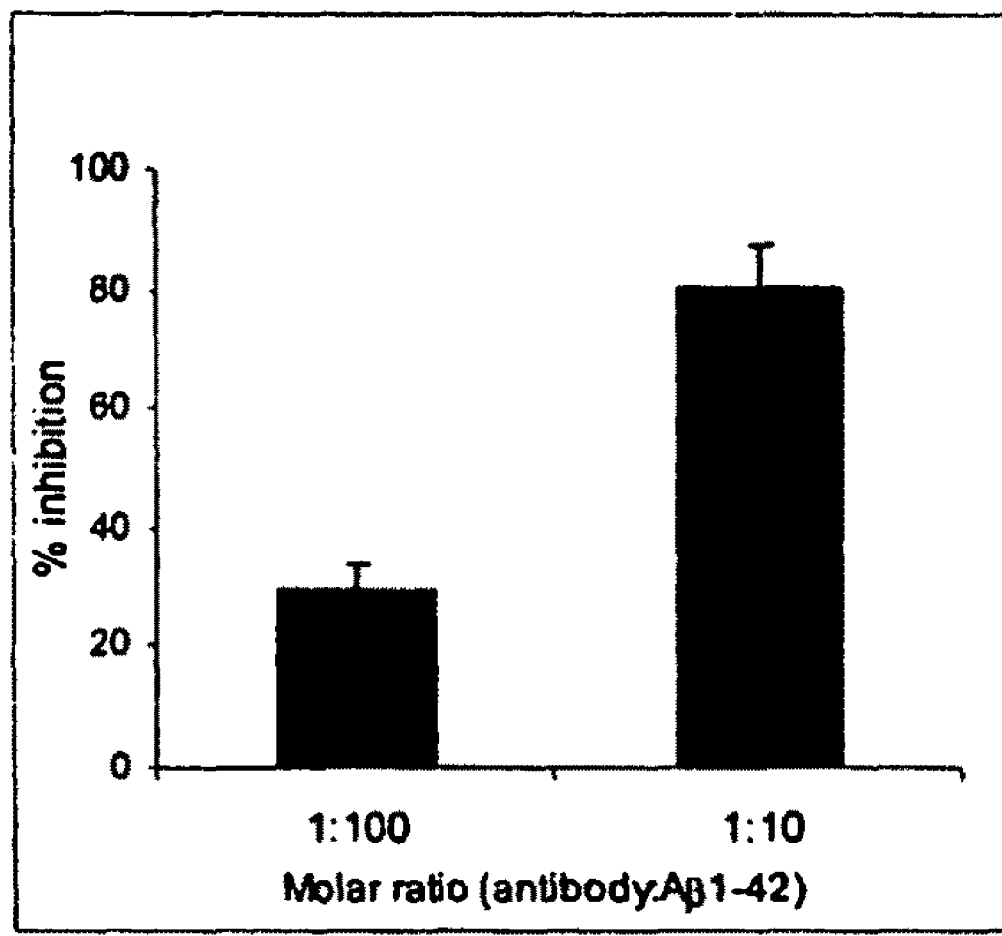
Figure 17:
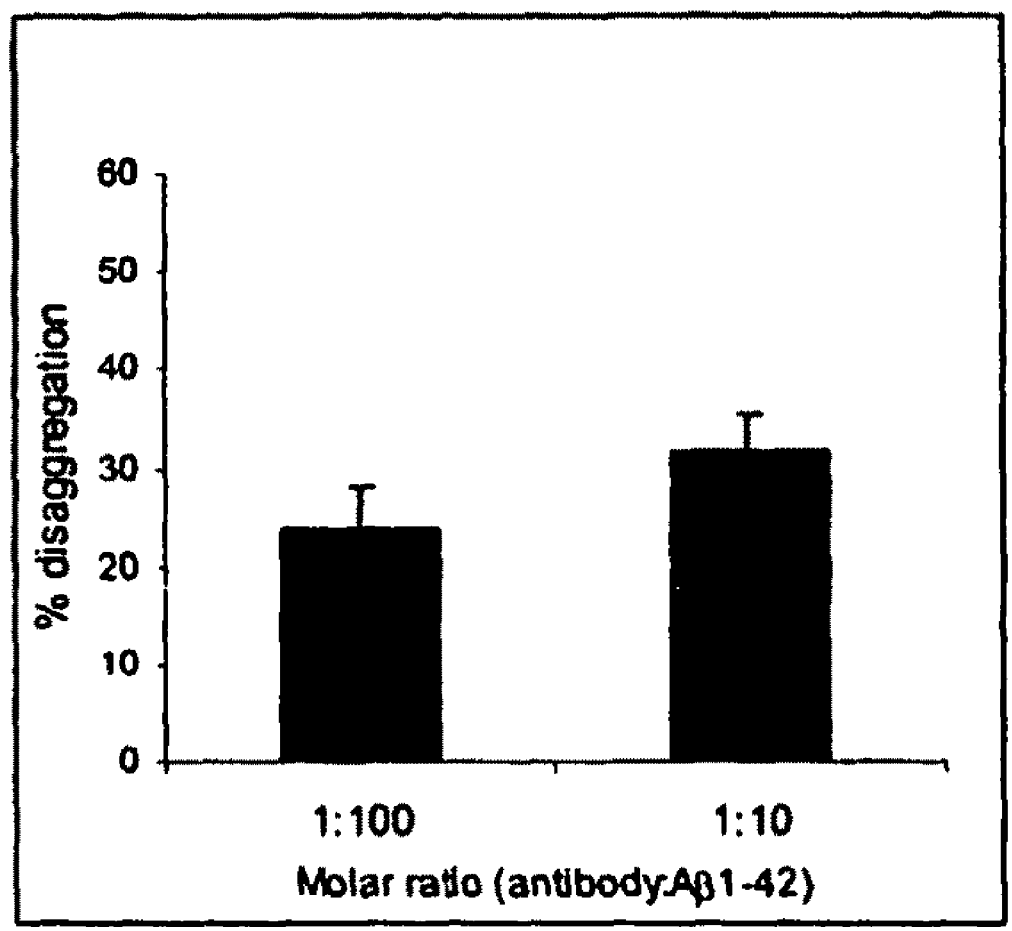
Figure 18:
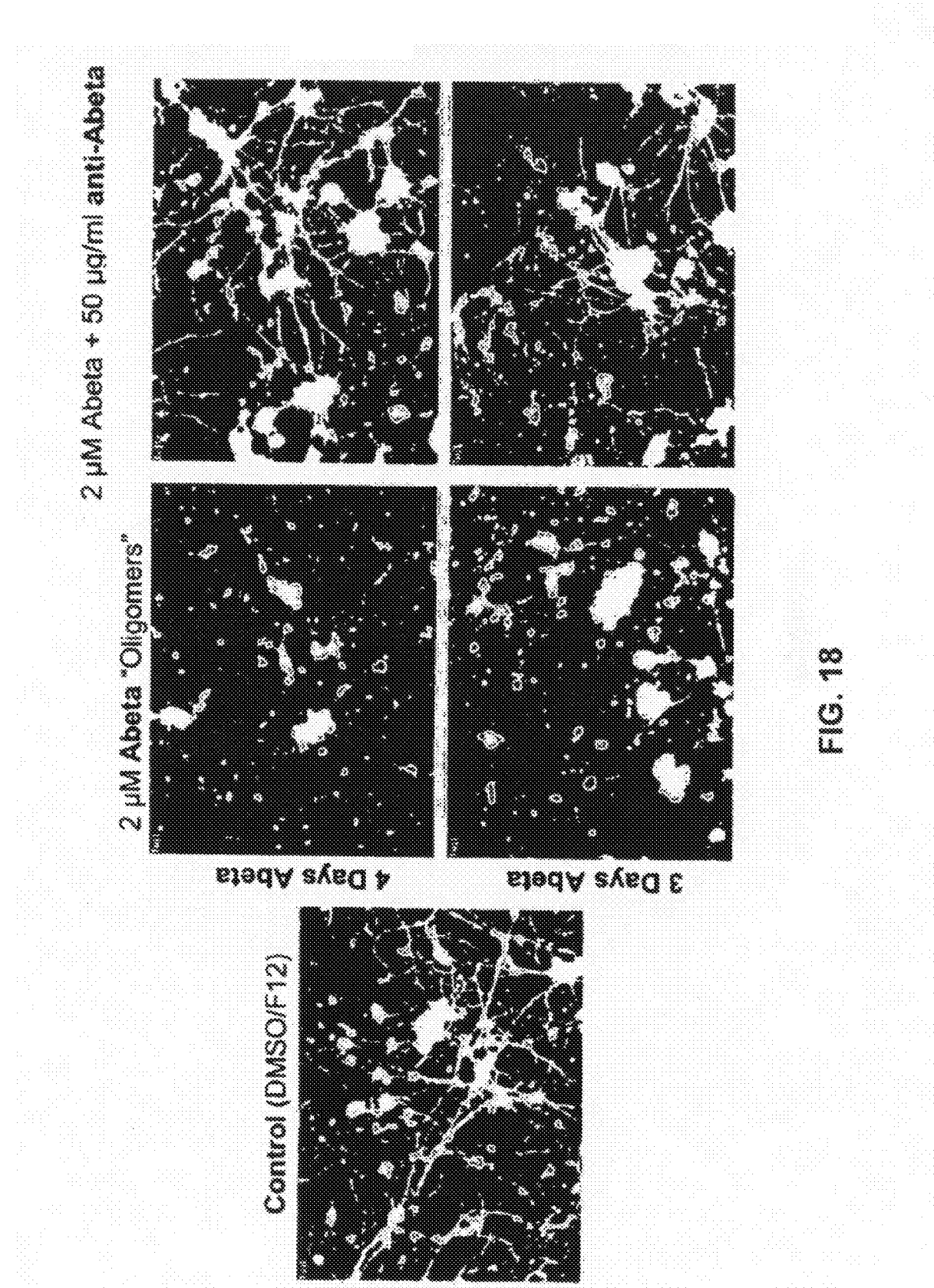
Figure 20A:
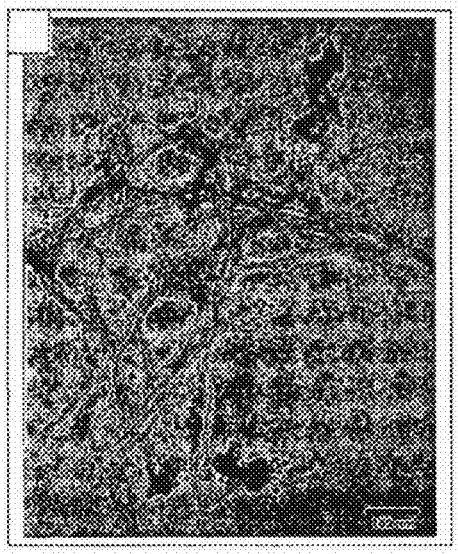
Figure 20B:
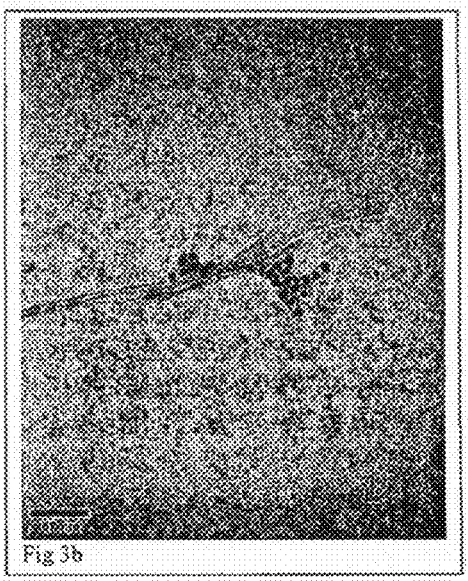

FIG. 1 (Example 2): Expression Cassette of the mouse light chain variable region of the Chimeric Antibody;

FIG. 2 (Example 2): Expression Cassette of the mouse heavy chain variable region of the Chimeric Antibody;

FIG. 3 (Example 5.2): Comparison of the mouse heavy chain variable region to the closest murine germ line sequence;

FIG. 4 (Example 8): Activity of purified humanized C2 antibodies;

FIG. 5 (Example 9): Binding activity of antibodies produced by transient expression of C2 modified CDRL2 constructs in conjunction with C2 chimeric heavy chain, compared to chimeric antibody C2ChVHAF/ChVK, produced by transient transfection and purified antibody;

FIG. 6 (Example 11): Results of Immunohistochemical Binding Assay with chimeric antibody AF and humanized antibody H4K1;

FIG. 7 (Example 12): Functionality of mC2 on Amyloid fibers;

FIG. 8 (Example 12): Binding Affinity of humanized C2 in ELISA;

FIG. 9 (Example 14): Conformation specific binding of mC2 to different classes of amyloid protein. Pellet preparation in the legend to this figure refers to $A\beta_{1-42}$ fibers, supernatant preparation refers to amyloid monomers;

FIG. 10: Humanized C2 VK sequences compared to murine sequence and human acceptor sequences DPK15 AND $J_K 1$;

FIG. 11: Humanized C2 VH sequences compared to murine sequence and human acceptor sequences DP54 AND $J_H 6$;

Figure 12:
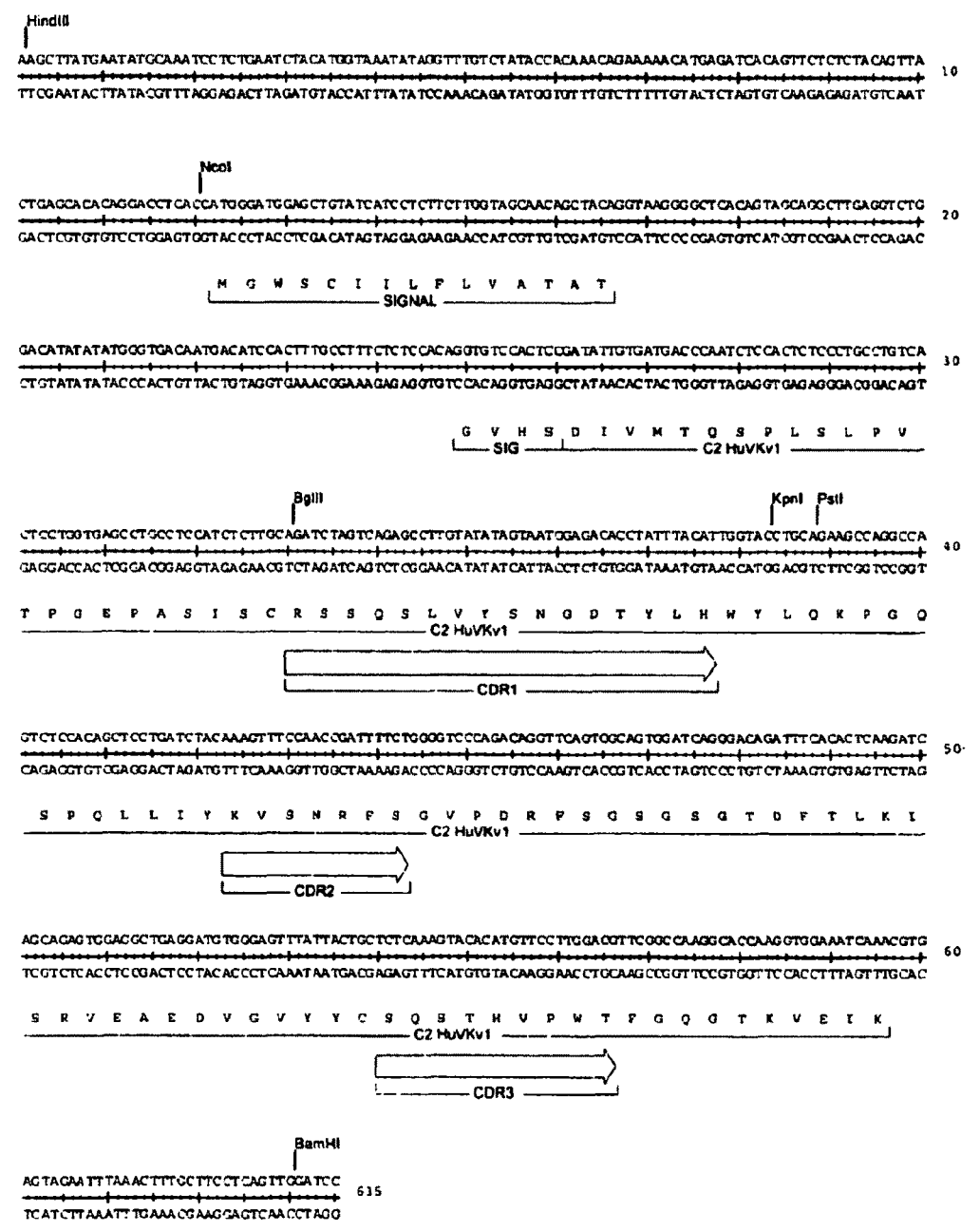

FIG. 12: Complete DNA and protein sequence of light chain variable region of C2 humanized antibody, C2HuVK1;

FIG. 13: Complete DNA and protein sequence of light chain constant region (human C Kappa) of humanized C2 antibody;

FIG. 14: Complete DNA and protein sequence of heavy chain constant region (human IgG4 ser228-pro) of humanized C2 antibody;

FIG. 15A-C (Example 15): Results of Epitope Mapping experiments;

FIG. 16 (Example 13): Results of aggregation assay experiments;

FIG. 17 (Example 13): Results of disaggregation assay experiments;

FIG. 18: (Example 16): Results of neuroprotection experiments with humanized antibody C2;

FIG. 19: Binding of mACI-01-Ab7 C2 monoclonal antibody to amyloid species in Western blot and Dot blot;

FIG. 20: Binding of mACI-01-Ab7 C2 monoclonal antibody to amyloid fibers by transmission electronic microscopy;

FIG. 21: Results of a head-to-head-experiment between Th-T fluorescent assay and solid-state NMR of U-$^{13}$C Tyr10 and Val12-labeled β-amyloid 1-42 peptide.

SEQ ID NO: 1 Amino acid sequence of C2 HuVH AF 4 humanized heavy chain variable region (CDR1)

SEQ ID NO: 2 Amino acid sequence of C2 HuVH AF 4 humanized heavy chain variable region (CDR2)

SEQ ID NO: 3 Amino acid sequence of C2 HuVH AF 4 humanized heavy chain variable region (CDR3)

SEQ ID NO: 4 Amino acid sequence of C2 HuVK 1 humanized light chain variable region (CDR1)

SEQ ID NO: 5 Amino Acid Sequence of C2 HuVK 1 Humanized Light Chain Variable Region (CDR2)

SEQ ID NO: 6 Amino Acid Sequence of C2 HuVK 1 Humanized Light Chain Variable Region (CDR3)

SEQ ID NO: 7 Amino Acid Sequence of Aβ Epitope Region 2

SEQ ID NO: 8 Amino acid sequence of Aβ epitope region 1

SEQ ID NO: 9 Amino acid sequence of Aβ epitope region 2 modified

SEQ ID NO: 10 Amino acid sequence of Aβ epitope region 1 modified

SEQ ID NO: 11 Amino acid sequence of Epitope region modified complete

SEQ ID NO: 12 Amino acid sequence of C2 HuVK 1 humanized light chain variable region SEQ ID NO: 13 Amino acid sequence of C2 humanized light chain SEQ ID NO: 14 Amino acid sequence of humanized C2 light chain constant region SEQ ID NO: 15 Amino acid sequence of C2 HuVH AF 4 humanized heavy chain variable region SEQ ID NO: 16 Amino acid sequence of C2 humanized heavy chain SEQ ID NO: 17: Amino acid sequence of IG GAMMA-4 CHAIN C REGION modified
SEQ ID NO: 18: Nucleotide sequence of CDR2 of C2 HuVH AF 4 humanised heavy chain variable region
SEQ ID NO: 19: Nucleotide sequence of CDR3 of C2 HuVH AF 4 humanised heavy chain variable region
SEQ ID NO: 20: Nucleotide sequence of CDR1 of C2 HuVK 1 humanised light chain variable region
SEQ ID NO: 21: Nucleotide sequence of C2 HuVK 1 humanized light chain variable region
SEQ ID NO: 22: Nucleotide sequence of C2 humanized light chain
SEQ ID NO: 23: Nucleotide sequence of C2 humanized light chain constant region
SEQ ID NO: 24: Nucleotide sequence of C2 HuVH AF 4 humanized heavy chain variable region
SEQ ID NO: 25: Nucleotide sequence of C2 humanized heavy chain
SEQ ID NO: 26: Nucleotide sequence of C2 humanized heavy chain constant region
SEQ ID NO: 27: Amino acid sequence of Mouse C2 Light Chain Variable Region
SEQ ID NO: 28: Amino acid sequence of Mouse C2 Heavy Chain Variable Region
SEQ ID NO: 29: Nucleotide sequence of Mouse C2 Light Chain Variable Region
SEQ ID NO: 30: Nucleotide sequence of Mouse C2 Light Chain
SEQ ID NO: 31: Nucleotide sequence of Mouse C2 Heavy Chain Variable Region
SEQ ID NO: 32: Nucleotide sequence of Mouse C2 Heavy Chain
SEQ ID NO: 33-40: Amino acid sequence variants of epitopic region on the Aβ peptide
SEQ ID NO: 41: Amino acid sequence of Mouse C2 Light Chain
SEQ ID NO: 42: Amino acid sequence of Mouse C2 Heavy Chain
SEQ ID NO: 43: Antigenic peptide $A\beta_{1-15}$
SEQ ID NO: 44: Antigenic peptide $A\beta_{1-16}$
SEQ ID NO: 45: Antigenic peptide $A\beta_{1-16(\Delta 14)}$
SEQ ID NO: 46: Antigenic peptide $A\beta_{22-35}$
SEQ ID NO: 47: Antigenic peptide $A\beta_{29-40}$
SEQ ID NO: 48: Antigenic peptide $A\beta_{1-17}$

DEFINITIONS

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

The language "diseases and disorders which are caused by or associated with amyloid or amyloid-like proteins" includes, but is not limited to, diseases and disorders caused by the presence or activity of amyloid-like proteins in monomeric, fibril, or polymeric state, or any combination of the three. Such diseases and disorders include, but are not limited to, amyloidosis, endocrine tumors, and macular degeneration.

The term "amyloidosis" refers to a group of diseases and disorders associated with amyloid plaque formation including, but not limited to, secondary amyloidosis and age-related amyloidosis such as diseases including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes, and senile cardiac amyloidosis; and various eye diseases including macular degeneration, drusen-related optic neuropathy, and cataract due to beta-amyloid deposition.

The terms "detecting" or "detected" as used herein mean using known techniques for detection of biologic molecules such as immunochemical or histological methods and refer to qualitatively or quantitatively determining the presence or concentration of the biomolecule under investigation.

"Polymeric soluble amyloid" refers to multiple aggregated monomers of amyloid peptides, or of amyloid-like peptides, or of modified or truncated amyloid peptides or of other derivates of amyloid peptides forming oligomeric or polymeric structures which are soluble in the mammalian or human body more particularly in the brain, but particularly to multiple aggregated monomers of amyloid β (Aβ) or of modified or truncated amyloid β (Aβ) peptides or of derivatives thereof, which are soluble in the mammalian or human body more particularly in the brain.

"Amyloid β, Aβ or β-amyloid" is an art recognized term and refers to amyloid β proteins and peptides, amyloid β precursor protein (APP), as well as modifications, fragments and any functional equivalents thereof. In particular, by amyloid as used herein is meant any fragment produced by proteolytic cleavage of APP but especially those fragments which are involved in or associated with the amyloid pathologies including, but not limited to, $A\beta_{1-38}$, $A\beta_{1-39}$, $A\beta_{1-40}$, $A\beta_{1-41}$ $A\beta_{1-42}$ and $A\beta_{1-43}$.

The structure and sequences of the amyloid β peptides as mentioned above are well known to those skilled in the art and methods of producing said peptides or of extracting them from brain and other tissues are described, for example, in Glenner and Wong, Biochem Biophys Res Comm 129, 885-890 (1984). Moreover, amyloid /3 peptides are also commercially available in various forms.

By "isolated" is meant a biological molecule free from at least some of the components with which it naturally occurs.

The terms "antibody" or "antibodies" as used herein are art-recognized terms and are understood to refer to molecules or active fragments of molecules that bind to known antigens, particularly to immunoglobulin molecules and to immunologically active portions of immunoglobulin molecules, i.e molecules that contain a binding site that specifically binds an antigen. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Also subclasses of the heavy chain are known. For example, IgG heavy chains in humans can be any of IgG1, IgG2, IgG3 and IgG4 subclass. The immunoglobulin according to the invention can be of any class (IgG, IgM, IgD, IgE, IgA and IgY) or subclass (IgG1, IgG2, IgG3, IgG4, IgA1 and IgA2) of immunoglobulin molecule.

As used herein "specifically binds" in reference to an antibody means that the antibody binds to its target antigen with greater affinity that it does to a structurally different antigen(s).

A typical immunoglobulin structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as full length intact antibodies or as a number of well-characterized fragments produced by digestion with various peptidases or chemicals. Thus, for example, pepsin digests an antibody below the disulfide linkages in the hinge region to produce F(ab')$_2$, a dimer of Fab which itself is a light chain joined to $V_H$-CH$_1$ by a disulfide bond. The F(ab')$_2$ may be reduced under mild conditions to break the disulfide linkage in the hinge region thereby converting the F(ab')$_2$ dimer into an Fab' monomer. The Fab' monomer is essentially a Fab fragment with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that any of a variety of antibody fragments may be synthesized de novo either chemically or by utilizing recombinant DNA methodology. Thus, the term antibody, as used herein also includes antibody fragments either produced by the modification of whole antibodies or synthesized de novo or antibodies and fragments obtained by using recombinant DNA methodologies.

"Antibodies" are intended within the scope of the present invention to include monoclonal antibodies, polyclonal antibodies, chimeric, single chain, bispecific, simianized, human and humanized antibodies as well as active fragments thereof. Examples of active fragments of molecules that bind to known antigens include separated light and heavy chains, Fab, Fab/c, Fv, Fab', and F(ab')$_2$ fragments, including the products of an Fab immunoglobulin expression library and epitope-binding fragments of any of the antibodies and fragments mentioned above.

These active fragments can be derived from an antibody of the present invention by a number of techniques. For example, monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

Recombinantly made antibodies may be conventional full length antibodies, active antibody fragments known from proteolytic digestion, unique active antibody fragments such as Fv or single chain Fv (scFv), domain deleted antibodies, and the like. An Fv antibody is about 50 Kd in size and comprises the variable regions of the light and heavy chain. A single chain Fv ("scFv") polypeptide is a covalently linked VH::VL heterodimer which may be expressed from a nucleic acid including VH- and VL-encoding sequences either joined directly or joined by a peptide-encoding linker. See Huston, et al. (1988) Proc. Nat. Acad. Sci. USA, 85:5879-5883. A number of structures for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513, 5,132,405 and 4,956,778.

The combining site refers to the part of an antibody molecule that participates in antigen binding. The antigen binding site is formed by amino acid residues of the N-terminal variable ("V") regions of the heavy ("H") and light ("L") chains. The antibody variable regions comprise three highly divergent stretches referred to as "hypervariable regions" or "complementarity determining regions" (CDRs) which are interposed between more conserved flanking stretches known as "framework regions" (FRs). In an antibody molecule, the three hypervariable regions of a light chain (LCDR1, LCDR2, and LCDR3) and the three hypervariable regions of a heavy chain (HCDR1, HCDR2 and HCDR3) are disposed relative to each other in three dimensional space to form an antigen binding surface or pocket. The antibody combining site therefore represents the amino acids that make up the CDRs of an antibody and any framework residues that make up the binding site pocket.

The identity of the amino acid residues in a particular antibody that make up the combining site can be determined using methods well known in the art. For example, antibody CDRs may be identified as the hypervariable regions originally defined by Kabat et al. (see, "Sequences of Proteins of Immunological Interest," E. Kabat et al., U.S. Department of Health and Human Services; Johnson, G and Wu, T T (2001) Kabat Database and its applications: future directions. Nucleic Acids Research, 29: 205-206; http://immuno.bme.nwa.edu). The positions of the CDRs may also be identified as the structural loop structures originally described by Chothia and others, (see Chothia and Lesk, J. Mol. Biol. 196, 901 (1987), Chothia et al., Nature 342, 877 (1989), and Tramontano et al., J. Mol. Biol. 215, 175 (1990)). Other methods include the "AbM definition" which is a compromise between Kabat and Chothia and is derived using Oxford Molecular's AbM antibody modeling software (now Accelrys) or the "contact definition" of CDRs by Macallum et al., ("Antibody-antigen interactions: contact analysis and binding site topography," J Mol Biol. 1996 Oct. 11; 262(5):732-45). The following chart identifies CDRs based upon various known definitions.

| Loop | Kabat | AbM | Chothia | Contact |
|---|---|---|---|---|
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B | H26--H35B | H26--H32 . . . 34 | H30--H35B |
| | | (Kabat Numbering) | | |
| H1 | H31--H35 | H26--H35 | H26--H32 | H30--H35 |
| | | (Chothia Numbering) | | |
| H2 | H50--H65 | H50--H58 | H52--H56 | H47--H58 |
| H3 | H95--H102 | H95--H102 | H95--H102 | H93--H101 |

General guidelines by which one may identify the CDRs in an antibody from sequence alone are as follows:

LCDR1:

Start—Approximately residue 24.

Residue before is always a Cys.

Residue after is always a Trp. Typically TRP is followed with TYR-GLN, but also may be followed by LEU-GLN, PHE-GLN, or TYR-LEU.

Length is 10 to 17 residues.

LCDR2:

Start—16 residues after the end of L1.

Sequence before is generally ILE-TYR, but also may be VAL-TYR, ILE-LYS, or ILE-PHE.

Length is generally 7 residues.

LCDR3:

Start—generally 33 residues after end of L2.

Residue before is a Cys.

Sequence after is PHE-GLY-X-GLY.

Length is 7 to 11 residues.

HCDR1:

Start—at approximately residue 26 (four residues after a CYS) [Chothia/AbM definition] Kabat definition starts 5 residues later.

Sequence before is CYS-X-X-X.

Residues after is a TRP, typically followed by VAL, but also followed by ILE, or ALA.

Length is 10 to 12 residues under AbM definition while Chothia definition excludes the last 4 residues.

HCDR2:

Start—15 residues after the end of Kabat/AbM definition of CDR-H1.

Sequence before typically LEU-GLU-TRP-ILE-GLY (SEQ ID NO. 1), but a number of variations are possible.

Sequence after is LYS/ARG-LEU/ILE/VAL/PHE/THR/ALA-THR/SER/ILE/ALA

Length is 16 to 19 residues under Kabat definition (AbM definition ends 7 residues earlier).

HCDR3:

Start—33 residues after end of CDR-H2 (two residues after a CYS).

Sequence before is CYS-X-X (typically CYS-ALA-ARG).

Sequence after is TRP-GLY-X-GLY.

Length is 3 to 25 residues.

The identity of the amino acid residues in a particular antibody that are outside the CDRs, but nonetheless make up part of the combining site by having a side chain that is part of the lining of the combining site (i.e., it is available to linkage through the combining site), can be determined using methods well known in the art such as molecular modeling and X-ray crystallography. See e.g., Riechmann et al., (1988) Nature, 332:323-327.

Chimeric antibodies are those in which one or more regions of the antibody are from one species of animal and one or more regions of the antibody are from a different species of animal. A preferred chimeric antibody is one which includes regions from a primate immunoglobulin. A chimeric antibody for human clinical use is typically understood to have variable regions from a non-human animal, e.g. a rodent, with the constant regions from a human. In contrast, a humanized antibody uses CDRs from the non-human antibody with most or all of the variable framework regions from and all the constant regions from a human immunoglobulin. A human chimeric antibody is typically understood to have the variable regions from a rodent. A typical human chimeric antibody has human heavy constant regions and human light chain constant regions with the variable regions of both the heavy and light coming from a rodent antibody. A chimeric antibody may include some changes to a native amino acid sequence of the human constant regions and the native rodent variable region sequence. Chimeric and humanized antibodies may be prepared by methods well known in the art including CDR grafting approaches (see, e.g., U.S. Pat. Nos. 5,843,708; 6,180,370; 5,693,762; 5,585,089; 5,530,101), chain shuffling strategies (see e.g., U.S. Pat. No. 5,565,332; Rader et al., Proc. Natl. Acad. Sci. USA (1998) 95:8910-8915), molecular modeling strategies (U.S. Pat. No. 5,639,641), and the like.

A "humanized antibody" as used herein in the case of a two chain antibody is one where at least one chain is humanized. A humanized antibody chain has a variable region where one or more of the framework regions are human. A humanized antibody which is a single chain is one where the chain has a variable region where one or more of the framework regions are human. The non-human portions of the variable region of the humanized antibody chain or fragment thereof is derived from a non-human source, particularly a non-human antibody, typically of rodent origin. The non-human contribution to the humanized antibody is typically provided in form at least one CDR region which is interspersed among framework regions derived from one (or more) human immunoglobulin(s). In addition, framework support residues may be altered to preserve binding affinity.

The humanized antibody may further comprise constant regions (e.g., at least one constant region or portion thereof, in the case of a light chain, and preferably three constant regions in the case of a heavy chain). The constant regions of a humanized antibody if present generally are human.

Methods to obtain "humanized antibodies" are well known to those skilled in the art. (see, e.g., Queen et al., Proc. Natl Acad Sci USA, 86:10029-10032 (1989), Hodgson et al., Bio/Technology, 9:421 (1991)).

A "humanized antibody" may also be obtained by a novel genetic engineering approach that enables production of affinity-matured human-like polyclonal antibodies in large animals such as, for example, rabbits and mice. See, e.g. U.S. Pat. No. 6,632,976.

The term constant region (CR) as used herein refers to constant regions genes of the immunoglobulin. The constant region genes encode the portion of the antibody molecule which confers effector functions. For Chimeric human antibodies and humanized antibodies, typically non-human (e.g., murine), constant regions are substituted by human constant regions. The constant regions of the subject chimeric or humanized antibodies are typically derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region, antibodies with desired effector function can be produced. Constant regions that may be used within the scope of this invention are gamma 1 (IgG1), particularly an Fc region of the gamma 1 (IgG1) isotype, gamma 3 (IgG3) and especially gamma 4 (IgG4). The light chain constant region can be of the kappa or lambda type, preferably of the kappa type. In one embodiment the light chain constant region is the human kappa constant chain (Heiter et al. (1980) Cell 22:197-207) and the heavy constant chain is the human IgG4 constant chain.

The term "monoclonal antibody" is also well recognized in the art and refers to an antibody that is the product of a single cloned antibody producing cell. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces the antibody.

For the purpose of the present invention, "monoclonal antibody" is also to be understood to comprise antibodies that are produced by a mother clone which has not yet reached full monoclonality.

"Functionally equivalent antibody" is understood within the scope of the present invention to refer to an antibody which substantially shares at least one major functional property with an antibody mentioned above and herein described comprising: binding specificity to the β-amyloid protein, particularly to the $A\beta_{1-42}$ protein, and more particularly to the 16-21 epitope region of the $A\beta_{1-42}$ protein, immunoreactivity in vitro, inhibition of aggregation of the $A\beta_{1-42}$ monomers into high molecular polymeric fibrils and/or disaggregation of preformed $A\beta_{1-42}$ polymeric fibrils, and/or a β-sheet breaking property and alleviating the effects of amyloidosis, a group of diseases and disorders associated with amyloid plaque formation including secondary amyloidosis and age-related amyloidosis such as diseases including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration, when administered prophylactically or therapeutically. The antibodies can be of any class such as IgG, IgM, or IgA, etc or any subclass such as IgG1, IgG2a, etc and other subclasses mentioned herein above or known in the art, but particularly of the IgG4 class. Further, the antibodies can be produced by any method, such as phage display, or produced in any organism or cell line, including bacteria, insect, mammal or other type of cell or cell line which produces antibodies with desired characteristics, such as humanized antibodies. The antibodies can also be formed by combining a Fab portion and an Fc region from different species.

The term "hybridize" as used refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 70° C., preferably at 65° C. (regarding the definition of SSPE, SSC and Denhardts solution see Sambrook et al. loc. cit.). Stringent hybridization conditions as for instance described in Sambrook et al, supra, are particularly preferred. Particularly preferred stringent hybridization conditions are for instance present if hybridization and washing occur at 65° C. as indicated above. Non-stringent hybridization conditions, for instance with hybridization and washing carried out at 45° C. are less preferred and at 35° C. even less.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

The antibody according to the invention may be an immunoglobulin or antibody, which is understood to have each of its binding sites identical (if multivalent) or, in the alternative, may be a "bispecific" or "bifunctional antibody".

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc and/or Fv fragments. The term "antigen-binding fragment" refers to a polypeptide fragment of an immunoglobulin or antibody that binds antigen or competes with intact antibody (i.e., with the intact antibody from which they were derived) for antigen binding (i.e., specific binding).

Binding fragments are produced by recombinant DNA techniques, or by enzymatic or chemical cleavage of intact immunoglobulins. Binding fragments include Fab, Fab', $F(ab')_2$, Fabc, Fv, single chains, and single-chain antibodies.

"Fragment" also refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide.

The term "antigen" refers to an entity or fragment thereof which can bind to an antibody. An immunogen refers to an antigen which can elicit an immune response in an organism, particularly an animal, more particularly a mammal including a human. The term antigen includes regions known as antigenic determinants or epitopes which refers to a portion of the antigen (which are contacted or which play a significant role in supporting a contact reside in the antigen responsible for antigenicity or antigenic determinants.

As used herein, the term "soluble" means partially or completely dissolved in an aqueous solution.

Also as used herein, the term "immunogenic" refers to substances which elicit the production of antibodies, T-cells and other reactive immune cells directed against an antigen of the immunogen.

An immune response occurs when an individual produces sufficient antibodies, T-cells and other reactive immune cells against administered immunogenic compositions of the present invention to moderate or alleviate the disorder to be treated.

The term immunogenicity as used herein refers to a measure of the ability of an antigen to elicit an immune response (humoral or cellular) when administered to a recipient. The present invention is concerned with approaches that reduce the immunogenicity of the subject human chimeric or humanized antibodies.

Humanized antibody of reduced immunogenicity refers to a humanized antibody exhibiting reduced immunogenicity relative to the parent antibody, e.g., the murine antibody.

Humanized antibody substantially retaining the binding properties of the parent antibody refers to a humanized antibody which retains the ability to specifically bind the antigen recognized by the parent antibody used to produce such humanized antibody. Preferably the humanized antibody will exhibit the same or substantially the same antigen-binding affinity and avidity as the parent antibody. Ideally, the affinity of the antibody will not be less than 10% of the parent antibody affinity, more preferably not less than about 30%, and most preferably the affinity will not be less than 50% of the parent antibody. Methods for assaying antigen-binding affinity are well known in the art and include half-maximal binding assays, competition assays, and Scatchard analysis. Suitable antigen binding assays are described in this application.

A "back mutation" is a mutation introduced in a nucleotide sequence which encodes a humanized antibody, the mutation results in an amino acid corresponding to an amino acid in the parent antibody (e.g., donor antibody, for example, a murine antibody). Certain framework residues from the parent antibody may be retained during the humanization of the antibodies of the invention in order to substantially retain the binding properties of the parent antibody, while at the same time minimizing the potential immunogenicity of the resultant antibody. In one embodiment of the invention, the parent antibody is of mouse origin. For example, the back mutation changes a human framework residue to a parent murine residue. Examples of framework residues that may be back mutated include, but are not limited to, canonical residues, interface packing residues, unusual parent residues which are close to the binding site, residues in the "Vernier Zone" (which forms a platform on which the CDRs rest) (Foote & Winter, 1992, *J. Mol. Biol.* 224, 487-499), and those close to CDR H3.

As used herein a "conservative change" refers to alterations that are substantially conformationally or antigenically neutral, producing minimal changes in the tertiary structure of the mutant polypeptides, or producing minimal changes in the antigenic determinants of the mutant polypeptides, respectively, as compared to the native protein. When referring to the antibodies and antibody fragments of the invention, a conservative change means an amino acid substitution that does not render the antibody incapable of binding to the subject receptor. Those of ordinary skill in the art will be able to predict which amino acid substitutions can be made while maintaining a high probability of being conformationally and antigenically neutral. Such guidance is provided, for example in Berzofsky, (1985) *Science* 229:932-940 and Bowie et al. (1990) *Science* 247:1306-1310. Factors to be considered that affect the probability of maintaining conformational and antigenic neutrality include, but are not limited to: (a) substitution of hydrophobic amino acids is less likely to affect antigenicity because hydrophobic residues are more likely to be located in a protein's interior; (b) substitution of physiochemically similar, amino acids is less likely to affect conformation because the substituted amino acid structurally mimics the native amino acid; and (c) alteration of evolutionarily conserved sequences is likely to adversely affect conformation as such conservation suggests that the amino acid sequences may have functional importance. One of ordinary skill in the art will be able to assess alterations in protein conformation using well-known assays, such as, but not limited to microcomplement fixation methods (Wasserman et al. (1961) J. Immunol. 87:290-295; Levine et al. (1967) Meth. Enzymol. 11:928-936) and through binding studies using conformation-dependent monoclonal antibodies (Lewis et al. (1983) Biochem. 22:948-954).

Further, the term "therapeutically effective amount" refers to the amount of antibody which, when administered to a human or animal, which is sufficient to result in a therapeutic effect in said human or animal. The effective amount is readily determined by one of skill in the art following routine procedures.

As used herein, the terms "treat," "prevent," "preventing," and "prevention" refer to the prevention of the recurrence or onset of one or more symptoms of a disorder in a subject resulting from the administration of a prophylactic or therapeutic agent.

Construction of Humanized Antibodies

The present invention may be understood more readily by reference to the following detailed description of specific embodiments included herein. Although the present invention has been described with reference to specific details of certain embodiments, thereof, it is not intended that such details should be regarded as limitations upon the scope of the invention.

The present invention provides novel methods and compositions comprising highly specific and highly effective antibodies having the ability to specifically recognize and bind to specific epitopes from a range of β-amyloid antigens. The antibodies enabled by the teaching of the present invention are particularly useful for the treatment of amyloidosis, a group of diseases and disorders associated with amyloid plaque formation including secondary amyloidosis and age-related amyloidosis including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, hereditary cerebral hemorrhage with amyloidosis Dutch type, Parkinson's disease, HIV-related dementia, ALS (amyotropic lateral sclerosis), Adult Onset Diabetes; senile cardiac amyloidosis; endocrine tumors, and others, including macular degeneration, to name just a few.

A fully humanized or reshaped variable region according to the present invention may be created within the scope of the invention by first designing a variable region amino acid sequence that contains non-human-, particularly rodent-derived CDRs, but especially CDRs derived from murine antibody ACI-01-Ab7C2 (named "mC2" throughout the application and deposited 1 Dec. 2005 with the "Deutsche Sammlung von Mikroorganismen and Zellkulturen GmbH (DSMZ) in Braunschweig, Mascheroder Weg 1 B, 38124 Branuschweig, under the provisions of the Budapest Treaty and given accession no DSM ACC2750) embedded in human-derived framework sequences. The non-human-, particularly the rodent-derived CDRs, which may be obtained from the antibody according to the present invention, provide the desired specificity. Accordingly, these residues are to be included in the design of the reshaped variable region essentially unchanged. Any modifications should thus be restricted to a minimum and closely watched for changes in the specificity and affinity of the antibody. On the other hand, framework residues in theory can be derived from any human variable region.

In order to create a reshaped antibody which shows an acceptable or an even improved affinity, a human framework sequences should be chosen, which is equally suitable for creating a reshaped variable region and for retaining antibody affinity.

In order to achieve this goal, the best-fit strategy was developed. As it is known that the framework sequences serve to hold the CDRs in their correct spatial orientation for interaction with antigen, and that framework residues can sometimes even participate in antigen binding, this strategy aims at minimizing changes that may negatively effect the three-dimensional structure of the antibody by deriving the human framework sequence used for antibody reshaping from the human variable region that is most homologous or similar to the non-human-, particularly the rodent-derived variable region. This will also maximise the likelihood that affinity will be retained in the reshaped antibody.

At its simplest level, the "best fit" strategy involves comparing the donor rodent V-region with all known human V-region amino acid sequences, and then selecting the most homologous to provide the acceptor framework regions for the humanization exercises. In reality there are several other factors which should be considered, and which may influence the final selection of acceptor framework regions. Molecular modelling predictions may be used in this regard prior to any experimental work in an attempt to maximise the affinity of the resultant reshaped antibody. Essentially, the goal of the modelling is to predict which key residues (if any) of the most homologous human framework should be left as in the rodent to obtain the best affinity in the reshaped antibody.

In one embodiment of the invention, the CDRs are obtainable from mouse monoclonal antibody, particularly from mouse monoclonal antibody ACI-01-Ab7C2 (named "mC2" throughout the application) described in co-pending application EP 05 02 7092.5 filed Dec. 12, 2005, the disclosure of which is incorporated herein by reference.

Hybridoma cells FP-12H3-C2, producing mouse monoclonal antibody ACI-01-Ab7C2 (named "mC2" and hC2 for the humanized C2 antibody, throughout the application) were deposited 1 Dec. 2005 in co-pending application no EP05027092.5 with the "Deutsche Sammlung von Mikroorganismen and Zellkulturen GmbH (DSMZ) in Braunschweig, Mascheroder Weg 1 B, 38124 Braunschweig, under the provisions of the Budapest Treaty and given accession no DSM ACC2750.

The mouse antibody may be raised against a supramolecular antigenic construct comprising an antigenic peptide corresponding to the amino acid sequence of the β-amyloid peptide, particularly of β-amyloid peptide $A\beta_{1-15}$, $A\beta_{1-16}$ and $A\beta_{1-16(\Delta 14)}$, modified with a hydrophobic moiety such as, for example, palmitic acid or a hydrophilic moiety such as, for example, polyethylene glycol (PEG) or a combination of both, wherein the hydrophobic and hydrophilic moiety, respectively, is covalently bound to each of the termini of the antigenic peptide through at least one, particularly one or two amino acids such as, for example, lysine, glutamic acid and cysteine or any other suitable amino acid or amino acid analogue capable of serving as a connecting device for coupling the hydrophobic and hydrophilic moiety to the peptide fragment. When a PEG is used as the hydrophilic moiety, the free PEG termini is covalently bound to phosphatidylethanolamine or any other compound suitable to function as the anchoring element, for example, to embed the antigenic construct in the bilayer of a liposome.

In particular, a mouse antibody may be raised against a supramolecular antigenic construct comprising an antigenic peptide corresponding to the amino acid sequence of the β-amyloid peptide $A\beta_{1-16}$ modified with a hydrophilic moiety such as, for example, polyethylene glycol (PEG) hydrophilic moiety is covalently bound to each of the termini of the antigenic peptide through at least one, particularly one or two amino acids such as, for example, lysine, glutamic acid and cysteine or any other suitable amino acid or amino acid analogue capable of serving as a connecting device for coupling the hydrophobic and hydrophilic moiety to the peptide fragment. When a PEG is used as the hydrophilic moiety, the free PEG termini are covalently bound to phosphatidylethanolamine or any other compound suitable to function as the anchoring element, for example, to embed the antigenic construct in the bilayer of a liposome.

In an embodiment of the invention, a chimeric antibody or a fragment thereof, or a humanized antibody or a fragment thereof is provided which comprises in the variable region at least one CDR of non-human origin embedded in one or more human- or primate-derived framework regions and combined with a constant region derived from a human or primate source antibody, which chimeric antibody or a fragment thereof, or a humanized antibody or a fragment thereof is capable of specifically recognizing and binding β-amyloid monomeric peptide.

The CDRs contain the residues most likely to bind antigen and must be retained in the reshaped antibody. CDRs are defined by sequence according to Kabat et al., Sequence of Proteins of Immunological Interest, 5th Edition, The United States Department of Health and Human Services, The United States Government Printing Office, 1991. CDRs fall into canonical classes (Chothia et al, 1989 Nature, 342, 877-883) where key residues determine to a large extent the structural conformation of the CDR loop. These residues are almost always retained in the reshaped antibody.

In the process for preparing a humanized antibody according to the invention, the amino acid sequences of the C2 heavy chain and light chain variable regions ($V_H$ and $V_K$) are compared to rodent antibody $V_H$ and $V_K$ sequences in the NCBI and Kabat databases.

The closest match mouse germ line gene to C2 $V_K$ is bb1, Locus MMU231201, (Schable et al, 1999). A comparison reveals that two amino acids differ from this germ line sequence, both located within CDRL1. Mature murine antibodies with similar, but not identical, sequence can be found. Several have an identical CDRL2 and identical CDRL3, but the CDRL1 of C2 seems to be unique. Comparison with human germ line $V_K$ sequences shows that genes from subgroup $V_K$II are the best match for C2 $V_K$ (Cox et al, 1994). C2 $V_K$ can thus be assigned to Kabat subgroup $MuV_K$II.Sequence.

DPK15 together with the human J region $HuJ_K1$ may be selected to provide the acceptor framework sequences for the humanized $V_K$.

The residues at the interface between the variable light and heavy chains have been defined (Chothia et al, 1985 *J. Mol. Biol.*, 186, 651-663). These are usually retained in the reshaped antibody. The Phe at position 87 of mouse C2 $V_K$ is unusual at the interface, where a Tyr is more common in the $V_K$II subgroup, indicating that this framework residue may be important for antibody activity. Tyr 87 is present in the human germline and humanized C2VK.

The humanized $V_K$ sequences thus may be designed such that the C2HuVK1 consists of mouse C2 $V_K$ CDRs with frameworks from DPK 15 and human $J_K1$. In a specific embodiment of the invention, murine residues may be substituted in the human framework region at positions 45, and/or 87. In the CDR2 region obtainable from a mouse monoclonal antibody, particularly murine antibody ACI-01-Ab7C2, amino acid substitutions may be made at Kabat positions 50 and/or 53. Residue 45 may be involved in supporting the conformation of the CDRs. Residue 87 is located at the interface of the $V_H$ and $V_K$ domains. Therefore these residues may be critical for maintenance of antibody binding.

The closest match mouse germ line gene to C2 $V_H$ AF is VH7183, Locus AF120466, (Langdon et al, 2000). Comparison with human germ line $V_H$ sequences shows that genes from subgroup $V_H$III are the best match for C2 $V_H$. C2 $V_H$ AF can be assigned to Kabat subgroup $MuV_H$IIID. Sequence DP54 together with the human J region $HuJ_H6$ can be selected to provide the acceptor framework sequences for the humanized $V_H$.

The comparison shows that there are nine amino acid differences between the C2 VH sequences and the human acceptor germ line sequence DP54 and $J_H6$, most being located within CDRH2. Mature murine antibodies with identical or similar (one residue different) CDRH1 or with similar CDRH2 (one residue different) are found, but none with all three CDRs identical to C2 $V_H$ AF. CDRH3 of C2 antibody is unusually short, consisting of only three residues. However, other antibodies are found in the database with CDRH3 of this length. Residue 47 of C2 $V_H$ is Leu rather than the more common Trp, and residue 94 is Ser rather than the normal Arg, indicating that these framework residues may be important for antibody activity.

Various humanized $V_H$ sequences may be designed. C2HuVH1 consists of C2 $V_H$ AF CDRs with frameworks from DP54 and $HuJ_H6$. In a specific embodiment of the invention, murine residues may be substituted in the human framework region at positions 47 or 94 or both. Residue 47 in framework 2 makes contact both with the CDRs and with the $V_K$ domain. Residue 94 may be involved in supporting the conformation of the CDRs. Therefore these residues may be critical for maintenance of antibody binding.

Different HCVR and LCVR regions may be designed which comprise the non-human CDRs obtainable from the donor antibody, for example, a murine antibody, embedded into the native or modified human- or primate-derived framework regions. The modification may particularly concern an exchange of one or more amino acid residues within the framework region by non-human residues, particularly murine residues, more commonly found in this position in the respective subgroups or by residues which have similar properties to the ones more commonly found in this position in the respective subgroups.

The modification of the framework region the framework sequences serve to hold the CDRs in their correct spatial orientation for interaction with antigen, and that framework residues can sometimes even participate in antigen binding. In one embodiment of the invention measures are taken to further adapt the selected human framework sequences to make them most similar to the sequences of the rodent frameworks in order to maximise the likelihood that affinity will be retained in the reshaped antibody.

Accordingly, murine residues in the human framework region may be substituted. In particular, murine residues may be substituted in the human framework region of the Heavy Chain Variable (HCVR) region at positions 47 or 94 or both and in the human framework region of the Light Chain Variable (LCVR) region at positions 45 and/or 87. In the CDR2 region obtainable from a mouse monoclonal antibody, particularly murine antibody ACI-01-Ab7C2, amino acid substitutions may be made at Kabat positions 50 and/or 53.

The residues found in the above indicated positions in the human framework region may be exchanged by murine residues more commonly found in this position in the respective subgroups. In particular, the Trp in Kabat position 47 in the human- or primate-derived framework region of the Heavy Chain Variable Region as shown in SEQ ID NO: 15 may be replaced by an Leu or by an amino acid residue that has similar properties and the substitution of which leads to alterations that are substantially conformationally or antigenically neutral, producing minimal changes in the tertiary structure of the mutant polypeptides, or producing minimal changes in the antigenic determinants. In particular, the Trp in Kabat position 47 in the human- or primate-derived framework region of the Heavy Chain Variable Region as shown in SEQ ID NO: 15 may further be replaced by an amino acid selected from the group consisting of norleucine, Ile, Val, Met, Ala, and Phe, particularly by Ile. Alternative conservative substitutions may be contemplated which are conformationally and antigenically neutral.

The Arg in Kabat position 94 in the human- or primate-derived framework region of the Heavy Chain Variable Region as shown in SEQ ID NO: 15 may be replaced by Ser or by an amino acid residue that has similar properties and the substitution of which leads to alterations that are substantially conformationally or antigenically neutral, producing minimal changes in the tertiary structure of the mutant polypeptides, or producing minimal changes in the antigenic determinants. In particular, the Arg in Kabat position 94 in the human- or primate-derived framework region of the Heavy Chain Variable Region as shown in SEQ ID NO: 15 may alternatively be replaced by Thr.

In another embodiment of the invention, both residues may be replaced in the humanized antibody.

The Gln in Kabat position 45 in the human- or primate-derived framework region of the Light Chain Variable Region as shown in SEQ ID NO: 12 may be replaced by Lys or by an amino acid residue that has similar properties and the substitution of which leads to alterations that are substantially conformationally or antigenically neutral, producing minimal changes in the tertiary structure of the mutant polypeptides, or producing minimal changes in the antigenic determinants. In particular, the Gln in Kabat position 45 in the human- or primate-derived framework region of the Light Chain Variable Region as shown in SEQ ID NO: 12 may be replaced by an amino acid selected from the group consisting of Arg, Gln, and Asn, particularly by Arg.

The Leu in Kabat position 50 in the human- or primate-derived framework region of the Light Chain Variable Region as shown in SEQ ID NO: 12 may be replaced by Lys or by an amino acid residue that has similar properties and the substitution of which leads to alterations that are substantially conformationally or antigenically neutral, producing minimal changes in the tertiary structure of the mutant polypeptides, or producing minimal changes in the antigenic determinants. In particular, the Leu in Kabat position 50 in the human- or primate-derived framework region of the Light Chain Variable Region as shown in SEQ ID NO: 12 may be replaced by an amino acid selected from the group consisting of Arg, Gln, and Asn, particularly by Arg.

The Asn in Kabat position 53 in the human- or primate-derived framework region of the Light Chain Variable Region as shown in SEQ ID NO: 12 may be replaced by His and Gln or by an amino acid residue that has similar properties and the substitution of which leads to alterations that are substantially conformationally or antigenically neutral, producing minimal changes in the tertiary structure of the mutant polypeptides, or producing minimal changes in the antigenic determinants. In particular, the Asn in Kabat position 53 in the human- or primate-derived framework region of the Light Chain Variable Region as shown in SEQ ID NO: 12 may be replaced by an amino acid selected from the group consisting of Gln, His, Lys and Arg.

The Thr in Kabat position 87 in the human- or primate-derived framework region of the Light Chain Variable Region as shown in SEQ ID NO: 12 may be replaced by Phe or by an amino acid residue that has similar properties and the substitution of which leads to alterations that are substantially conformationally or antigenically neutral, producing minimal changes in the tertiary structure of the mutant polypeptides, or producing minimal changes in the antigenic determinants. In particular, the Tyr in Kabat position 87 in the human- or primate-derived framework region of the Light Chain Variable Region as shown in SEQ ID NO: 12 may be replaced by an amino acid selected from the group consisting of Leu, Val, Ile, and Ala, particularly by Leu.

The so obtained variable region comprising at least one CDR of non-human origin embedded in one or more human- or primate-derived framework regions may then be combined with a constant region derived from a human or primate source antibody, particularly with human IgG4 or κ constant regions respectively. The IgG4 constant region may be modified by, for example, changing Serine at position 228 in the hinge region to Proline (HuIgG4 Ser-Pro). This mutation stabilizes the interchain disulphide bond and prevents the formation of half molecules that may occur in native human IgG4 preparations. The IgG4 constant region may be further modified by deletion of the terminal Lys in position 439 as shown in SEQ ID NO: 16.

The modified variable regions may be constructed by method known in the art such as, for example overlapping PCR recombination. The expression cassettes for the chimeric antibody, C2 ChV$_H$ AF and C2 ChV$_K$, may be used as templates for mutagenesis of the framework regions to the required sequences. Sets of mutagenic primer pairs are synthesized encompassing the regions to be altered. The humanized V$_H$ and V$_K$ expression cassettes produced may be cloned into appropriate cloning vectors know in the art such as, for example, pUC19. After the entire DNA sequence is confirmed to be correct for each V$_H$ and V$_K$, the modified heavy and light chain V-region genes can be excised from the cloning vector as expression cassettes. These can then be transferred to appropriate expression vectors such as pSVgpt and pSVhyg which include human IgG4 Ser-Pro or x constant regions respectively.

Expression Vectors

Expression vector pSVgpt is based on pSV$_2$gpt (Mulligan and Berg, 1980) and includes the ampicillin resistance gene for selection in bacterial cells, the gpt gene for selection in mammalian cells, the murine heavy chain immunoglobulin enhancer region, genomic sequence encoding the constant region gene and SV40 poly A sequences. The heavy chain variable region for expression is inserted as a HindIII to BamHI fragment.

Expression vector pSVhyg includes the ampicillin resistance gene for selection in bacterial cells, the hyg gene for selection in mammalian cells, the murine heavy chain immunoglobulin enhancer region, genomic sequence encoding the kappa constant region gene and including the kappa enhancer and SV40 poly A sequences. The light chain variable region for expression is inserted as a HindIII to BamHI fragment.

The DNA sequence is then to be confirmed to be correct for the humanized V$_H$ and V$_K$ in the expression vectors.

For antibody production the humanized heavy and light chain expression vectors may be introduced into appropriate production cell lines know in the art such as, for example, NS0 cells. Introduction of the expression vectors may be accomplished by co-transfection via electroporation or any other suitable transformation technology available in the art. Antibody producing cell lines can then be selected and expanded and humanized antibodies purified. The purified antibodies can then be analyzed by standard techniques such as SDS-PAGE.

Antibody with Improved Affinity, Specificity, Stability

The CDRL2 sequence ("KVSNRFS") of the mouse C2 antibody may be modified slightly without adversely affecting antibody activity. Conservative substitutions may be made through exchange of R for K at position 50 and S for N at position 53. The two alternative CDRL2 sequences are therefore "RVSNRFS" and "KVSSRFS", respectively. These are incorporated into the murine V$_K$ sequence with no other changes, as C2 VK-R and C2 VK-S, respectively.

The affinity, specificity and stability of an antibody according to the invention as described herein before or a fragment thereof can be modified by change of its glycosylation profile or pattern resulting in improved therapeutic values.

To achieve this change in glycosylation pattern, host cells may be engineered such that they are capable of expressing a preferred range of a glycoprotein-modifying glycosyl transferase activity which increases complex N-linked oligosaccharides carrying bisecting GlcNAc. Further, modified glycoforms of glycoproteins may be obtained, for example antibodies, including whole antibody molecules, antibody fragments, or fusion proteins that include a region equivalent to the Fc region of an immunoglobulin, having an enhanced Fc-mediated cellular cytotoxicity.

Methods of obtaining antibodies with modified glycosylation pattern are known to those skilled in the art and described, for example, in EP1071700, US2005272128, Ferrara et al (2006) J Biol Chem 281(8), 5032-5036); Ferrara et al (2006) Biotechnology and Bioengineering 93(5), 851-861.

Pharmaceutical Preparation and Administration

The antibodies according to the invention, but particularly a monoclonal antibody according the invention, can be prepared in a physiologically acceptable formulation and may comprise a pharmaceutically acceptable carrier, diluent and/or excipient using known techniques. For example, the antibody according to the invention and as described herein before including any functionally equivalent antibody or functional parts thereof, in particular, the monoclonal antibody including any functionally equivalent antibody or functional parts thereof is combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions, various types of wetting agents, sterile solutions, etc.

Formulation of the pharmaceutical composition according to the invention can be accomplished according to standard methodology know to those skilled in the art.

The compositions of the present invention may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal, interdermal, intraperitoneal, or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

It is well know to those skilled in the pertinent art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

The composition may be administered in combination with other compositions comprising an biologically active substance or compound, particularly at least one compound selected from the group consisting of compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), α-secretase activators, β- and γ-secretase inhibitors, tau proteins, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine, M1 agonists and other drugs including any amyloid or tau modifying drug and nutritive supplements such as, for example, vitamin B12, cysteine, a precursor of acetylcholine, lecithin, choline, Ginkgo biloba, acyetyl-L-carnitine, idebenone, propentofylline, or a xanthine derivative, together with an antibody according to the present invention and, optionally, a pharmaceutically acceptable carrier and/or a diluent and/or an excipient and procedures for the treatment of diseases.

Proteinaceous pharmaceutically active matter may be present in amounts between 1 ng and 10 mg per dose. Generally, the regime of administration should be in the range of between 0.1 µg and 10 mg of the antibody according to the invention, particularly in a range 1.0 µg to 1.0 mg, and more particularly in a range of between 1.0 µg and 100 µg, with all individual numbers falling within these ranges also being part of the invention. If the administration occurs through continuous infusion a more proper dosage may be in the range of between 0.01 µg and 10 mg units per kilogram of body weight per hour with all individual numbers falling within these ranges also being part of the invention.

Administration will generally be parenterally, eg intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

The pharmaceutical composition may further comprise proteinaceous carriers such as, for example, serum albumin or immunoglobulin, particularly of human origin. Further biologically active agents may be present in the pharmaceutical composition of the invention dependent on its the intended use.

When the binding target is located in the brain, certain embodiments of the invention provide for the antibody or active fragment thereof to traverse the blood-brain barrier. Certain neurodegenerative diseases are associated with an increase in permeability of the blood-brain barrier, such that the antibody or active fragment thereof can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or active fragment thereof across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002)) and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989))), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody or antigen-binding fragment (see, e.g., U.S. Patent Publication No. 2003/0083299).

Lipid-based methods of transporting the antibody or active fragment thereof across the blood-brain barrier include, but are not limited to, encapsulating the antibody or active fragment thereof in liposomes that are coupled to antibody binding fragments that bind to receptors on the vascular endothelium of the blood-brain barrier (see, e.g., U.S. Patent Application Publication No. 20020025313), and coating the antibody or active fragment thereof in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the antibody or active fragment thereof across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

Detection/Diagnosis

In a further embodiment the present invention provides methods and kits for the detection and diagnosis of amyloid-associated diseases or conditions. These methods include known immunological methods commonly used for detecting or quantifying substances in biological samples or in an in situ condition.

Diagnosis of an amyloid-associated disease or condition in a patient may be achieved by detecting the immunospecific binding of a monoclonal antibody or an active fragment thereof to an epitope of the amyloid protein in a sample or in situ, which includes bringing the sample or a specific body part or body area suspected to contain the amyloid protein into contact with an antibody which binds an epitope of the amyloid protein, allowing the antibody to bind to the amyloid protein to form an immunological complex, detecting the formation of the immunological complex and correlating the presence or absence of the immunological complex with the presence or absence of amyloid protein in the sample or specific body part or area optionally comparing the amount of said immunological complex to a normal control value, wherein an increase in the amount of said aggregate compared to a normal control value indicates that said patient is suffering from or is at risk of developing an amyloid-associated disease or condition.

Monitoring minimal residual disease in a patient following treatment with an antibody or a vaccine composition according to the invention may be achieved by detecting the immunospecific binding of a monoclonal antibody or an active fragment thereof to an epitope of the amyloid protein in a sample or in situ, which includes bringing the sample or a specific body part or body area suspected to contain the amyloid antigen into contact with an antibody which binds an epitope of the amyloid protein, allowing the antibody to bind to the amyloid antigen to form an immunological complex, detecting the formation of the immunological complex and correlating the presence or absence of the immunological complex with the presence or absence of amyloid antigen in the sample or specific body part or area, optionally comparing the amount of said immunological complex to a normal control value, wherein an increase in the amount of said aggregate compared to a normal control value indicates that said patient may still suffer from a minimal residual disease.

Predicting responsiveness of a patient to a treatment with a vaccine composition according to the invention may be achieved by detecting the immunospecific binding of a monoclonal antibody or an active fragment thereof to an epitope of the amyloid protein in a sample or in situ, which includes bringing the sample or a specific body part or body area suspected to contain the amyloid antigen into contact with an antibody which binds an epitope of the amyloid protein, allowing the antibody to bind to the amyloid antigen to form an immunological complex, detecting the formation of the immunological complex and correlating the presence or absence of the immunological complex with the presence or absence of amyloid antigen in the sample or specific body part or area, optionally comparing the amount of said immunological complex before and after onset of the treatment, wherein an decrease in the amount of said aggregate indicates that said patient has a high potential of being responsive to the treatment.

Biological samples that may be used in the diagnosis of an amyloid-associated disease or condition are, for example, fluids such as serum, plasma, saliva, gastric secretions, mucus, cerebrospinal fluid, lymphatic fluid and the like or tissue or cell samples obtained from an organism such as neural, brain, cardiac or vascular tissue. For determining the presence or absence of the amyloid protein in a sample any immunoassay known to those of ordinary skill in the art. (See Harlow and Lane, Antibodies: A Laboratory Manual (Cold Spring Harbor Laboratory, New York 1988 555-612) may be used such as, for example, assays which utilize indirect detection methods using secondary reagents for detection, ELISA's and immunoprecipitation and agglutination assays. A detailed description of these assays is, for example, given in WO96/13590 to Maertens and Stuyver, Zrein et al. (1998) and WO96/29605.

For in situ diagnosis, the antibody or any active and functional part thereof may be administered to the organism to be diagnosed by methods known in the art such as, for example, intravenous, intranasal, intraperitoneal, intracerebral, intraarterial injection such that a specific binding between the antibody according to the invention with an eptitopic region on the amyloid protein may occur. The antibody/antigen complex may be detected through a label attached to the antibody or a functional fragment thereof.

The immunoassays used in diagnostic applications typically rely on labelled antigens, antibodies, or secondary reagents for detection. These proteins or reagents can be labelled with compounds generally known to those skilled in the art including enzymes, radioisotopes, and fluorescent, luminescent and chromogenic substances including colored particles, such as colloidal gold and latex beads. Of these, radioactive labelling can be used for almost all types of assays and with most variations. Enzyme-conjugated labels are particularly useful when radioactivity must be avoided or when quick results are needed. Fluorochromes, although requiring expensive equipment for their use, provide a very sensitive method of detection. Antibodies useful in these assays include monoclonal antibodies, polyclonal antibodies, and affinity purified polyclonal antibodies.

Alternatively, the antibody may be labelled indirectly by reaction with labelled substances that have an affinity for immunoglobulin, such as protein A or G or second antibodies. The antibody may be conjugated with a second substance and detected with a labelled third substance having an affinity for the second substance conjugated to the antibody. For example, the antibody may be conjugated to biotin and the antibody-biotin conjugate detected using labelled avidin or streptavidin. Similarly, the antibody may be conjugated to a hapten and the antibody-hapten conjugate detected using labelled anti-hapten antibody.

Those of ordinary skill in the art will know of these and other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1-31), and Schurs, A. H. W. M., et al. 1977 (Clin. Chim Acta 81:1-40). Coupling techniques mentioned in the latter are the glutaraldehyde method, the periodate method, the dimaleimide method, and others, all of which are incorporated by reference herein.

Current immunoassays utilize a double antibody method for detecting the presence of an analyte, wherein. The antibody is labeled indirectly by reactivity with a second antibody that has been labeled with a detectable label. The second antibody is preferably one that binds to antibodies of the animal from which the monoclonal antibody is derived. In other words, if the monoclonal antibody is a mouse antibody, then the labeled, second antibody is an anti-mouse antibody. For the monoclonal antibody to be used in the assay described below, this label is preferably an antibody-coated bead, particularly a magnetic bead. For the polyclonal antibody to be employed in the immunoassay described herein, the label is preferably a detectable molecule such as a radioactive, fluorescent or an electrochemiluminescent substance.

An alternative double antibody system often referred to as fast format systems because they are adapted to rapid determinations of the presence of an analyte, may also be employed within the scope of the present invention. The system requires high affinity between the antibody and the analyte. According to one embodiment of the present invention, the presence of the amyloid protein is determined using a pair of antibodies, each specific for amyloid protein. One of said pairs of antibodies is referred to herein as a "detector antibody" and the other of said pair of antibodies is referred to herein as a "capture antibody". The monoclonal antibody of the present invention can be used as either a capture antibody or a detector antibody. The monoclonal antibody of the present invention can also be used as both capture and detector antibody, together in a single assay. One embodiment of the present invention thus uses the double antibody sandwich method for detecting amyloid protein in a sample of biological fluid. In this method, the analyte (amyloid protein) is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Exemplary solid phase substances include, but are not limited to, microtiter plates, test tubes of polystyrene, magnetic, plastic or glass beads and slides which are well known in the field of radioimmunoassay and enzyme immunoassay. Methods for coupling antibodies to solid phases are also well known to those skilled in the art. More recently, a number of porous material such as nylon, nitrocellulose, cellulose acetate, glass fibers and other porous polymers have been employed as solid supports.

The present invention also relates to a diagnostic kit for detecting amyloid protein in a biological sample comprising a composition as defined above. Moreover, the present invention relates to the latter diagnostic kit which, in addition to a composition as defined above, also comprises a detection reagent as defined above. The term "diagnostic kit" refers in general to any diagnostic kit known in the art. More specifically, the latter term refers to a diagnostic kit as described in Zrein et al. (1998).

It is still another object of the present invention to provide novel immunoprobes and test kits for detection and diagnosis of amyloid-associated diseases and conditions comprising antibodies according to the present invention. For immunoprobes, the antibodies are directly or indirectly attached to a suitable reporter molecule, e.g., an enzyme or a radionuclide. The test kit includes a container holding one or more antibodies according to the present invention and instructions for using the antibodies for the purpose of binding to amyloid protein to form an immunological complex and detecting the formation of the immunological complex such that presence or absence of the immunological complex correlates with presence or absence of amyloid protein.

EXAMPLES

Materials

The development and preparation of mouse monoclonal antibody ACI-01-Ab7C2 (named "mC2" and hC2 for the humanized C2 antibody, throughout the application) is described in co-pending application EP 05 02 7092.5 filed Dec. 12, 2005, the disclosure of which is incorporated herein by reference.

Hybridoma cells FP-12H3-C2, producing mouse monoclonal antibody ACI-01-Ab7C2 (named "mC2" and hC2 for the humanized C2 antibody, throughout the application) were deposited 1 Dec. 2005 in co-pending application no EP05027092.5 with the "Deutsche Sammlung von Mikroorganismen and Zellkulturen GmbH (DSMZ) in Braunschweig, Mascheroder Weg 1 B, 38124 Braunschweig, under the provisions of the Budapest Treaty and given accession no DSM ACC2750.

Hybridoma cells were cultured in Dulbecco's modified Eagle Medium (DMEM) supplemented with 10% foetal bovine serum and antibiotics (Penicillin/Streptomycin). The isotype of the antibody produced was checked and found to be mouse IgG2b/kappa, as expected.

Assay

An ELISA for binding to Amyloid Beta provided a reliable measure of the potency of C2 antibodies. Positive control antibodies, murine FP-12H3-C2 antibody (Genovac Lot No: AK379/01), and standard Chemicon antibody 1560 (Lot no: 0508008791).

Choice of Human Constant Regions

As immune system recruitment is not desirable for the clinical antibody candidate, the selected human constant region for the heavy chain was human IgG4, modified to change Serine at position 228 in the hinge region to Proline (HuIgG4 Ser-Pro). This mutation stabilizes the interchain disulphide bond and prevents the formation of half molecules that may occur in native human IgG4 preparations. The antibody expressed from the production cell lines will also have the terminal lysine removed. The sequences of human constant regions HuIgG4 Ser-Pro and human Kappa are given in SEQ ID NO: 17 and 14, respectively.

Example 1

Cloning and Sequencing of Antibody Variable Regions

Total RNA was prepared from $3 \times 10^6$ hybridoma cells (one T175 flask) using the Qiagen RNeasy mini kit (Cat No: 74104). RNA was eluted in 50 µL water and checked on a 1.2% agarose gel. The conditioned medium from the cells was retained and a sample used for testing in the antibody activity assay.

$V_H$ and $V_K$ cDNAs were prepared using reverse transcriptase with mouse IgG and κ constant region primers. The first strand cDNAs were amplified by PCR using a large set of signal sequence primers. The amplified DNAs were gel-purified and cloned into the vector pGem® T Easy (Promega). The $V_H$ and $V_K$ clones obtained were screened for inserts of the expected size by PCR and the DNA sequence of selected clones determined by automated DNA sequencing. The locations of the complementarity determining regions (CDRs) in the sequences were determined with reference to other antibody sequences (Kabat E A et al., 1991). The numbering convention of Kabat for antibody variable regions is used throughout this application; hence residue numbers may differ from the strict linear number.

The DNA sequence and deduced amino acid sequence for mC2 $V_K$ is shown in SEQ ID NO: 29 and 27, respectively. Four clones gave this identical productive sequence. A non-productive aberrant $V_K$ sequence that arises from the hybridoma fusion partner was also found in a number of clones.

For mC2 $V_H$, two different productive sequences were isolated. The mC2 $V_H$ AF sequence (see SEQ ID NO: 30) was found in a total of 29 clones, with 14 single base pair changes in individual clones. The mC2 $V_H$ B sequence was found in a total of 8 clones. Five of these represented the majority sequence, with the other 3 clones being variations on this. It is possible that these similar $V_H$ B sequences arose as an artifact of the PCR amplification. A non-productive aberrant $V_H$ was also obtained from the C2 hybridoma and is attributed to defective V-D-J joining.

In order to determine which is the correct active mC2 $V_H$, two chimeric antibodies were prepared with the two different $V_H$ sequences, AF and B, combined with the mC2 $V_K$, to be tested for the correct antibody activity.

Example 2

Construction of Chimeric Antibody Genes

A human chimeric antibody in its most common form consists of human constant regions linked to murine (or other non-human) variable regions. A chimeric antibody provides a very useful tool, firstly for confirmation that the correct variable regions have been identified, secondly for use as a control antibody in antigen binding assays with the same effector functions and utilizing the same secondary detection reagents as a humanized or engineered antibody, and also may be used to investigate the pharmacokinetic and other properties of the human constant regions with reference to the particular target for the antibody.

Two chimeric heavy chain expression vectors were constructed consisting of mC2 $V_H$ AF or mC2 $V_H$ B variable regions linked to HuIgG4 (Ser-Pro) constant region in the expression vector pSVgpt. This is based on pSV$_2$gpt (Mulligan and Berg, 1980) and includes the ampicillin resistance gene for selection in bacterial cells, the gpt gene for selection in mammalian cells, the murine heavy chain immunoglobulin enhancer region, genomic sequence encoding the constant region gene and SV40 poly A sequences. The heavy chain variable region for expression is inserted as a HindIII to BamHI fragment.

A chimeric light chain vector was constructed consisting of C2 VK linked to human C Kappa constant region in the expression vector pSVhyg. (Hieter P A et al, 1980) pSVhyg includes the ampicillin resistance gene for selection in bacterial cells, the hyg gene for selection in mammalian cells, the murine heavy chain immunoglobulin enhancer region, genomic sequence encoding the kappa constant region gene and including the kappa enhancer and SV40 poly A sequences. The light chain variable region for expression is inserted as a HindIII to BamHI fragment.

Expression cassettes for the murine C2 VH and VK sequences were constructed by addition of 5' flanking sequence including the leader signal peptide, leader intron and the murine immunoglobulin promoter, and 3' flanking sequence including the splice site and intron sequence, using the vectors VH-PCR1 and VK-PCR1 as templates (Riechmann et al., 1988). The DNA sequence was confirmed to be correct for the VH and VK in the chimeric expression vectors. The DNA and amino acid sequences of the VH and VK genes in the expression cassettes are shown in FIGS. 1 and 2.

Example 3

Expression of Chimeric Antibodies 3.1 Expression in Stable Cell Lines

The host cell line for antibody expression was NS0, a non-immunoglobulin producing mouse myeloma, obtained from the European Collection of Animal Cell Cultures, Porton UK (ECACC No 85110503). The heavy and light chain expression vectors were co-transfected into NS0 cells by electroporation. Colonies expressing the gpt gene were selected in Dulbecco's Modified Eagle's Medium (DMEM) supplemented with 10% foetal bovine serum (FBS), 0.8 µg/ml mycophenolic acid and 250 µg/ml xanthine. Transfected cell clones were screened for production of human antibody by ELISA for human IgG. Cell lines secreting antibody were expanded and the highest producers selected and frozen down in liquid nitrogen. The best producing cell lines for each antibody were expanded in medium as above but with only 5% FBS. Chimeric antibodies were purified using Prosep®-A (Bioprocessing Ltd). The concentration was determined by ELISA for human IgGκ antibody. The antibodies were also analyzed by SDS-PAGE.

3.2 Transient Expression of Chimeric Antibodies

To expedite the testing of the different chimeric antibodies, transient expression was used to produce quickly small quantities of cell supernatant containing recombinant antibody for testing. The mC2 $V_H$ and $V_K$ expression cassettes were transferred to vectors based on pcDNA3.1 (Invitrogen) for transient expression. The heavy chain vector included a human IgG constant region. The light chain vector included a human kappa constant region. Both mC2 $V_H$ AF and mC2 $V_H$ B were transfected with mC2 $V_K$ into human embryonic kidney (HEK 298) cells with Lipofectamine 2000 reagent (Invitrogen Cat No: 11668) according to the protocol supplied by the manufacturer. Conditioned medium was harvested from cells 3 days after transfection. The amount of antibody produced was determined by ELISA for human IgGκ antibody.

Example 4

Activity of Chimeric C2 Antibodies 4.1 Activity of Chimeric C2 Antibodies Produced by Transient Transfection Samples of conditioned medium from transient transfection for the two different chimeric antibodies were tested in the ELISA for binding to Amyloid Beta. The results clearly indicate that the C2 VH AF is the correct sequence. The C2 $V_H$ AF/C2 $V_K$ chimeric antibody binds well in the assay, but the C2 $V_H$ B/C2 $V_K$ does not show any binding at all. The Chemicon 1560 murine control antibody showed good binding, but binding by the purified murine C2 antibody supplied was low. It should be noted that a different secondary antibody was employed for the murine antibodies with the mouse constant regions compared to the chimeric antibodies with human constant regions, so the results are not directly comparable. Conditioned medium from the C2 hybridoma was later found to give a good result in the assay.

4.2 Activity of Purified Chimeric C2 Antibodies

The two different C2 chimeric antibodies were purified from stable NS0 cell lines as described and tested using the Amyloid Beta ELISA. The results obtained are in accordance with the results obtained with transiently expressed antibody. The C2 ChVH AF/ChVK antibody binds well in the ELISA and the C2 ChVH B/ChVK antibody does not bind at all.

Example 5

Design of Humanized C2 Antibody Genes

The mC2 $V_H$ and $V_K$ amino acid sequences were compared to rodent antibody $V_H$ and $V_K$ sequences in the NCBI and Kabat databases.

5.1 Light Chain Variable Region

The closest match mouse germ line gene to mC2 $V_K$ is bb1, Locus MMU231201, (Schable et al, 1999). Only two amino acids differ from this germ line sequence, both located within CDRL1. Mature murine antibodies with similar, but not identical, sequence are found. Several have an identical CDRL2 and identical CDRL3, but the CDRL1 of mC2 seems to be unique. mC2 $V_K$ can be assigned to Kabat subgroup MuV$_K$II. Position 87 of mC2 $V_K$ is F rather than the Y that is more common in the subgroup, indicating that this framework residue may be important for antibody activity. Comparison with human germ line $V_K$ sequences shows that genes from subgroup $V_K$II are the best match for mC2 $V_K$ (Cox et al, 1994). Sequence DPK15 together with the human J region HuJ$_K$1 were selected to provide the acceptor framework sequences for the humanized $V_K$.

Four humanized $V_K$ sequences were designed. C2HuVK1 consists of mC2 $V_K$ CDRs with frameworks from DPK 15 and human J$_K$1. In versions 2, 3 and 4 murine residues have been substituted in the framework at positions 45 or 87 or both. Residue 45 may be involved in supporting the conformation of the CDRs. Residue 87 is located at the interface of the $V_H$ and $V_K$ domains. Therefore these residues may be critical for maintenance of antibody binding.

The positions and changes that have been made in the light chain framework regions are shown in Table 6. A comparison of the humanized sequences with mC2 $V_K$ sequence, and with DPK15 and human J$_K$1

5.2 Heavy Chain Variable Region

The closest match mouse germ line gene to mC2 $V_H$ AF is VH7183, Locus AF120466, (Langdon et al, 2000). The comparison is shown in FIG. 3. Nine amino acids differ from this germ line sequence, most being located within CDR2. Mature murine antibodies with identical or similar (one residue different) CDR1 or with similar CDR2 (one residue different) are found, but none with all three CDRs identical to mC2 $V_H$ AF. CDR3 of mC2 antibody is unusually short, consisting of only three residues. However, other antibodies are found in the database with CDR3 of this length. mC2 $V_H$ AF can be assigned to Kabat subgroup MuV$_{H111}$D. Residue 47 of mC2 $V_H$ is L rather than the more common W, and residue 94 is S rather than the normal R, indicating that these framework residues may be important for antibody activity. Comparison with human germ line $V_H$ sequences shows that genes from subgroup V$_H$III are the best match for mC2 $V_H$. Sequence DP54 together with the human J region HuJ$_H$6 was selected to provide the acceptor framework sequences for the humanized $V_H$.

Four humanized $V_H$ sequences were designed. C2HuVH1 consists of mC2 $V_H$ AF CDRs with frameworks from DP54 and HuJ$_H$6. In versions 2, 3 and 4 murine residues have been substituted in the framework at positions 47 or 94 or both. Residue 47 in framework 2 makes contact both with the CDRs and with the $V_K$ domain. Residue 94 may be involved in supporting the conformation of the CDRs. Therefore these residues may be critical for maintenance of antibody binding.

The positions and changes that have been made in the heavy chain framework regions are shown in Table 7.

Example 6

Construction of Humanized Antibody Genes

The modified variable regions were constructed by the method of overlapping PCR recombination. The expression cassettes for the chimeric antibody, C2 ChV$_H$ AF and C2 ChV$_K$ were used as templates for mutagenesis of the framework regions to the required sequences. Sets of mutagenic primer pairs were synthesized encompassing the regions to be altered. The humanized V$_H$ and V$_K$ expression cassettes produced were cloned into pUC19 and the entire DNA sequence was confirmed to be correct for each V$_H$ and V$_K$. The modified heavy and light chain V-region genes were excised from pUC19 as HindIII to BamHI expression cassettes. These were transferred to the expression vectors pSVgpt and pSVhyg which include human IgG4 Ser-pro or κ constant regions respectively, as for the chimeric antibody vectors. The DNA sequence was confirmed to be correct for the humanized V$_H$ and V$_K$ in the expression vectors.

Example 7

Expression of Humanized Antibodies 7.1 Expression in Stable Cell Lines

The humanized heavy and light chain expression vectors were co-transfected into NS0 cells by electroporation, as for the expression of chimeric antibodies. Antibody producing cell lines were selected and expanded and humanized antibodies purified, exactly as for the chimeric antibody. The purified antibodies were analyzed by SDS-PAGE.

7.2 Transient Expression of Humanized Antibodies

To expedite testing of the different humanized V$_H$ and V$_K$ constructs, the C2 humanized V$_H$ and V$_K$ expression cassettes were also transferred to the vectors for transient expression described in section 7.2. The four humanized C2 $V_K$ constructs were co-transfected with the chimeric C2 $V_H$ construct into HEK293 cells. Similarly, the four humanized C2 $V_H$ constructs were co-transfected with the chimeric C2 $V_K$ construct into HEK293 cells. Conditioned medium was harvested from cells three days after transfection. The amount of antibody produced was determined by ELISA for human IgGκ antibody.

Example 8

Activity of Humanized C2 Antibodies 8.1 Activity of Humanized C2 Antibodies Produced by Transient Transfection Samples of conditioned medium from the transient transfection were tested in the Amyloid Beta ELISA. The results obtained clearly indicate that the humanized VH constructs C2 HuVH AF versions 2 and 4 are functional when combined with the chimeric C2 kappa chain, and are comparable to the chimeric C2 antibody in the assay. In contrast, the antibodies containing C2 HuVH AF versions 1 and 3 combined with the chimeric C2 kappa chain show no binding at all in the assay. This indicates that the substitution of the murine residue at position 94 is essential for antibody activity. Antibodies containing the chimeric C2 heavy chain combined with the four humanized C2 kappa chains all showed good binding, comparable to the chimeric antibody, in the ELISA.

8.2 Activity of Purified Humanized C2 Antibodies

Eight different humanized C2 antibodies comprising all combinations of two humanized heavy chains and four humanized light chains were purified from stable NS0 cell lines as described and tested using the Amyloid Beta ELISA (FIG. 4).

The results obtained clearly indicate that C2 HuVH4 antibodies perform better in the assay than C2 HuVH2 antibodies. Of the C2 HuVH2 antibodies, C2 HuVH2/HuVK3 shows the best binding activity, but this is approximately 2 fold reduced compared to the chimeric control antibody C2 ChVHAF/ChVK. C2 HuVH2/HuVK2 activity is four to five fold reduced compared to the control. The activities of the antibodies comprising C2HuVH4 with the four different humanized light chains are similar. The highest activity is observed for C2HuVH4/HuVK1 and all four antibodies are close to the control chimeric antibody in the assay.

Example 9

Modifications to CDRL2

9.1 Design Light Chain with Modified CDR 2

As noted above, many antibodies share the same CDRL2 sequence ("KVSNRFS") as the C2 antibody. It was decided to test whether CDRL2 could be modified slightly without adversely affecting antibody activity. Two conservative substitutions were selected: R for K at position 50 and S for N at position 53. The two alternative CDRL2 sequences are therefore "RVSNRFS" and "KVSSRFS". These were incorporated into the murine $V_K$ sequence with no other changes, as mC2 VK-R and mC2 VK-S respectively.

9.2 Transient Expression of Modified CDRL2 Antibody

The two C2 light chain constructs with modified CDRL2 described in Section 11.2.1 were cloned into the light chain vector for transient expression. Each was co-transfected with the chimeric C2 $V_H$ vector into HEK293 cells. Conditioned medium was harvested from cells three days after transfection. The amount of antibody produced was determined by ELISA for human IgGκ antibody.

9.3 Activity of C2 Antibody with Modified CDRL2

Samples of conditioned medium from the transient transfection of mC2 $V_K$S with modified CDRL2 combined with mC2 $V_H$ were tested in the Amyloid Beta ELISA. (FIG. 5) Both the VK-R and the VK-S antibodies are comparable to the chimeric C2 antibody, indicating that the individual modifications to CDRL2 chosen do not markedly affect the activity of the antibody in the assay.

Example 10

Affinity Determination

To assess the binding specificity and affinity of mouse (ACI-01-Ab-7-C2) chimeric (AF) and humanized antibodies (H4K1; H4K4), BIACORE® analysis was performed using amyloid beta 1-42 monomers and fibers as antigen immobilized on a CM5 chip. BIACORE® technology utilizes changes in the refractive index at the surface layer upon binding of the antibody to the antigen immobilized on the layer. Binding is detected by surface plasmon resonance (SPR) of laser light refracting from the surface. Analysis of the signal kinetics on rate and off rate allows the discrimination between non-specific and specific interaction. The concentration of antibody used was in the range of 0.05 µM to 1.0 µM.

TABLE 1

Binding specificity and affinity of mouse (ACI-01-Ab-7-C2) chimeric (AF) and humanized antibodies (H4K1; H4K4) for amyloid beta 1-42 monomers and fibers

|  | Monomers | | | Fibers | | |
| --- | --- | --- | --- | --- | --- | --- |
|  | $k_a$(1/Ms) | $k_d$(1/s) | KD (M) | $k_a$(1/Ms) | $k_d$(1/s) | KD (M) |
| Mouse ACI-01-Ab-7-C2 | 1.8E+04 | 2.7E−03 | 1.5E−07 | 2.4E+04 | 9.9E−04 | 4.1E−08 |
| chimeric AF | 4.7E+04 | 9.5E−04 | 2E−08 | 5.1E+04 | 3.3E−04 | 6.5E−09 |
| humanized H4K1 | 5.0E+04 | 9.5E−04 | 1.9E−08 | 4.9E+04 | 2.3E−04 | 4.7E−09 |
| humanized H4K4 | 2.5E+04 | 4.4E−04 | 1.8E−08 | 1.3E+05 | 3.0E−04 | 2.3E−09 |

Example 11

Immunohistochemical Binding Assay 11.1 Human Brain Sections

Brains from healthy, non-demented pre-AD and AD patients were obtained from the Universitätsklinik in Bonn after ethical approval. Brains were fixed in formaldehyde and the hippocampus region was dehydrated, embedded in paraffin and 5 µm sections were cut with a microtome. Paraffin sections were stored at RT until use. For fresh material, 5 μm cryosections were cut with a cryostat and sections stored at −80° C. until use.

11.2 Immunohistochemistry

Paraffin sections were deparaffinized and rehydrated by bathing slides in xylene followed by 100% ethanol, 90% ethanol and 70% ethanol. Background was decreased by 30 minutes incubation in 10% $H_2O_2$, 10% methanol in water. Antigen retrieval was obtained by incubating the slides in 100% formic acid for 3 minutes. After 3 washes in Tris buffered saline (TBS, pH 7.5), non-specific labeling was blocked by a 2 hour incubation of the slides in 10% BSA, 0.25% Triton X-100 in TBS. After washing (3 washes in TBS) blocking of endogenous antibodies was performed by adding a non-labeled anti-human IgG (Biomeda) and incubating slides in humid chambers overnight at RT. After another 3 washes, the primary human anti amyloid antibody was added to the slides and incubated another 24 hours at RT. Following washing, an alkaline phosphatase labeled secondary anti human IgG (Sigma) was added to the slides and incubated for 2 hours at RT. After washing, slides were developed with Liquid permanent Red (Dakocytomation) washed with water and air-dried before mounting with permanent mounting media (corbitbalsam).

Cryosection were fixed in methanol for 30 minutes at −80° C. and background decreased by adding $H_2O_2$ to the cold methanol to a final concentration of 10% and incubating for 30 minutes at RT. After 3 washes in Tris buffered saline (TBS, pH7.5), non-specific labeling was blocked by a 2 hour incubation of the slides in 10% BSA, 0.25% Triton X 100 in TBS as above and the same staining procedure as above was carried out.

Sections were examined with a Leica DMLB microscope and photographed using a Leica DC500 camera and Leica FireCam1.2.0 software.

Both human antibodies A and C labeled plaques of brains from AD disease patients (FIG. 6). Both diffuse and cored plaques were labeled. Moreover, diffuse plaques in non-demented pre-AD patients could also be detected by the A and C antibodies. Amyloid in cerebral amyloid angiopathy (CAA) was labeled with both antibodies and some staining of neurons which may correspond to intracellular amyloid was also detected. No labeling was seen on control brains from healthy patient. Plaques could be detected on paraffin sections pretreated with formic acid but no plaques were labeled on paraffin sections without formic acid pretreatment and on cryosections fixed in methanol. The human antibody B did not detect plaques on paraffin sections and the mouse antibody did not stain either paraffin or cryosections of human brains.

Abbreviations:
A=binding chimeric antibody AF (IgG4) (mC2ChVHAF)
B=non-binding chimeric antibody B (IgG4) (mC2VHB)
C=binding humanized antibody H4K1 (IgG4) (HuVH4/HuVK1)
Mouse=ACI-01-Ab-C2 mouse antibody (IgG2b)

Example 12

Functionality of mC2 on Amyloid Fibers 12.1 Modification of Conformation of Aâ1-42 Fibers and Initiation of Disaggregation after Binding of the mC2 Antibody In order to evaluate the mechanism by which the antibody is capable to disaggregate preformed beta-amyloid ($A\beta_{1-42}$) fibers a head-to-head comparison of Thioflavin-T (Th-T) fluorescent assay was performed measuring disaggregation and solid-state Nuclear Magnetic Resonance (NMR) of U-$^{13}$C Tyrosine10 and Valine12-labeled Aβ1-42 peptide analysing secondary conformation (FIG. 7A). The mC2 antibody solubilised 35.4% of the preformed Aβ1-42 fibers and simultaneously induced a shift in secondary conformation from beta sheet to random coiled. The reduction in the population of the beta sheet conformation with respect to the random coil is of the order of 35% and is therefore in close agreement with that measured using fluorescence Th-T assay (FIG. 7B). These data indicate that the binding of the mC2 antibody initiates a transition of the secondary structure which potentially causes a destabilization of the parallel intermolecular arrangement of the beta sheets affecting a break of elongated fibers into smaller fragments.

12.2 Conformation-Dependent Binding Affinity of mC2 Antibody

Since it is well known in the scientific literature that a proportion of the antibody-antigen binding energy can be used for energy-dependent modification of the conformation of an antigen (Blond and Goldberg, 1987), a comparison experiment of the binding affinity of the C2 antibody to the whole $A\beta_{1-42}$ protein and to a smaller, nine amino acid long, peptide comprising the antibody's epitope was performed (FIG. 8). For this comparison the affinities of the humanized antibody C2 were analyzed by ELISA using biotinylated peptides covering the complete amino-acid sequence of the C2's epitope (produced by Mimotopes and purchased from ANAWA Trading SA) and a biotinylated complete Aβ1-42 peptide (Bachem). The analysis was done according to the manufacturer's (Mimotopes) instructions. As demonstrated in FIG. 8 and Table 2, the antibody binds with a 36.0% higher affinity to the peptide comprising its specific epitope (aminoacids 13-21 of the $A\beta_{1-42}$ sequence) than to the whole Aβ1-42 protein. It is therefore suggested that the difference in binding affinity energy was used for the energy-consuming transition of the secondary conformation of the amyloid protein to present the antigen in a more acceptable position for the antibody interaction. This explains why the affinity of the antibody is lower for the native (the whole amyloid protein) than for the isolated subunit.

TABLE 2

| | O.D | |
|---|---|---|
| | Amyloid beta 13-21 | Amyloid beta 1-42 |
| hC2 | 1.225 | 0.9005 |
| Control IgG | 0.171 | 0.196 |

Example 13

Effects of the Anti-Amyloid hC2 on the Aggregation of Amyloid Beta 1-42 Peptide

To evaluate the ability of the humanized anti-human amyloid beta monoclonal antibody hC2 to mediate anti-aggregating and disaggregating effects on amyloid beta (Aβ) a thioflavin T spectrofluorescence assay was accomplished.

13.1 Inhibition of Aggregation Assay

Aβ1-42 lyophilized powder was reconstituted in hexafluoroisopropanol (HFIP) to 1 mM. The peptide solution was sonicated for 15 min at room temperature, agitated overnight, and aliquots made into non-siliconized microcentrifuge tubes. The HFIP was then evaporated under a stream of argon. The resulting peptide film was vacuum dried for 10 min and stored at −80° C. until used.

To assay for the antibody-mediated inhibition of Aβ1-42 aggregation the hC2 antibody was pre-diluted in PBS and an assay solution containing the following components was made in a non-siliconized incubation tube: 3.3 or 0.33 µM pre-diluted antibody, 10 µM thioflavin T, 33 µM Aβ1-42, and 8.2% DMSO. Therefore the final molar ratios of antibody to Aβ1-42 were 1:10 and 1:100. Appropriate control solutions were also prepared. The solutions were then incubated for 24 hrs at 37° C., and the spectrofluorescence (relative fluorescence units; RFU) read in six replicates in black 384-well plates (Perkin-Elmer) on a Perkin-Elmer FluoroCount spectrofluorometer. The spectrofluorescence was then measured and % disaggregation calculated as described below.

13.2 Disaggregation Assay

To assay for antibody-mediated disaggregation of pre-aggregated Aβ1-42, a low-molecular weight Aβ1-42, prepared as described above, was made up as a 110 µM solution in 27% DMSO and 1×PBS. This solution was then allowed to aggregate at 37° C. for 24 hrs after which the following were added: 3.3 or 0.33 µM pre-diluted antibody, and 110 µM thioflavin T. This resulted in a molar ratio of 1:10 and 1:100 antibody to Aβ1-42. This solution was then incubated for additional 24 hrs at 37° C. The spectrofluorescence was then measured and % disaggregation calculated as described below.

13.3 Calculation

Inhibition of aggregation or disaggregation is expressed as mean % inhibition or disaggregation, respectively, ±standard error of the mean (SEM) according to the following equation:

$$\% \text{ inhibition} = \frac{(RFU \text{ of pos contrl} - RFU \text{ of neg contrl}) - (RFU \text{ of sample with } A\beta 1\text{-}42 - RFU \text{ of sample without } A\beta 1\text{-}42)}{(RFU \text{ of pos contrl} - RFU \text{ of neg contrl})} \times 100\%$$

13.4 Result 13.4.1 Inhibition of Aβ1-42 Aggregation

Inhibition of Aβ1-42 aggregation using the hC2 antibody is shown in Table 3 and FIG. 11. At an antibody to Aβ1-42 molar ratio of 1:100 the inhibition averaged 30% (2 independent experiments), whereas at a 1:10 molar ratio the inhibition was 80% (2 independent experiments; see Table 3).

TABLE 3 hC2-mediated inhibition of Aβ1-42 aggregation at a
1:100 and 1:10 antibody to Aβ1-42 molar ratios.

| Antibody | Molar ratio (antibody to Aβ1-42) | |
| --- | --- | --- |
| | 1:100 | 1:10 |
| hC2 | 30.0 ± 4.1% | 80.4 ± 6.9% |

13.9.2 Disaggregation of Pre-Aggregated Aβ1-42

Disaggregation of pre-aggregated Aβ1-42 using the hC2 antibody is shown in Table 4 and FIG. 12. At an antibody to Aβ1-42 molar ratio of 1:100 the disaggregation averaged 24%, whereas at a 1:10 molar ratio the disaggregation was 32% (3 independent experiments; see Table 4).

TABLE 4 hC2-mediated disaggregation of pre-aggregated Ab1-42 at
a 1:100 and 1:10 antibody to Aβ1-42 molar ratios.

| Antibody | Molar ratio (antibody to Aβ1-42) | |
| --- | --- | --- |
| | 1:100 | 1:10 |
| hC2 | 23.9 ± 4.4% | 31.9 ± 3.5% |

Using the thioflavin T assay, the bi-functional properties of the anti-Aβ humanized antibody hC2 can be demonstrated, namely to inhibit the aggregation of Aβ1-42 into pathogenic protofibrillar conformation and in addition to disaggregate preformed Aβ1-42 protofibrils. hC2 inhibited Aβ1-42 aggregation by 80% at an antibody to Aβ1-42 molar ratio of 1:10. The ability of hC2 to disaggregate pre-aggregated protofibrils of Aβ1-42 at a 1:10 molar ratio was shown to be 32%.

Example 14

Conformation-Specific Binding of mC2 to Different Classes of Amyloid Protein

In order to evaluate the specificity of mC2 to different stages of polymerized amyloid protein, monomeric, polymeric soluble and fibrillic amyloid, an ELISA coated with these different stages of polymeric beta-amyloid was performed (FIG. 9). Monomers were prepared according to a modified method published by (Klein, 2002), soluble polymeric amyloid beta according to (Barghorn et al., 2005), whereas fibers were performed by incubation of amyloid (Bachem, Switzerland) with a final concentration of 1 µg/µl in Tris/HCl pH 7.4 at 37° C. for 5 days followed by a centrifugation step (10,000 rpm for 5 minutes). Then amyloid polymers were coated on an ELISA plates with a final concentration of 55 µg/ml and binding affinity ELISA by using an anti-mouse IgG monoclonal antibody (Jackson) labelled with alkaline phosphate was performed. As demonstrated in Table 5 the mC2 antibody binds with higher affinity to soluble polymeric amyloid beta than to fibers and with the lowest to monomers. These data indicate that the antibody's binding is influenced by the amyloid epitope and by the conformation of the different amyloid aggregates.

TABLE 5

Conformation-specific binding of mC2 to
Amyloid Monomers, Oligomers and Fibres

| mC2 Ab Conc | O.D | | |
| --- | --- | --- | --- |
| (ug/ml) | Oligomer | Fibers | Monomers |
| 0.625 | 2.806 | 1.620 | 1.155 |
| 0.312 | 1.724 | 0.989 | 0.649 |
| 0.156 | 1.036 | 0.631 | 0.397 |
| 0.078 | 0.652 | 0.499 | 0.333 |

Example 15

Epitope Mapping of AC Immune's Monoclonal Antibody hC2

Epitope mapping of the humanized monoclonal antibody hC2 was performed by ELISA using three different peptide libraries. One library comprised a total of 33 biotinylated peptides covering the complete amino acid (aa) sequence of Aβ1-42 (produced by Mimotopes and purchased from ANAWA Trading SA), the second library contains biotinylated peptides using peptide 12 (aa12-20 of Aβ) from the first peptide library and substituting each aa in the sequence by an alanine (see table 8 below), and the third library contains biotinylated peptides 13, 14, or 15 (aa 13-21, 14-22 or 15-23 of Aβ) and substituting in each case the last amino acids to an alanine or to a glycine for aa 21 which is already an alanine (see table 9 below). A biotinylated complete Aβ1-42 peptide was used as positive control (Bachem). Epitope mapping was done according to the manufacturer's (Mimotopes) instructions. Briefly, Streptavidin coated plates (NUNC) were blocked with 0.1% BSA in PBS overnight at 4° C. After washing with PBS-0.05% Tween 20, plates were coated for 1 hour at RT with the different peptides from the library, diluted in 0.1% BSA, 0.1% Sodium Azide in PBS to a final concentration of 10 μM. After washing, plates were incubated for 1 hour at RT with the hC2 antibody or a non Aβ binding chimeric IgG4 antibody diluted to 200 ng/ml in 2% BSA, 0.1% Sodium Azide in PBS. Plates were washed again and incubated with alkaline phosphatase conjugated goat anti human IgG for 1 h at RT. After final washing, plates were incubated with phosphatase substrate (pNPP) and read at 405 nm using an ELISA plate reader.

It was shown that the humanized monoclonal antibody hC2 bound specifically to peptides 12,13,14,15 and 16 of the first peptide library. These peptides comprise aa 12-20, 13-21, 14-22, 15-23 and 16-24 respectively of Aβ1-42, suggesting that the epitope lies in region 12-24 of Aβ. A second library with alanine substitutions was used to determine the critical aa for binding to Aβ12-20 (VHHQKLVFF). The binding of the hC2 antibody is lost completely when amino acids 16, 17, 19 or 20 are substituted by an alanine, indicating that these aa are absolutely critical for binding of the antibody to Aβ. The binding of the hC2 antibody is partially lost when aa 15 and 18 are substituted.

The binding was also almost completely lost when aa 14 was substituted for an alanine, indicating that aa 14 is also very important for binding.

Finally, a third library was used to determine whether aa 21, 22 or 23 are critical for binding to the epitope. The binding of the antibody to aa 15-23 was reduced when aa 23 was substituted for an alanine, indicating that aa 23 is also important for binding. The binding was partially lost when aa 21 was substituted for a glycine and slightly lost when aa 22 was substituted for an alanine.

Example 16

Neuroprotection by the hC2 Antibody

The ability of antibody hC2 to protect neurons from Abeta oligomer-induced degeneration was assessed in an in vitro assay. Embryonic day 16.5-17.5 mouse cortical neurons were isolated, dissociated, and cultured in vitro in N3-F12 media. The cells were grown for nine days in total, and were fed on day 3 and on the day that Abeta oligomer, or Abeta oligomer plus anti-Abeta antibody hC2 was added. At day five ("4 days Abeta") or day six ("3 days Abeta"), certain wells of cells were treated with either 2 μM Abeta oligomer alone, or a combination of 2 μM Abeta oligomer and 50 μg/mL anti-Abeta antibody hC2.

The Abeta oligomer was prepared by dissolving Abeta 1-42 (rPeptide) in HFIP, from which Abeta peptides were aliquoted into 10 μl aliquots at 1 mg/ml and then evaporated in a fume hood for 30 minutes and peptide films were stored at −80 C until use. Upon use, the peptide film was dissolved in 10 μl of DMSO, then 78.6 μl of HAMS F12, and the Abeta peptide solution was incubated at 4 C for 24-48 hours (25 μM final concentration of Abeta).

For control cells, DMSO-F12 alone was added at the same volume as Abeta-DMSO at day 5, and the cells were cultured for an additional 4 days without any additional treatment. On day 9, neurons from all culture conditions were fixed and stained with Tuj1 (an anti-beta-tubulin antibody), followed by staining with secondary antibodies labeled with FITC to visualize microtubules, and thus neuronal processes in general. The results are shown in FIG. 13.

Untreated mouse embryonic cortical neurons showed normal morphology after nine days of culture (FIG. 13, leftmost panel). Treatment of the cells with Abeta oligomer for three days induced axon degeneration and caused a decrease in the total number of axons (FIG. 13, lower center panel), and this effect was even more pronounced at four days of treatment (FIG. 13, upper center panel). In contrast, the cells treated with the combination of Abeta oligomer and anti-Abeta antibody hC2 looked similar to control cells (FIG. 13, upper and lower right panels). These results indicate that anti-Abeta antibody hC2 was able to protect embryonic mouse cortical neurons from Abeta oligomer-induced degeneration.

TABLE 6

Positions and changes made in the humanized C2 light chain framework regions

| Position Light chain | 45 | 87 | 50 | 53 |
|---|---|---|---|---|
| Mouse C2V$_K$ | K | F | K | N |
| Humanized C2HuV$_K$1 | Q | Y | K | N |
| Humanized C2HuV$_K$2 | Q | F | K | N |
| Humanized C2HuV$_K$3 | K | Y | K | N |
| Humanized C2HuV$_K$4 | K | F | K | N |
| Human Germline dpk15 | Q | Y | L | N |
| Mouse C2V$_K$-R | | | R | |
| Mouse C2V$_K$-S | | | | S |

TABLE 7

Positions and changes made in the humanized C2 heavy chain framework regions

| Position Heavy chain | 47 | 94 |
|---|---|---|
| Mouse C2VHAF | L | S |
| Humanized C2HuVHAF1 | W | R |
| Humanized C2HuVHAF2 | W | S |
| Humanized C2HuVHAF3 | L | R |
| Humanized C2HuVHAF4 | L | S |
| Human Germline DP-54 | W | R |

A total of 8 different antibodies were constructed with light chains Humanized C2HuV$_K$1, C2HuV$_K$2, C2HuV$_K$3, C2HuV$_K$4 and heavy chains C2HuVHAF4 and C2HuVHAF2

TABLE 8

Summary of peptides used in the second library

| p12-20 | V | H | H | Q | K | L | V | F | F |
|---|---|---|---|---|---|---|---|---|---|
| A12 | A | H | H | Q | K | L | V | F | F |
| A13 | V | A | H | Q | K | L | V | F | F |
| A14 | V | H | A | Q | K | L | V | F | F |
| A15 | V | H | H | A | K | L | V | F | F |
| A16 | V | H | H | Q | A | L | V | F | F |
| A17 | V | H | H | Q | K | A | V | F | F |

TABLE 8-continued

Summary of peptides used in the second library

| A18 | V | H | H | Q | K | L | *A* | F | F |
|---|---|---|---|---|---|---|---|---|---|
| A19 | V | H | H | Q | K | L | V | *A* | F |
| A20 | V | H | H | Q | K | L | V | F | *A* |
| aa no. | 12 | 13 | *14* | *15* | 16 | 17 | *18* | 19 | 20 | aa that are important for binding are marked in italics and underscore and aa absolutely critical for binding are marked in italics and bold.

TABLE 9

Summary of peptides used in the third library.

| p13-21 |  | H | H | Q | K | L | V | F | F | A |  |  |
|---|---|---|---|---|---|---|---|---|---|---|---|---|
| p13-21 | G21 | H | H | Q | K | L | V | F | F | G |  |  |
| p14-22 |  |  | H | Q | K | L | V | F | F | A | E |  |
| p14-22 | A22 |  | H | Q | K | L | V | F | F | A | A |  |
| p15-23 |  |  |  | Q | K | L | V | F | F | A | E | D |
| p15-23 | A23 |  |  | Q | K | L | V | F | F | A | E | A |
| aa no. |  | 13 | *14* | *15* | 16 | 17 | *18* | 19 | *20* | 21 | 22 | *23* | aa that are important for binding are marked in italics and underscore and aa absolutely critical for binding are marked in italics and bold

Example 17

Binding of AC Immune's Monoclonal Antibody mACI-01-Ab7 C2 to Amyloid Species in Western Blot and Dot Blot To determine whether the binding of the mouse antibody mACI-01-Ab7 C2 is dependent on the native conformation of Aβ a comparison of the binding to linearized amyloid by Western Blot or native amyloid on Dot Blot was performed (FIGS. 2a and 2b)

Amyloid monomers were generated by dissolving Aβ1-42 peptide in HFIP and the solvent evaporated under argon. Dried peptide film was stored at −80° C. until use. For preparation of monomers, the peptide film was resuspended in DMSO to a concentration of 2.75 µg/µl and diluted in PBS to 1 µg/µl. For preparation of oligomers, dried peptide film was resuspended in DMSO to 5 mM, sonicated and PBS added to reach 400 uM amyloid followed by the addition of SDS to a final concentration of 0.2%. After 6 hour incubation at 37° C., the amyloid was diluted in water to a final concentration of 100 µM and incubated another 18 h at 37° C. The amyloid oligomers were precipitated with ice-cold 33% methanol, 4% acetic acid solution for 1 h at 4° C., spun down at 16200 g for 10 minutes and the pellet resuspended in 5 mM Na2H2PO4, 35 mM NaCl pH 7.4 to a final concentration of 1 µg/µl. For preparation of fibers, peptide film was diluted in Tris-HCl 50 mM buffer to get a concentration of 1 mg/ml of amyloid and incubated at 37° C. for 5 days. The tubes were spun at 10000 g for 5 minutes and the pellet resuspended in 0.1M carbonate buffer pH 9.6 to reach 1 µg/µl.

1 or 5 µg of monomers, oligomers or fibers were diluted in PBS and in loading buffer and applied to a 12% SDS-PAGE and the gel transferred to nitrocellulose membranes. Alternatively, 3 or 1 µg or 100 and 10 ng of amyloid species were diluted in PBS and were dotted directly onto the nitrocellulose membrane and the membranes dried at RT for 1 hour. After blocking for 30 minutes with Casein solution (Vector), the membranes were incubated for 30 minutes with mACI-01-Ab7 C2 or 6E10 (Chemicon) antibodies diluted to 1 µg/ml in Casein solution. After 3 washes in Casein solution, the membranes were incubated at RT for 30 minutes with HRP-labeled goat anti-mouse IgG (Dako Cytomation) diluted in Casein solution, washed 3 times and developed with DAB substrate (Dako Cytomation).

The monoclonal mouse antibody mACI-01-Ab7 C2 bound specifically to monomers, oligomers and fibers in the Dot Blot assay as did the positive control antibody 6E10. In contrast, the mACI-01-Ab7C2 antibody did not detect linearized amyloid species by Western Blot in contrast to the 6E10 antibody which clearly recognized all linearized peptides. This result demonstrates that the binding of mACI-0'-Ab7 C2 to amyloid is dependent on the native conformation of amyloid.

Example 18 mACI-01Ab7 C2-Aβ$_{1-42}$ Interactions

The interactions between AC immune's lead antibody mACI-01-Ab7 C2 (mC2) with amyloid peptide Aβ$_{1-42}$ was studies using surface plasmon resonance. The binding of the mouse antibody mACI-01-Ab7 C2 to either monomers or fibers of Aβ$_{1-42}$ were determined.

All SPR experiments were carried out on a Biacore X instrument (Biacore AB). Reagents for immobilization (EDC, NHS and ethanolamine), sensor chips CM5 and SA as well as running and sample buffer HBS-EP were purchased from Biacore AB. Sodium acetate (10 mM, pH 5.0) was used as coupling buffer to increase coupling yield. Fibrillar Aβ$_{1-42}$ (BAchem) was prepared by adding PBS buffer to Aβ$_{1-42}$ to a final concentration of 3 mg/ml and leaving the vials at 37° C. for 7 days. Fibrillar Aβ$_{1-42}$ was coupled to a CM5 sensor chip containing a surface-bound carboxymethyl dextran matrix. Biotinylated monomeric Aβ$_{1-42}$ (Bachem) was coupled to a Sensor chip SA consisting of carboxymethyl dextran matrix with covalently attached Streptavidin. Typically four or five concentrations of mAb were assayed by serial dilutions using running buffer. Injections were performed starting from the lowest concentration and were passed over both fc 1 and 2 at a flow rate of 30 µL'min for 3 min. Flow cell 2 was underivatised and responses were subtracted from fc 1 to correct for instrument noise and bulk refractive changes. After injection was finished, the surfaces were washed immediately with running buffer for 5 min. To remove remaining bound antibody from the Aβ$_{1-42}$ fibrils, surface regeneration was performed by injecting pulses of 10 mM NaOH. Kinetic analysis was performed using algorithms for numerical integration and global analysis using BIAevaluation 3.0. The curves obtained for injections of analyte at different concentrations were overlaid and the baselines adjusted to zero. For curve fitting, all data were fit simultaneously to a 1:1 homogeneous complex.

Binding of the mouse mACI-01-Ab7 C2 antibody to amyloid was determined to be relatively strong. As demonstrated in Table 2, the mouse antibody mACI-01-Ab7 C2 bound specifically to immobilized Aβ$_{1-42}$ fibers with an average association constant (ka) of $3.8 \times 10^{-4}$ M/s, a dissociation constant (kd) of $1.1 \times 10^{-3}$ s$^{-1}$ and therefore with the resulting average KD of $3.5 \times 10^{-8}$ M. Association of the mACI-01-Ab7 C2 to Aβ monomers was similar or slightly faster with an average ka of $1.6 \times 10^{-4}$ M/s but the dissociation was more rapid giving a KD of $2.5 \times 10^{-7}$ M.

TABLE 2

| | Monomers | | | Fibers | | |
|---|---|---|---|---|---|---|
| | $k_a$(1/Ms) | $k_d$(1/s) | KD (M) | $k_a$(1/Ms) | $k_d$(1/s) | KD (M) |
| mACI-01-Ab7 C2 exp. 1 | 1.8E+04 | 2.7E−03 | 1.5E−07 | 2.4E+04 | 9.9E−04 | 4.1E−08 |
| mACI-01-Ab7 C2 exp. 2 | 1.5E+04 | 5.3E−03 | 3.5E−07 | 5.60E+04 | 9.66E−04 | 1.73E−08 |
| mACI-01-Ab7 C2 exp. 3 | | | | 3.26E+04 | 1.49E−03 | 4.58E−08 |
| average mACI-01-Ab7 C2 | 1.6E+04 ±0.21 | 4.0E−03 1.84 | 2.5E−07 1.41 | 3.8E+04 1.66 | 1.1E−03 0.3 | 3.5E−08 1.53 |

Example 19

Binding of mACI-01-Ab7 C2 Monoclonal Antibody to Amyloid Fibers

To analyze the molecular binding side of the antibody on pre-formed fibers negatively contrasted transmission electronic microscopy (TEM) was performed (FIGS. 3a and 3b).

The antibody, mACI-01-Ab7 C2, was coupled with 8 nm colloidal gold according to[4,5]. For the co-incubation of amyloid 1-42 (Aβ1-42) fibers 6.65 uM fibers were incubated for 24 h at RT with the gold-labeled antibody with the molar ratio of 1:100. Subsequently 5 µl of sample were incubated on the fresh glow-discharged Cu grid (mesh 200) covered with parlodium/C film for 45 seconds, washed 3 times with water and 1 times with 2% fresh diluted and filtered uranyl acetate. Samples were stained in 2% uranyl acetate for 15-20 sec. Excess of stain on the grids was sucked and consequently air-dried. Three grids of each sample were prepared. The grids were analyzed in transmission electron microscopy Hitachi 7000.

The monoclonal antibody, mACI-01-Ab7 C2, binds directly to $A\beta_{1-42}$ fibers. Interestingly the antibody exhibits no symmetric binding to axis of single fibers but binds to particular and not all areas of side branches of the fiber network. It seemed to be the antibody targets specific regions within the side branches. The potential explanation is a specific secondary structure which occurs only in this specific side branches. This hypothesis is supported by NMR data demonstrating that the antibody induced transition on conformation and therefore it is likely that its binding is dependent on a conformation of the amyloid fiber comprising a β-sheet structure.

Example 20

Epitope Mapping of Monoclonal Antibody mACI-01-Ab7 C2

Epitope mapping of the monoclonal antibody mACI-01-Ab7 C2 was performed by ELISA using three different peptide libraries. One library comprises a total of 33 biotinylated peptides covering the complete amino acid (aa) sequence of Aβ1-42 (produced by Mimotopes and purchased from ANAWA Trading SA), the second library contains biotinylated peptides using peptide 12 (aa12-20 of Aβ) from the first peptide library and substituting each amino acid in the sequence by an alanine (see table 41 below), and the third library contains biotinylated peptides 13, 14, or 15 (aa 13-21, 14-22 or 15-23 of Aβ) and substituting in each case the last amino acids to an alanine or to a glycine for aa 21 which is already an alanine (see table 5 below). A biotinylated complete Aβ1-42 peptide was used as positive control (Bachem).

Epitope mapping was done according to the manufacturer's (Mimotopes) instructions. Briefly, Streptavidin coated plates (NUNC) were blocked with 0.1% BSA in PBS overnight at 4° C. After washing with PBS-0.05% Tween 20, plates were coated for 1 hour at RT with the different peptides from the library, diluted in 0.1% BSA, 0.1% Sodium Azide in PBS to a final concentration of 10 µM. After washing, plates were incubated for 1 hour at RT with the mACI-01-Ab7 C2 antibody or an isotype control mouse IgG2b antibody, diluted to 10 µg/ml in 2% BSA, 0.1% Sodium Azide in PBS. Plates were washed again and incubated with alkaline phosphatase conjugated goat anti mouse IgG for 1 h at RT. After final washing, plates were incubated with phosphatase substrate (pNPP) and read at 405 nm using an ELISA plate reader.

It was shown that the monoclonal antibody mACI-01-Ab7 C2 bound specifically to peptides 12, 13, 14 and 15 of the first peptide library. These 4 peptides comprise as 12-20 (VHHQKLVFF), 13-21 (HHQKLVFFA), 14-22 (HQKLVFFAE) and 15-23 (QKLVFFAED) of Aβ1-42 suggesting that the epitope lies in region 12-23 of Aβ. A second library with alanine substitutions was used to determine the critical as for binding to peptide 12-20 (VHHQKLVFF). The binding of the mACI-01-Ab7 C2 antibody is lost completely when as 16, 17, 19 or 20 are substituted by an alanine, indicating that these as are absolutely critical for binding of the antibody to Aβ. The binding of the mACI-01-Ab7 C2 antibody is partially lost when aa 15 and 18 are substituted.

The binding was also almost completely lost when aa 14 was substituted for an alanine, indicating that aa 14 is also very important for binding.

Finally, a third library was used to determine whether aa 21, 22 or 23 are critical for binding to the epitope. The binding of the antibody to aa 15-23 was reduced when aa 23 was substituted for an alanine, indicating that aa 23 is also important for binding. The binding was partially lost when aa 21 was substituted for a glycine and slightly lost when aa 22 was substituted for an alanine.

TABLE 4

Summary of peptides used in the second library.

| p12-20 | V | H | H | Q | K | L | V | F | F |
|---|---|---|---|---|---|---|---|---|---|
| A12 | A | H | H | Q | K | L | V | F | F |
| A13 | V | A | H | Q | K | L | V | F | F |
| A14 | V | H | *A* | Q | K | L | V | F | F |
| A15 | V | H | H | *A* | K | L | V | F | F |
| A16 | V | H | H | Q | A | L | V | F | F |
| A17 | V | H | H | Q | K | A | V | F | F |
| A18 | V | H | H | Q | K | L | *A* | F | F |
| A19 | V | H | H | Q | K | L | V | A | F |
| A20 | V | H | H | Q | K | L | V | F | A |
| aa no. | 12 | 13 | *14* | *15* | 16 | 17 | *18* | 19 | 20 | aa that are important for binding are marked in italics and underscored and aa absolutely critical for binding are marked in italics and bold and underscored

TABLE 5

Summary of peptides used in the third library.

| | | | | | | | | | | | |
|---|---|---|---|---|---|---|---|---|---|---|---|
| p13-21 | | H | H | Q | K | L | V | F | F | A | |
| p13-21 | G21 | H | H | Q | K | L | V | F | F | G | |
| p14-22 | | | H | Q | K | L | V | F | F | A | E |
| p14-22 | A22 | | H | Q | K | L | V | F | F | A | A |
| p15-23 | | | | Q | K | L | V | F | F | A | E | D |
| p15-23 | A23 | | | Q | K | L | V | F | F | A | E | A |
| aa no. | | 13 | 14 | 15 | 16 | 17 | 18 | 19 | 20 | 21 | 22 | 23 | aa that are important for binding are marked in italics and underscored and aa absolutely critical for binding are marked in italics and bold and underscored

Example 21

Influence of Passive Vaccination with mACI-01-Ab7 C2 on Brain Amyloid Load in Single Transgenic hAPP Mice To assess the in vivo capacity of the mACI-01-Ab7 C2 monoclonal antibody to bind and clear soluble amyloid out of the brain, 6 month old single hAPP mice[9], gender and age matched, were used for a passive immunization study with different dose. Soluble Amyloid load was analyzed at the end of the study by harvesting the brain of the animals and by performing an Aβ1-40 and Aβ1-42 specific ELISA (TGC, Germany).

8-13 animals per group received two injections at an interval of one week of 100, 300 and 1000 µg monoclonal antibody in 200 µl PBS whereas injection of PBS alone served as control. One day after the second injection animals were sacrificed for biochemical analysis of soluble amyloid fraction. To quantify the amount of human Aβ1-40 and human Aβ1-42 in the soluble fraction of the brain homogenates and/or in cerebrospinal fluid (CSF), commercially available Enzyme-Linked-Immunosorbent-Assay (ELISA) kits were used (h Amyloid β40 or β42 ELISA high sensitive, TGC, Switzerland). The ELISA was performed according to the manufacturer's protocol. Briefly, standards (a dilution of synthetic Aβ1-40 or Aβ1-42) and samples were prepared in a 96-well polypropylene plate without protein binding capacity (Greiner, Germany). The standard dilutions with final concentrations of 1000, 500, 250, 125, 62.5, 31.3 and 15.6 pg/ml and the samples were prepared in the sample diluent, furnished with the ELISA kit, to a final volume of 60 µl. Since amyloid levels increase with the age of the mouse and since the actual evaluation requires that the readings of the samples are within the linear part of the standard curve, the samples for Aβ 40 analysis were diluted 2:3, the samples for Aja 42 analysis were not diluted.

Samples, standards and blanks (50 µl) were added to the anti-Aβ-coated polystyrol plate (capture antibody selectively recognizes the C-terminal end of the antigen) in addition with a selective anti-Aβ-antibody conjugate (biotinylated detection antibody) and incubated overnight at 4° C. in order to allow formation of the antibody-Amyloid-antibody-complex. The following day, a Streptavidine-Peroxidase-Conjugate was added, followed 30 minutes later by the addition of a TMB/peroxide mixture, resulting in the conversion of the substrate into a colored product and the color intensity was measured by means of photometry with an ELISA-reader with a 450 nm filter. Quantification of the Aβ content of the samples was obtained by comparing absorbance to the standard curve made with synthetic Aβ1-40 or Aβ1-42. Data were expressed as individual changes to mean control value (in percent to control).

The total amount of Aβ40 in brain homogenates could be significantly reduced and roughly non-significantly for Aβ42 when single hAPP mice were passively immunized by two i.p. injections of monoclonal antibody ACI-01-Ab7 C2 at a dose of 300 µg (Aβ40: −27.3±13.9% with p<0.05; Aβ42: −8.6±22.4 with p=0.56; unpaired Student's T test), whereas 100 and 1,000 µg didn't reach significance. Immunization with 100 µg lead to an increase for Aβ40 and Aβ42 in brain homogenates (Aβ40: 32.3±36.8%; Aβ42: 38.3±51.4%) whereas treatment with 1,000 µg elicited the right tendency of amyloid burden lowering and could be potentially effective with an increased number of animals per group (Aβ40: −2.2±26.0%; Aβ42: −9.3±15.9%). These data demonstrate that in an acute immunization protocol the antibody mACI-01-Ab7 C2 is capable to decrease the total amount of soluble Aβ in the brain of this murine AD model. Interestingly, it seems to be that the dose-relationship is transient but more studies with larger groups must be performed in order to gain significant data.

Example 22

Influence of Chronic Passive Administration of mACI-01-Ab7 C2 on Plaque Load in Double Transgenic hAPPxPS1 Mice To assess the in vivo capacity of the mACI-01-Ab7 C2 monoclonal antibody to bind and reduce amyloid plaques in the brain, 3.5 month old double transgenic hAPPxPS1 mice[10], gender and age matched, were used for a 4 month long chronic passive immunization study. Amyloid plaques were analyzed at the end of the study by histochemistry of the brain of the animals by binding of Thioflavin S.

15 transgenic animals received 16 weekly injections of 500 µg monoclonal antibody in PBS. 15 animals were injected with PBS alone, serving as controls. All injections were given intra-peritoneally. At sacrifice, mice were anaesthetized and flushed trans-cardially with physiological serum at 4° C. to remove blood from the brain vessels. Subsequently, the brain was removed from the cranium and hindbrain and forebrain were separated with a cut in the coronal/frontal plane. The forebrain was divided evenly into left and right hemisphere by using a midline sagittal cut. One hemisphere was post-fixed overnight in 4% paraformaldehyde for histology. Sagittal vibratome sections (40 µm) were cut for free floating incubations and stored at 4° C. until staining in PBS with 0.1% sodium azide. Five sections at different levels were stained for dense plaques with Thioflavin S. Sections of all animals used were randomized for staining and blind quantification. Images were acquired with a Leica DMR microscope equipped with a Sony DXC-9100P camera and analyzed with a computer using Leica Q-Win software. Light intensity and condenser settings for the microscope were kept constant throughout the image acquisition process. All acquired images were subjected to the same computer subroutines to minimize investigator bias. Density slice thresholding was applied uniformly throughout analysis. The area of the subiculum was selected for automatic quantification of the amyloid load in the Thioflavin S staining.

The total plaque load and the number of plaques in the area of subiculum could be significantly reduced when double hAPP/PS1 mice were passively immunized for 4 months as described above. In plaque load a significant decrease of 31% (mACI-01-Ab7 C2: 1.11±0.21% and control: 1.61±0.35%; p=0.003, Mann-Whitney U-Test) could be achieved whereas the chronic passive immunization significantly reduced the amount of plaques by 19% (mACI-01-Ab7 C2: 8.73±1.36 and control: 10.78±1.36; p=0.006, Mann-Whitney U-Test), indicating that plaque solubilization occurred to a slightly lesser degree than plaque disruption.

Example 23

Influence of Passive Vaccination with mACI-01-Ab7 C2 on Memory Capacity in Single Transgenic hAPP Mice To analyze the in vivo capacity of the mACI-01-Ab7 C2 antibody to modify or increase cognitive functionality, 9 month old single hAPP mice, gender and age matched, were used for passive immunization study. Non-spatial cognition was measured at the end of the immunization period assessed by new Object Recognition Task (ORT).

12 animals per group received two intra peritoneal injections of 400 µg monoclonal antibody in 200 µl PBS whereas injection of PBS alone served as control. One day after the second injection cognitive capability were studied in a new Object Recognition Task (ORT)[12,13]. For ORT enrollment mice were placed for 10 minutes into a behavioral arena and faced to a new unknown object. Exploration time was recorded. Three hours later the same animals were re-placed into the same arena for a $2^{nd}$ session but faced with the old, previously explored, and additionally with a new object. Again, exploration times for both objects were recorded and resulting cognition index was calculated as the ratio of exploration time for the new object related to total exploration time and expressed as proportional changes to the control.

Passive vaccination with mACI-0'-Ab7 C2 leads to a significant increase of cognitive memory capacities in single transgenic AD mice (mACI-01-Ab7 C2: 131.6±9.1% and control: 100.0±9.2% with p<0.05; unpaired Student's T test and n=12 per each group).

REFERENCE LIST

Barghorn S, Nimmrich V, Striebinger A, Krantz C, Keller P, Janson B, Bahr M, Schmidt M, Bitner R S, Harlan J, Barlow E, Ebert U, Hillen H (2005) Globular amyloid beta-peptide oligomer—a homogenous and stable neuropathological protein in Alzheimer's disease. J Neurochem 95:834-847.

Blond and Goldberg, 1987, PNAS Mar. 1, 1987 Vol. 84|no. 5| 1147-1151

Cox J P L, Tomlinson I M and Winter G. Eur. J. Immunol. 1994; 24: 827-836. A directory of human germ-line Vκ segments reveals a strong bias in their usage.

Hieter P A, Max E E, Seidman J G, Maizel J V Jr, Leder P. Cloned human and mouse kappa immunoglobulin constant and J region genes conserve homology in functional segments. Cell. 1980 November; 22(1 Pt 1):197-207.

Kabat E A, Wu T T, Perry H M, Gottesman K S, Foeller C. Sequences of proteins of Immunological Interest, US Department of Health and Human Services, 1991.

Klein W L (2002) Abeta toxicity in Alzheimer's disease: globular soluble polymeric amyloid beta (ADDLs) as new vaccine and drug targets. Neurochem Int 41(5):345-352.

Langdon S D, Inaioki M, Kelsoe G. and Tedder T F. Immunogenetics 2000; 51: 241-245. Germline sequences of V(H)7183 gene family members in C57BL16 mice demonstrate natural selection of particular sequences during recent evolution Mulligan R C and Berg P. Science 1980; 209: 1422-1427. Expression of a bacterial gene in mammalian cells.

Riechmann L, Clark M, Waldmann H, Winter G, Nature 1988; 332: 323-327. Reshaping human antibodies for therapy.

Schable K F, Thiebe R, Bensch A, Brensing-Kueppers J, Heim V, Kirschbaum T, Lamm R, Ohnrich M, Pourrajabi S, Roschenthaler F, Schwendinger J, Wichelhaus D, Zocher I and Zachau H G. Eur. J. Immunol. 1999; 29: 2082-2086. Characteristics of the immunoglobulin V kappa genes, pseudogenes, relics and orphons in the mouse genome.

Tomlinson I M, Walter G, Marks J D, Llewelyn M B and Winter G. J. Mol. Biol. 1992; 227: 776-798. The repertoire of human germline $V_H$ sequences reveals about 50 groups of $V_H$ segments with different hypervariable loops

The invention claimed is:

1. A method for monitoring minimal residual disease in a patient following treatment with a pharmaceutical composition which comprises a humanized antibody or a fragment thereof that specifically binds to β-amyloid protein, wherein said method comprises:
   a. bringing a sample suspected to contain β-amyloid antigen into contact with a humanized antibody or a fragment thereof which specifically binds β-amyloid protein, wherein said humanized antibody or fragment thereof comprises a Light Chain Variable Region (LCVR) comprising SEQ ID NO:12 and a Heavy Chain Variable Region (HCVR) comprising SEQ ID NO:15;
   b. allowing the humanized antibody or fragment thereof to bind to β-amyloid antigen to form an immunological complex;
   c. detecting the formation of the immunological complex;
   d. correlating the presence or absence of the immunological complex with the presence or absence of amyloid antigen in the sample; and
   e. comparing the amount of said immunological complex to a normal control value, wherein an increase in the amount of said immunological complex compared to a normal control value indicates that said patient still suffers from a minimal residual disease.

2. A method for predicting responsiveness of a patient being treated with a pharmaceutical composition which comprises a humanized antibody or a fragment thereof that specifically binds to β-amyloid protein, wherein said method comprises
   a. bringing a sample suspected to contain β-amyloid antigen into contact with a humanized antibody or a fragment thereof, which specifically binds β-amyloid protein wherein said humanized antibody or fragment thereof comprises an LCVR comprising SEQ ID NO:12 and an HCVR comprising SEQ ID NO:15;
   b. allowing the humanized antibody or fragment thereof to bind to β-amyloid antigen to form an immunological complex;
   c. detecting the formation of the immunological complex;
   d. correlating the presence or absence of the immunological complex with the presence or absence of β-amyloid antigen in the sample; and
   e. comparing the amount of said immunological complex before and after onset of the treatment,
wherein a decrease in the amount of said immunological complex after said treatment as compared to the amount of said immunological complex before said treatment indicates that said patient has a high potential of being responsive to the treatment.

3. The method of claim 1 or 2, wherein the patient is a human.

4. The method of claim 3, wherein the human has Alzheimer's Disease.

5. The method of claim 3, wherein the human has a disease or condition associated with increased concentration of β-amyloid in the brain.

6. The method of claim 5, wherein the disease or condition is mild cognitive impairment, Down's syndrome, or hereditary cerebral hemorrhage with amyloidosis (Dutch type).

7. The method of claim 1 or 2 wherein the humanized antibody or fragment thereof of step (a) comprises a light chain comprising SEQ ID NO: 13 and a heavy chain having the amino acid sequence of SEQ ID NO: 16.

8. A method for monitoring minimal residual disease in a patient following treatment with a pharmaceutical composition which comprises a humanized antibody or a fragment thereof that specifically binds to β-amyloid protein, wherein said method comprises:
   a. bringing a sample suspected to contain β-amyloid antigen into contact with a humanized antibody or a fragment thereof which specifically binds β-amyloid protein, wherein said humanized antibody or fragment thereof comprises a Light Chain Variable Region (LCVR) comprising SEQ ID NO:12;
   b. allowing the humanized antibody or fragment thereof to bind to β-amyloid antigen to form an immunological complex;
   c. detecting the formation of the immunological complex;
   d. correlating the presence or absence of the immunological complex with the presence or absence of amyloid antigen in the sample; and
   e. comparing the amount of said immunological complex to a normal control value, wherein an increase in the amount of said immunological complex compared to a normal control value indicates that said patient still suffers from a minimal residual disease.

9. A method for predicting responsiveness of a patient being treated with a pharmaceutical composition which comprises a humanized antibody or a fragment thereof that specifically binds to β-amyloid protein, wherein said method comprises
   a. bringing a sample suspected to contain β-amyloid antigen into contact with a humanized antibody or a fragment thereof, which specifically binds β-amyloid protein wherein said humanized antibody or fragment thereof comprises an LCVR comprising SEQ ID NO:12;
   b. allowing the humanized antibody or fragment thereof to bind to β-amyloid antigen to form an immunological complex;
   c. detecting the formation of the immunological complex; and
   d. correlating the presence or absence of the immunological complex with the presence or absence of β-amyloid antigen in the sample,
   e. comparing the amount of said immunological complex before and after onset of the treatment,
wherein a decrease in the amount of said immunological complex after said treatment as compared to the amount of said immunological complex before said treatment indicates that said patient has a high potential of being responsive to the treatment.

10. A method for monitoring minimal residual disease in a patient following treatment with a pharmaceutical composition which comprises a humanized antibody or a fragment thereof that specifically binds to β-amyloid protein, wherein said method comprises:
   a. bringing a sample suspected to contain β-amyloid antigen into contact with a humanized antibody or a fragment thereof which specifically binds β-amyloid protein, wherein said humanized antibody or fragment thereof comprises an HCVR comprising SEQ ID NO:15;
   b. allowing the humanized antibody or fragment thereof to bind to β-amyloid antigen to form an immunological complex;
   c. detecting the formation of the immunological complex;
   d. correlating the presence or absence of the immunological complex with the presence or absence of amyloid antigen in the sample; and
   e. comparing the amount of said immunological complex to a normal control value, wherein an increase in the amount of said immunological complex compared to a normal control value indicates that said patient still suffers from a minimal residual disease.

11. A method for predicting responsiveness of a patient being treated with a pharmaceutical composition which comprises a humanized antibody or a fragment thereof that specifically binds to β-amyloid protein, wherein said method comprises
   a. bringing a sample suspected to contain β-amyloid antigen into contact with a humanized antibody or a fragment thereof, which specifically binds β-amyloid protein wherein said humanized antibody comprises an HCVR comprising SEQ ID NO:15;
   b. allowing the humanized antibody or fragment thereof to bind to β-amyloid antigen to form an immunological complex;
   c. detecting the formation of the immunological complex;
   d. correlating the presence or absence of the immunological complex with the presence or absence of β-amyloid antigen in the sample; and
   e. comparing the amount of said immunological complex before and after onset of the treatment, wherein a decrease in the amount of said immunological complex after said treatment as compared to the amount of said immunological complex before said treatment indicates that said patient has a high potential of being responsive to the treatment.

\* \* \* \* \*